US011739297B2

(12) United States Patent
Klichinsky et al.

(10) Patent No.: US 11,739,297 B2
(45) Date of Patent: Aug. 29, 2023

(54) METHOD OF INCREASING TUMOR KILLING ACTIVITY OF MACROPHAGES OR MONOCYTES COMPRISING CHIMERIC ANTIGEN RECEPTOR

(71) Applicant: Carisma Therapeutics Inc., Philadelphia, PA (US)

(72) Inventors: Michael Klichinsky, Philadelphia, PA (US); Nicholas G. Minutolo, Philadelphia, PA (US); Nicholas R. Anderson, Philadelphia, PA (US)

(73) Assignee: Carisma Therapeutics Inc., Philadelphia, PA (US)

( * ) Notice: Subject to any disclaimer, the term of this patent is extended or adjusted under 35 U.S.C. 154(b) by 0 days.

(21) Appl. No.: 17/477,494

(22) Filed: Sep. 16, 2021

(65) Prior Publication Data
US 2022/0000918 A1  Jan. 6, 2022

Related U.S. Application Data

(63) Continuation of application No. PCT/US2021/035991, filed on Jun. 4, 2021.

(60) Provisional application No. 63/082,584, filed on Sep. 24, 2020, provisional application No. 63/044,934, filed on Jun. 26, 2020, provisional application No. 63/034,873, filed on Jun. 4, 2020.

(51) Int. Cl.
| | |
|---|---|
| *C12N 5/0786* | (2010.01) |
| *C07K 16/28* | (2006.01) |
| *C07K 14/725* | (2006.01) |
| *A61K 35/15* | (2015.01) |
| *A61K 39/00* | (2006.01) |
| *C07K 16/32* | (2006.01) |
| *A61P 35/00* | (2006.01) |
| *C12N 15/86* | (2006.01) |
| *C07K 14/735* | (2006.01) |
| *C07K 14/47* | (2006.01) |
| *C07K 14/705* | (2006.01) |
| *A61K 38/00* | (2006.01) |

(52) U.S. Cl.
CPC ............ *C12N 5/0645* (2013.01); *A61K 35/15* (2013.01); *A61P 35/00* (2018.01); *C07K 14/4703* (2013.01); *C07K 14/7051* (2013.01); *C07K 14/70517* (2013.01); *C07K 14/70521* (2013.01); *C07K 14/70535* (2013.01); *C07K 14/70596* (2013.01); *C07K 16/2896* (2013.01); *C07K 16/32* (2013.01); *C12N 15/86* (2013.01); *A61K 38/00* (2013.01); *A61K 2039/5156* (2013.01); *A61K 2039/5158* (2013.01); *C07K 2317/53* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2501/24* (2013.01); *C12N 2501/52* (2013.01); *C12N 2510/00* (2013.01); *C12N 2740/15043* (2013.01)

(58) Field of Classification Search
CPC .......................... A61K 35/15; C07K 14/7051
See application file for complete search history.

(56) References Cited

U.S. PATENT DOCUMENTS

| | | | |
|---|---|---|---|
| 7,994,298 | B2 | 8/2011 | Zhang et al. |
| 8,450,112 | B2 | 5/2013 | Li et al. |
| 9,132,153 | B2 | 9/2015 | Li et al. |
| 9,149,519 | B2 | 10/2015 | Landau et al. |
| 9,669,058 | B2 | 6/2017 | Li et al. |
| 11,034,749 | B2 | 6/2021 | Gill et al. |
| 11,312,939 | B2 | 4/2022 | Klichinsky et al. |
| 2004/0053873 | A1 | 3/2004 | Barman et al. |
| 2011/0223240 | A1 | 9/2011 | Masliah et al. |
| 2011/0305638 | A1 | 12/2011 | Ting et al. |
| 2013/0287748 | A1 | 10/2013 | June et al. |
| 2014/0161799 | A1 | 6/2014 | Frazier et al. |
| 2014/0242701 | A1 | 8/2014 | Shiku et al. |
| 2014/0322212 | A1 | 10/2014 | Brogdon et al. |
| 2016/0207989 | A1 | 7/2016 | Short |
| 2016/0340406 | A1 | 11/2016 | Zhao et al. |
| 2017/0123556 | A1 | 5/2017 | Lin et al. |
| 2017/0151281 | A1 | 6/2017 | Wagner et al. |
| 2017/0166657 | A1 | 6/2017 | O'Neill et al. |
| 2017/0216354 | A1 | 8/2017 | Wagner et al. |
| 2017/0258837 | A1 | 9/2017 | Li et al. |
| 2018/0028567 | A1 | 2/2018 | Li et al. |
| 2018/0186878 | A1 | 7/2018 | Rosenthal |
| 2018/0244748 | A1 | 8/2018 | Gill et al. |
| 2018/0353588 | A1 | 12/2018 | Boyd et al. |
| 2019/0346444 | A1* | 11/2019 | Klein ................... G01N 33/563 |

(Continued)

FOREIGN PATENT DOCUMENTS

| | | |
|---|---|---|
| CN | 101668777 A | 3/2010 |
| CN | 104829733 A | 8/2015 |

(Continued)

OTHER PUBLICATIONS

Miki et al. 4-1BBL regulates the polarization of macrophages and inhibition of 4-1BBL signaling alleviates imiquimodinduced psoriasis. J. Immunol. 204, 1892-1903, 2020. (Year: 2020).*

Suttles et al. Macrophage CD40 signaling: A pivotal regulator of disease protection and pathogenesis. Semin. Immunol. 21, 257-264, 2009. (Year: 2009).*

Luheshi et al., Th1 cytokines are more effective than Th2 cytokines at licensing anti-tumor functions in CD40-activated human macrophages in vitro. Eur. J. Immunol. 44, 162-172, 2014. (Year: 2014).*

(Continued)

*Primary Examiner* — Elly-Gerald Stoica

(74) *Attorney, Agent, or Firm* — Choate, Hall & Stewart LLP; Brian E. Reese; Melissa M. Adams

(57) ABSTRACT

The present disclosure pertains to immune cells comprising chimeric antigen receptors (CARs) and methods of using immune cells comprising CARs.

10 Claims, 204 Drawing Sheets

Specification includes a Sequence Listing.

(56) References Cited

U.S. PATENT DOCUMENTS

| | | | |
|---|---|---|---|
| 2020/0002676 A1* | 1/2020 | O'Neill | C07K 16/40 |
| 2020/0247870 A1 | 8/2020 | Gill et al. | |
| 2021/0046110 A1 | 2/2021 | Gill et al. | |
| 2022/0000917 A1 | 1/2022 | Klichinsky et al. | |
| 2022/0002675 A1 | 1/2022 | Klichinsky et al. | |

FOREIGN PATENT DOCUMENTS

| | | |
|---|---|---|
| EP | 3334764 A2 | 6/2018 |
| JP | 2004/529636 A | 9/2004 |
| JP | 2009-523007 A | 6/2009 |
| JP | 2013-525305 A | 6/2013 |
| RU | 2434882 C2 | 11/2011 |
| WO | WO-02/077029 A2 | 10/2002 |
| WO | WO-2006/040330 A2 | 4/2006 |
| WO | WO-2007/012614 A2 | 2/2007 |
| WO | WO-2008/103947 A2 | 8/2008 |
| WO | WO-2011/130566 A2 | 10/2011 |
| WO | WO-2013/051718 A1 | 4/2013 |
| WO | WO-2014/153114 A1 | 9/2014 |
| WO | WO-2016/033331 A1 | 3/2016 |
| WO | WO-2016/149254 A1 | 9/2016 |
| WO | WO-2016/176651 A2 | 11/2016 |
| WO | WO-2016/193696 A1 | 12/2016 |
| WO | WO-2016/210447 A1 | 12/2016 |
| WO | WO-2017/009852 A1 | 1/2017 |
| WO | WO-2017/019848 A1 | 2/2017 |
| WO | WO-2017/044487 A1 | 3/2017 |
| WO | WO-2017/123556 A1 | 7/2017 |
| WO | WO-2019/152781 A1 | 8/2019 |
| WO | WO-2020/047371 A1 | 3/2020 |
| WO | WO-2021/248061 A1 | 12/2021 |

OTHER PUBLICATIONS

Richards et al., Concepts for agonistic targeting of CD40 in immuno-oncology. Human Vaccines and immunotherapeutics, 16, 377-387, 2020. (Year: 2020).*

International Search Report for PCT/US2021/35991, 3 pages (dated Oct. 19, 2021).

Andreesen, et al., Adoptive transfer of tumor cytotoxic macrophages generated in vitro from circulating blood monocytes: a new approach to cancer immunotherapy, Cancer Res. 50(23), Dec. 1990, 7450-7456.

Batrakova, et al., Cell-Mediated Drugs Delivery, Expert Opin Drug Deliv., 8(4):415-433 (2011).

Biglari, A. et al., Human monocytes expressing a CEA-specific chimeric CD64 receptor specifically target CEA-expressing tumour cells in vitro and in vivo, Gene Therapy, 13:602-610 (2006).

Extended European Search Report for European Patent Application No. 16831340.1 dated Mar. 6, 2019.

Gill Saar, et al., 31st Annual Meeting and Associated Programs of the Society for Immunotherapy of Cancer (SITC 2016): part one; Journal for ImmunoTherapy of Cancer, 4(Suppl 1): P23, Dec. 2016, Abstract Only.

International Search Report for PCT/US19/48989, 5 pages (dated Jan. 2, 2020).

International Search Report for PCT/US2016/044440 (Modified Monocytes/Macrophage Expressing Chimeric Antigen Receptors and Uses Thereof, filed Jul. 28, 2016), issued by ISA/US, 2 pages (dated Oct. 21, 2016).

International Search Report for PCT/US2019/016253 (Modified Monocytes/Macrophages/Dendritic Cells Expressing Chimeric Antigen Receptors and Uses in Diseases and Disorders Associated With Protein Aggregates, filed Feb. 1, 2019), issued by ISA/US, 3 pages (dated Apr. 24, 2019).

Khramtsova, et al., The M2/Alternatively Activated Macrophage Phenotype Correlates with Aggressive Histopathologic Features and Poor Clinical Outcome in Early Stage Breast Cancer, Cancer Research 69(24) Suppl. 3, Dec. 2009.

Klichinsky et al., Human Chimeric Antigen Receptor Macrophages for Cancer Immunotherapy, Nature Biotechnology, pp. 1-13 (2020).

Klichinsky, M. et al., Abstract 4575: Chimeric antigen receptor macrophages (CARMA) for adoptive cellular immunotherapy of solid tumors, Proceedings: AACR Annual Meeting Washington D.C., Apr. 1-5, 4 pages (2017).

Levine, et al., Global Manufacturing of CAR T Cell Therapy, Mol. Ther. Methods Clin. Dev., pp. 92-101 (2017).

Maude, et al., Chimeric Antigen Receptor T Cells for Sustained Remissions in Leukemia, N. Engl. J. Med., 371(16):1507-1517 (2014).

Search Report for Singapore Patent Application No. 11201800339R dated Apr. 22, 2019.

Sharma, A. et al., HER-2 Pulsed Dendritic Cell Vaccine Can Eliminate HER-2 Expression and Impact DCIS, Cancer, 118(17):4354-4362 (2012).

Villanueva, Macrophages Get a CAR, Nature, p. 308 (2020).

Wei, et al., Cancer immunotherapy using in vitro genetically modified targeted dendritic cells, Cancer Research, 68:3854-3862 (2008).

Weiskopf et al., Engineered SIRP variants as immunotherapeutic adjuvants to anti-cancer antibodies, Science, 341(88):88-91 (2013).

Weiskopf, K. and Weissman, I., Macrophages are critical effectors of antibody therapies for cancer, mAbs, 7(2):303-310 (2015).

Written Opinion for PCT/US19/48989, 6 pages (dated Jan. 2, 2020).

Written Opinion for PCT/US2016/044440 (Modified Monocytes/Macrophage Expressing Chimeric Antigen Receptors and Uses Thereof, filed Jul. 28, 2016), issued by ISA/US, 9 pages (dated Oct. 21, 2016).

Written Opinion for PCT/US2019/016253 (Modified Monocytes/Macrophages/Dendritic Cells Expressing Chimeric Antigen Receptors and Uses in Diseases and Disorders Associated With Protein Aggregates, filed Feb. 1, 2019), issued by ISA/US, 6 pages (dated Apr. 24, 2019).

Xu, Jing, Viral and Plasmid Transduction Systems: Methods to Modify Immune Cells for Cancer Immunotherapy, Biology Education Centre and Department of Immunology, Genetics and Pathology (IGP), Rudbeck Laboratory, Uppsala University, 29 pages (2011).

Yong, C. et al., Using Electroporation to Determine Function of a Chimeric Antigen Receptor in T Cell and Macrophage Cell Lines, The Open Gene Therapy Journal, 5:1-11 (2013).

Bobadilla, S. et al., Efficient transduction of myeloid cells by a lentiviral vector that packages the Vpx accessory protein, Gene Therapy, 20(5):514-520 (2013).

Whilding, L. and Maher, J., CAR T-cell immunotherapy: The path from the by-road to the freeway?, Molecular Oncology, 9:1994-2012 (2015).

Alabanza, L. et al., The Impact of Different Hinge and Transmembrane Components on the Function of a Novel Fully-Human Anti-CD19 Chimeric Antigen Receptor, Molecular Therapy, 24(1):S32-S33 (2016).

Harding, S.A. et al., Increased CD40 ligand and platelet-monocyte aggregates in patients with type 1 diabetes mellitus, Atherosclerosis, 176:321-325 (2004).

Kiener, P.A. et al., Stimulation of CD40 with purified soluble gp39 induces proinflammatory responses in human monocytes, J. Immunol., 1155:4917-4925 (1995).

Lukasik, M. et al., Chronic hyper-reactivity of platelets resulting in enhanced monocyte recruitment in patients after ischaemic stroke, Platelets, 23(2):132-142 (2012).

Michelson, A. et al., Circulating Monocyte-Platelet Aggregates Are a More Sensitive Marker of In Vivo Platelet Activation Than Platelet Surface P-Selectin, Circulation, 104:1533-1537 (2001).

Parameswaran, N. and Patial, S., Tumor Necrosis Factor-Signaling in Macrophages, Crit. Rev. Eukaryot Gene Expr., 20(2):87-103 (2010).

Beatty, G. L. et al., CD40 Agonists Alter Tumor Stroma and Show Efficacy Against Pancreatic Carcinoma in Mice and Humans, Science, 331:1612-1616 (2011).

Fujiwara, K. et al., Hinge and Transmembrane Domains of Chimeric Antigen Receptor Regulate Receptor Expression and Signaling Threshold, Cells, 9:1-17 (2020).

(56) References Cited

OTHER PUBLICATIONS

Jackaman, C. et al., IL-2/CD40-driven NK cells install and maintain potency in the anti-mesothelioma effector/memory phase, International Immunology, 24(6):357-368 (2012).

Vonderheide, R. H. et al., Clinical Activity and Immune Modulation in Cancer Patients Treated with CP-870,893, a Novel CD40 Agonist Monoclonal Antibody, Journal of Clinical Oncology, 25(7):876-883 (2007).

Zernegar, B. et al., Unique CD40-mediated biological program in B cell activation requires both type 1 and type 2 NF-kb activation pathways, PNSAS, 101(21):8108-8113 (2004).

\* cited by examiner

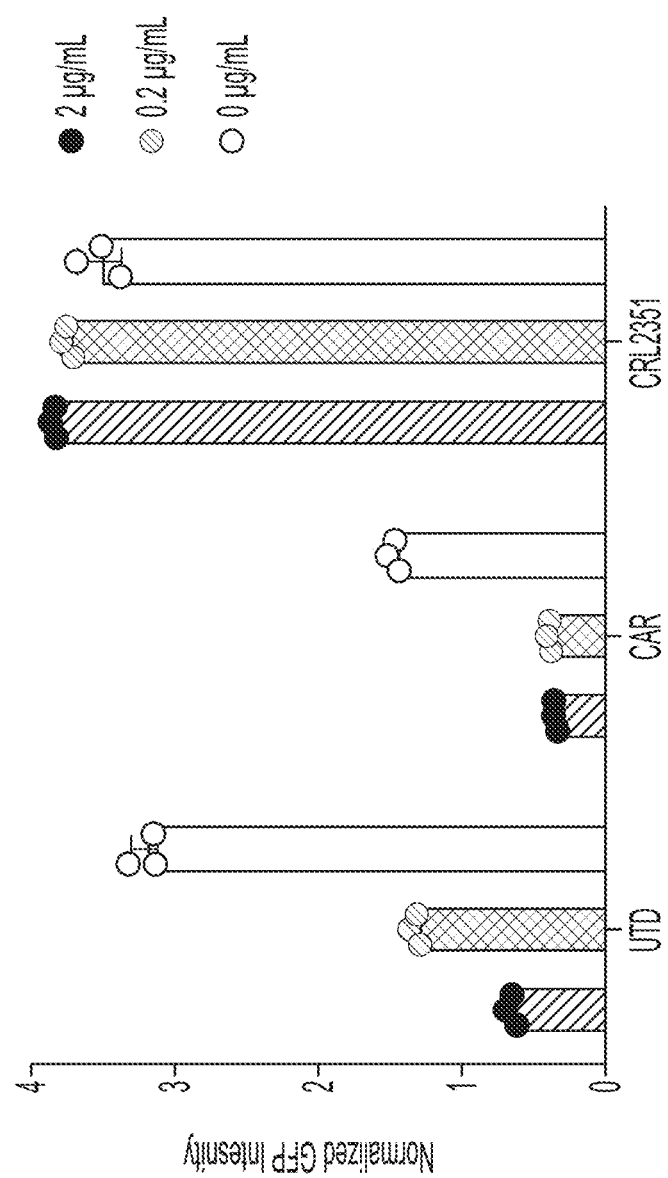

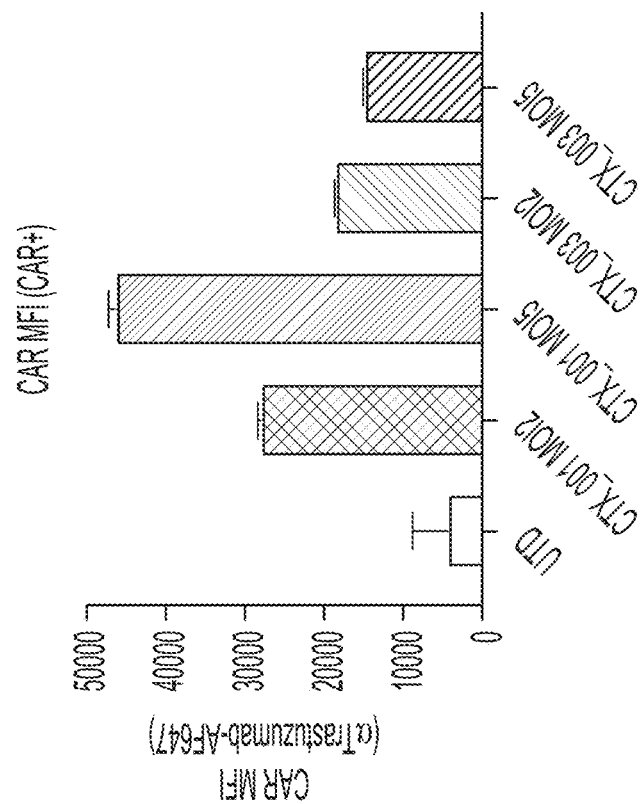
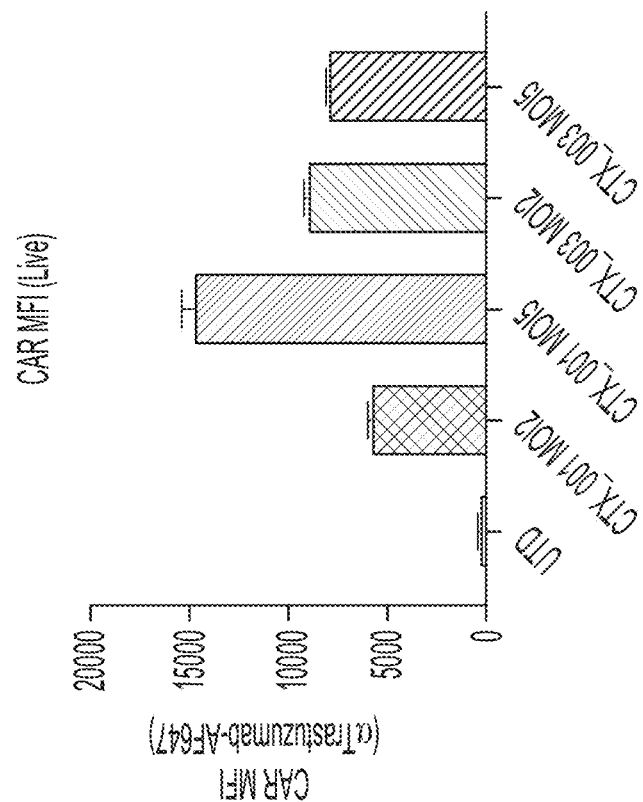
FIG. 142

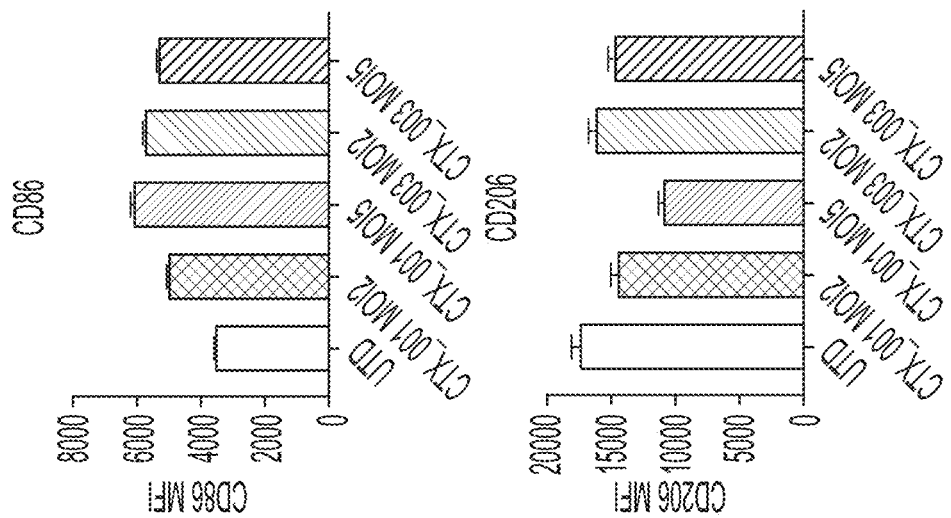
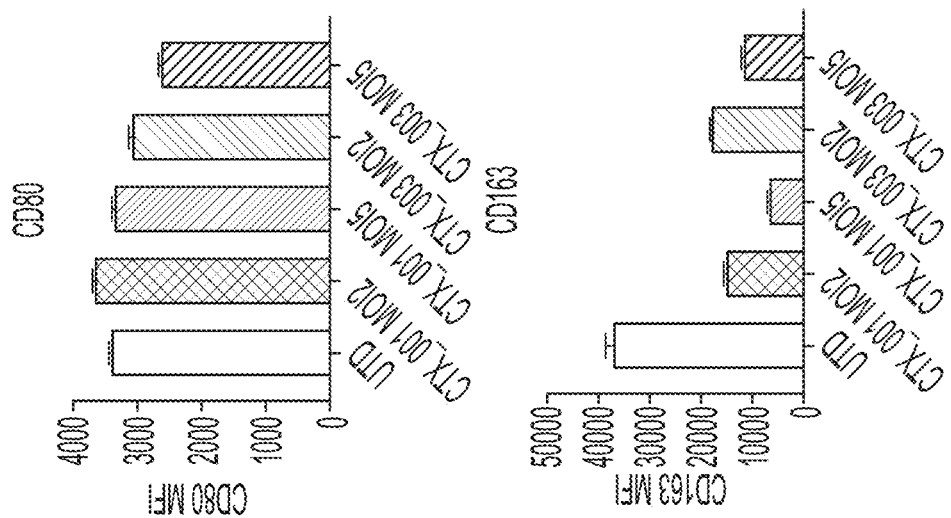
FIG. 143

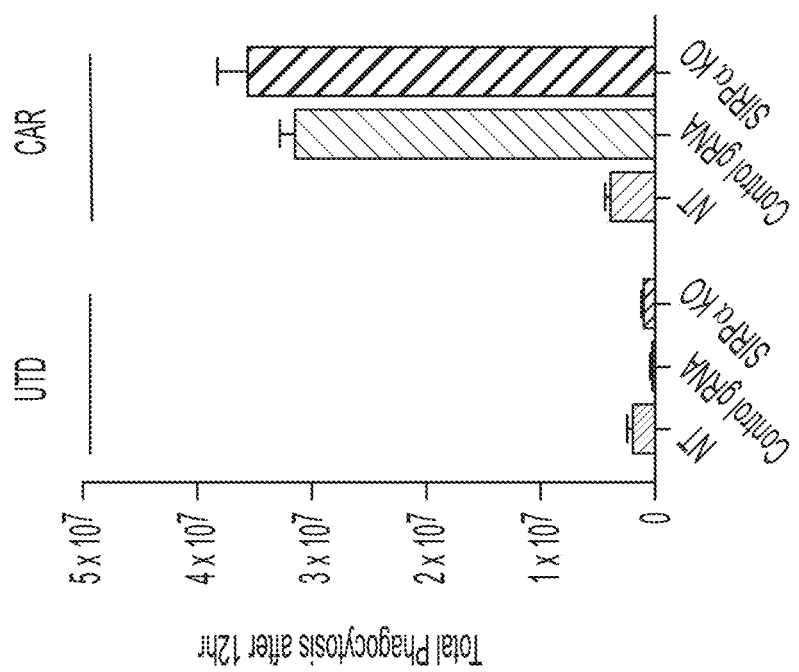

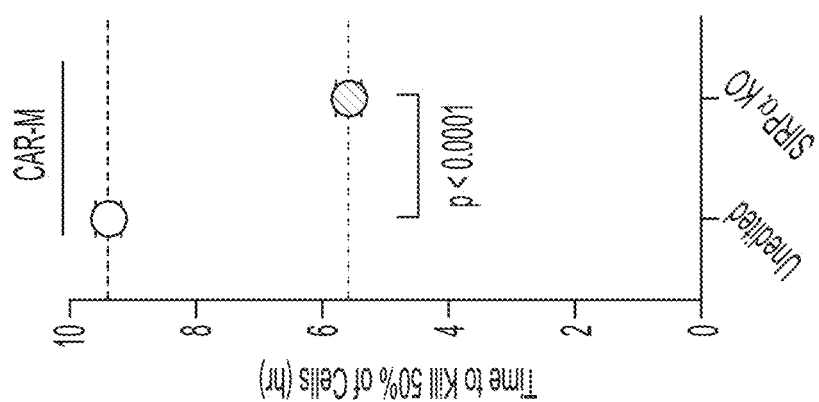

SEQUENCE LISTING

```
<160> NUMBER OF SEQ ID NOS: 4

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gagcccgccg gcccggcccc                                                  20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gugcuuaccu gaccaggcgc                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgggctcagg cctctcagac                                                  20

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Gly Ser Gly Gly Gly Gly Ser
1               5                   10                  15
```

METHOD OF INCREASING TUMOR KILLING ACTIVITY OF MACROPHAGES OR MONOCYTES COMPRISING CHIMERIC ANTIGEN RECEPTOR

CROSS REFERENCE TO RELATED APPLICATIONS

This application is a continuation of PCT/US21/35991, which claims priority to and the benefit of U.S. Provisional Patent Application Nos. 63/034,873, filed Jun. 4, 2020; 63/044,934, filed Jun. 26, 2020; and 63/082,584, filed Sep. 24, 2020; the contents of each of which are incorporated herein by reference in their entirety.

SEQUENCE LISTING

The present specification makes reference to a Sequence Listing (submitted electronically as a .txt file named "Sequence_Listing.txt" on Sep. 16, 2021). The .txt file was generated on Jul. 13, 2021 and is 1,338 bytes in size. The entire contents of the Sequence Listing are herein incorporated by reference.

BACKGROUND

Although immunotherapies have been investigated for many diseases and disorders, including cancer, Alzheimer's disease, Parkinson's disease, amyotrophic lateral sclerosis (ALS), systemic amyloidosis, prion disease, cardiovascular disease, atherosclerosis, fibrosis, functional limitations that have been encountered still need to be addressed.

Therefore, a need exists for the development of new therapeutic modalities optimized to target specific antigens.

SUMMARY OF THE INVENTION

In one aspect, the disclosure provides modified immune cells comprising a chimeric antigen receptor (CAR) comprising: (a) an extracellular domain, (b) a transmembrane domain, and (c) an intracellular domain, wherein the immune cell comprises a macrophage, monocyte, or dendritic cell. While a variety of CARs have been developed in multiple cells types and for treatment of multiple indications, the present disclosure encompasses the recognition that maximizing CAR and/or effector activity in monocytes, macrophages and/or dendritic cells requires the use of customized CAR components. Accordingly, the present disclosure provides several examples of such CARs and supporting agents, moieties, and adjunct compositions that are particularly useful in treating any of a variety of conditions including, for example, various cancers, diseases or disorders of the central nervous system (e.g. Alzheimer's Disease, Parkinson's Disease, and/or ALS), cardiovascular disease, fibrosis, and others.

In another aspect, the disclosure provides methods of modifying a macrophage, monocyte or dendritic cell comprising: delivering to the macrophage, monocyte or dendritic cell a viral vector comprising one or more nucleic acid sequences encoding: (a) an extracellular domain, (b) a transmembrane domain, and (c) an intracellular domain, wherein the viral vector is packaged with at least one Vpx protein, wherein the modified macrophage, monocyte or dendritic cell comprises a chimeric engineered receptor (CAR) comprising (a) through (c), and wherein the modified macrophage, monocyte or dendritic cell exhibits increased CAR expression relative to a modified macrophage, monocyte or dendritic cell comprising a CAR that was delivered a viral vector encoding the CAR that was not packaged with at least one Vpx protein.

In some embodiments, a viral vector is or comprises a lentiviral vector. In some embodiments, a viral vector is delivered at a multiplicity of infection (MOI) of about 1 to about 50. In some embodiments, a viral vector is delivered at a MOI of about 1, about 2, about 3, about 4, about 5, about 6, about 7, about 8, about 9, or about 10.

In some embodiments, a modified macrophage, monocyte or dendritic cell exhibits increased CAR expression of about 20%, about 30%, about 40%, about 40%, about 50%, about 60%, about 70%, about 80%, about 90%, or greater relative to a modified macrophage, monocyte or dendritic cell comprising a CAR that was delivered a viral vector encoding the CAR that was not packaged with at least one Vpx protein.

In some embodiments, a modified macrophage, monocyte or dendritic cell exhibits CAR expression for an extended time period relative to an unmodified macrophage, monocyte or dendritic cell. In some embodiments, an extended time period of CAR expression is for at least 5 days, at least 10 days, at least 15 days, at least 20 days, at least 25 days, at least 30 days, or longer. In some embodiments, a modified macrophage, monocyte or dendritic cell exhibits increased effector activity relative to an unmodified macrophage, monocyte or dendritic cell. In some embodiments, a modified macrophage, monocyte or dendritic cell exhibits increased tumor killing ability or phagocytosis relative to an unmodified macrophage, monocyte or dendritic cell.

In some embodiments, a modified macrophage, monocyte or dendritic cell does not exhibit increased polarization to a M1 phenotype relative to a macrophage, monocyte or dendritic cell comprising a CAR that was delivered a viral vector encoding the CAR that was not packaged with at least one Vpx protein (e.g., an adeno-associated viral vector (e.g., Ad5 vector, e.g., Ad5f35)). In some embodiments, a modified macrophage, monocyte or dendritic cell does not exhibit increased expression of one or more markers of M1 phenotype relative to a macrophage, monocyte or dendritic cell comprising a CAR that was delivered a viral vector encoding the CAR that was not packaged with at least one Vpx protein (e.g., an adeno-associated viral vector (e.g., Ad5 vector, e.g., Ad5f35)). In some embodiments, one or more markers of M1 phenotype comprise or are one, two, three, four, five, six, seven, eight, nine, 10, 11, 12, 13, 14, 15, 16, 17, or 18 of CD86, CD80, MHC II, IL-1R, TLR2, TLR4, iNOS, SOCS3, CD83, PD-L1, CD69, MHC I, CD64, CD32, CD16, IL1R, a IFIT family member, or an ISG family member.

In some embodiments, a modified macrophage, monocyte or dendritic cell exhibits increased production of one or more inflammatory cytokines relative to an unmodified macrophage, monocyte or dendritic cell. In some embodiments, one or more inflammatory cytokines comprise or are one, two, three, four, five, six, seven, eight, nine, 10, 11, or 12 of TNFα, IL-6, IL-1a, IL-1b, IL-12, IL-18, IL-8, IL-2, IL-23, IFNα, IFNβ, IFNγ, IL-2, IL-8, IL33, CCL3, CXCL12, CCL22, CCL4, CXCL10, or CCL2.

In some embodiments, a modified macrophage, monocyte or dendritic cell exhibits reduced SIRPα activity relative to an unmodified macrophage, monocyte or dendritic cell. In some embodiments, a modified macrophage, monocyte or dendritic cell comprises deletion of SIRPα using one or more endonucleases. In some embodiments, one or more endonucleases comprise or are one or more of a CRISPR/Cas system, zinc finger nuclease (ZFN), transcription activator-like effector-based nuclease (TALEN), or meganuclease. In some embodiments, a CRISPR/Cas system comprises Cas9, Cas12a, or C2c2. In some embodiments, a modified macrophage, monocyte or dendritic cell has been treated with one or more anti-SIRPα antibodies. In some embodiments, a modified macrophage, monocyte or dendritic cell comprises one or more anti-SIRPα antibodies. In some embodiments, a modified macrophage, monocyte or dendritic cell comprises one or more siRNAs that downregulate SIRPα.

In some embodiments, an extracellular domain of a CAR comprises one or more antigen binding domains and an FcR extracellular domain, and/or a transmembrane domain of a CAR comprises an FcR transmembrane domain, and/or an intracellular domain of a CAR comprises an FcR intracellular domain. In some embodiments, a CAR comprises, from N-terminus to C-terminus, one or more extracellular binding domains, an FcR extracellular domain, an FcR transmembrane domain, and an FcR intracellular domain. In some embodiments, one or more of a FcR extracellular domain, a FcR transmembrane domain and a FcR intracellular domain is or comprises a human FcR domain. In some embodiments, an FcR extracellular domain, a FcR transmembrane domain and a FcR intracellular domain together comprise a full-length FcR. In some embodiments, an FcR extracellular domain comprises a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain. In some embodiments, an FcR transmembrane domain comprises a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain. In some embodiments, a FcR intracellular domain comprises a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain.

In some embodiments, an extracellular domain of a CAR comprises one or more antigen binding domains and a toll-like receptor (TLR) extracellular domain and/or a transmembrane domain of a CAR comprises a TLR transmembrane domain and/or a intracellular domain of a CAR comprises a TLR intracellular domain. In some embodiments, a CAR comprises, from N-terminus to C-terminus, one or more extracellular binding domains, a TLR extracellular domain, a TLR transmembrane domain, and a TLR intracellular domain. In some embodiments, one or more of a TLR extracellular domain, a TLR transmembrane domain and a TLR intracellular domain is or comprises a human TLR domain. In some embodiments, a TLR extracellular domain, a TLR transmembrane domain and a TLR intracellular domain together comprise a full-length TLR. In some embodiments, a TLR extracellular domain comprises a TLR1, TLR2, TLR3, TLR4, TLR5, TLR6, TLR7, TLR8, or TLR9 domain. In some embodiments, a TLR transmembrane domain comprises a TLR1, TLR2, TLR3, TLR4, TLR5, TLR6, TLR7, TLR8, or TLR9 domain. In some embodiments, a TLR intracellular domain comprises a TLR1, TLR2, TLR3, TLR4, TLR5, TLR6, TLR7, TLR8, or TLR9 domain.

In some embodiments, a chimeric antigen receptor further comprises one or more of: (d) one or more extracellular leader domains, (e) one or more extracellular hinge domains, and (f) one or more intracellular co-stimulatory domains. In some embodiments, one or more extracellular leader domains comprise a CD8 extracellular leader domain.

In some embodiments, one or more extracellular antigen binding domains comprise a scFv, centyrin, or darpin.

In some embodiments, one or more extracellular hinge domains comprise a CD28 extracellular hinge domain, CD8a extracellular hinge domain, or an IgG4 extracellular hinge domain.

In some embodiments, a transmembrane domain comprises a CD28, CD8a, CD64, CD32a, CD32c, CD16a, TRL1, TLR2, TLR3, TRL4, TLR5, TLR6, TLR7, TLR8, or TLR9 transmembrane domain.

In some embodiments, an intracellular domain comprises one or more intracellular signaling domains. In some embodiments, one or more intracellular signaling domains comprise a CD3-zeta, FcR γ, CD64, CD32a, CD32c, CD16a, TLR1, TLR2, TLR3, TLR4, TLR5, TLR6, TLR7, TLR8, TLR9, ALK, AXL, DDR2, EGFR, EphA1, INSR, cMET, MUSK, PDGFR, PTK7, RET, ROR1, ROS1, RYK, TIE2, TRK, VEGFR, CD40, CD19, CD20, 41BB, CD28, OX40, GITR, TREM-1, TREM-2, DAP12, MR, ICOS, MyD88, V/I/LxYxxL/V, SIRPα, CD45, Siglec-10, PD1, SHP-1, SHP-2, KIR-2DL, KIR-3DL, NKG2A, CD170, CD33, BTLA, CD32b, SIRPb, CD22, PIR-B, LILRB1, 41BBL (TNFSF9), CD27, OX40L, CD32b, CD11b, ITGAM, SLAMF7, CD206, CD163, CD209, Dectin-2, IL1R, IL2R, IL3R, IL4R, IL5R, IL6R, IL7R, IL8R, IL9R, IL10R, IL11R, IL12R, IL13R, IL14R, IL15R, IL17R, IFNaR, IFNgR, TNFR, CSF1R, CSF2R, Dap10, CD36, Dectin-1, ICOSL and/or Syk intracellular signaling domain. In some embodiments, one or more intracellular signaling domains comprises at least one intracellular co-stimulatory domain In another aspect, the disclosure provides pharmaceutical compositions comprising an immune cell of any aspect or embodiment described herein. In some embodiments, a pharmaceutical composition comprises a pharmaceutically acceptable carrier.

In another aspect, the disclosure provides nucleic acid constructs (e.g., viral vectors) comprising one or more nucleic acid sequences encoding: (a) an extracellular domain, (b) a transmembrane domain, and (c) an intracellular domain, wherein the nucleic acid construct encodes a chimeric antigen receptor (CAR) comprising (a) through (c). In some embodiments, a nucleic acid construct further comprises one or more nucleic acid sequences encoding: (e) one or more extracellular leader domains, (f) one or more extracellular hinge domains, (g) one or more intracellular co-stimulatory domains, (h) a cleavage peptide, and (i) one or more peptide agents. In some embodiments, a cleavage peptide is or comprises a P2A, F2A, E2A or T2A peptide.

In another aspect, the disclosure provides pharmaceutical compositions comprising a nucleic acid construct of any aspect or embodiment described herein. In some embodiments, a pharmaceutical composition comprises a pharmaceutically acceptable carrier.

In another aspect, the disclosure provides pharmaceutical compositions comprising a macrophage, monocyte or dendritic cell modified by a method of any aspect or embodiment described herein. In some embodiments, a pharmaceutical composition comprises a pharmaceutically acceptable carrier.

In another aspect, the disclosure provides methods of treating a disease or disorder in a subject, comprising: delivering to the subject a therapeutically effective amount of a pharmaceutical composition of any aspect or embodiment described herein.

In another aspect, the disclosure provides methods of modifying an immune cell, the method comprising: delivering to the immune cell a nucleic acid construct comprising one or more nucleic acid sequences encoding: (a) an extracellular domain, (b) a transmembrane domain, and (c) an intracellular domain, wherein the modified immune cell comprises a chimeric engineered receptor comprising (a) through (c), and wherein the modified immune cell comprises a macrophage, monocyte or dendritic cell.

In some embodiments, a modified macrophage, monocyte or dendritic cell exhibits reduced SIRPα activity relative to an unmodified macrophage, monocyte or dendritic cell. In some embodiments, a modified macrophage, monocyte or dendritic cell comprises or expresses at least one CAR comprising one, two, three, or four of an anti-HER2 scFv, CD8 hinge, CD8 transmembrane domain, or CD3-zeta intracellular signaling domain. In some embodiments, at least one CAR comprises a CD8a signal peptide. In some embodiments, delivering a nucleic acid construct encoding (a)-(c) to a modified macrophage, monocyte or dendritic cell comprises transduction with a viral vector. In some embodiments, a viral vector comprises or is an adenoviral vector, an adeno-associated viral vector, or a retroviral vector (e.g., a lentiviral vector or a gammaretroviral vector). In some embodiments, an adeno-associated viral vector comprise or is an Ad5 vector (e.g., Ad5f35 viral vector).

In some embodiments, a modified macrophage, monocyte or dendritic cell comprises deletion of SIRPα using one or more endonucleases. In some embodiments, one or more endonucleases comprise or are one or more of a CRISPR/Cas system, zinc finger nuclease (ZFN), transcription activator-like effector-based nuclease (TALEN), or meganuclease. In some embodiments, a CRISPR/Cas system comprises one or more of Cas9, Cas12a, or C2c2. In some embodiments, a modified macrophage, monocyte or dendritic cell has been treated with one or more anti-SIRPα antibodies. In some embodiments, a modified macrophage, monocyte or dendritic cell comprises one or more anti-SIRPα antibodies. In some embodiments, a modified macrophage, monocyte or dendritic cell comprises one or more siRNAs that downregulate SIRPα.

BRIEF DESCRIPTION OF THE DRAWING

The drawings are for illustration purposes only, not for limitation.

FIGS. 6A-6B are graphs showing tumor killing ability (FIG. 6A) and induction of expression of M1 and M2 markers (FIG. 6B) after incubation of macrophages and CAR macrophages with 4-1BB.

FIG. 125A shows results from macrophages transfected with CAR mRNA with or without priming with various concentrations of IFN-β. FIG. 125B shows results from macrophages transfected with CAR mRNA comprising a variety of modifications and treated with IFN-β. FIG. 125C shows results from macrophages transfected with CAR mRNA and treated with interferon cytokines.

FIG. 127A shows results from tests of viability and CAR expression in CAR macrophages that had been treated with interferon cytokines. FIG. 127B and FIG. 127C show tumor growth results from cancer cells cultured with macrophages electroporated with CAR mRNA and treated with interferon cytokines.

FIG. 128A shows viability, CAR expression and M1 marker expression of macrophages transfected with CAR mRNA and treated with interferons. FIG. 128B and FIG. 128C show tumor killing results from cancer cells cultured with macrophages electroporated with CAR mRNA and treated with interferon cytokines.

FIG. 130A shows mCherry expression in transfected macrophages after treatment with IFN-γ and the RNaseL inhibitor sunitinib. FIG. 130B shows a tumor growth curve for cancer cells cultured with CAR macrophages treated with sunitinib.

FIG. 130C shows tumor killing activity of CAR macrophages treated with sunitinib.

FIG. 8) in macrophages transduced with and without VPX lentivirus at MOI of 0-50. Untransduced (UTD) macrophages were used as control.

FIG. 142 is a series of graphs of MFI showing viability (live) and CAR expression (CAR+) of CTX_001 and CTX_003 in macrophages transduced with VPX lentivirus at MOI of 2 and MOI of 5 as assessed using αTrastuzumab-A F647. UTD macrophages were used as control.

FIG. 143 is a series of graphs of MFI of M2 macrophage markers (CD163 and CD206) and M1 macrophage markers (CD80 and CD86) of CTX_001 and CTX_003 macrophages transduced with VPX lentivirus at MOI of 2 and MOI of 5. UTD macrophages were used as control.

FIG. 156A-D are a series of graphs showing SIRPα knockout in CTX_001 macrophages with Cas9 and gRNA targeting SIRPα using flow cytometry (FIG. 156A), expression of CTX_001 in SIRPα knockout macrophages using flow cytometry (FIG. 156B), phagocytosis by SIRPα knockout CTX_001 macrophages of HCC-1954 human breast cancer cells over 12 hours (FIG. 156C), and total phagocytosis measured over 12 hours quantified as area under the curve (FIG. 156D). NT CAR macrophages, gRNA only, and UTD macrophages were used as controls.

FIG. 157A-E are a series of graphs showing SIRPα knockout in CTX_001 macrophages from different donor cells with Cas9 and gRNA targeting SIRPα using flow cytometry (FIG. 157A), expression of CTX_001 in SIRPα knockout macrophages using flow cytometry (FIG. 157B), SIRPα knockout CTX_001 macrophages killing SKOV-3 cells expressing nuclight green fluorescent protein over 24 hours as indicated by normalized tumor burden (FIG. 157C), tumor killing kinetics based on hours required for clearance of 50% of target tumor cells (FIG. 157D), and total phagocytosis measured over 12 hours (FIG. 157E). NT CAR macrophages, gRNA only, and UTD macrophages were used as controls.

DEFINITIONS

Figure 1A:
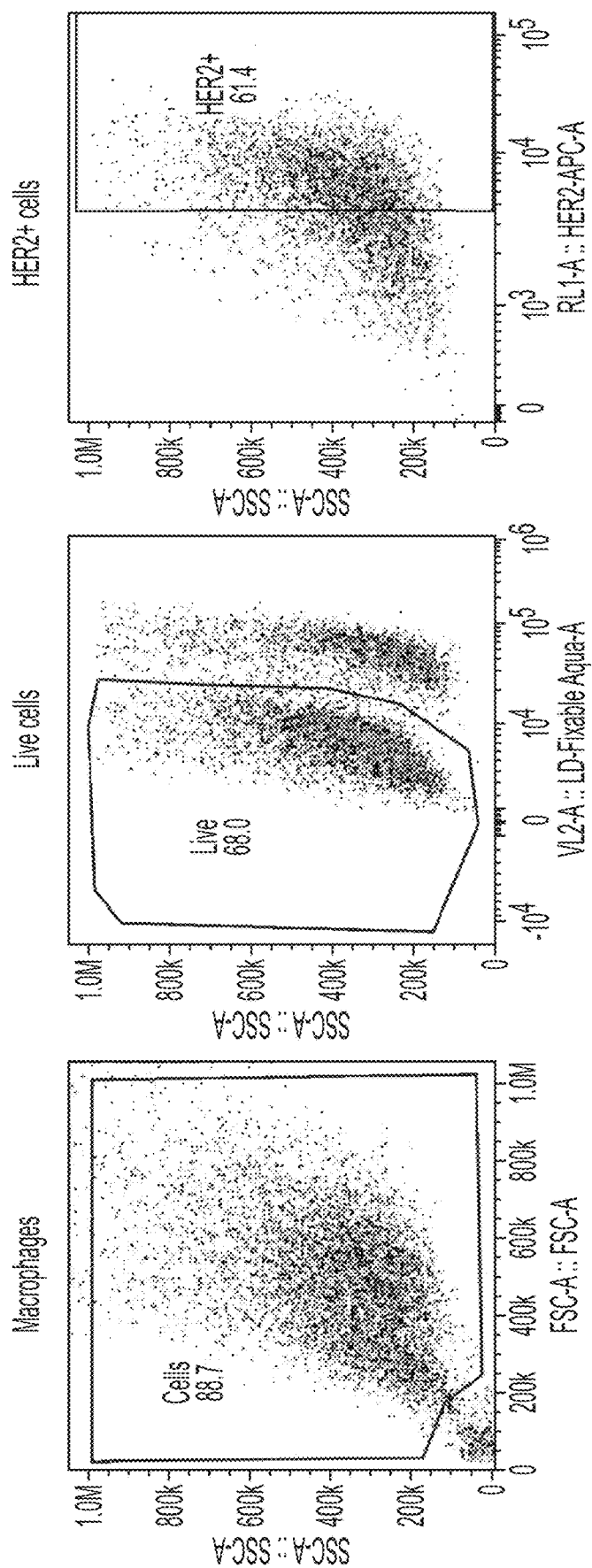
FIGS. 1A-1B are graphs showing HER2 expression from macrophages transfected with constructs described herein (see FIGS. 8-44). Live cell percentage and CAR:HER2 expression are shown in the dot plots for selected samples (FIG. 1A) and for all samples (FIG. 1B).

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

The articles "a" and "an" are used herein to refer to one or to more than one (i.e., to at least one) of the grammatical object of the article. By way of example, "an element" means one element or more than one element.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Activation: As used herein, the term "activation" refers to the state of a cell, for example a monocyte, macrophage, or dendritic cell that has been sufficiently stimulated to induce detectable cellular proliferation or has been stimulated to exert its effector function. Activation can also be associated with induced cytokine production, cytokine secretion, phagocytosis, cell signaling (e.g., gene expression changes), target cell killing, metabolic changes, production of inflammatory mediators, proliferation, epigenetic reprogramming, phenotypic switching of macrophages (e.g., M1 polarization), suppression of pro-tumor or M2 macrophages, phenotypic switching of pro-tumor or M2 macrophages, and/or antigen processing and presentation.

Activated monocytes/macrophages/dendritic cells: As used herein, the term "activated monocytes/macrophages/dendritic cells" refers to, among other things, monocyte/macrophage/dendritic cells that are undergoing cell division or exerting effector function. The term "activated monocytes/macrophages/dendritic cells" refers to, among others thing, cells that are performing an effector function or exerting any activity not seen in the resting state, including phagocytosis, cytokine secretion, proliferation, gene expression changes, metabolic changes, production of inflammatory mediators, proliferation, epigenetic reprogramming, phenotypic switching of macrophages (e.g., M1 polarization), suppression of pro-tumor or M2 macrophages, phenotypic switching of pro-tumor or M2 macrophages, and other functions.

Agent: As used herein, the term "agent" (or "biological agent" or "therapeutic agent"), refers to a molecule that may be expressed, released, secreted or delivered to a target by a modified cell described herein. An agent includes, but is not limited to, a nucleic acid, an antibiotic, an anti-inflammatory agent, an antibody or fragments thereof, an antibody agent or fragments thereof, a growth factor, a cytokine, an enzyme, a protein, a peptide, a fusion protein, a synthetic molecule, an organic molecule (e.g., a small molecule), a carbohydrate, a lipid, a hormone, a microsome, a derivative or a variation thereof, a formulation or composition including one or more thereof, and any combinations thereof. An agent may bind any cell moiety, such as a receptor, an antigenic determinant, or other binding site present on a target or target cell. An agent may diffuse or be transported into a cell, where it may act intracellularly.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprising two identical heavy chain polypeptides (about 50 kD each) and two identical light chain polypeptides (about 25 kD each) that associate with each other into what is commonly referred to as a "Y-shaped" structure. Each heavy chain comprises at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain comprises two domains—an amino-terminal variable (VL) domain, followed by a carboxy-terminal constant (CL) domain, separated from one another by another "switch". Intact antibody tetramers comprises two heavy chain-light chain dimers in which the heavy and light chains are linked to one another by a single disulfide bond; two other disulfide bonds connect the heavy chain hinge regions to one another, so that the dimers are connected to one another and a tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complementarity determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including, for example, effector cells that mediate cytotoxicity. Affinity and/or other binding attributes of Fc regions for Fc receptors can be modulated through glycosylation or other modification. In some embodiments, antibodies produced and/or utilized in accordance with the present invention (e.g., as a component of a CAR) include glycosylated Fc domains, including Fc domains with modified or engineered glycosylation. In some embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal. In some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody", as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.].

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, in some embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody agent may lack a covalent modification (e.g., attachment of a glycan) that it would have if produced naturally. In some embodiments, an antibody agent may contain a covalent modification (e.g., attachment of a glycan, a payload [e.g., a detectable moiety, a therapeutic moiety, a catalytic moiety, etc], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is not and/or does not comprise a polypeptide whose amino acid sequence includes structural elements recognized by those skilled in the art as an immunoglobulin variable domain. In some embodiments, an antibody agent may be or comprise a molecule or composition which does not include immunoglobulin structural elements (e.g., a receptor or other naturally occurring molecule which includes at least one antigen binding domain).

Antibody fragment: As used herein, the term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments and human and humanized versions thereof.

Antibody heavy chain: As used herein, the term "antibody heavy chain" refers to the larger of the two types of polypeptide chains present in all antibody molecules in their naturally occurring conformations.

Antibody light chain: As used herein, the term "antibody light chain" refers to the smaller of the two types of polypeptide chains present in all antibody molecules in their naturally occurring conformations.

Synthetic antibody: As used herein, the term "synthetic antibody" refers to an antibody that is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

Antigen: As used herein, the term "antigen" or "Ag" refers to a molecule that is capable of provoking an immune response. This immune response may involve either antibody production, the activation of specific immunologically-competent cells, or both. A skilled artisan will understand that any macromolecule, including virtually all proteins or peptides, can serve as an antigen. Furthermore, antigens can be derived from recombinant or genomic DNA. A skilled artisan will understand that any DNA that comprises a nucleotide sequences or a partial nucleotide sequence encoding a protein that elicits an immune response encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

Anti-tumor effect: As used herein, the term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of a tumor in the first place.

Autologous: As used herein, the term "autologous" refers to any material derived from an individual to which it is later to be re-introduced into the same individual.

Allogeneic: As used herein, the term "allogeneic" refers to a graft (e.g., a population of cells) derived from a different animal of the same species.

Xenogenic: As used herein, the term "xenogeneic" refers to a graft (e.g., a population of cells) derived from an animal of a different species.

Cancer: As used herein, the term "cancer" refers to a disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

Conservative sequence modifications: As used herein, the term "conservative sequence modifications" refers to amino acid modifications that do not significantly affect or alter the binding characteristics of an antibody containing the amino acid sequence. Such conservative modifications include amino acid substitutions, additions and deletions. Modifications can be introduced into an antibody compatible with various embodiments by standard techniques known in the art, such as site-directed mutagenesis and PCR-mediated mutagenesis. Conservative amino acid substitutions are ones in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

Co-stimulatory ligand: As used herein, the term "co-stimulatory ligand" refers to a molecule on an antigen presenting cell (e.g., an APC, dendritic cell, B cell, and the like) that specifically binds a cognate co-stimulatory molecule on a monocyte/macrophage/dendritic cell, thereby providing a signal which mediates a monocyte/macrophage/dendritic cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a monocyte/macrophage/dendritic cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

Cytotoxic: As used herein, the term "cytotoxic" or "cytotoxicity" refers to killing or damaging cells. In one embodiment, cytotoxicity of the metabolically enhanced cells is improved, e.g. increased cytolytic activity of macrophages.

Effective amount: As used herein, "effective amount" and "therapeutically effective amount" are interchangeable, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

Effector function: As used herein, "effector function" or "effector activity" refers to a specific activity carried out by an immune cell in response to stimulation of the immune cell. For example, an effector function of macrophages to engulf and digest cellular debris, foreign substances, microbes, cancer cells and other unhealthy cells by phagocytosis.

Encoding: As used herein, "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Endogenous: As used herein "endogenous" refers to any material from or produced inside a particular organism, cell, tissue or system.

Exogenous: As used herein, the term "exogenous" refers to any material introduced from or produced outside a particular organism, cell, tissue or system.

Expand: As used herein, the term "expand" refers to increasing in number, as in an increase in the number of monocytes/macrophages. In one embodiment, monocytes, macrophages, or dendritic cells that are expanded ex vivo increase in number relative to the number originally present in the culture. In another embodiment, monocytes, macrophages, or dendritic cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

Expression: As used herein, the term "expression" of a nucleic acid sequence refers to generation of any gene product from a nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Expression vector: As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses (e.g., Ad5 vector, e.g., Ad5f35) that incorporate the recombinant polynucleotide.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences.

Identity: As used herein, the term "identity" refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

Substantial identity: As used herein, the term "substantial identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

Immunoglobulin: As used herein, the term "immunoglobulin" or "Ig," refers to a class of proteins that function as antibodies. Antibodies expressed by B cells are sometimes referred to as a BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is an immunoglobulin that has no known antibody function, but may serve as an antigen receptor. IgE is an immunoglobulin that mediates immediate hypersensitivity by causing release of mediators from mast cells and basophils upon exposure to allergen.

Immune response: As used herein the term "immune response" refers to a cellular response to an antigen that occurs when lymphocytes identify antigenic molecules as foreign and induce the formation of antibodies and/or activate lymphocytes to remove the antigen.

Isolated: As used herein, the term "isolated" refers to something altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Lentivirus: As used herein, the term "lentivirus" refers to a genus of the Retroviridae family. Lentiviruses are unique among the retroviruses in being able to infect non-dividing cells; they can deliver a significant amount of genetic information into the DNA of a host cell, so they are one of the most efficient methods of a gene delivery vector. HIV, SIV, and FIV are all examples of lentiviruses. Vectors derived from lentiviruses offer the means to achieve significant levels of gene transfer in vivo.

Modified: As used herein, the term "modified" refers to a changed state or structure of a molecule or cell of the invention. Molecules may be modified in many ways, including chemically, structurally, and functionally. Cells may be modified through the introduction of nucleic acids.

Modulating: As used herein the term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Operably linked: As used herein, the term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Overexpressed tumor antigen: As used herein, the term "overexpressed" tumor antigen or "overexpression" of a tumor antigen refers to an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

Polynucleotide: As used herein, the term "polynucleotide" refers to a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

Polypeptide: As used herein, the term "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Signal transduction pathway: As used herein, the term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

Single chain antibodies: As used herein, the term "single chain antibodies" refers to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

Specifically binds: As used herein, the term "specifically binds," with respect to an antigen binding domain, such as an antibody agent, refers to an antigen binding domain or antibody agent which recognizes a specific antigen, but does not substantially recognize or bind other molecules in a sample. For example, an antigen binding domain or antibody agent that specifically binds to an antigen from one species may also bind to that antigen from one or more species. But, such cross-species reactivity does not itself alter the classification of an antigen binding domain or antibody agent as specific. In another example, an antigen binding domain or antibody agent that specifically binds to an antigen may also bind to different allelic forms of the antigen. However, such cross reactivity does not itself alter the classification of an antigen binding domain or antibody agent as specific. In some instances, the terms "specific binding" or "specifically binding," can be used in reference to the interaction of an antigen binding domain or antibody agent, a protein, or a peptide with a second chemical species, to mean that the interaction is dependent upon the presence of a particular structure (e.g., an antigenic determinant or epitope) on the chemical species; for example, an antigen binding domain or antibody agent recognizes and binds to a specific protein structure rather than to proteins generally. If an antigen binding domain or antibody agent is specific for epitope "A", the presence of a molecule containing epitope A (or free, unlabeled A), in a reaction containing labeled "A" and the antigen binding domain or antibody agent, will reduce the amount of labeled A bound to the antibody.

Stimulation: As used herein, the term "stimulation," refers to a primary response induced by binding of a stimulatory molecule (e.g., an FcR complex, a TLR complex, or a TCR/CD3 complex) with its cognate ligand thereby mediating a signal transduction event, such as, but not limited to, signal transduction via Fc receptor machinery or via a synthetic CAR. Stimulation can mediate altered expression of certain molecules, such as downregulation of TGF-beta, and/or reorganization of cytoskeletal structures, and the like. As used herein, the term "stimulatory molecule," refers to a molecule of a monocyte, macrophage, or dendritic cell that specifically binds with a cognate stimulatory ligand present on an antigen presenting cell. In some embodiments, a stimulatory molecule comprises an FcR extracellular domain comprising a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain. In some embodiments, a stimulatory molecule comprises a TLR extracellular domain comprising a TLR1, TLR2, TLR3, TLR4, TLR5, TLR6, TLR7, TLR8, or TLR9 domain. As used herein, the term "stimulatory ligand," refers to a ligand that when present on an antigen presenting cell (e.g., an aAPC, a macrophage, a dendritic cell, a B-cell, and the like) or tumor cell can specifically bind with a cognate binding partner (referred to herein as a "stimulatory molecule") on a monocyte, macrophage, or dendritic cell thereby mediating a response by the immune cell, including, but not limited to, activation, initiation of an immune response, proliferation, and the like. Stimulatory ligands are well-known in the art and encompass, inter alia, Toll-like receptor (TLR) ligand, an anti-toll-like receptor antibody, an agonist, and an antibody for a monocyte/macrophage receptor. In addition, cytokines, such as interferon-gamma, are potent stimulants of macrophages.

Subject: As used herein, the term "subject" refers to an organism, for example, a mammal (e.g., a human, a non-human mammal, a non-human primate, a primate, a laboratory animal, a mouse, a rat, a hamster, a gerbil, a cat, a dog). In some embodiments a human subject is an adult, adolescent, or pediatric subject. In some embodiments, a subject is suffering from a disease, disorder or condition, e.g., a disease, disorder or condition that can be treated as provided herein, e.g., a cancer or a tumor listed herein. In some embodiments, a subject is susceptible to a disease, disorder, or condition; in some embodiments, a susceptible subject is predisposed to and/or shows an increased risk (as compared to the average risk observed in a reference subject or population) of developing the disease, disorder or condition. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

Substantially purified: As used herein, the term "substantially purified", for example as applied to a cell, refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

Target: As used herein, the term "target" refers to a cell, tissue, organ, or site within the body that is in need of treatment or is preferentially bound by, for example, an antibody (or fragment thereof) or a CAR.

Target site: As used herein, the term "target site" or "target sequence" refers to a genomic nucleic acid sequence that defines a portion of a nucleic acid to which a binding molecule may specifically bind under conditions sufficient for binding to occur.

T cell receptor: As used herein, the term "T cell receptor" or "TCR" refers to a complex of membrane proteins that participate in the activation of T cells in response to the presentation of antigen. A TCR is responsible for recognizing antigens bound to major histocompatibility complex molecules. A TCR comprises a heterodimer of an alpha (α) and beta (β) chain, although in some cells the TCR comprises gamma and delta (γ/δ) chains. TCRs may exist in alpha/beta and gamma/delta forms, which are structurally similar but have distinct anatomical locations and functions. Each chain comprises two extracellular domains, a variable and constant domain. In some embodiments, a TCR may be modified on any cell comprising a TCR, including, for example, a helper T a cytotoxic T cell, a memory T cell, regulatory T cell, natural killer T cell, and gamma delta T cell.

Therapeutic: As used herein, the term "therapeutic" refers to a treatment and/or prophylaxis. A therapeutic effect is obtained by suppression, remission, or eradication of a disease state.

Transfected: As used herein, the term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Treat: As used herein, the term "treat," "treatment," or "treating" refers to partial or complete alleviation, amelioration, delay of onset of, inhibition, prevention, relief, and/or reduction in incidence and/or severity of one or more symptoms or features of a disease, disorder, and/or condition. In some embodiments, treatment may be administered to a subject who does not exhibit signs or features of a disease, disorder, and/or condition (e.g., may be prophylactic). In some embodiments, treatment may be administered to a subject who exhibits only early or mild signs or features of the disease, disorder, and/or condition, for example for the purpose of decreasing the risk of developing pathology associated with the disease, disorder, and/or condition. In some embodiments, treatment may be administered to a subject who exhibits established, severe, and/or late-stage signs of the disease, disorder, or condition.

Tumor: As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer. In some embodiments, a tumor may be a disperse tumor or a liquid tumor. In some embodiments, a tumor may be a solid tumor.

Vector: As used herein, the term "vector" refers to a composition of matter that comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DETAILED DESCRIPTION

Immune Cells

The present disclosure, among other things, provides modified immune cells (e.g., macrophages, monocytes, or dendritic cells) comprising at least one chimeric antigen receptor (CAR) as described herein. Accordingly, in some embodiments, an immune cell comprising at least one CAR comprises: (a) an extracellular domain (e.g., an extracellular domain as described herein), (b) a transmembrane domain (e.g., a transmembrane domain as described herein), and (c) an intracellular domain (e.g., an intracellular domain as described herein).

As used herein, the term "immune cell," refers to a cell that is involved in an immune response, e.g., promotion of an immune response. Examples of immune cells include, but are not limited to, macrophages, monocytes, dendritic cells, neutrophils, eosinophils, mast cells, platelets, large granular lymphocytes, Langerhans' cells, natural killer (NK) cells, T-lymphocytes, or B-lymphocytes. A source of immune cells (e.g., macrophages, monocytes, or dendritic cells) can be obtained from a subject. Examples of subjects include humans, monkeys, chimpanzees, dogs, cats, mice, rats, and transgenic species thereof.

In some embodiments, a population of immune cells as described herein comprises monocytes, macrophages, dendritic cells, and/or precursors thereof. In some embodiments, a population of immune cells comprises a purified population of monocytes, macrophages, or dendritic cells, or a cell line.

In some embodiments, an immune cell is activated, e.g., an immune cell exhibits increased cytokine production, chemokine production, phagocytosis, cell signaling, target cell killing, and/or antigen presentation, e.g., relative to an inactive cell. In some embodiments, an activated immune cell exhibits changes in gene expression, e.g., an induction of pro-inflammatory gene expression (e.g., one, two, three, four, five, six, or seven of TNF, IL-12, IFN, GM-CSF, G-CSF, M-CSF, or IL-1), e.g., relative to an inactive cell. In certain embodiments, activated immune cells are undergoing cell division. In some embodiments, targeted effector activity of an immune cell is enhanced by inhibition of CD47 and/or SIRPα activity. CD47 and/or SIRPα activity may be inhibited by treating an immune cell with an anti-CD47 or anti-SIRPα antibody or by any method known to those skilled in the art.

In some embodiments, immune cells (e.g., macrophages, monocytes, or dendritic cells) are obtained (e.g., isolated) from a subject. Immune cells may be autologous or sourced from allogeneic or universal donors. Cells can be obtained from a number of sources including peripheral blood mononuclear cells, bone marrow, lymph node tissue, spleen tissue, umbilical cord, tumors, and/or induced pluripotent stem cells, such as embryonic stem cells (ESCs). In certain embodiments, cells can be obtained from a unit of blood collected from a subject using any number of separation techniques known to a skilled artisan, such as Ficoll separation. In some embodiments, cells from circulating blood of a subject are obtained by apheresis or leukapheresis. Cells collected by apheresis may be washed to remove a plasma fraction and resuspended in a variety of buffers (e.g., phosphate buffered saline (PBS)) or culture media. In some embodiments, enrichment of immune cells (e.g. monocytes) comprises plastic adherence. In some embodiments, following enrichment, differentiation of immune cells (e.g. monocytes) comprises stimulation with GM-CSF. In some embodiments, a composition comprising blood cells (e.g., monocytes, lymphocytes, platelets, plasma, and/or red blood cells), such as a leukapheresis composition (e.g., a leukopak) is used for enrichment. In some embodiments, a leukapheresis composition (e.g., a leukopak) comprises a sample from a healthy human donor. In certain embodiments, apheresis of immune cells (e.g. monocytes) is followed by mobilization with GM-CSF. In certain embodiments, selection of immune cells (e,g, monocytes) comprises CD14 positive selection using microbeads (e.g., MACS® MicroBeads on a CliniMACS Prodigy device). In some embodiments, an immune cell precursor (e.g., precursors to macrophages, monocytes, or dendritic cells) is used in compositions and methods described herein. Immune cell precursors may be differentiated in vivo or ex vivo into immune cells. Non-limiting examples of precursor immune cells include hematopoietic stem cells, common myeloid progenitors, myeloblasts, monoblasts, promonocytes, or intermediates thereof. For example, induced pluripotent stem cells may be used to generate monocytes, macrophages, and/or dendritic cells. Induced pluripotent stem cells (iPSCs) may be derived from normal human tissue, such as peripheral blood, fibroblasts, skin, keratinocytes, or renal epithelial cells. Autologous, allogeneic, or universal donor iPSCs could be differentiated toward a myeloid lineage (e.g., a monocyte, macrophage, dendritic cell, or precursor thereof).

Immune cells (e.g., macrophages, monocytes, or dendritic cells) as described herein can be isolated from peripheral blood, for example, by lysing red blood cells and depleting lymphocytes and red blood cells, such as by centrifugation through a PERCOLL™ gradient. Alternatively, immune cells can be isolated from umbilical cord tissue. A specific subpopulation of immune cells can be further isolated by positive or negative selection techniques. In some embodiments, immune cells can be depleted of cells expressing certain antigens, including, but not limited to, CD34, CD3, CD4, CD8, CD56, CD66b, CD19, or CD20. In some embodiments, enrichment of an immune cell population, for example, by negative selection can be accomplished using a combination of antibodies directed to surface markers unique to the negatively selected cells. By way of non-limiting example, cell selection can also comprise negative magnetic immunoadherence or flow cytometry that uses a cocktail of monoclonal antibodies directed to cell surface markers present on negatively selected cells.

During isolation of a desired population of immune cells (e.g., macrophages, monocytes, or dendritic cells) as described herein by positive or negative selection, immune cell concentration and surface (e.g., particles, such as beads) can be varied. It may be desirable to significantly decrease volume in which beads and cells are mixed together to ensure maximum contact area of cells and beads.

In some embodiments, prior to administration, immune cells (e.g., macrophages, monocytes, or dendritic cells) as described herein (e.g., comprising a CAR described herein) are treated with a pro-inflammatory agent. In some embodiments, treatment with a pro-inflammatory agent increases anti-tumor activity of immune cells described herein. In some embodiments, treatment with at least one pro-inflammatory agent promotes M1 phenotype (e.g., a switch from M2 to M1 phenotype) in immune cells described herein. In some embodiments, at least one pro-inflammatory agent comprises or is a CD40 agonist (e.g., CD40L). In some embodiments, at least one pro-inflammatory agent comprises or is a 41BB-ligand agonist (e.g., 4-1BB). In some embodiments, at least one pro-inflammatory agent comprises or is a CD40 agonist (e.g., CD40L) and a 41BB-ligand agonist (e.g., 4-1BB).

In some embodiments, a modified macrophage, monocyte, or dendritic cell comprises a CAR described herein (e.g., a CAR comprising one or more extracellular domains, one or more transmembrane domains, and one or more intracellular domains). In some embodiments, a modified macrophage, monocyte, or dendritic cell has been treated with one or more pro-inflammatory agents. In some embodiments, a modified macrophage, monocyte, or dendritic cell exhibits increased anti-tumor activity relative to an unmodified cell of the same type. In some embodiments, one or more pro-inflammatory agents comprises or is a CD40 agonist (e.g., CD40L). In some embodiments, one or more pro-inflammatory agents comprises or is a 41BB-ligand agonist (e.g., 4-1BB). In some embodiments, one or more pro-inflammatory agents comprises or is a CD40 agonist (e.g., CD40L) and a 41BB-ligand agonist (e.g., 4-1BB). The disclosure provides methods of treating a disease or disorder in a subject, comprising: delivering to the subject a therapeutically effective amount of a pharmaceutical composition comprising a modified macrophage, monocyte, or dendritic cell described herein.

The disclosure also provides methods of modifying a macrophage, monocyte, or dendritic cell comprising a CAR described herein (e.g., a CAR comprising one or more extracellular domains, one or more transmembrane domains, and one or more intracellular domains), wherein the method comprises treating a macrophage, monocyte, or dendritic cell with one or more pro-inflammatory agents, thereby producing a modified macrophage, monocyte, or dendritic cell that exhibits increased anti-tumor activity relative to an unmodified cell of the same type. In some embodiments, one or more pro-inflammatory agents comprises or is a CD40 agonist (e.g., CD40L). In some embodiments, one or more pro-inflammatory agents comprises or is a 41BB-ligand agonist (e.g., 4-1BB). In some embodiments, one or more pro-inflammatory agents comprises or is a CD40 agonist (e.g., CD40L) and a 41BB-ligand agonist (e.g., 4-1BB). The disclosure provides methods of treating a disease or disorder in a subject, comprising: delivering to the subject a therapeutically effective amount of a pharmaceutical composition comprising a macrophage, monocyte, or dendritic cell modified by methods described herein.

In some embodiments, immune cells (e.g., macrophages, monocytes, or dendritic cells) as described herein (e.g., comprising a CAR described herein) are administered to a subject in combination with a pro-inflammatory agent. In some embodiments, immune cells (e.g., macrophages, monocytes, or dendritic cells) as described herein (e.g., comprising a CAR described herein) are administered to a subject substantially simultaneously, before, or after a pro-inflammatory agent. In some embodiments, administration with a pro-inflammatory agent increases anti-tumor activity of immune cells described herein. In some embodiments, administration with a pro-inflammatory agent promotes M1 phenotype (e.g., a switch from M2 to M1 phenotype) in immune cells described herein. In some embodiments, a pro-inflammatory agent comprises or is a CD40 agonist (e.g., CD40L). In some embodiments, a pro-inflammatory agent comprises or is a 41BB-ligand agonists (e.g., 4-1BB).

Macrophages

Macrophages are immune cells specialized for detection, phagocytosis, and destruction of target cells, such as pathogens or tumor cells. Macrophages are potent effectors of the innate immune system and are capable of at least three distinct anti-tumor functions: phagocytosis of dead and dying cells, microorganisms, cancer cells, cellular debris, or other foreign substances; cytotoxicity against tumor cells; and presentation of tumor antigens to orchestrate an adaptive anti-tumor immune response.

Accumulating evidence suggests that macrophages are abundant in the tumor microenvironment of numerous cancers and can adopt a number of phenotypes that are collectively referred to as tumor-associated macrophages (TAMs). The immunosuppressive nature of the tumor microenvironment typically results in more M2-like TAMs, which further contribute to the general suppression of anti-tumor immune responses. Recent studies, however, have identified that TAMs are able to be "reprogrammed" via pro-inflammatory signals, and that the switch from a M2 phenotype to a more M1 phenotype is associated with productive anti-tumor immune responses. Inducing endogenous TAMs to switch to M1-type cells and engineering macrophages that cannot be subverted into M2 would greatly enhance anti-tumor immunotherapy and represent a significant advance in the field.

In some embodiments, a macrophage comprises or is an undifferentiated or M0 macrophage. In certain embodiments, a macrophage comprises or expresses one, two, three, four, five, or six of CD14, CD16, CD64, CD68, CD71, or CCR5. Exposure to various stimuli can induce M0 macrophages to polarize into several distinct populations, which may be identified by macrophage phenotype markers, cytokine production, and/or chemokine secretion.

In some embodiments, a macrophage comprises or is a polarized macrophage. Under classical conditions of activation, M0 macrophages can be exposed to pro-inflammatory signals, such as LPS, IFNγ, and GM-CSF, and polarize into M1 macrophages. Generally, M1 macrophages are associated with pro-inflammatory immune responses, such as Th1 and Th17 T cell responses. Exposure to other stimuli can polarize macrophages into a diverse group of "alternatively activated" or M2 macrophages.

In some embodiments, a macrophage comprises or is an M1 macrophage. In some embodiments, a macrophage expresses one or more markers of M1 macrophages (e.g., one, two, three, four, five, six, seven, eight, nine, 10, 11, 12, 13, 14, 15, 16, 17, or 18 of CD86, CD80, MHC II, IL-1R, TLR2, TLR4, iNOS, SOCS3, CD83, PD-L1, CD69, MHC I, CD64, CD32, CD16, IL1R, a IFIT family member, or an ISG family member).

In some embodiments, a macrophage comprising or expressing at least one CAR described herein secretes relatively high levels of one or more inflammatory cytokines (e.g., one, two, three, four, five, six, seven, eight, nine, 10, 11, or 12 of IL-1, TNF, IL-12, IL-18, IL-23, IFNα, IFNβ, IFNγ, IL-2, IL-6, IL-8, or IL33) or chemokines (e.g., one or both of CC or CXC chemokines) (e.g., one, two, three, four, five, six, seven, eight, nine, 10, 11, 12, 13, 14, 15, or 16 of the CXC chemokines; e.g., one, two, three, four, five, six, seven, eight, nine, 10, 11, 12, 13, 14, 15, 16, 17, 18, 19, 20, 21, 22, 23, 24, 25, 26, 27, or 28 of the CC chemokines; eg., one of the CX3C chemokines, e.g., one or both of the C chemokines), e.g., relative to a macrophage without a CAR as described herein. In some embodiments, a macrophage comprising or expressing at least one CAR described herein stimulates an immune response and/or inflammation, e.g., relative to a macrophage without a CAR as described herein. In some embodiments, a macrophage comprises or is an M2 macrophage (e.g., an M2a, M2b, M2c, and M2d macrophage). An M2a macrophage can be induced by IL-4, IL-13, and/or fungal infection. An M2b macrophage can be induced by IL-1R ligands, an immune complex, and/or LPS. An M2c macrophage can be induced by IL-10 and/or TGFβ. An M2d macrophage can be induced by IL-6 and/or adenosine. In some embodiments, a macrophage comprising or expressing at least one CAR described herein decreases an immune response in a subject, e.g., relative to a macrophage without a CAR as described herein. In some embodiments, a macrophage expresses one or more markers of M2 macrophages (e.g., one, two, or three of CD206, CD163, or CD209). In some embodiments, a macrophage comprising or expressing at least one CAR described herein exhibits increased secretion of one or more anti-inflammatory cytokines (e.g., one or both of IL-10 or TGFβ), e.g., relative to a macrophage without a CAR as described herein.

In some embodiments, a macrophage comprises at least one upregulated M1 marker and/or at least one downregulated M2 marker. In some embodiments, at least one M1 marker (e.g., HLA DR, CD86, CD80, PD-L1, CD83, CD69, MHC I, CD64, CD32, CD16, IL1R, a IFIT family member, and/or an ISG family member) is upregulated in a macrophage. In some embodiments, at least one M2 marker (e.g., CD206, CD163, and/or CD209) is downregulated in a macrophage.

In some embodiments, a macrophage comprising or expressing at least one CAR described herein exhibits increased phagocytosis, e.g., relative to a macrophage without a CAR as described herein. In some embodiments, a macrophage comprising or expressing at least one CAR described herein exhibits increased cytotoxicity against a tumor cell, e.g., relative to a macrophage without a CAR as described herein. In some embodiments, a macrophage comprising or expressing at least one CAR described herein exhibits increased tumor antigen presentation (e.g., post-phagocytosis presentation) and/or increased antigen processing, e.g., relative to a macrophage without a CAR as described herein. In some embodiments, a macrophage comprising or expressing at least one CAR described herein exhibits increased tumor killing (e.g., by phagocytosis, lysis, apoptosis, or production of tumor killing cytokines (e.g., TNFα), e.g., relative to a macrophage without a CAR as described herein.

In some embodiments, a macrophage comprising or expressing at least one CAR described herein exhibits one or both of increased expression of favorable genes (e.g., CD80, CD86, MHC-I, MHC-II, CD40, 41BBL, TNF, IFNa, IFNb, IFNg, IL2, IL12, IL6, IL8, IL1b, and/or CXCL12) or decreased expression of unfavorable genes (e.g., CD163, CD206, TGFb, IL10, and/or IL4), e.g., relative to a macrophage without a CAR as described herein. In some embodiments, a macrophage comprising or expressing at least one CAR described herein exhibits increased production of ROS, e.g., relative to a macrophage without a CAR as described herein. In some embodiments, a macrophage comprising or expressing at least one CAR described herein exhibits metabolic reprogramming (e.g., of an interferon signaling pathway, TH1 pathway, PTEN signaling, PI3K signaling, MTOR signaling, TLR signaling, CD40 signaling, 41BB signaling, 41BBL signaling, macrophage maturation signaling, dendritic cell maturation signaling, CD3-zeta signaling, FcR γ signaling, CD64 signaling, CD32a signaling, CD32c signaling, CD16a signaling, TLR1 signaling, TLR2 signaling, TLR3 signaling, TLR4 signaling, TLR5 signaling, TLR6 signaling, TLR7 signaling, TLR8 signaling, TLR9 signaling, ALK signaling, AXL signaling, DDR2 signaling, EGFR signaling, EphA1 signaling, INSR signaling, cMET signaling, MUSK signaling, PDGFR signaling, PTK7 signaling, RET signaling, ROR1 signaling, ROS1 signaling, RYK signaling, TIE2 signaling, TRK signaling, VEGFR signaling, CD40 signaling, CD19 signaling, CD20 signaling, 41BB signaling, CD28 signaling, OX40 signaling, GITR signaling, TREM-1 signaling, TREM-2 signaling, DAP12 signaling, MR signaling, ICOS signaling, MyD88 signaling, V/I/LxYxxL/V signaling, SIRPα signaling, CD45 signaling, Siglec-10 signaling, PD1 signaling, SHP-1 signaling, SHP-2 signaling, KIR-2DL signaling, KIR-3DL signaling, NKG2A signaling, CD170 signaling, CD33 signaling, BTLA signaling, CD32b signaling, SIRPb signaling, CD22 signaling, PIR-B signaling, and/or LILRB1 signaling), e.g., relative to a macrophage without a CAR as described herein. In some embodiments, a macrophage comprising or expressing at least one CAR described herein exhibits induction of cell survival mechanisms, e.g., relative to a macrophage without a CAR as described herein. In some embodiments, a macrophage comprising or expressing at least one CAR described herein exhibits induction of cell death mechanisms, e.g., relative to a macrophage without a CAR as described herein. In some embodiments, a macrophage comprising or expressing at least one CAR described herein exhibits one, two, three, four, or five of increased resistance to phagocytic checkpoints, increased expression of chemokine receptors to aid in trafficking, increased expression of chemokines to recruit other immune cells, increased expression of ECM degrading enzymes (e.g., MMPs to degrade tumor ECM and/or exhibit anti fibrotic activity), or increased proliferation, e.g., relative to a macrophage without a CAR as described herein. In some embodiments, a macrophage comprising or expressing at least one CAR described herein exhibits one, two, three, or four of improved duration of CAR expression, improved stability of the CAR on the cell surface, increased level of CAR expression, or decreased background activity of the CAR, e.g., relative to a macrophage without a CAR as described herein.

In some embodiments, a macrophage comprising or expressing at least one CAR described herein decreases infection (e.g., of an infectious agent) in a subject, e.g., relative to a macrophage without a CAR as described herein. In some embodiments, an infectious agent comprises or is a virus, a protozoa (e.g., trypanosome, malaria, or *toxoplasma*), a bacteria (e.g., *mycobacterium, salmonella*, or *listeria*), a fungi (e.g., *Candida*), or a combination thereof. In some embodiments, a virus comprises hepatitis virus (e.g., hepatitis A, hepatitis B, hepatitis C, or hepatitis E), retrovirus, human immunodeficiency virus (e.g., HIV1 or HIV2), T cell leukemia virus, a Lymphotropic virus (e.g., HTLV1 or HTLV2), herpes simplex virus (e.g., herpes simplex virus type 1 or type 2), Epstein-Barr virus, cytomegalovirus, varicella-zoster virus, poliovirus, measles virus, Rubella virus, Japanese encephalitis virus, mumps virus, influenza virus, adenovirus, enterovirus, rhinovirus, coronavirus (e.g., severe acute respiratory syndrome (SARS) virus, Middle East respiratory syndrome (MERS) virus, or Coronavirus disease 2019 (COVID-19)), Ebola virus, West Nile virus, or a variant or combination thereof.

In some embodiments, a macrophage comprising or expressing at least one CAR described herein decreases formation and/or degrades existing aggregates via phagocytosis of at least one protein aggregate in a subject (e.g., a subject having a neurodegenerative disease, an inflammatory disease, a cardiovascular disease, a fibrotic disease, amyloidosis, or a combination thereof), e.g., relative to a macrophage without a CAR as described herein. In some embodiments, a neurodegenerative disease is selected from the group consisting of tauopathy, a-synucleopathy, presenile dementia, senile dementia, Alzheimer's disease, progressive supranuclear palsy (PSP), Pick's disease, primary progressive aphasia, frontotemporal dementia, corticobasal dementia, Parkinson's disease, dementia with Lewy bodies, Down's syndrome, multiple system atrophy, amyotrophic lateral sclerosis (ALS), Hallervorden-Spatz syndrome, polyglutamine disease, trinucleotide repeat disease, and prion disease. In some embodiments, an inflammatory disease is selected from the group consisting of systemic lupus erythematosus, vasculitis, rheumatoid arthritis, periodontitis, ulcerative colitis, sinusitis, asthma, tuberculosis, Crohn's disease, chronic infection, hereditary periodic fever, a malignancy, systemic vasculitides, cystic fibrosis, bronchiectasis, epidermolysis bullosa, cyclic neutropenia, an immunodeficiency, Muckle-Wells (MWS) disease, and Familiar Mediterranean Fever (FMF). In some embodiments, amyloidosis is selected from the group consisting of Primary Amyloidosis (AL), Secondary Amyloidosis (AA), Familial Amyloidosis (ATTR), Beta-2 Microglobulin Amyloidosis, Localized Amyloidosis, Heavy Chain Amyloidosis (AH), Light Chain Amyloidosis (AL), Primary Systemic Amyloidosis, ApoAI Amyloidosis, ApoAII Amyloidosis, ApoAIV Amyloidosis, Apolipoprotein C2 Amyloidosis, Apolipoprotein C3 Amyloidosis, Corneal lactoferrin amyloidosis, Transthyretin-Related Amyloidosis, Dialysis amyloidosis, Fibrinogen amyloidosis, Lect2 amyloidosis (ALECT2), and Lysozyme amyloidosis. In some embodiments, a cardiovascular disease is selected from the group consisting of atherosclerosis, coronary artery disease, peripheral artery disease, hypertensive heart disease, metabolic syndrome, hypertension, cerebrovascular disease, and heart failure. In some embodiments, a fibrotic disease is selected from the group consisting of pulmonary fibrosis, idiopathic pulmonary fibrosis, cirrhosis, cystic fibrosis, scleroderma, cardiac fibrosis, radiation-induced lung injury, steatohepatitis, glomerulosclerosis, interstitial lung disease, liver fibrosis, mediastinal fibrosis, retroperitoneal cavity fibrosis, bone marrow fibrosis, and skin fibrosis.

Monocytes

Monocytes are multipotent cells that circulate in the blood, bone marrow, and spleen, and generally do not proliferate when in a steady state. Monocytes can vary in size significantly in the range of about 10-30 μm in diameter. A ratio of nucleus to cytoplasm for a monocyte can range from about 2:1 to about 1:1. Typically, monocytes comprise chemokine receptors and pathogen recognition receptors that mediate migration from blood to tissues, such as during an infection. Monocytes can produce inflammatory cytokines, take up cells and/or toxic molecules, and differentiate into dendritic cells or macrophages.

In some embodiments, a monocyte comprises or expresses one or more phenotypic markers. Exemplarily phenotypic markers for human monocyte cells include, but are not limited to, CD9, CD11b, CD11c, CDw12, CD13, CD15, CDw17, CD31, CD32, CD33, CD35, CD36, CD38, CD43, CD49b, CD49e, CD49f, CD63, CD64, CD65s, CD68, CD84. CD85, CD86, CD87, CD89, CD91, CDw92, CD93, CD98, CD101, CD102, CD111, CD112, CD115, CD116, CD119, CDw121b, CDw123, CD127, CDw128, CDw131, CD147, CD155, CD156a, CD157, CD162 CD163, CD164, CD168, CD171, CD172a, CD180, CD206, CD131a1, CD213 2, CDw210, CD226, CD281, CD282, CD284, and CD286. Exemplarily phenotypic markers for mouse monocyte cells include, but are not limited to, CD11a, CD11b, CD16, CD18, CD29, CD31, CD32, CD44, CD45, CD49d, CD115, CD116, Cdw131, CD281, CD282, CD284, CD286, F4/80, and CD49b. In certain embodiments monocytes comprises one, two, or three of CD11b, CD14, or CD16. In certain embodiments, monocytes comprises CD14+ CD16− monocytes, CD14+ CD16+ monocytes, or CD14− CD16+ monocytes.

In some embodiments, a monocyte differentiates into a macrophage. In some embodiments, a monocyte differentiates into a dendritic cell (DC). Monocytes can be differentiated into macrophages or DCs by any technique known in the art. For example, differentiation of monocytes into macrophages can be induced by macrophage colony stimulating factor (M-CSF). Differentiation of monocytes into DCs can be induced by granulocyte-macrophage colony stimulating factor (GM-CSF) in combination with IL-4.

In some embodiments, a monocyte comprising or expressing at least one CAR described herein exhibits increased secretion of one or more cytokines (e.g., one, two, three, four, five, six, or seven of TNF, IL-12, IFN, GM-CSF, G-CSF, M-CSF, or IL-1), e.g., relative to a monocyte without a CAR as described herein. In some embodiments, a monocyte comprising or expressing at least one CAR described herein exhibits increased phagocytosis, e.g., relative to a monocyte without a CAR as described herein. In some embodiments, a monocyte comprising or expressing at least one CAR described herein exhibits enhanced survival, e.g., relative to a monocyte without a CAR as described herein. In some embodiments, a monocyte comprising or expressing at least one CAR described herein exhibits enhanced differentiation into macrophages (e.g., M1 or M2 macrophages), e.g., relative to a monocyte without a CAR as described herein. In some embodiments, a monocyte comprising or expressing at least one CAR described herein exhibits enhanced differentiation into DCs (e.g., resident or migrating DCs and/or in lymphoid and non-lymphoid tissue), e.g., relative to a monocyte without a CAR as described herein. In some embodiments, a monocyte comprising or expressing at least one CAR described herein exhibits increased cytotoxicity against a tumor cell, e.g., relative to a monocyte without a CAR as described herein. In some embodiments, a monocyte comprising or expressing at least one CAR described herein exhibits increased tumor antigen presentation (e.g., post-phagocytosis presentation) and/or increased antigen processing, e.g., relative to a monocyte without a CAR as described herein. In some embodiments, a monocyte comprising or expressing at least one CAR described herein exhibits increased tumor killing (e.g., by phagocytosis, lysis, apoptosis, or production of tumor killing cytokines (e.g., TNFα), e.g., relative to a monocyte without a CAR as described herein.

In some embodiments, a monocyte comprising or expressing at least one CAR described herein exhibits one or both of increased expression of favorable genes or decreased expression of unfavorable genes, e.g., relative to a monocyte without a CAR as described herein. In some embodiments, a monocyte comprising or expressing at least one CAR described herein exhibits increased production of ROS, e.g., relative to a monocyte without a CAR as described herein. In some embodiments, a monocyte comprising or expressing at least one CAR described herein exhibits metabolic reprogramming, e.g., relative to a monocyte without a CAR as described herein. In some embodiments, a monocyte comprising or expressing at least one CAR described herein exhibits induction of cell survival mechanisms, e.g., relative to a monocyte without a CAR as described herein. In some embodiments, a monocyte comprising or expressing at least one CAR described herein exhibits induction of cell death mechanisms, e.g., relative to a monocyte without a CAR as described herein. In some embodiments, a monocyte comprising or expressing at least one CAR described herein exhibits one, two, three, four, or five of increased resistance to phagocytic checkpoints, increased expression of chemokine receptors to aid in trafficking, increased expression of chemokines to recruit other immune cells, increased expression of ECM degrading enzymes (e.g., MMPs to degrade tumor ECM and/or exhibit anti fibrotic activity), or increased proliferation, e.g., relative to a monocyte without a CAR as described herein. In some embodiments, a monocyte comprising or expressing at least one CAR described herein exhibits one, two, three, or four of improved duration of CAR expression, improved stability of the CAR on the cell surface, increased level of CAR expression, or decreased background activity of the CAR, e.g., relative to a monocyte without a CAR as described herein.

Dendritic Cells

Dendritic cells (DCs) are bone marrow-derived, specialized antigen presenting cells that are involved in initiating immune responses and maintaining tolerance of the immune system to self-antigens. Dendritic cells may be found in both lymphoid and non-lymphoid organs and are generally thought to arise from lymphoid or myeloid lineages.

In some embodiments, a DC comprises or expresses one or more phenotypic markers. Exemplarily phenotypic markers for DCs include, but are not limited to, CD11c, CD83, CD1a, CD1c, CD141, CD207, CLEC9a, CD123, CD85, CD180, CD187, CD205, CD281, CD282, CD284, CD286 and partially CD206, CD207, CD208 and CD209.

Immature DCs can be characterized by a high capacity for antigen capture, but relatively low T cell stimulatory capability. Inflammatory mediators promote DC maturation. Once DCs reach the mature stage, there is a dramatic change in properties relative to immature DCs, such as a decrease in antigen capture ability and/or an increased ability to stimulate T cells. In some embodiments, a DC comprises or is an immature DC. In other embodiments, a DC comprises or is a mature DC.

Without wishing to be bound by theory, it is believed that modification of a DC cell to comprise or express at least one CAR described herein can allow mature DCs to simultaneously exhibit increased antigen capture ability and T cell stimulation, e.g., relative to a DC without a CAR described herein. In some embodiments, a DC comprising or expressing at least one CAR described herein mediates tumor antigen presentation, e.g., increased tumor antigen presentation relative to a DC without a CAR as described herein. In some embodiments, a DC comprising or expressing at least one CAR described herein mediates tumor T cell stimulation, e.g., increased T cell stimulation relative to a DC without a CAR as described herein.

In some embodiments, a DC comprising or expressing at least one CAR described herein exhibits increased secretion of one or more cytokines (e.g., one, two, three, four, five, six, or seven of TNF, IL-12, IFN, GM-CSF, G-CSF, M-CSF, or IL-1), e.g., relative to a DC without a CAR as described herein. In some embodiments, a DC comprising or expressing at least one CAR described herein exhibits increased phagocytosis, e.g., relative to a DC without a CAR as described herein. In some embodiments, a DC comprising or expressing at least one CAR described herein exhibits increased tumor antigen presentation (e.g., post-phagocytosis presentation), increased antigen processing, increased antigen cross presentation, increased T cell priming, and/or stimulation of T cells, e.g., relative to a DC without a CAR as described herein.

In some embodiments, a DC comprising or expressing at least one CAR described herein exhibits one or both of increased expression of favorable genes or decreased expression of unfavorable genes, e.g., relative to a DC without a CAR as described herein. In some embodiments, a DC comprising or expressing at least one CAR described herein exhibits increased production of ROS, e.g., relative to a DC without a CAR as described herein. In some embodiments, a DC comprising or expressing at least one CAR described herein exhibits metabolic reprogramming, e.g., relative to a DC without a CAR as described herein. In some embodiments, a DC comprising or expressing at least one CAR described herein exhibits induction of cell survival mechanisms, e.g., relative to a DC without a CAR as described herein. In some embodiments, a DC comprising or expressing at least one CAR described herein exhibits induction of cell death mechanisms, e.g., relative to a DC without a CAR as described herein. In some embodiments, a DC comprising or expressing at least one CAR described herein exhibits one, two, three, four, or five of increased resistance to phagocytic checkpoints, increased expression of chemokine receptors to aid in trafficking, increased expression of chemokines to recruit other immune cells, increased expression of ECM degrading enzymes (e.g., MMPs to degrade tumor ECM and/or exhibit anti fibrotic activity), or increased proliferation, e.g., relative to a DC without a CAR as described herein. In some embodiments, a DC comprising or expressing at least one CAR described herein exhibits one, two, three, or four of improved duration of CAR expression, improved stability of the CAR on the cell surface, increased level of CAR expression, or decreased background activity of the CAR, e.g., relative to a DC without a CAR as described herein.

Chimeric Antigen Receptors (CAR)

The term "chimeric antigen receptor" or "CAR," as used herein, refers to an artificial cell surface receptor that is engineered to be expressed on an immune effector cell and specifically targets a cell and/or binds an antigen. CARs may be used, for example, as a therapy with adoptive cell transfer. For example, in some embodiments, monocytes, macrophages and/or dendritic cells are removed from a patient (e.g., from blood, tumor or ascites fluid) and modified so that they express a receptor specific to a particular form of antigen. In some embodiments, CARs have been expressed with specificity to an antigen, for example, a tumor associated antigen. In some embodiments, a CAR comprises an extracellular domain, a transmembrane domain and an intracellular domain.

In some embodiments, a modified immune cell, for example, a modified macrophage, monocyte, or dendritic cell, is generated by expressing a CAR therein. In some embodiments, an immune cell comprises a CAR comprising an extracellular domain, a transmembrane domain, and an intracellular domain, wherein the immune cell comprises a macrophage, monocyte, or dendritic cell.

In some embodiments, a CAR may further comprise one or more of: one or more extracellular leader domains, one or more extracellular hinge domains and one or more intracellular co-stimulatory domains.

In some embodiments, a CAR comprises a spacer domain or hinge between an extracellular domain and a transmembrane domain. In some embodiments, a CAR comprises a spacer domain or hinge between an intracellular domain and a transmembrane domain. As used herein, the term "spacer domain" or "hinge" refers to any oligo- or polypeptide that functions to link a transmembrane domain to either an extracellular domain or to an intracellular domain in a polypeptide chain. In some embodiments, a spacer domain or hinge may comprise up to 300 amino acids, preferably 10 to 100 amino acids and most preferably 25 to 50 amino acids. In some embodiments, a short oligo- or polypeptide linker, preferably between 2 and 10 amino acids in length, may form a linkage between a transmembrane domain and an intracellular domain of a CAR. An example of a linker includes a glycine-serine doublet.

In some embodiments, an immune cell comprising a CAR may comprise one or more control systems including, but not limited to: a safety switch (e.g., an on switch, and off switch, a suicide switch), a logic gate, for example an AND gate (e.g., two or more CARs, each of which lacks one or more signaling domains such that activation of both/all CARs is required for full immune cell (e.g., macrophage, monocyte, or dendritic cell) activation or function), an OR gate (e.g., two or more CARs, each with an intracellular domain such as CD3ζ and a co-stimulatory domain), and/or a NOT gate (e.g., two or more CARs, one of which includes an inhibitory domain that antagonizes the function of the other CAR[s]).

The present disclosure also provides immune cells comprising a nucleic acid sequence (e.g., an isolated nucleic acid sequence) encoding a CAR, wherein the nucleic acid sequence comprises a nucleic acid sequence encoding an extracellular domain, a nucleic acid sequence encoding a transmembrane domain and a nucleic acid sequence encoding an intracellular domain, wherein the cell is a monocyte, macrophage or a dendritic cell that expresses the CAR.

In some embodiments, a CAR comprises an extracellular domain is operably linked to another domain of the CAR, such as a transmembrane domain or an intracellular domain, for expression in an immune cell. In some embodiments, a nucleic acid encoding an extracellular domain is operably linked to a nucleic acid encoding a transmembrane domain and the nucleic acid encoding the transmembrane domain is operably linked to a nucleic acid encoding an intracellular domain.

In some embodiments, an effector activity of an immune cell comprising a CAR is directed against a target cell comprising an antigen that specifically binds an antigen binding domain of the CAR. In some embodiments, a targeted effector activity directed against a target cell is or comprises phagocytosis, targeted cellular cytotoxicity, antigen presentation, or cytokine secretion.

In some embodiments, a CAR described herein comprises at least one domain (e.g., an extracellular domain, a transmembrane domain, and/or an intracellular domain) that inhibits anti-phagocytic signaling in an immune cell described herein (e.g., a macrophage, monocyte, or dendritic cell). In some embodiments, a CAR described herein improves effector activity of an immune cell described herein (e.g., a macrophage, monocyte, or dendritic cell), e.g., by enhancing inhibition of CD47 and/or SIRPα activity, relative to a cell of the same type without a CAR. In some embodiments, a CAR described herein binds CD47, e.g., and serves as a dominant negative receptor, inhibiting SIRPα activity (e.g., a CD47 sink). In some embodiments, a CAR described herein that binds SIRPα, e.g., comprises an activating receptor (e.g., comprises a CD3z intracellular domain). A CAR described herein inhibits at least one interaction of CD47 and SIRPα. In some embodiments, a CAR is or comprises a phagocytic logic gate.

In some embodiments, an immune cell described herein (e.g., comprising or expressing a CAR described herein) comprises or expresses at least one variant or fragment of: SIRPα (e.g., a dominant negative SIRPα or a high-affinity engineered variant of SIRPα (e.g., CV1)), 5F9 scFv, B6H12 scFv (e.g., a humanized B6H12 scFv), PD1 (e.g., a dominant negative PD1 or HAC-I), anti-PD1 scFv (e.g., E27 or durvalumab), a Siglec (e.g., Siglec-10, Siglec-9, and/or Siglec-11), and/or SHP-1. In some embodiments, a variant or fragment comprises a mutated intracellular domain. In some embodiments, a variant or fragment does not comprise or express at least one intracellular domain (e.g., an immune cell comprises or expresses an anti-CD47 scFv, CD8 hinge domain, and CD8 transmembrane). In some embodiments, an immune cell described herein (e.g., comprising or expressing a CAR described herein) comprises a dominant negative receptor, e.g., blocking an inhibitory checkpoint.

In some embodiments, a CAR described herein further comprises a cleavage peptide (e.g., a P2A, F2A, E2A and/or T2A peptide) and at least one second CAR comprising at least one inhibitory domain of anti-phagocytic signaling. In some embodiments, at least one second CAR comprises a SIRPα (e.g., a high-affinity engineered variant of SIRPα (e.g., CV1)), 5F9 scFv, B6H12 scFv (e.g., a humanized B6H12 scFv), or a CD47 binding extracellular domain or a fragment thereof. In some embodiments, at least one second CAR comprises a SIRPα transmembrane domain or a fragment thereof. In certain embodiments, a second CAR further comprises a hinge domain (e.g., a CD8 hinge domain). In certain embodiments, at least one second CAR comprises: (i) a leader sequence (e.g., a CD8 leader); ii) an extracellular domain (e.g., a SIRPα, CV1, 5F9 scFv, or B6H12 scFv (e.g., a humanized B6H12 scFv) extracellular domain); and ii) a transmembrane domain (e.g., a SIRPα transmembrane domain). In some embodiments, a CAR described herein further comprises a cleavage peptide (e.g., a P2A peptide) and at least one marker protein (e.g., CD20 or a fragment thereof, CD19 or a fragment thereof, NGFR or a fragment thereof, a synthetic peptide, and/or a fluorescent protein).

In some embodiments, an immune cell described herein (e.g., comprising or expressing a CAR described herein) comprises or expresses one or more phosphatase dead domains (e.g. a phosphatase dead Shp1, phosphatase dead 72-5ptase (INPPSE), phosphatase dead Shp2, and/or phosphatase dead SHIP-1 domain) and/or a constitutively active kinase domain (e.g., a constitutively active LYN domain). In some embodiments, a CAR described herein further comprises a cleavage peptide (e.g., a P2A, F2A, E2A and/or T2A peptide) and one or more phosphatase dead domains (e.g. a phosphatase dead Shp1, phosphatase dead 72-5ptase (INPP5E), phosphatase dead Shp2, and/or phosphatase dead SHIP-1 domain) and/or a constitutively active kinase domain (e.g., a constitutively active LYN domain).

Extracellular Domains

The present disclosure provides chimeric antigen receptors (CAR) comprising extracellular domains. In some embodiments, an extracellular domain comprises an Fc receptor (FcR) extracellular domain. In some embodiments, an extracellular domain comprises a toll-like receptor (TLR) extracellular domain. In some embodiments, an extracellular domain comprises a leader domain. In some embodiments, an extracellular domain comprises an antigen binding domain. In some embodiments, an extracellular domain comprises a hinge domain. In some embodiments, an extracellular domain comprises one or more of an FcR extracellular domain, a TLR extracellular domain, a leader domain, an antigen binding domain and a hinge domain. In some embodiments, an extracellular domain may be a domain that is endogenous to a particular immune cell type (e.g., a modified immune cell as provided herein). In some embodiments, an extracellular domain may be a domain that is not endogenous to a particular immune cell type (e.g., a modified immune cell as provided herein).

FcR Extracellular Domains

In some embodiments, an FcR extracellular domain comprises a full-length FcR extracellular domain. In some embodiments, an FcR extracellular domain comprises a portion of a full-length FcR extracellular domain. In some embodiments, an FcR extracellular domain (or portion thereof) is or comprises a human FcR extracellular domain. In some embodiments, an FcR extracellular domain may be a domain that is endogenous to a particular immune cell type (e.g., a modified immune cell as provided herein). In some embodiments, an FcR extracellular domain may be a domain that is not endogenous to a particular immune cell type (e.g., a modified immune cell as provided herein). In some embodiments, an FcR extracellular domain comprises a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain.

TLR Extracellular Domains

In some embodiments, a TLR extracellular domain comprises a full-length TLR extracellular domain. In some embodiments, a TLR extracellular domain comprises a portion of a full-length TLR extracellular domain. In some embodiments, a TLR extracellular domain (or portion thereof) is or comprises a human TLR extracellular domain. In some embodiments, a TLR extracellular domain may be a domain that is endogenous to a particular immune cell type (e.g., a modified immune cell as provided herein). In some embodiments, a TLR extracellular domain may be a domain that is not endogenous to a particular immune cell type (e.g., a modified immune cell as provided herein). In some embodiments, a TLR extracellular domain comprises a TLR1, TLR2, TLR3, TLR4, TLR5, TLR6, TLR7, TLR8, or TLR9 domain.

Leader Domains

In some embodiments, a CAR comprises one or more extracellular leader domains. In some embodiments, a nucleic acid encoding a CAR comprises a nucleic acid sequence encoding an extracellular leader domain, but the extracellular leader domain is cleaved from the CAR before the CAR is expressed in an immune cell. In some embodiments, an extracellular leader domain is or comprises a human extracellular leader domain. In some embodiments, an extracellular leader domain may be a domain that is endogenous to a particular immune cell type (e.g., a modified immune cell as provided herein). In some embodiments, an extracellular leader domain may be a domain that is not endogenous to a particular immune cell type (e.g., a modified immune cell as provided herein). In some embodiments, an extracellular leader domain comprises a CD8 extracellular leader domain. In some embodiments, an extracellular leader domain comprises a leader domain from a stimulatory or co-stimulatory domain (e.g., a TLR1, TLR2, TLR3, TLR4, TLR5, TLR6, TLR7, TLR8, TLR9, ALK, AXL, DDR2, EGFR, EphA1, INSR, cMET, MUSK, PDGFR, PTK7, RET, ROR1, ROS1, RYK, TIE2, TRK, VEGFR, CD40, CD19, CD20, 41BB, CD28, OX40, GITR, TREM-1, TREM-2, DAP12, MR, ICOS, MyD88 domain).

Antigen Binding Domains

In some embodiments, a CAR comprises an antigen binding domain that binds to an antigen, for example, on a target cell. In some embodiments, a CAR comprises an antigen binding domain that binds to an antigen associated with viral infection, bacterial infection, parasitic infection, autoimmune disease, and/or cancer cells. In some embodiments, an antigen binding domain recognizes an antigen that acts as a cell surface marker on a target cell associated with a particular disease state.

In some embodiments, an antigen binding domain binds to a tumor antigen, such as an antigen that is specific for a tumor or cancer of interest. In some embodiments a tumor antigen comprises one or more antigenic cancer epitopes. In some embodiments, a tumor antigen comprises CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8) aNeu5Ac(2-3)bDGalp(1-4)bDGlcp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4) bDGlcp(1-1)Cer); transglutaminase 5 (TGS5); high molecular weight-melanoma-associated antigen (HMW-MAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAXS); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); or immunoglobulin lambda-like polypeptide 1 (IGLL1). In certain embodiments, a tumor antigen comprises ERBB2 (Her2/neu). In certain embodiments, a tumor antigen comprises PSMA. In certain embodiments, a tumor antigen comprises Mesothelin. In some embodiments, an antigen binding domain binds to a misfolded protein antigen or a protein of a protein aggregate, such as a protein that is specific for a disease/disorder of interest. In some embodiments, the disease/disorder is a neurodegenerative disease/disorder, an inflammatory disease/disorder, a cardiovascular disease/disorder, a fibrotic disease/disorder, or amyloidosis (e.g., mediated by protein aggregates of immunoglobulin light chains or of transthyretin). In some embodiments, the neurodegenerative disease/disorder is selected from the group consisting of tauopathy, asynucleopathy, presenile dementia, senile dementia, Alzheimer's disease (mediated by protein aggregates of beta-amyloid), Parkinsonism linked to chromosome 17 (FTDP-17), progressive supranuclear palsy (PSP), Pick's disease, primary progressive aphasia, frontotemporal dementia, corticobasal dementia, Parkinson's disease, Parkinson's disease with dementia, dementia with Lewy bodies, Down syndrome, multiple system atrophy, amyotrophic lateral sclerosis (ALS), Hallervorden-Spatz syndrome, polyglutamine disease, trinucleotide repeat disease, Familial British dementia, Fatal Familial Insomnia, Gerstmann-Straussler-Scheinker Syndrome, Hereditary cerebral hemorrhage with amyloidosis (Icelandic) (HCHW A-I), Sporadic Fatal Insomnia (sFI), Variably Protease-Sensitive Prionopathy (VPSPr), Familial Danish dementia, and prion disease (such as Creutzfeldt-Jakob disease, CJD and Variant Creutzfeldt-Jakob Disease (vCJD)).

In some embodiments, an antigen binding domain comprises any domain that binds to an antigen. In some embodiments, an antigen binding domain is or comprises a monoclonal antibody, a polyclonal antibody, a synthetic antibody, a human antibody, a humanized antibody, a non-human antibody, or any fragment thereof, for example an scFv. In some embodiments, an antigen binding domain is or comprises an aptamer, a darpin, a centyrin, a naturally occurring or synthetic receptor, an affibody, or other engineered protein recognition molecule. In some embodiments, an antigen binding domain is or comprises a mammalian antibody or a fragment thereof. In some embodiments, an antigen binding domain is derived, in whole or in part, from the same species in which the CAR will ultimately be used. For example, for use in humans, an antigen binding domain of a CAR comprises a human antibody, a humanized antibody, or a fragment thereof (e.g. a scFv). In some embodiments, an antigen binding domain may be a domain that is endogenous to a particular immune cell type (e.g., a modified immune cell as provided herein). In some embodiments, an antigen binding domain may be a domain that is not endogenous to a particular immune cell type (e.g., a modified immune cell as provided herein).

In some embodiments, a CAR comprises one or more antigen binding domains. In some embodiments, a CAR comprises two or more antigen binding domains. In some embodiments, a CAR is a bispecific CAR. In some embodiments, an immune cell comprises two or more different CARs comprising one or more antigen binding domains. In some embodiments, an immune cell comprising a bispecific CAR and/or comprising two or more different CARs comprising one or more antigen binding domains can reduce off-target and/or on-target off-tissue effects by requiring that two antigens are present. In some embodiments, an immune cell comprises a bispecific CAR and/or comprises two or more different CARs comprising one or more antigen binding domains, wherein the CARs provide distinct signals that in isolation are insufficient to mediate activation of the modified cell, but are synergistic together, stimulating activation of the modified cell. In some embodiments, such a construct may be referred to as an 'AND' logic gate.

In some embodiments, an immune cell comprising a bispecific CAR and/or comprising two or more different CARs comprising one or more antigen binding domains can reduce off-target and/or on-target off-tissue effects by requiring that one antigen is present and a second, normal protein antigen is absent before the cell's activity is stimulated. In some embodiments, such a construct may be referred to as a 'NOT' logic gate. In contrast to AND gates, NOT gated CAR-modified cells are activated by binding to a single antigen. However, the binding of a second receptor to the second antigen functions to override the activating signal being perpetuated through the CAR. Typically, such an inhibitory receptor would be targeted against an antigen that is abundantly expressed in a normal tissue but is absent in tumor tissue.

Hinge Domains

In some embodiments, a CAR comprises one or more extracellular hinge domains. In some embodiments, an extracellular hinge domain is or comprises a human extracellular hinge domain. In some embodiments, an extracellular hinge domain may be a domain that is endogenous to a particular immune cell type (e.g., a modified immune cell as provided herein). In some embodiments, an extracellular hinge domain may be a domain that is not endogenous to a particular immune cell type (e.g., a modified immune cell as provided herein). In some embodiments, one or more extracellular hinge domains comprise a CD8a extracellular hinge domain or an IgG4 or a CD28 extracellular hinge domain. In some embodiments, one or more extracellular hinge domains comprise a CD28 extracellular hinge domain. In some embodiments, an extracellular hinge domain optimizes the physicochemical parameters of a CAR, e.g., optimal size relative to tumor antigen (e.g., allowing for exclusion of inhibitory molecules), optimal flexibility, optimal protein folding, optimal protein stability, optimal binding, optimal homodimerization, and/or lack of homodimerization.

Transmembrane Domains

In some embodiments, a CAR comprises a transmembrane domain, for example, that connects an extracellular domain to an intracellular domain. In some embodiments, a transmembrane domain is naturally associated with one or more other domain(s) of a CAR. In some embodiments, a transmembrane domain can be modified to avoid binding to transmembrane domains of other surface membrane proteins, in order to minimize interactions with other members of a receptor complex. In some embodiments, a transmembrane domain may be derived either from a naturally-occurring or from a synthetic source. In some embodiments a transmembrane domain is derived from a naturally-occurring membrane-bound or transmembrane protein. In some embodiments, a transmembrane domain is or comprises a human transmembrane domain. In some embodiments, a transmembrane domain may be a domain that is endogenous to a particular immune cell type (e.g., a modified immune cell as provided herein). In some embodiments, a transmembrane domain may be a domain that is not endogenous to a particular immune cell type (e.g., a modified immune cell as provided herein). In some embodiments, a transmembrane domain comprises a CD28, CD8a, CD64, CD32a, CD32c, CD16a, TRL1, TLR2, TLR3, TRL4, TLR5, TLR6, TLR7, TLR8, TLR9, ALK, AXL, DDR2, EGFR, EphA1, INSR, cMET, MUSK, PDGFR, PTK7, RET, ROR1, ROS1, RYK, TIE2, TRK, VEGFR, CD40, CD19, CD20, 41BB, CD28, OX40, GITR, TREM-1, TREM-2, DAP12, MR, ICOS, MyD88, CD3-zeta, FcR γ, V/I/LxYxxL/V, SIRPα, CD45, Siglec-10, PD1, SHP-1, SHP-2, KIR-2DL, KIR-3DL, NKG2A, CD170, CD33, BTLA, CD32b, SIRPb, CD22, PIR-B, LILRB1, CD36, or Syk transmembrane domain.

FcR Transmembrane Domains

In some embodiments, an FcR transmembrane domain comprises a full-length FcR transmembrane domain. In some embodiments, an FcR transmembrane domain comprises a portion of a full-length FcR transmembrane domain. In some embodiments, an FcR transmembrane domain is or comprises a human FcR transmembrane domain, or portion thereof. In some embodiments, an FcR transmembrane domain may be a domain that is endogenous to a particular immune cell type (e.g., a modified immune cell as provided herein). In some embodiments, an FcR transmembrane domain may be a domain that is not endogenous to a particular immune cell type (e.g., a modified immune cell as provided herein). In some embodiments, an FcR transmembrane domain comprises a CD64 (FcγRI), CD32a (FcγRIIa), CD32b (FcγRIIb), CD32c, CD16a (FcγRIIIa), CD16b (FcγRIIIb), FcεRI, FcεRII, or FcαRI (CD89) domain.

TLR Transmembrane Domains

In some embodiments, a TLR transmembrane domain comprises a full-length TLR transmembrane domain. In some embodiments, a TLR transmembrane domain comprises a portion of a full-length TLR transmembrane domain. In some embodiments, a TLR transmembrane domain is or comprises a human TLR transmembrane domain, or portion thereof. In some embodiments, a TLR transmembrane domain may be a domain that is endogenous to a particular immune cell type (e.g., a modified immune cell as provided herein). In some embodiments, a TLR transmembrane domain may be a domain that is not endogenous to a particular immune cell type (e.g., a modified immune cell as provided herein). In some embodiments, a TLR transmembrane domain comprises a TLR1, TLR2, TLR3, TLR4, TLR5, TLR6, TLR7, TLR8, or TLR9 domain.

Intracellular Domains

In some embodiments, a CAR comprises one or more intracellular domains. In some embodiments, an intracellular domain is or comprises a human intracellular domain, or portion thereof. In some embodiments, an intracellular domain may be a domain that is endogenous to a particular immune cell type (e.g., a modified immune cell as provided herein). In some embodiments, an intracellular domain may be a domain that is not endogenous to a particular immune cell type (e.g., a modified immune cell as provided herein). In some embodiments, an intracellular domain and/or other cytoplasmic domain of a CAR is responsible for activation of the cell in which the CAR is expressed (e.g., an immune cell). In some embodiments, an intracellular domain of a CAR is responsible for signal activation and/or transduction in an immune cell comprising said CAR.

In some embodiments, an intracellular domain of a CAR includes at least one domain responsible for signal activation and/or transduction. In some embodiments, an intracellular domain is or comprises at least one of a co-stimulatory molecule and a signaling domain. In some embodiments, an intracellular domain of a CAR comprises dual signaling domains. In some embodiments, an intracellular domain of a CAR comprises more than two signaling domains.

In some embodiments, an intracellular domain comprises a cytoplasmic portion of a surface receptor. In some embodiments, an intracellular domain comprises a co-stimulatory molecule. In some embodiments, an intracellular domain comprises a molecule that acts to initiate signal transduction in an immune cell.

In some embodiments, an intracellular domain of a CAR includes any portion of one or more co-stimulatory molecules, such as at least one signaling domain from CD3, Fc epsilon RI gamma chain, any derivative or variant thereof, any synthetic sequence thereof that has the same functional capability, and any combination thereof.

FcR Intracellular Domains

In some embodiments, an FcR intracellular domain comprises a full-length FcR intracellular domain. In some embodiments, an FcR intracellular domain comprises a portion of a full-length FcR intracellular domain. In some embodiments, an FcR intracellular domain is or comprises a human FcR intracellular domain, or portion thereof. In some embodiments, an FcR intracellular domain may be a domain that is endogenous to a particular immune cell type (e.g., a modified immune cell as provided herein). In some embodiments, an FcR intracellular domain may be a domain that is not endogenous to a particular immune cell type (e.g., a modified immune cell as provided herein). In some embodiments, an FcR intracellular domain comprises a CD64 (FcγRI), CD32a (FcγRIIa), CD32b (FcγRIIb), CD32c (Fc gamma RIIc), CD16a (FcγRIIIa), CD16b (FcγRIIIb), FcεRI, FcεRII, or FcαRI (CD89) domain.

TLR Intracellular Domains

In some embodiments, a TLR intracellular domain comprises a full-length TLR intracellular domain. In some embodiments, a TLR intracellular domain comprises a portion of a full-length TLR intracellular domain. In some embodiments, a TLR intracellular domain is or comprises a human TLR intracellular domain, or portion thereof. In some embodiments, a TLR intracellular domain may be a domain that is endogenous to a particular immune cell type (e.g., a modified immune cell as provided herein). In some embodiments, a TLR intracellular domain may be a domain that is not endogenous to a particular immune cell type (e.g., a modified immune cell as provided herein). In some embodiments, a TLR intracellular domain comprises a TLR1, TLR2, TLR3, TLR4, TLR5, TLR6, TLR7, TLR8, or TLR9 domain.

Signaling Domains

In some embodiments, a CAR comprises one or more intracellular signaling domains. In some embodiments, an intracellular signaling domain is or comprises a human intracellular signaling domain, or portion thereof. In some embodiments, a signaling domain may be a domain that is endogenous to a particular immune cell type (e.g., a modified immune cell as provided herein). In some embodiments, a signaling domain may be a domain that is not endogenous to a particular immune cell type (e.g., a modified immune cell as provided herein).

In some embodiments, one or more intracellular signaling domains comprise a CD3-zeta, FcR γ, CD64, CD32a, CD32c, CD16a, TLR1, TLR2, TLR3, TLR4, TLR5, TLR6, TLR7, TLR8, TLR9, ALK, AXL, DDR2, EGFR, EphA1, INSR, cMET, MUSK, PDGFR, PTK7, RET, ROR1, ROS1, RYK, TIE2, TRK, VEGFR, CD40, CD19, CD20, 41BB, CD28, OX40, GITR, TREM-1, TREM-2, DAP12, MR, ICOS, MyD88, V/I/LxYxxL/V, SIRPα, CD45, Siglec-10, PD1, SHP-1, SHP-2, KIR-2DL, KIR-3DL, NKG2A, CD170, CD33, BTLA, CD32b, SIRPb, CD22, PIR-B, LILRB1, Syk, 41BB ligand (41BBL; TNFSF9), CD27, OX40L, CD32b, CD11b, ITGAM, SLAMF7, CD206, CD163, CD209, Dectin-2, or one or more cytokine receptor signaling domains (e.g., an IL1R, an IL2R, an IL3R, an IL4R, an IL5R, an IL6R, an IL7R, an IL8R, an IL9R, an IL10R, an IL11R, an IL12R, an IL13R, an IL14R, an IL15R, an IL17R, an IFNaR, an IFNgR, an TNFR, an CSF1R, an CSF2R, Dap10, CD36, Dectin-1, or ICOSL intracellular signaling domain)

In some embodiments, an intracellular domain of a CAR comprises dual signaling domains, such as 41BB, CD28, ICOS, TLR1, TLR2, TLR3, TLR4, TLR5, TLR6, TLR7, TLR8, TLR9, TLR10, TLR11, CD116 receptor beta chain, CSF1-R, LRP1/CD91, SR-A1, SR-A2, MARCO, SR-CL1, SR-CL2, SR-C, SR-E, CR1, CR3, CR4, dectin 1, DEC-205, DC-SIGN, CD14, CD36, LOX-1, CD11b, together with any of the signaling domains listed in the above paragraph in any combination.

Co-Stimulatory Domains

As used herein, a "co-stimulatory molecule" or "co-stimulatory domain" refers to a molecule in an immune cell that is used to heighten or dampen an initial stimulus. For example, pathogen-associated pattern recognition receptors, such as TLR or the CD47/SIRPα axis, are molecules on immune cells that, respectively, heighten or dampen an initial stimulus. In some embodiments, a co-stimulatory domain comprises TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combinations thereof.

In some embodiments, a co-stimulatory domain may be a domain that is endogenous to a particular immune cell type (e.g., a modified immune cell as provided herein). In some embodiments, a co-stimulatory domain may be a domain that is not endogenous to a particular immune cell type (e.g., a modified immune cell as provided herein).

As used herein, a "co-stimulatory signal" refers to a signal, which in combination with a primary signal, such as activation of a CAR on an immune cell, leads to activation of the immune cell.

Cleavage Peptides

As used herein, a cleavage peptide refers to a peptide that can induce the cleaving of a recombinant protein in a cell. In some embodiments, a cleavage peptide is a 2A peptide. In some embodiments, a cleavage peptide is or comprises a P2A, F2A, E2A or T2A peptide. In some embodiments, a nucleic acid as described herein comprises one or more nucleic acid sequences encoding one or more cleavage peptides. In some embodiments, a nucleic acid comprising a nucleic acid sequence encoding a cleavage peptide also comprises one or more nucleic acid sequences encoding one or more intracellular domains and one or more nucleic acid sequences comprising one or more peptide agents, wherein translation of the nucleic acid results in a protein comprising one or more intracellular domains separated from one or more peptide agents by a cleavage peptide. In some embodiments, a first promoter is operably linked to one or more nucleic acids encoding a CAR and a second promoter is operably linked to one or more nucleic acids encoding a peptide agent. In some embodiments, a nucleic acid sequence comprising a CAR, and optionally one or more peptide agents, further comprises an internal ribosome entry site (IRES) sequence. An IRES sequence may be any viral, chromosomal or artificially designed sequence that initiates cap-independent ribosome binding to mRNA facilitates the initiation of translation.

Peptide Agents

As used herein, a peptide agent refers to a peptide co-expressed with a CAR in an immune cell. In some embodiments, a peptide agent is co-expressed with a CAR to ensure stoichiometric balance and optimal signaling of a CAR. In some embodiments, a peptide agent forms a homodimer with an identical peptide agent. In some embodiments, a peptide agent forms a heterodimer with a different peptide agent. In some embodiments, a nucleic acid as described herein comprises one or more nucleic acid sequences encoding one or more peptide agents. In some embodiments, a peptide agent is or comprises an FcR gamma chain.

In some embodiments, a peptide agent comprises any peptide, protein, receptor, secreted antibody or a fragment thereof (e.g., an scFv, Fab, Fab', F(ab')2, Fc, or nanobody). In some embodiments, a peptide agent comprises one or more cytokines (e.g., one or more of IL-1, IL-2, IL-6, IL-8, TNF-a, IFNa, IFNb, IFN-y, GMCSF, or MCSF), CD40-L, dominant negative SIRPα, dominant negative PD1, dominant negative CD45, dominant negative SIGLEC 10, or dominant negative LILRB.

Fc Receptors (FcR)

In some embodiments, a CAR comprises one or more antigen binding domains and an FcR extracellular domain, and/or the transmembrane domain of the CAR comprises an FcR transmembrane domain, and/or the intracellular domain of the CAR comprises an FcR intracellular domain. In some embodiments, a CAR comprises, from N-terminus to C-terminus, one or more extracellular binding domains, an FcR extracellular domain, an FcR transmembrane domain, and an FcR intracellular domain. In some embodiments, one or more of the FcR extracellular domain, the FcR transmembrane domain and the FcR intracellular domain is or comprises a human FcR domain. In some embodiments, an FcR extracellular domain, an FcR transmembrane domain and an FcR intracellular domain together comprise a full-length FcR. In some embodiments, an FcR extracellular domain, an FcR transmembrane domain and an FcR intracellular domain together comprise a portion of a full-length FcR. In some embodiments, an FcR extracellular domain comprises a portion of a full-length FcR extracellular domain. In some embodiments, an FcR transmembrane domain comprises a portion of a full-length FcR transmembrane domain. In some embodiments, an FcR intracellular domain comprises a portion of a full-length FcR intracellular domain.

Toll-Like Antigen Receptors (TLR)

In some embodiments, a CAR comprises one or more antigen binding domains and a toll-like receptor (TLR) extracellular domain and/or the transmembrane domain of the CAR comprises a TLR transmembrane domain and/or the intracellular domain of the CAR comprises a TLR intracellular domain. In some embodiments, a CAR comprises, from N-terminus to C-terminus, one or more extracellular binding domains, a TLR extracellular domain, a TLR transmembrane domain, and a TLR intracellular domain. In some embodiments, one or more of the TLR extracellular domain, the TLR transmembrane domain and the TLR intracellular domain is or comprises a human TLR domain. In some embodiments, a TLR extracellular domain, a TLR transmembrane domain and a TLR intracellular domain together comprise a full-length TLR. In some embodiments, a TLR extracellular domain, a TLR transmembrane domain and a TLR intracellular domain together comprise portion of a full-length TLR. In some embodiments, a TLR extracellular domain comprises a portion of a full-length TLR extracellular domain. In some embodiments, a TLR transmembrane domain comprises a portion of a full-length TLR transmembrane domain. In some embodiments, a TLR intracellular domain comprises a portion of a full-length TLR intracellular domain.

Nucleic Acid Constructs

The present disclosure, among other things, provides nucleic acid molecules encoding at least one CAR described herein or a fragment thereof. An immune cell can comprise a nucleic acid molecule (e.g., an exogenous nucleic acid molecule) encoding at least one CAR described herein. In some embodiments, a nucleic acid molecule encoding at least one CAR comprises: (a) an extracellular domain (e.g., an extracellular domain as described herein), (b) a transmembrane domain (e.g., a transmembrane domain as described herein), and (c) an intracellular domain (e.g., an intracellular domain as described herein).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s). The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "operably linked" or "transcriptional control" refers to functional linkage between a regulatory sequence and a heterologous nucleic acid sequence resulting in expression of the heterologous nucleic acid sequence. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

As used herein, the terms "fragment" or "portion" refers to a structure that includes a discrete portion of the whole, but lacks one or more moieties found in the whole structure. In some embodiments, a fragment consists of such a discrete portion. In some embodiments, a fragment consists of or comprises a characteristic structural element or moiety found in the whole. In some embodiments, a nucleotide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, or more monomeric units (e.g., nucleic acids) as found in the whole nucleotide. In some embodiments, a nucleotide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99%, or more of the monomeric units (e.g., residues) found in the whole nucleotide. The whole material or entity may in some embodiments be referred to as the "parent" of the whole.

Nucleic acid molecules encoding at least one CAR described herein or a fragment thereof can be a DNA molecule, an RNA molecule, or a combination thereof. In some embodiments, a nucleic acid molecule comprises or is a messenger RNA (mRNA) transcript encoding at least one CAR described herein or a fragment thereof. In some embodiments, a nucleic acid molecule comprises or is a DNA construct encoding at least one CAR described herein or a fragment thereof.

In some embodiments, all or a fragment of a CAR described herein is encoded by a codon optimized nucleic acid molecule, e.g., for expression in a cell (e.g., a mammalian cell). A variety of codon optimization methods are known in the art, e.g., as disclosed in U.S. Pat. Nos. 5,786,464 and 6,114,148, each of which is hereby incorporated by reference in its entirety.

In some embodiments, a vector comprises a nucleic acid molecule encoding at least one CAR as described herein or a fragment thereof. In some embodiments, a vector comprises a plasmid, viral vector, phagemid, retrotransposon (e.g. piggyback or sleeping beauty), site directed insertion vector (e.g. CRISPR/Cas systems (e.g., CRISPR/Cas systems comprising one or more of Cas9, Cas12a, or C2c2), Zn finger nucleases, or TALEN for insertion of a template donor DNA comprising a nucleic acid sequence encoding at least one CAR as described herein), suicide expression vector, or any other vector known in the art. Vectors can be suitable for replication and integration in eukaryotes. Vectors can include expression vectors, replication vectors, probe generation vectors, and sequencing vectors.

A vector can comprise an origin of replication, a promoter sequence (e.g., a constitutive or inducible promoter), and/or convenient restriction endonuclease sites (See, e.g., WO 01/96584; WO 01/29058; and U.S. Pat. No. 6,326,193, each of which are hereby incorporated by reference in their entirety). A vector can also include, e.g., a signal sequence to facilitate secretion, a polyadenylation signal and transcription terminator (e.g., a Bovine Growth Hormone (BGH) polyadenylation signal), an element allowing episomal replication and replication in prokaryotes (e.g., SV40 origin and/or ColE1), elements to allow selection (e.g., an ampicillin resistance gene and/or zeocin marker), and/or reporter genes (e.g., luciferase, beta-galactosidase, chloramphenicol acetyl transferase, secreted alkaline phosphatase, or green fluorescent protein).

Expression of nucleic acids as described herein may be achieved by operably linking a nucleic acid encoding a CAR polypeptide or fragment thereof to a promoter in an expression vector. Exemplary promoters (e.g., constitutive promoters) include, but are not limited to, an elongation factor-1α promoter (EF-1a) promoter, immediate early cytomegalovirus (CMV) promoter, ubiquitin C promoter, phosphoglycerokinase (PGK) promoter, simian virus 40 (SV40) early promoter, mouse mammary tumor virus (MMTV) promoter, human immunodeficiency virus (HIV) long terminal repeat (LTR) promoter, Moloney murine leukemia virus (Mo-MuLV) promoter, an avian leukemia virus promoter, an Epstein-Barr virus immediate early promoter, a Rous sarcoma virus promoter, an actin promoter, a myosin promoter, a hemoglobin promoter, or a creatine kinase promoter. Examples of inducible promoters include, but are not limited to a metallothionine promoter, a glucocorticoid promoter, a progesterone promoter, and a tetracycline promoter. A vector can also comprise additional promoter elements, e.g., enhancers, to regulate the frequency of transcriptional initiation.

In some embodiments, a vector comprising a nucleic acid molecule encoding at least one CAR as described herein or a fragment thereof comprises or is a viral vector. Viral vector technology is well known in the art and is described, e.g., in Sambrook et al., 2012, MOLECULAR CLONING: A LABORATORY MANUAL, volumes 1-4, Cold Spring Harbor Press, NY). Examples of viral vectors include, but are not limited to, adenoviral vectors, adeno-associated viral vectors, or retroviral vectors (e.g., a lentiviral vector or a gammaretroviral vector). In some embodiments, a vector comprises a lentiviral vector (e.g., as described in U.S. Pat. No. 9,149,519 or International Publication No. WO 2017/044487, each of which is hereby incorporated by reference in its entirety).

In some embodiments, a viral vector comprises an adenoviral vector. Adenoviruses are a large family of viruses containing double stranded DNA. They replicate within the nucleus of a host cell, using the host's cell machinery to synthesize viral RNA, DNA and proteins. Adenoviruses are known in the art to affect both replicating and non-replicating cells, to accommodate large transgenes, and to code for proteins without integrating into the host cell genome. In some embodiments, an adenoviral vector comprises an Ad2 vector or an Ad5 vector (e.g., Ad5f35 adenoviral vector, e.g., a helper-dependent Ad5F35 adenoviral vector).

In some embodiments, a viral vector is an adeno-associated virus (AAV) vector. AAV systems are generally well known in the art (see, e.g., Kelleher and Vos, Biotechniques, 17(6):1110-17 (1994); Cotten et al., P.N.A.S. U.S.A., 89(13):6094-98 (1992); Curiel, Nat Immun, 13(2-3):141-64 (1994); Muzyczka, Curr Top Microbiol Immunol, 158:97-129 (1992); and Asokan A, et al., Mol. Ther., 20(4):699-708 (2012)). Methods for generating and using recombinant AAV (rAAV) vectors are described, for example, in U.S. Pat. Nos. 5,139,941 and 4,797,368.

Several AAV serotypes have been characterized, including AAV1, AAV2, AAV3 (e.g., AAV3B), AAV4, AAV5, AAV6, AAV7, AAV8, AAV9, AAV10, and AAV11, as well as variants thereof. Generally, any AAV serotype may be used to deliver at least one CAR described herein. In some embodiments, an AAV serotype has a tropism for a particular tissue.

In some embodiments, CRISPR/Cas9 system has recently been shown to facilitate high levels of precise genome editing using adeno associated viral (AAV) vectors to serve as donor template DNA during homologous recombination (HR).

In some embodiments, a vector comprises a gammaretroviral vector (e.g., as described in Tobias Maetzig et al., "Gammaretroviral Vectors: Biology, Technology and Application" Viruses. 2011 June; 3(6): 677-713, which is hereby incorporated by reference in its entirety). Exemplary gammaretroviral vectors include Murine Leukemia Virus (MLV), Spleen-Focus Forming Virus (SFFV), and Myeloproliferative Sarcoma Virus (MPSV), and vectors derived therefrom.

In some embodiments, a vector comprises two or more nucleic acid sequences encoding a CAR, e.g., at least one CAR described herein, and a second CAR, e.g., a different CAR described herein. In some embodiments, two or more nucleic acid sequences encoding a CAR and a second CAR are encoded by a single nucleic molecule, e.g., in same frame and as a single polypeptide chain. In some embodiments, two or more CARs are separated by one or more cleavage peptide sites (e.g., an auto-cleavage site or a substrate for an intracellular protease). In certain embodiments, a cleavage peptide comprises a porcine teschovirus-1 (P2A) peptide, Thosea asigna virus (T2A) peptide, equine rhinitis A virus (E2A) peptide, foot-and-mouth disease virus (F2A) peptide, or a variant thereof.

In some embodiments, a vector comprises at least one nucleic acid sequence encoding a CAR, e.g., at least one CAR described herein, and at least one nucleic acid encoding at least one gene co-expressed with a CAR, e.g., a cytokine described herein (e.g., TNF, IL-12, IFN, GM-CSF, G-CSF, M-CSF, and/or IL-1) or a stimulatory ligand described herein (e.g., CD7, B7-1 (CD80), B7-2 (CD86), PD-L1, PD-L2, 4-1BBL, OX40L, ICOS-L, ICAM, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor, and/or a B7-H3 ligand.

Pharmaceutical Compositions

The present disclosure, among other things, provides pharmaceutical compositions comprising immune cells as described herein (e.g., macrophages, monocytes, or dendritic cells) in combination with one or more pharmaceutically or physiologically acceptable carriers, diluents, or excipients.

When "a therapeutically effective amount, "an immunologically effective amount," "an anti-immune response effective amount," or "an immune response-inhibiting effective amount" is indicated, a precise amount of a pharmaceutical composition comprising immune cells as described herein (e.g., macrophages, monocytes, or dendritic cells) can be determined by a physician with consideration of individual differences in age, weight, immune response, and condition of the patient (subject).

Pharmaceutical compositions comprising immune cells as described herein (e.g., macrophages, monocytes, or dendritic cells) may comprise buffers including neutral buffered saline or phosphate buffered saline (PBS); carbohydrates, such as glucose, mannose, sucrose, dextrans, or mannitol; proteins, polypeptides, or amino acids (e.g., glycine); antioxidants; chelating agents, such as EDTA or glutathione; adjuvants (e.g., aluminum hydroxide); and preservatives. In some embodiments, a pharmaceutical composition is substantially free of contaminants, e.g., there are no detectable levels of a contaminant (e.g., an endotoxin).

Pharmaceutical compositions described herein may be administered in a manner appropriate to the disease, disorder, or condition to be treated or prevented. Quantity and frequency of administration will be determined by such factors as condition of a patient, and type and severity of a patient's disease, disorder, or condition, although appropriate dosages may be determined by clinical trials.

Pharmaceutical compositions described herein may be in a variety of forms. These include, for example, liquid, semi-solid and solid dosage forms, such as liquid solutions (e.g., injectable and infusible solutions), dispersions or suspensions, liposomes, and suppositories. Preferred compositions may be injectable or infusible solutions. Pharmaceutical compositions described herein can be formulated for administration intravenously, subcutaneously, intradermally, intratumorally, intranodally, intramedullary, intramuscularly, transarterially, or intraperitoneally.

In some embodiments, a pharmaceutical composition described herein is formulated for parenteral (e.g., intravenous, subcutaneous, intraperitoneal, or intramuscular) administration. In some embodiments, a pharmaceutical composition described herein is formulated for intravenous infusion or injection. In some embodiments, a pharmaceutical composition described herein is formulated for intramuscular or subcutaneous injection. Pharmaceutical compositions described herein can be formulated for administered by using infusion techniques that are commonly known in immunotherapy (See, e.g., Rosenberg et al., New Eng. J. of Med. 319:1676, 1988, which is hereby incorporated by reference in its entirety).

As used herein, the terms "parenteral administration" and "administered parenterally" refer to modes of administration other than enteral and topical administration, usually by injection or infusion, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intratumoral, and intrasternal injection and infusion.

Pharmaceutical compositions comprising immune cells as described herein may be administered at a dosage of about $10^4$ to about $10^9$ cells/kg body weight (e.g., about $10^5$ to about $10^6$ cells/kg body weight), including all integer values within those ranges). In some embodiments, a dose of immune cells as described herein (e.g., macrophages, monocytes, or dendritic cells) comprises at least about $1\times10^6$, about $1.1\times10^6$, about $2\times10^6$, about $3.6\times10^6$, about $5\times10^6$, about $1\times10^7$, about $1.8\times10^7$, about $2\times10^7$, about $5\times10^7$, about $1\times10^8$, about $2\times10^8$, about $5\times10^8$, about $1\times10^9$, about $2\times10^9$, or about $5\times10^9$ cells. Pharmaceutical compositions described herein may also be administered multiple times at a certain dosage. An optimal dosage and treatment regime for a particular patient can readily be determined by one skilled in the art by monitoring a patient for signs of a disease, disorder, or condition and adjusting treatment accordingly.

It may be desired to administer pharmaceutical compositions comprising immune cells (e.g., macrophages, monocytes, or dendritic cells) as described herein to a subject and then subsequently redraw blood (or have apheresis performed), activate collected immune cells, and reinfuse a subject with activated immune cells. This process can be performed multiple times, e.g., every few weeks. Immune cells (e.g., macrophages, monocytes, or dendritic cells) can be activated from blood draws of from about 10 cc to about 400 cc. In some embodiments, immune cells (e.g., macrophages, monocytes, or dendritic cells) are activated from blood draws of about 20 cc, about 30 cc, about 40 cc, about 50 cc, about 60 cc, about 70 cc, about 80 cc, about 90 cc, or about 100 cc. Without being bound by theory, methods comprising multiple blood draw and reinfusions as described herein may select for certain immune cell populations. In some embodiments, pharmaceutical compositions comprising immune cells as described herein (e.g., macrophages, monocytes, or dendritic cells) are administered in combination with (e.g., before, simultaneously, or following) a second therapy. For example, a second therapy can include, but is not limited to antiviral therapy (e.g., cidofovir, interleukin-2, Cytarabine (ARA-C), or natalizumab), chimeric antigen receptor-T cell (CAR-T) therapy, T-cell receptor (TCR)-T cell therapy, chemotherapy, radiation, an immunosuppressive agent (e.g., cyclosporin, azathioprine, methotrexate, mycophenolate, FK506 antibody, or glucocorticoids), an antagonist (e.g., one or more of a PD-1 antagonist, a PD-L1 antagonist, CTLA4 antagonist, CD47 antagonist, SIRPα antagonist, CD40 agonists, CSF1/CSF1R antagonist, or a STING agonist), or an immunoablative agent (e.g., an anti-CD52 antibody (e.g., alemtuzumab), an anti-CD3 antibody, cytoxin, fludaribine, cyclosporin, FK506, rapamycin, mycophenolic acid, a steroid, FR901228, or irradiation).

In some embodiments, pharmaceutical compositions comprising immune cells as described herein (e.g., macrophages, monocytes, or dendritic cells) are administered in combination with (e.g., before, simultaneously, or following) bone marrow transplantation or lymphocyte ablative therapy using a chemotherapy agent (e.g., fludarabine, external-beam radiation therapy (XRT), cyclophosphamide, or Rituxan). In certain embodiments, subjects undergo standard treatment with high dose chemotherapy followed by peripheral blood stem cell transplantation. In certain embodiments, following transplant, subjects receive an infusion of a pharmaceutical composition comprising immune cells as described herein. Pharmaceutical compositions described herein may be administered before or following surgery.

A dosage of any aforementioned therapy to be administered to a subject will vary with a disease, disorder, or condition being treated and based on a specific subject. Scaling of dosages for human administration can be performed according to art-accepted practices. For example, a dose of alemtuzumab will generally be about 1 mg to about 100 mg for an adult, usually administered daily for a period of between about 1 day to about 30 days, e.g., a daily dose of about 1 mg to about 10 mg per day (e.g., as described in U.S. Pat. No. 6,120,766, which is hereby incorporated by reference in its entirety).

Methods of Treatment

The present disclosure, among other things, provides methods of treating a disease or disorder (e.g., a disease or a disorder described herein) in a subject comprising delivering a pharmaceutical composition comprising immune cells as described herein (e.g., macrophages, monocytes, or dendritic cells). In some embodiments, a therapeutically effective amount of a pharmaceutical composition described herein is administered to a subject having a disease or disorder. Pharmaceutical compositions as described herein can be for use in the manufacture of a medicament for treating a disease or disorder in a subject or stimulating an immune response in a subject.

A subject to be treated with methods described herein can be a mammal, e.g., a primate, e.g., a human (e.g., a patient having, or at risk of having, a disease or disorder described herein). In some embodiments, immune cells (e.g., macrophages, monocytes, or dendritic cells) may be autologous, allogeneic, or xenogeneic with respect to a subject. Pharmaceutical compositions as described herein can be administered to a subject in accordance with a dosage regimen described herein, alone or in combination with one or more therapeutic agents, procedures, or modalities.

Pharmaceutical composition comprising immune cells as described herein (e.g., macrophages, monocytes, or dendritic cells) can be used to treat or prevent a disease associated with a tumor or cancer, a neurodegenerative disease or disorder, an inflammatory disease or disorder, a cardiovascular disease or disorder, a fibrotic disease or disorder, a disease associated with amyloidosis, and a combination of thereof.

A method of treating (e.g., one or more of reducing, inhibiting, or delaying progression of) a cancer or a tumor in a subject with a pharmaceutical composition comprising immune cells as described herein (e.g., macrophages, monocytes, or dendritic cells) is provided. A subject can have an adult or pediatric form of cancer. A cancer may be at an early, intermediate, or late stage, or a metastatic cancer. A cancer can include, but is not limited to, a solid tumor, a hematological cancer (e.g., leukemia, lymphoma, or myeloma, e.g., multiple myeloma), or a metastatic lesion. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma, e.g., a cutaneous melanoma), pancreas, and bones (e.g., a chordoma).

In some embodiments, a cancer is chosen from a lung cancer (e.g., a non-small cell lung cancer (NSCLC) (e.g., a non-small cell lung cancer (NSCLC) with squamous and/or non-squamous histology, or a NSCLC adenocarcinoma), or a small cell lung cancer (SCLC)), a skin cancer (e.g., a Merkel cell carcinoma or a melanoma (e.g., an advanced melanoma)), an ovarian cancer, a mesothelioma, a bladder cancer, a soft tissue sarcoma (e.g., a hemangiopericytoma (HPC)), a bone cancer (a bone sarcoma), a kidney cancer (e.g., a renal cancer (e.g., a renal cell carcinoma)), a liver cancer (e.g., a hepatocellular carcinoma), a cholangiocarcinoma, a sarcoma, a myelodysplastic syndrome (MDS), a prostate cancer, a breast cancer (e.g., a breast cancer that does not express one, two or all of estrogen receptor, progesterone receptor, or Her2/neu, e.g., a triple negative breast cancer), a colorectal cancer (e.g., a relapsed colorectal cancer or a metastatic colorectal cancer, e.g., a microsatellite unstable colorectal cancer, a microsatellite stable colorectal cancer, a mismatch repair proficient colorectal cancer, or a mismatch repair deficient colorectal cancer), a nasopharyngeal cancer, a duodenal cancer, an endometrial cancer, a pancreatic cancer, a head and neck cancer (e.g., head and neck squamous cell carcinoma (HNSCC)), an anal cancer, a gastro-esophageal cancer, a thyroid cancer (e.g., anaplastic thyroid carcinoma), a cervical cancer (e.g., a squamous cell carcinoma of the cervix), a neuroendocrine tumor (NET) (e.g., an atypical pulmonary carcinoid tumor), a lymphoproliferative disease (e.g., a post-transplant lymphoproliferative disease), a lymphoma (e.g., T-cell lymphoma, B-cell lymphoma, or a non-Hogdkin lymphoma), a myeloma (e.g., a multiple myeloma), or a leukemia (e.g., a myeloid leukemia or a lymphoid leukemia).

In some embodiments, a cancer is a brain tumor, e.g., a glioblastoma, a gliosarcoma, or a recurrent brain tumor. In some embodiments, a cancer is a pancreatic cancer, e.g., an advanced pancreatic cancer. In some embodiments, a cancer is a skin cancer, e.g., a melanoma (e.g., a stage II-IV melanoma, an HLA-A2 positive melanoma, an unresectable melanoma, or a metastatic melanoma), or a Merkel cell carcinoma. In some embodiments, a cancer is a renal cancer, e.g., a renal cell carcinoma (RCC) (e.g., a metastatic renal cell carcinoma). In some embodiments, a cancer is a breast cancer, e.g., a metastatic breast carcinoma or a stage IV breast carcinoma, e.g., a triple negative breast cancer (TNBC). In some embodiments, a cancer is a virus-associated cancer. In some embodiments, a cancer is an anal canal cancer (e.g., a squamous cell carcinoma of the anal canal). In some embodiments, a cancer is a cervical cancer (e.g., a squamous cell carcinoma of the cervix). In some embodiments, a cancer is a gastric cancer (e.g., an Epstein Barr Virus (EBV) positive gastric cancer, or a gastric or gastro-esophageal junction carcinoma). In some embodiments, a cancer is a head and neck cancer (e.g., an HPV positive and negative squamous cell cancer of the head and neck (SCCHN)). In some embodiments, a cancer is a nasopharyngeal cancer (NPC). In some embodiments, a cancer is a colorectal cancer, e.g., a relapsed colorectal cancer, a metastatic colorectal cancer, e.g., a microsatellite unstable colorectal cancer, a microsatellite stable colorectal cancer, a mismatch repair proficient colorectal cancer, or a mismatch repair deficient colorectal cancer.

In some embodiments, a cancer is a hematological cancer. In some embodiments, a cancer is a leukemia, e.g., acute myeloid leukemia, chronic myeloid leukemia, acute lymphoblastic leukemia, chronic lymphocytic leukemia, chronic leukemia, or acute leukemia. In some embodiments, a cancer is a lymphoma, e.g., Hodgkin lymphoma (HL), non-Hodgkin's lymphoma, lymphocytic lymphoma, or diffuse large B cell lymphoma (DLBCL) (e.g., a relapsed or refractory HL or DLBCL). In some embodiments, a cancer is a myeloma, e.g., multiple myeloma.

Pharmaceutical composition comprising immune cells as described herein (e.g., macrophages, monocytes, or dendritic cells) can be used to enhance or modulate an immune response in a subject. In one embodiment, a pharmaceutical composition described herein enhances, stimulates, or increases an immune response in a subject (e.g., a subject having, or at risk of, a disease or disorder described herein). In certain embodiments, a subject is, or is at risk of being, immunocompromised. For example, a subject is undergoing or has undergone a chemotherapeutic treatment and/or radiation therapy.

In some embodiments, a subject has, or is at risk of, developing an inflammatory disorder (e.g., a chronic or acute inflammatory disorder). In some embodiments, a subject has, or is at risk, of developing an autoimmune disease or disorder. Exemplary autoimmune diseases that can be treated with methods described herein include, but are not limited to, Alzheimer's disease, asthma (e.g., bronchial asthma), an allergy (e.g., an atopic allergy), Acquired Immunodeficiency Syndrome (AIDS), atherosclerosis, Behcet's disease, celiac, cardiomyopathy, Crohn's disease, cirrhosis, diabetes, diabetic retinopathy, eczema, fibromyalgia, fibromyositis, glomerulonephritis, graft vs. host disease (GVHD), Guillain-Barre syndrome, hemolytic anemia, multiple sclerosis, myasthenia gravis, osteoarthritis, polychondritis, psoriasis, rheumatoid arthritis, sepsis, stroke, vasculitis, ventilator-induced lung injury, transplant rejection, Raynaud's phenomena, Reiter's syndrome, rheumatic fever, sarcoidosis, scleroderma, Sjogren's syndrome, ulcerative colitis, uveitis, vitiligo, or Wegener's granulomatosis.

Administration of pharmaceutical compositions described herein may be carried out in any convenient manner (e.g., injection, ingestion, transfusion, inhalation, implantation, or transplantation). In some embodiments, a pharmaceutical compositions described herein is administered by injection or infusion. Pharmaceutical compositions described herein may be administered to a patient transarterially, subcutaneously, intravenously, intradermally, intratumorally, intranodally, intramedullary, intramuscularly, or intraperitoneally. In some embodiments, a pharmaceutical composition described herein is administered parenterally (e.g., intravenously, subcutaneously, intraperitoneally, or intramuscularly). In some embodiments, a pharmaceutical composition described herein is administered by intravenous infusion or injection. In some embodiments, a pharmaceutical composition described herein is administered by intramuscular or subcutaneous injection. Pharmaceutical compositions described herein may be injected directly into a site of inflammation, a local disease site, a lymph node, an organ, a tumor, or site of infection in a subject.

Methods of Immune Cell Modification

Methods can comprise delivering to an immune cell (e.g., a monocyte, macrophage, or dendritic cell), a nucleic acid construct comprising one or more nucleic acid sequences encoding: (a) an extracellular domain (e.g., an extracellular domain as described herein), (b) a transmembrane domain (e.g., a transmembrane domain as described herein), and (c) an intracellular domain (e.g., an intracellular domain as described herein), such that an immune cell comprises a CAR comprising (a)-(c). In some embodiments, a nucleic acid construct comprising one or more nucleic acid sequences further encodes one, two, or three of: (d) an extracellular leader domain (e.g., an extracellular leader domain as described herein), (e) an extracellular hinge domain (e.g., an extracellular hinge domain as described herein), or (f) an intracellular co-stimulatory domain (e.g., an intracellular co-stimulatory domain as described herein).

A nucleic acid construct comprising one or more nucleic acid sequences encoding at least one CAR as described herein can be introduced into an immune cell (e.g., a monocyte, macrophage, or dendritic cell) by physical, chemical, or biological methods. Physical methods for introducing a nucleic acid construct as described herein into an immune cell (e.g., a monocyte, macrophage, or dendritic cell) can comprise electroporation, calcium phosphate precipitation, lipofection, particle bombardment, microinjection, or a combination thereof. A nucleic acid construct can be introduced into immune cells using commercially available methods, including electroporation (Amaxa Nucleofector-II® (Amaxa Biosystems, Cologne, Germany), ECM 830 BTX (Harvard Instruments, Boston, Mass.) Gene Pulser II® (BioRad, Denver, Colo.), or Multiporator® (Eppendort, Hamburg Germany)). A nucleic acid construct can also be introduced into immune cells using mRNA transfection, e.g., cationic liposome-mediated transfection, lipofection, polymer encapsulation, peptide-mediated transfection, or biolistic particle delivery systems, such as "gene guns" (See, e.g., Nishikawa, et al. Hum Gene Ther., 12(8):861-70 (2001), which is hereby incorporated by reference in its entirety).

Biological methods for introducing a nucleic acid construct as described herein into an immune cell (e.g., a monocyte, macrophage, or dendritic cell) include use of DNA and RNA vectors. Viral vectors, and especially retroviral vectors, have become widely used for inserting genes into mammalian cells (e.g., human cells). Viral vectors can also be derived from lentivirus, poxviruses, herpes simplex virus I, adenoviruses (e.g. Adf535), or adeno-associated viruses (See, e.g., U.S. Pat. Nos. 5,350,674 and 5,585,362, which are hereby incorporated by reference in their entirety). Retroviral vectors, such as lentivirus, are suitable tools to achieve long-term gene transfer that allow for long-term, stable integration of a transgene and its propagation in daughter cells.

Chemical means for introducing a nucleic acid construct as described herein into an immune cell (e.g., a monocyte, macrophage, or dendritic cell) include colloidal dispersion systems, macromolecule complexes, nanocapsules, microspheres, beads, and lipid-based systems (e.g., oil-in-water emulsions, micelles, mixed micelles, nanoparticles, liposomes, and lipofectamine-nucleic acid complexes).

An exemplary system for delivery of a nucleic acid construct as described herein is a lipid-based system. A nucleic acid construct as described herein may be encapsulated in an aqueous interior of a liposome, interspersed within a lipid bilayer, attached to a liposome via a linking molecule, entrapped in a liposome, complexed with a liposome, dispersed in a solution or suspension comprising a lipid, mixed with a lipid, complexed with a micelle, or otherwise associated with a lipid. Lipids for use in methods described herein may be naturally occurring or synthetic lipids. Lipids can also be obtained from commercial sources. For example, dimyristyl phosphatidylcholine can be obtained from Sigma (St. Louis, Mo.); dicetyl phosphate can be obtained from K & K Laboratories (Plainview, N.Y.); cholesterol can be obtained from Calbiochem-Behring; and dimyristyl phosphatidylglycerol can be obtained from Avanti Polar Lipids, Inc. (Birmingham, Ala.). Stock solutions of lipids in chloroform or chloroform/methanol can be stored at about −20° C.

A variety of assays may be performed to confirm presence of a nucleic acid construct as described herein in an immune cell (e.g., a monocyte, macrophage, or dendritic cell). For example, such assays include molecular biological assays well known to those of skill in the art, such as Southern and Northern blotting, RT-PCR, and PCR; and biochemical assays, such as detecting the presence or absence of a particular peptide, e.g., by immunological means (ELISAs and Western blots).

VPX Mediated Viral Delivery of Nucleic Acids encoding CARs

Immune cells described herein (e.g., macrophages, monocytes, or dendritic cells) can be refractory to lentiviral transduction because of expression of a restriction factor, SAMHD1, which depletes nucleotide triphosphates available for reverse transcription. For example, SAMHD1 can restrict replication of human immunodeficiency virus type 1 (HIV-1) by depleting an intracellular pool of deoxynucleoside triphosphates. Viral protein X (Vpx), an accessory protein associated with simian immunodeficiency virus (SIV) and HIV-2, induces degradation of SAMHD1. Use of Vpx can allow for viral vectors, such as lentivirus, comprising one or more nucleic acid sequences encoding at least one CAR to immune cells described herein (e.g., macrophages, monocytes, or dendritic cells). In some embodiments, a viral vector comprising one or more nucleic acid sequences encoding at least one CAR and packaged with at least one Vpx protein can increase transfection of immune cells describes herein (e.g., macrophages, monocytes, or dendritic cells), e.g., relative to the same type of immune cell transfected with a viral vector comprising one or more nucleic acid sequences encoding at least one CAR and not packaged with at least one Vpx protein. In some embodiments, the Vpx lentivirus can lead to genomic integration of the CAR sequence, enabling long-term, permanent expression of the chimeric antigen receptor (CAR). Given that CARs are transmembrane proteins that regularly recycle into the intracellular space, the demonstration of permanent cell surface expression of the CAR with Vpx-lentivirus is a notable development in the field. Vpx-lentivirus transduced macrophages are not phenotypically impacted by viral transduction—a finding that enables the production of CAR macrophages with phenotypic plasticity. While other viral vectors (such as Ad5f35) induce an M1, pro-inflammatory phenotype, Vpx-lentivirus does not have an impact on the M1/M2 phenotype—enabling an M0 CAR macrophage product that may not have pro-inflammatory functions/toxicities at baseline. The Vpx-lentivirus transduced CAR macrophages retain phenotypic plasticity and may be further polarized to an M1 or M2 phenotype with cytokines, agonists, peptides, culture media, and other factors. Vpx-lentivirus transduced CAR macrophages can be exposed to pro-inflammatory signals (e.g., one or more pro-inflammatory cytokines, e.g., one or more of LPS, IFNa, IFNb, IFNγ, CpG, CD40L, GM-CSF, TNFα, IL-6, or a STING ligand (STING-L)) and polarize into M1 macrophages. Vpx-lentivirus transduced CAR macrophages can be exposed to immunosuppressive signals (e.g., one or more immunosuppressive cytokines (e.g., one or more of IL-4, IL-10, IL-13, or TGFb) and/or one or both of at least one prostaglandin or at least corticosteroid) and polarize into M2 macrophages.

In some embodiments, a lentiviral vector is packaged with a Vpx protein (e.g., as described in International Publication No. WO 2017/044487, which is hereby incorporated by reference in its entirety). In some embodiments, Vpx comprises a virion-associated protein (e.g., an accessory protein for viral replication). In some embodiments, a Vpx protein is encoded by human immunodeficiency virus type 2 (HIV-2). In some embodiments, a Vpx protein is encoded by simian immunodeficiency virus (SIV). In some embodiments, an immune cell as described herein (e.g., a monocyte, macrophage, or dendritic cell) is transfected with a lentiviral vector packaged with a Vpx protein. In some embodiments, Vpx inhibits at least one antiviral factor of an immune cell as described herein (e.g., a monocyte, macrophage, or dendritic cell).

In some embodiments, a lentiviral vector packaged with a Vpx protein exhibits increased transfection efficiency of an immune cell as described herein (e.g., a monocyte, macrophage, or dendritic cell), e.g., relative to a lentiviral vector not packaged with a Vpx protein. In some embodiments, an immune cell as described herein (e.g., a monocyte, macrophage, or dendritic cell) is one or both of electroporated or transfected with at least one VPX mRNA prior to transfection with a viral vector (e.g., an adenoviral vector, e.g., an Ad2 vector or an Ad5 vector (e.g., Ad5f35 adenoviral vector, e.g., a helper-dependent Ad5F35 adenoviral vector)).

Treatment and Culturing of Immune Cells During Modification

In some embodiments, methods of the present disclosure comprise one or more steps of treating an immune cell (e.g., a monocyte, macrophage, or dendritic cell) during the process of modifying the immune cell.

In some embodiments, methods of the present disclosure comprise a step of treating an immune cell (e.g., a monocyte, macrophage, or dendritic cell) with a modulator of a pathway activated by in vitro transcribed mRNA. In vitro transcribed (IVT) mRNA is recognized by various endosomal innate immune receptors (Toll-like receptor 3 (TLR3), TLR7 and TLR8) and cytoplasmic innate immune receptors (protein kinase RNA-activated (PKR), retinoic acid-inducible gene I protein (RIG-I), melanoma differentiation-associated protein 5 (MDA5) and 2'-5'-oligoadenylate synthase (OAS)). Signaling through these different pathways results in inflammation associated with type 1 interferon (IFN), tumor necrosis factor (TNF), interleukin-6 (IL-6), IL-12 and the activation of cascades of transcriptional programs. Overall, these create a pro-inflammatory microenvironment poised for inducing specific immune responses. Moreover, downstream effects such as slow-down of translation by eukaryotic translation initiation factor 2a (eIF2α) phosphorylation, enhanced RNA degradation by ribonuclease L (RNaseL), and overexpression and inhibition of replication of self-amplifying mRNA are of relevance for the pharmacokinetics and pharmacodynamics of IVT mRNA.

In some embodiments, a modulator of a pathway activated by in vitro transcribed mRNA comprises an RNase inhibitor. In some embodiments, a modulator of a pathway activated by in vitro transcribed mRNA comprises an RNaseL, RNase T2 or RNase1 inhibitor. In some embodiments, a modulator of a pathway activated by in vitro transcribed mRNA comprises an RNaseL inhibitor. In some embodiments, an RNaseL inhibitor comprises sunitinib. In some embodiments, an RNaseL inhibitor comprises ABCE1.

In some embodiments, treating an immune cell (e.g., a monocyte, macrophage, or dendritic cell) with an RNaseL inhibitor increases mRNA stability in a modified immune cell relative to mRNA stability in a modified immune cell of the same type that was not treated with an RNaseL inhibitor. In some embodiments, treating an immune cell (e.g., a monocyte, macrophage, or dendritic cell) with an RNaseL inhibitor increases CAR expression in a modified immune cell relative to CAR expression in a modified immune cell of the same type that was not treated with an RNaseL inhibitor. In some embodiments, treating an immune cell (e.g., a monocyte, macrophage, or dendritic cell) with an RNaseL inhibitor increases effector activity in a modified immune cell relative to effector activity in a modified immune cell of the same type that was not treated with an RNaseL inhibitor.

In some embodiments of the present disclosure, a step of treating an immune cell (e.g., a monocyte, macrophage, or dendritic cell) occurs before a step of delivering an mRNA to the immune cell.

In some embodiments, methods of the present disclosure comprise a step of culturing an immune cell (e.g., a monocyte, macrophage, or dendritic cell) with a cytokine or immune stimulating recombinant protein. In some embodiments, a cytokine comprises IFN-α, IFN-β, IFN-γ, TNFα, IL-6, STNGL, LPS, a CD40 agonist, a 4-1BB ligand, recombinant 4-1BB, a CD19 agonist, a TLR agonist (e.g., TLR-1, TLR-2, TLR-3, TLR-4, TLR-5, TLR-6, TLR-7, TLR-8 or TLR-9), TGF-β (e.g., TGF-β1, TGF-β2, or TGF-β3), a glucocorticoid, an immune complex, interleukin-1 alpha (IL-1α), IL-1β, IL-2, IL-3, IL-4, IL-5, IL-6, IL-7, IL-9, IL-10, IL-12, IL-13, IL-14, IL-15, IL-16, IL-17, IL-18, IL-20, granulocyte-macrophage colony-stimulating factor (GM-CSF), granulocyte colony-stimulating factor (G-CSF), Leukemia inhibitory factor (LIF), oncostatin M (OSM), TNF-β, CD154, lymphotoxin beta (LT-β), an A proliferation-inducing ligand (APRIL), CD70, CD153, glucocorticoid-induced TNF receptor ligand (GITRL), tumor necrosis factor superfamily member 14 (TNFSF14), OX40L (CD252), TALL-1 (Tumor necrosis factor ligand superfamily member 13B-TNFSF13B), TNF-related apoptosis-inducing ligand (TRAIL), TNF-related weak inducer of apoptosis (TWEAK), TNF-related activation-induced cytokine (TRANCE), erythropoietin (Epo), thyroid peroxidase precursor (Tpo), FMS-related tyrosine kinase 3 ligand (FLT-3L), stem cell factor (SCF), macrophage colony-stimulating factor (M-CSF), merozoite surface protein (MSP), a Nucleotide-binding oligomerization domain-containing protein (NOD) ligand (e.g., NOD1, NOD2, or NOD1/2 agonists), a RIG-I-like receptor (RLR) ligand (e.g., 5'ppp-dsRNA, 3p-hpRNA, Poly(I:C), or Poly(dA:dT)), a C-type lectin receptor (CLR) ligand (e.g., curdlan, β-glucan, HKCA, laminarin, pustulan, scleroglucan, WGP dispersible, WGP soluble, zymosan, zymosan depleted, furfurman, b-GlcCer, GlcC14C18, HKMT, TDB, TDB-HS15, or TDM), a cyclic dinucleotide sensor ligand (e.g., C-Gas agonist or stimulator of interferon gene (STING) ligand), an inflammasome inducer (e.g., alum, ATP, CPPD crystals, hemozoin, MSU crystals, Nano-SiO2, Nigericin, or TDB), an aryl hydrocarbon (AhR) ligand (e.g., FICZ, indirubin, ITE, or L-kynurenine), an alpha-protein kinase 1 (ALPK1) ligand, a multi-PRR ligand, an NFKB/NFAT activator (e.g., concavalin A, ionomycin, PHA-P, or PMA) or a combination thereof. In some embodiments, a cytokine comprises IFN-β.

In some embodiments of the present disclosure, a step of culturing an immune cell (e.g., a monocyte, macrophage, or dendritic cell) occurs after a step of delivering an mRNA to the immune cell.

In some embodiments, culturing a modified immune cell (e.g., a monocyte, macrophage, or dendritic cell) with a cytokine or immune stimulating recombinant protein increases the viability of the modified immune cell relative to a modified immune cell of the same type that was not cultured with the cytokine or immune stimulating recombinant protein. In some embodiments, culturing a modified immune cell (e.g., a monocyte, macrophage, or dendritic cell) with a cytokine or immune stimulating recombinant protein increases protein (e.g., CAR) expression of the modified immune cell relative to a modified immune cell of the same type that was not cultured with the cytokine or immune stimulating recombinant protein. In some embodiments, culturing a modified immune cell (e.g., a monocyte, macrophage, or dendritic cell) with a cytokine or immune stimulating recombinant protein increases longevity of protein (e.g., CAR) expression relative to a modified immune cell of the same type that was not cultured with the cytokine or immune stimulating recombinant protein. In some embodiments, culturing a modified immune cell (e.g., a monocyte, macrophage, or dendritic cell) with a cytokine or immune stimulating recombinant protein increases effector activity of the modified immune cell relative to a modified immune cell of the same type that was not cultured with the cytokine or immune stimulating recombinant protein. In some embodiments, culturing a modified immune cell (e.g., a monocyte, macrophage, or dendritic cell) with a cytokine or immune stimulating recombinant protein increases M1 polarization of the modified immune cell relative to a modified immune cell of the same type that was not cultured with the cytokine or immune stimulating recombinant protein.

All publications, patent applications, patents, and other references mentioned herein, including GenBank Accession Numbers, are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following example. An example is provided for illustrative purposes only. It is not to be construed as limiting the scope or content of the disclosure in any way.

EXAMPLES

The following examples are provided so as to describe to the skilled artisan how to make and use methods and compositions described herein, and are not intended to limit the scope of the present disclosure.

Example 1: Chimeric Antigen Receptor (CAR) Macrophages and Monocytes

A CAR transgene can be introduced into monocytes or macrophages via electroporation or transfection with DNA, mRNA, or chemically modified mRNA or through viral transduction with a lentiviral, adenoviral or alternative viral vector. Expression of the CAR will be confirmed using antigen specific staining via flow cytometry, real time PCR, or fluorescent microscopy. These techniques will also be used to determine the intensity and kinetics of expression of the CAR.

CAR constructs, which express on the surface of the macrophage, will be tested for activity in a tumor phagocytosis assay and/or tumor killing assay against a target positive cell line. Constructs, which cause phagocytosis and/or killing of the target cells, will be tested for cytokine secretion, chemokine secretion, immune cell recruitment ability, phenotypic alteration (i.e. self-polarization to M1/M2), and T cell stimulation/antigen presentation functionality.

Figure 8:
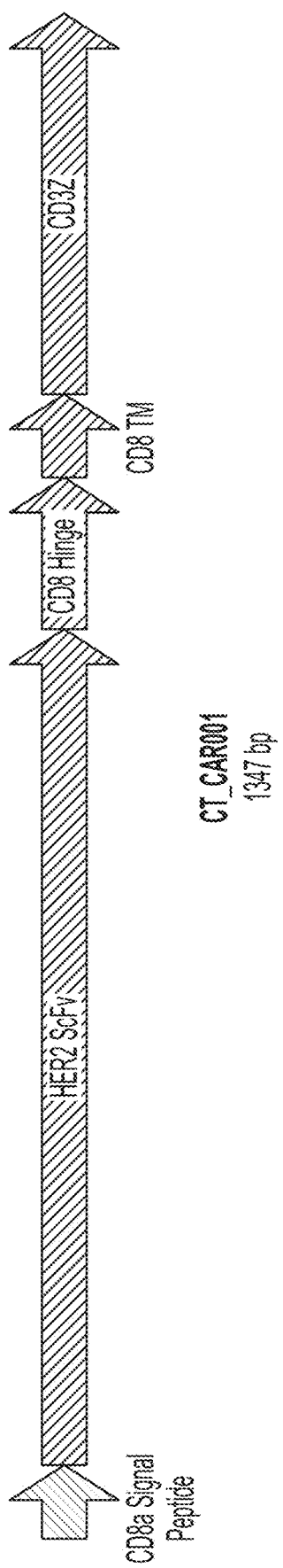
FIGS. 8-117 are schematics of exemplary chimeric antigen receptor (CAR) constructs, including those shown in the above figures.
Figure 9:
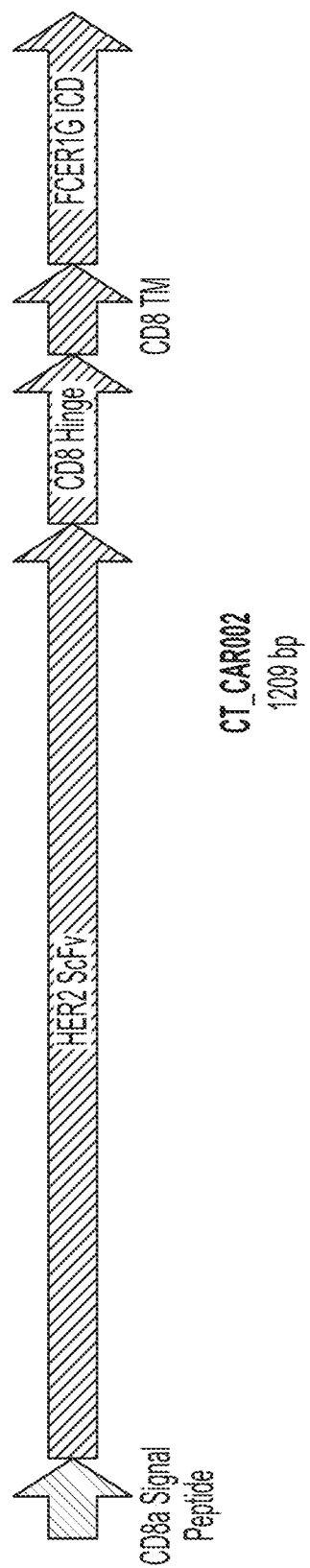
Figure 117:
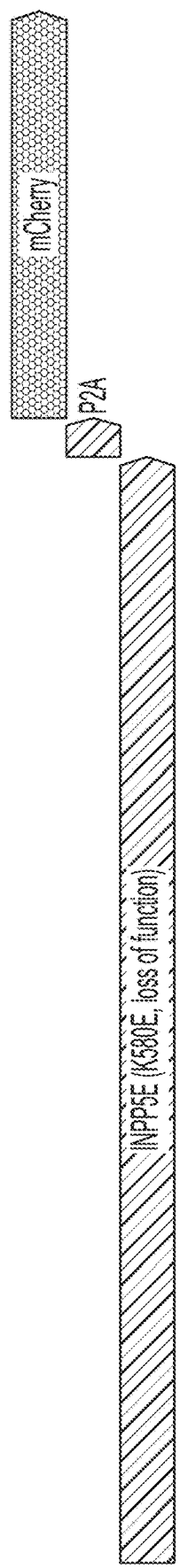
Figure 135:
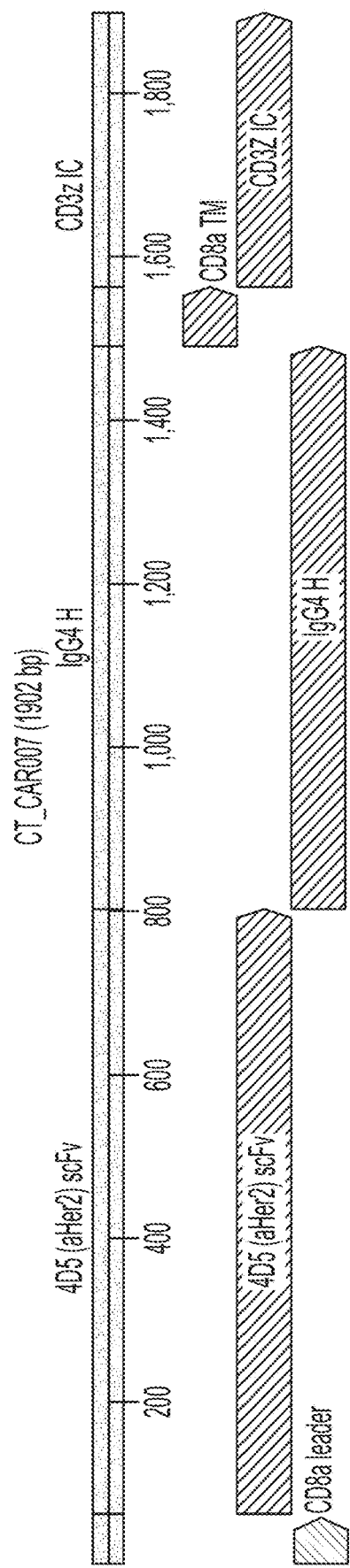
FIG. 135 is a schematic of an exemplary CAR construct.

Table 1 shows exemplary mRNA and polypeptide sequences used for CAR components described herein. Exemplary CAR constructs of CAR components are shown in FIGS. 8-117 and 135.

TABLE 1 mRNA and polypeptide sequences (GenBank accession numbers and UniProt KB codes, respectively) for CAR components described herein.

| Gene name | GenBank number (transcript variant 1) | UniProt KB code |
|---|---|---|
| CD8a | NM_001768.7 | P01732 |
| CD3z | NM_198053.3 | P20963 |
| FCER1G | NM_004106.2 | P30273 |
| IgG4 | AJ294733.1 | P01861 |
| CD64 | NM_001378804.1 | P12314 |
| CD32a | NM_001136219.3 | P12318 |

TABLE 1-continued mRNA and polypeptide sequences (GenBank accession numbers and UniProt KB codes, respectively) for CAR components described herein.

| Gene name | GenBank number (transcript variant 1) | UniProt KB code |
|---|---|---|
| CD32c | NM_201563.5 | P31995 |
| CD16 | NM_000569.8 | P08637 |
| TLR1 | NM_003263.4 | Q15399 |
| TLR2 | NM_001318787.2 | O60603 |
| TLR6 | NM_006068.4 | Q9Y2C9 |
| TLR4 | NM_138554.5 | O00206 |
| TLR5 | NM_003268.6 | O60602 |
| SIRPa | NM_001040022.1 | P78324 |
| Siglec 10 | NM_033130.5 | Q96LC7 |
| Siglec 9 | NM_001198558.1 | Q9Y336 |
| Siglec 11 | NM_052884.3 | Q96RL6 |
| 4-1BBL | NM_003811.4 | P41273 |
| CD27 | NM_001242.5 | P26842 |
| CD28 | NM_006139.4 | P10747 |
| CD36 | NM_001001548.2 | P16671 |
| CD80 | NM_005191.4 | P33681 |
| CD86 | NM_175862.5 | P42081 |
| CD209 | NM_021155.4 | Q9NNX6 |
| DAP10 | NM_014266.4 | Q9UBK5 |
| DAP12 | NM_003332.4 | O43914 |
| GITR | NM_004195.3 | Q9Y5U5 |
| ICOS | NM_012092.4 | Q9Y6W8 |
| ICOSL | NM_015259.6 | O75144 |
| OX40 | NM_003327.4 | P43489 |
| OX40L | NM_003326.5 | P23510 |
| PDL1 | NM_014143.4 | Q9NZQ7 |
| PD1 | NM_005018.3 | Q15116 |
| TLR2 | NM_001318787.2 | O60603 |
| TLR4 | NM_138554.5 | O00206 |
| TLR8 | NM_138636.5 | Q9NR97 |
| CD40 | NM_001250.6 | P25942 |
| Myd88 | NM_001172567.2 | Q99836 |
| IFNaR1 | NM_000629.3 | P17181 |
| GMCSFR | NM_006140.6 | P15509 |
| TREM1 | NM_018643.5 | Q9NP99 |
| TREM2 | NM_018965.4 | Q9NZC2 |
| SHP1 | NM_002831.6 | P29350 |
| SHP2 | NM_002834.5 | Q06124 |
| SHIP1 | NM_001017915.3 | Q92835 |
| Lyn | NM_002350.4 | P07948 |
| INPP5E | NM_019892.6 | Q9NRR6 |

Example 2: Viral Transduction of Primary Human Macrophages and Monocytes

For lentivirus production, HEK293T cells were plated at 3.5×106 cells/10 cm plate in 10 mL of DMEM media supplemented with 10% FBS and 1% pen/strep. After overnight growth, plates were transfected with pVSV-G (2.5 µg), RSV-Rev (2.5m), PMDL-Chp6 (10 µg), pVPX (1 µg), and the lentiviral transfer plasmid containing the desired insert sequence (14 µg) using calcium phosphate transfection. Supernatant was discarded 16 hours post-transfection, followed by addition of 6 mL DMEM. Supernatant was harvested 48 hours post-transfection, followed by centrifugation at 1,200×g for 5 minutes, and filtration through a 0.45 mm filter. Virus was stored at −80° C. for later use.

For lentiviral transduction of primary human macrophages, primary human macrophages were plated at a given density and incubated for 2 hours at 37° C. Lentivirus was then added to the macrophage culture at a specified multiplicity of infection (MOI). After 48-72 hours, media was exchanged and transduced macrophages were used for various assays.

Example 3: Receptor Expression from Monocytes and Macrophages

Figure 1B:
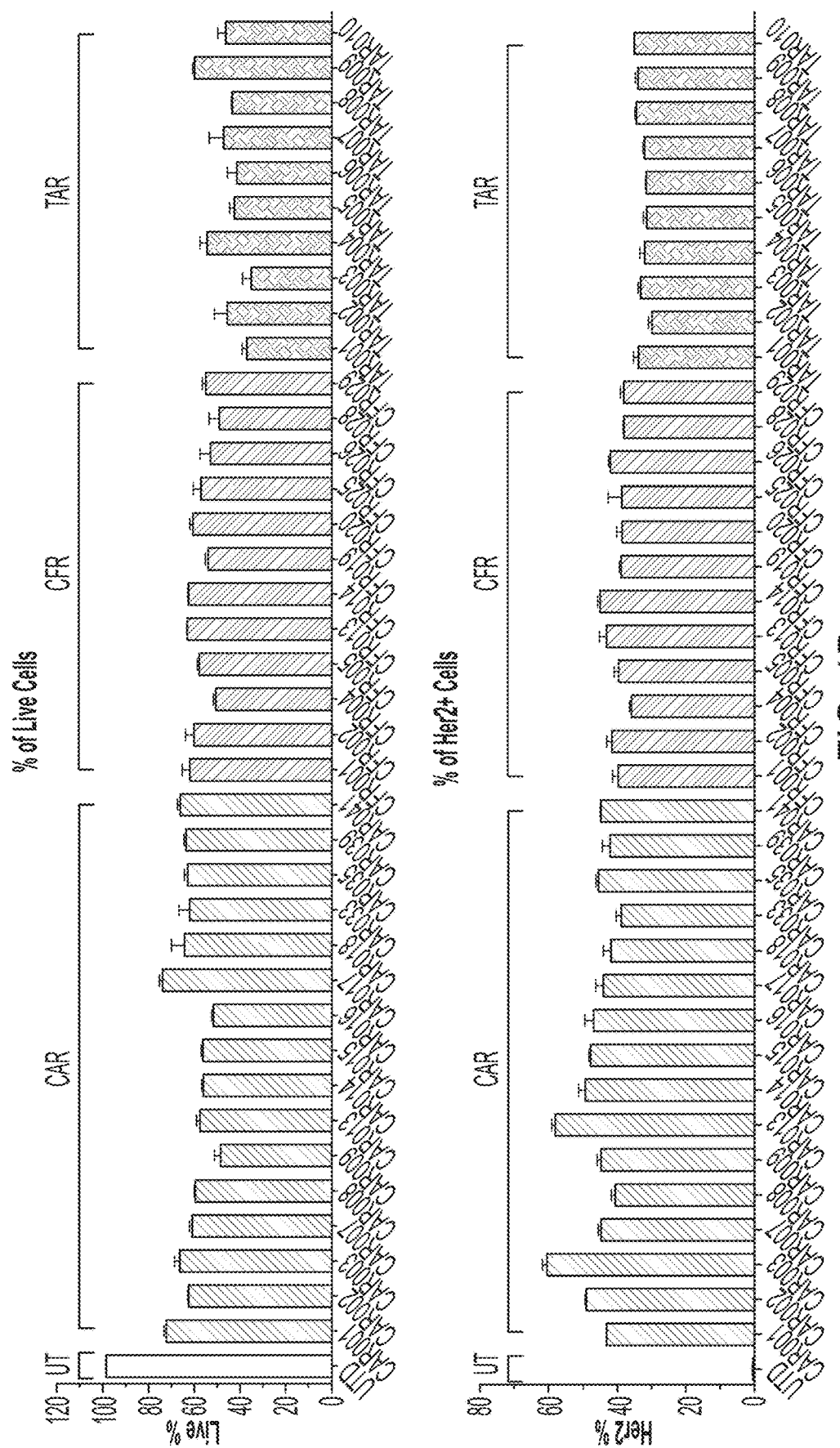

CD14+ Monocytes derived macrophages were plated with culture medium (10-20% FBS-TEX-MACS with 10 ng/ml of GM-CSF) and cultured overnight. 120 nM of CAR mRNA were transfected and incubated at 37° C. in a culture medium for one day, and CAR expression was detected with rHER2 binding by flow cytometry. About 60-70% of CAR and Chimeric FcR (CFR) transfected cells, and 40-60% of Toll-Like Antigen Receptor (TAR) transfected cells were viable (FIG. 1A). CAR:HER2 expression was 40-60% positive in CAR transfected cells and 30-40% positive in CFR and TAR transfected cells (FIG. 1B). CAR1 and CAR13 expression stood out amongst other constructs in primary human macrophages.

Figure 2A:
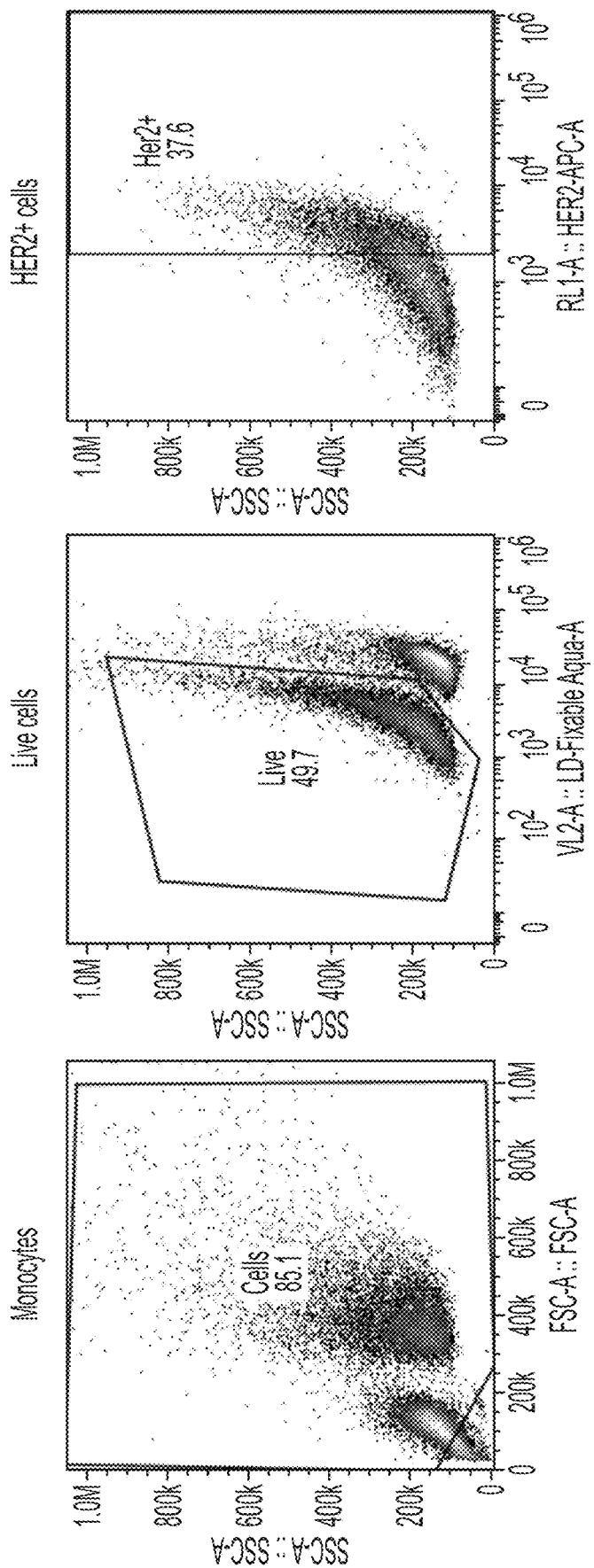
FIGS. 2A-2B are graphs showing HER2 expression from monocytes transfected with constructs described herein (see FIGS. 8-44). Live cell percentage and CAR:HER2 expression are shown in the dot plots for selected samples (FIG. 2A) and for all samples (FIG. 2B).
Figure 2B:
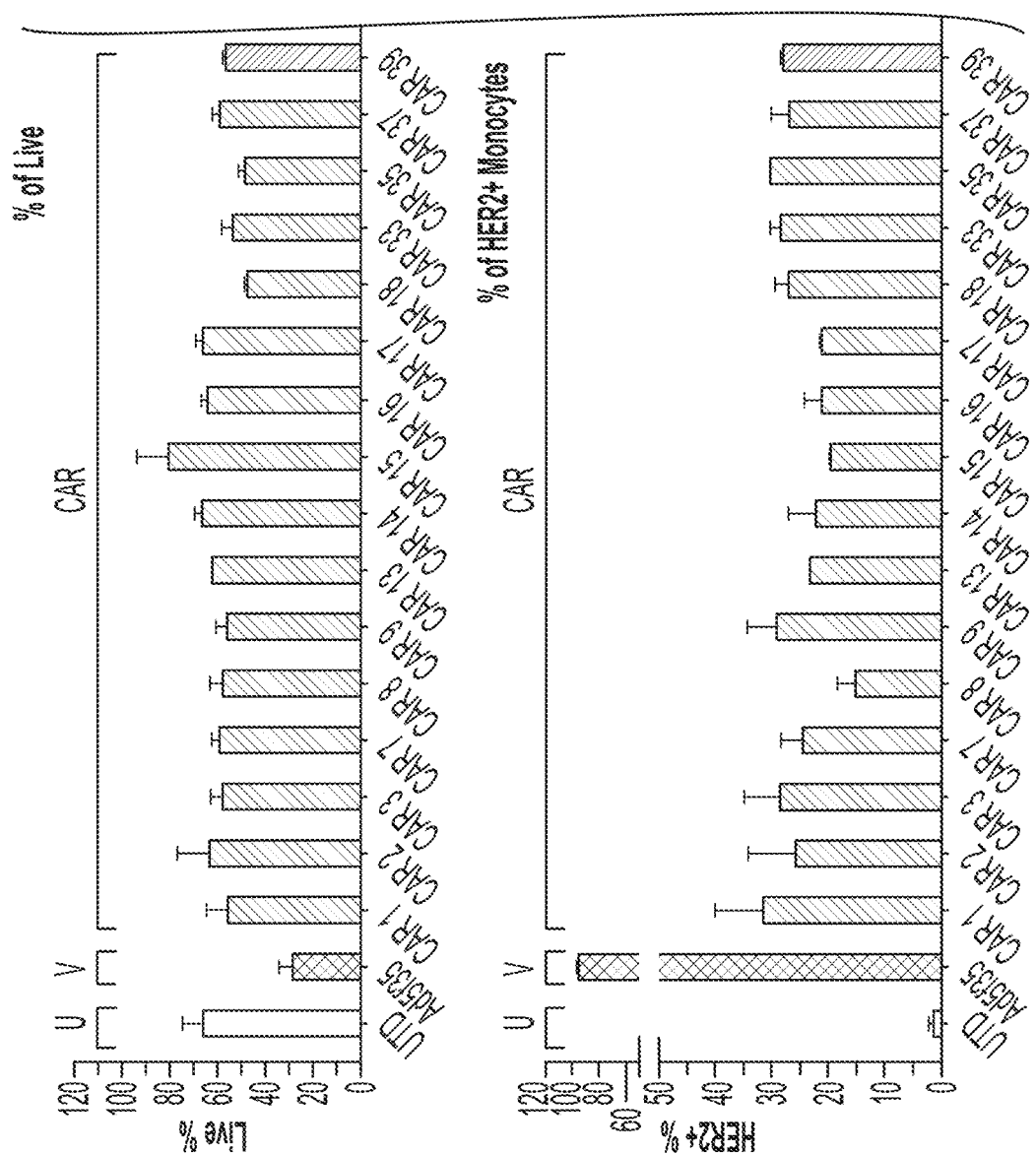
Figure 2B:
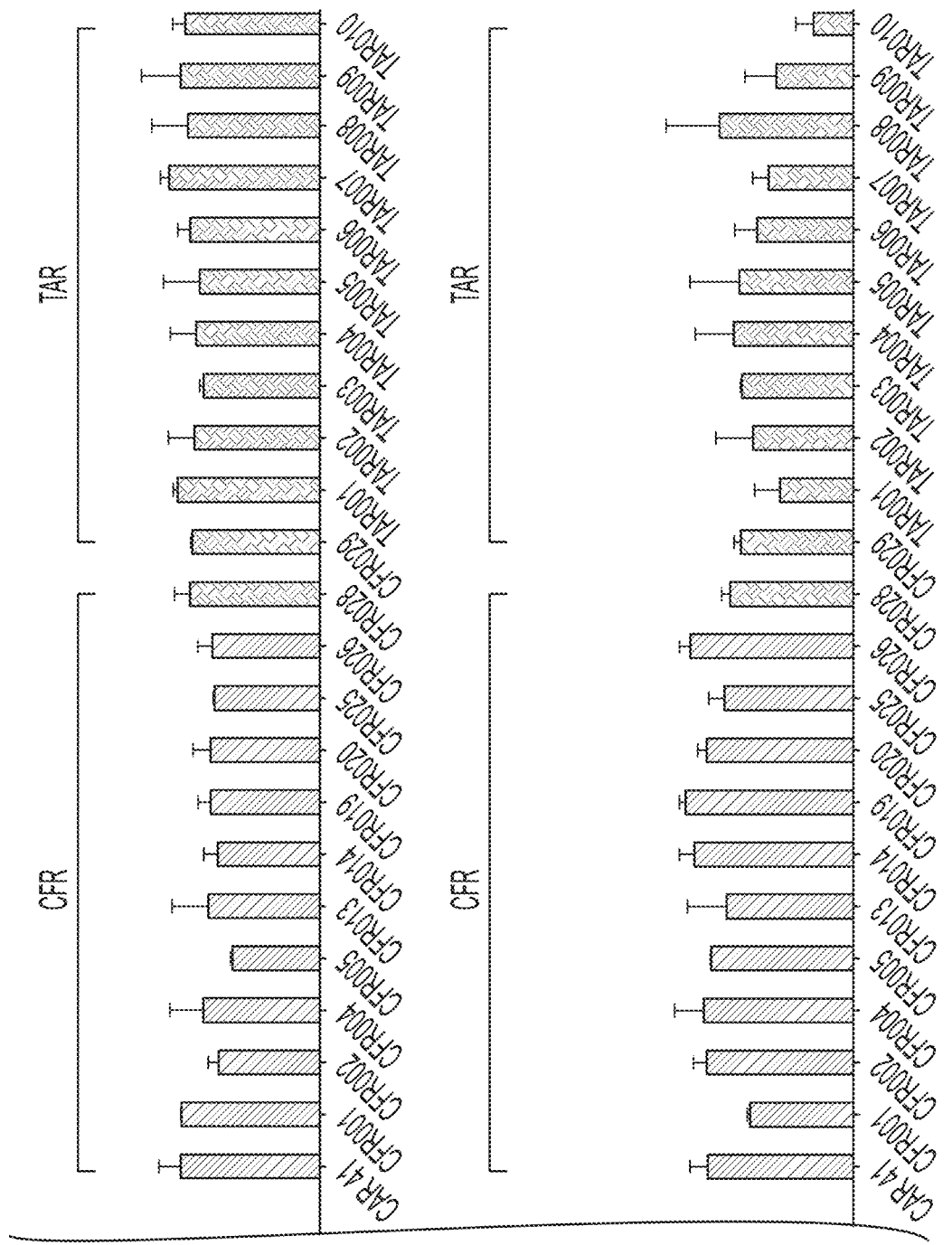

CD14+ Monocytes purified with MACS beads are rested in culture medium overnight. 40 nM of CAR mRNA was transfected and cells were incubated at 37° C. for three days, and CAR expression was detected with rHER2 binding by flow cytometry. Ad5f35 was used as a positive control. About 50-80% of CAR and TAR transfected cells, and 40-60% of CFR transfected cells were viable (FIG. 2A). CAR:HER2 expression were 15-30% positive in CAR, CFR and TAR transfected monocytes (FIG. 2B). These results show that CAR, CFR and TAR mRNA can be expressed in primary human monocytes; however, expression intensity is much lower than in macrophages.

Example 4: Receptor Expression and Tumor Cell Killing of CAR Macrophages

To generate receptor expressing macrophages, primary human macrophages were suspended in EP buffer containing 50-500 nM mRNA (or highest concentration possible based on mRNA stock) at a concentration of $1.0 \times 10^5$ to $1.0 \times 10^9$ cells/mL and electroporated. Cells were removed from the cassette, plated in TexMACS media containing 20% FBS and incubated overnight at 37° C. and 5% CO2. CAR, CFR, and TAR expression MFI, and percentage were detected after 24 hours with rHER2 binding by flow cytometry. Live percentage was detected using Live/Dead Aqua. For killing, macrophages were co-cultured with Her2+ CRL2351-NucGFP tumor cells at a 2:1 E:T ratio and monitored via Incucyte® for 72 hours. Tumor cell death was calculated by integrated GFP intensity per well relative to time 0.

Figure 3A:
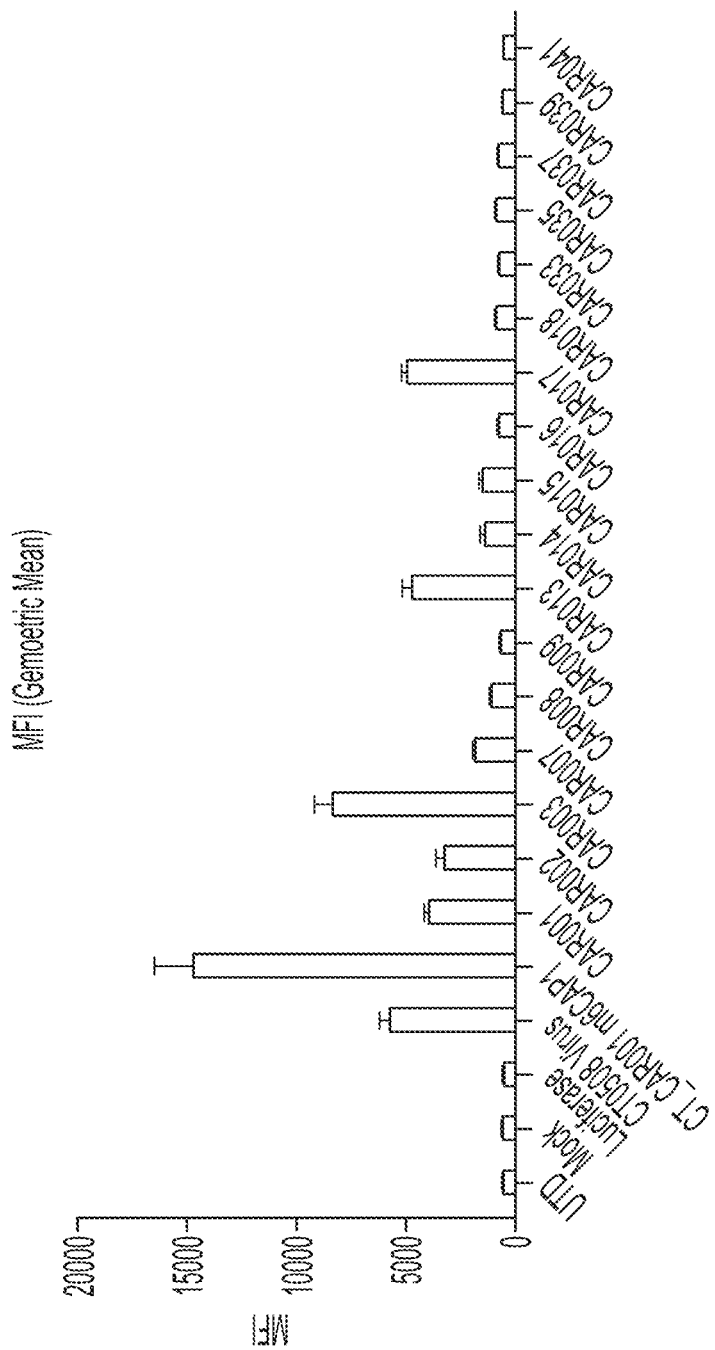
FIGS. 3A-3D are graphs showing CAR expression, CAR+ percentage, live percentage, and tumor killing ability of CAR macrophages.
Figure 3B:
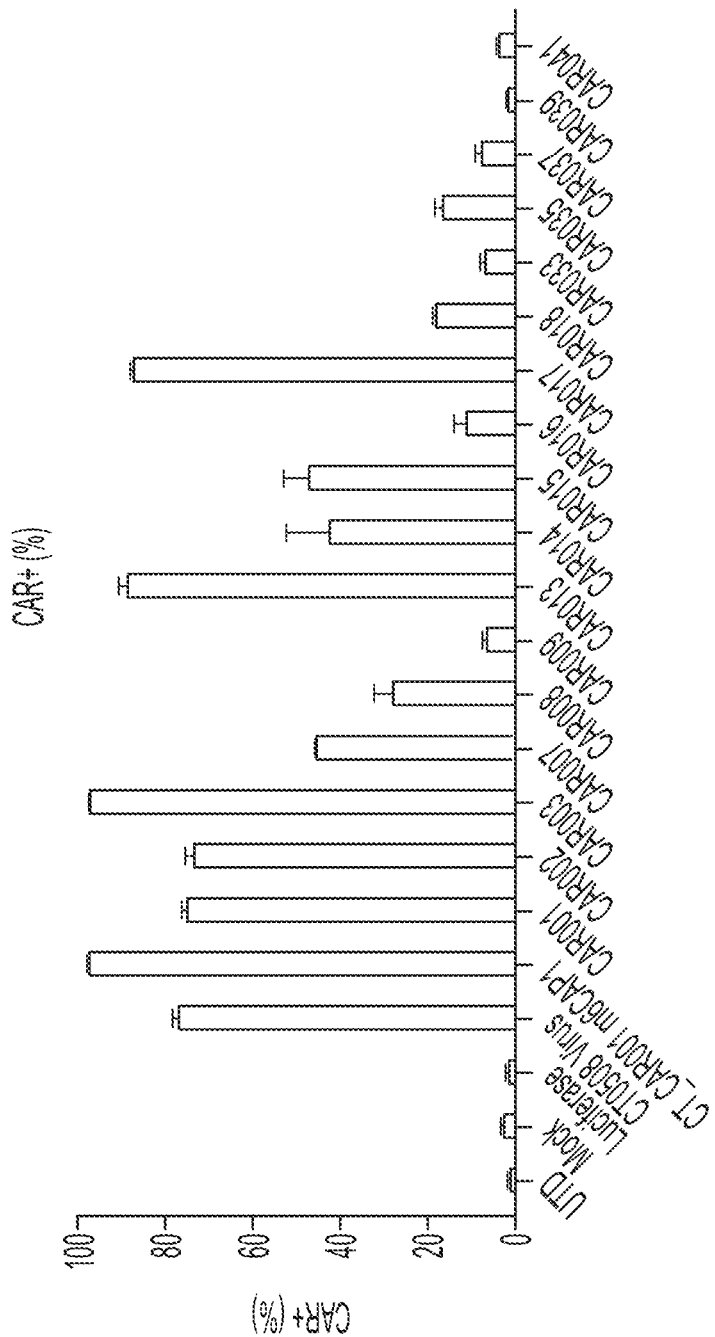
Figure 3C:
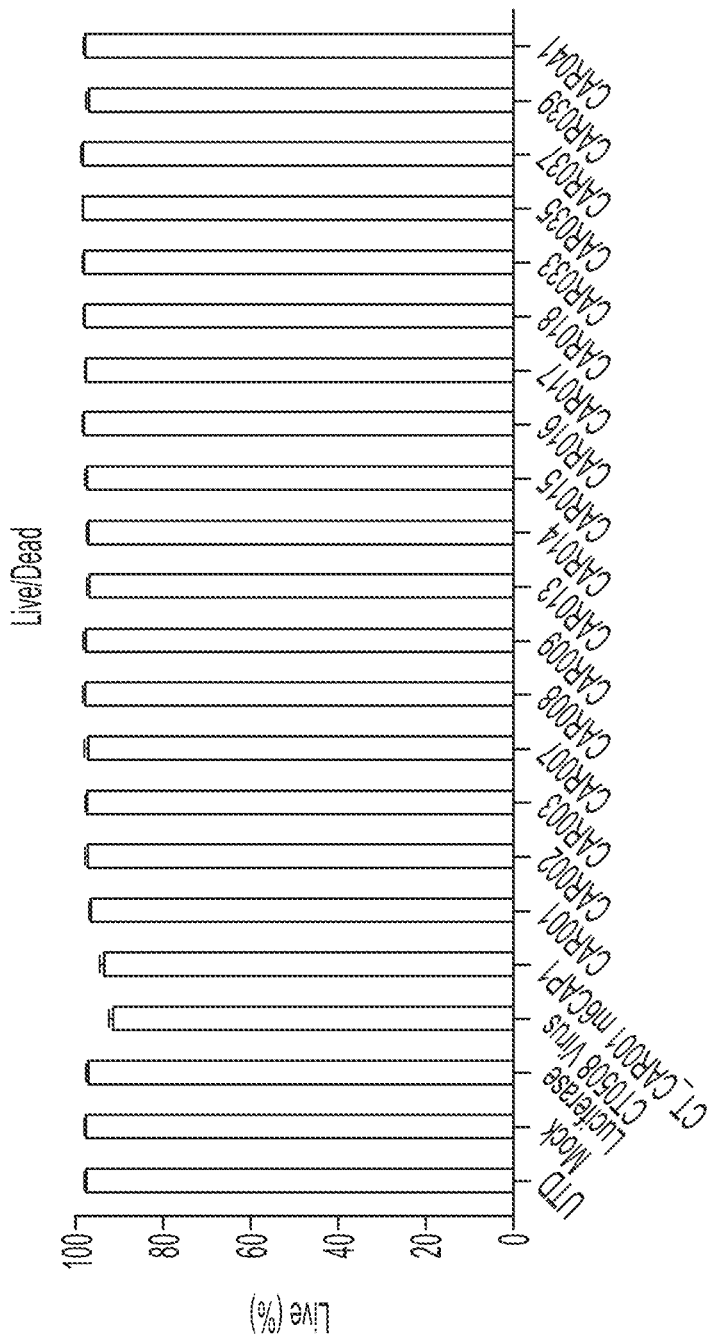
Figure 3D:
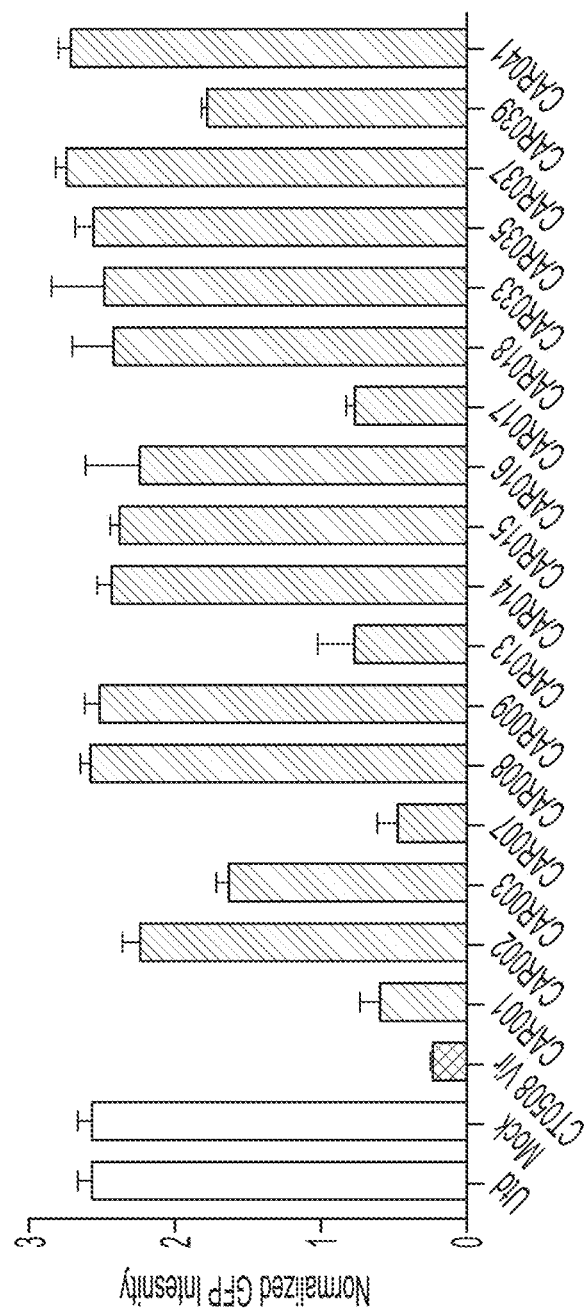
Figure 118:
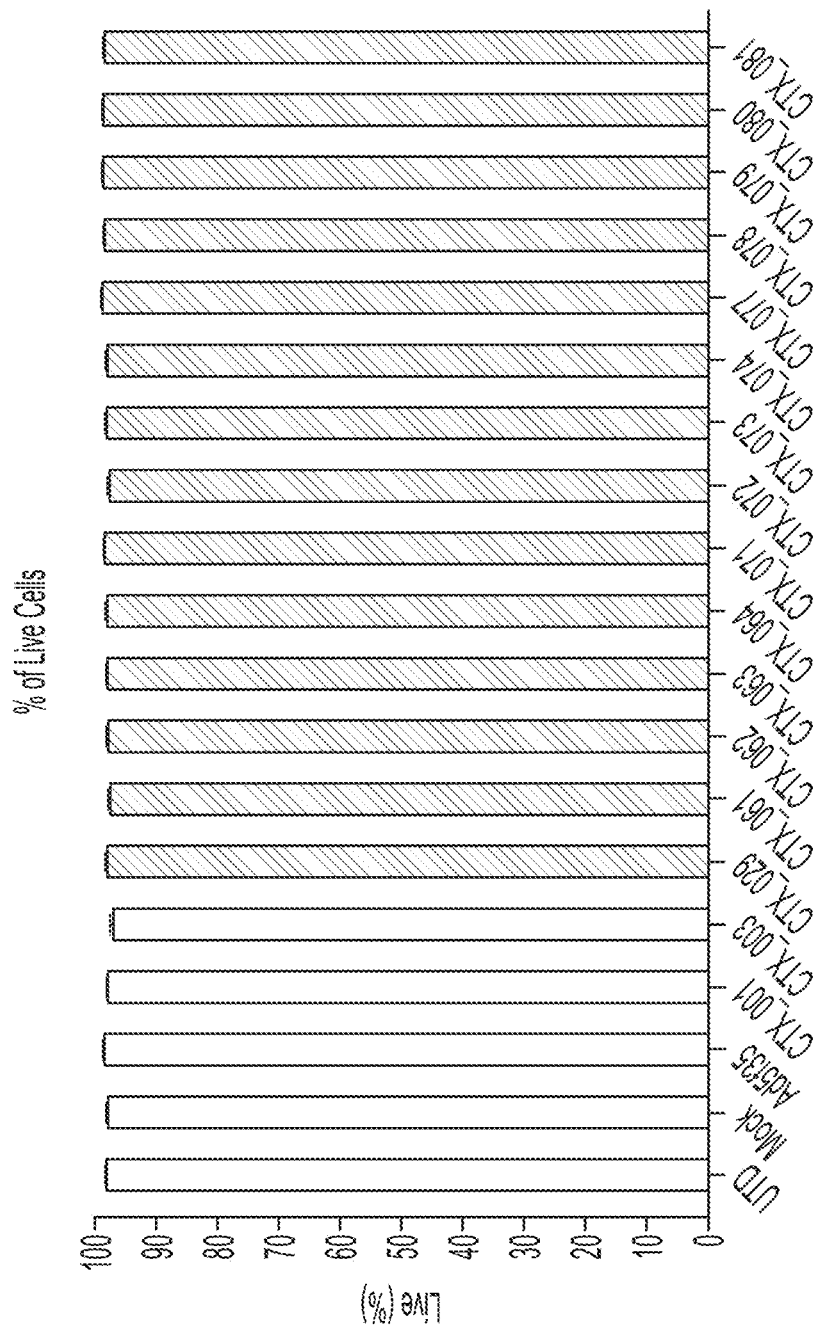
FIG. 118 is a graph showing live percentage of CAR macrophages expressing CAR029, CAR061, CAR062, CAR063, CAR064, CAR071, CAR072, CAR074, CAR074, CAR077, CAR078, CAR079, CAR080, and CAR081.
Figure 119:
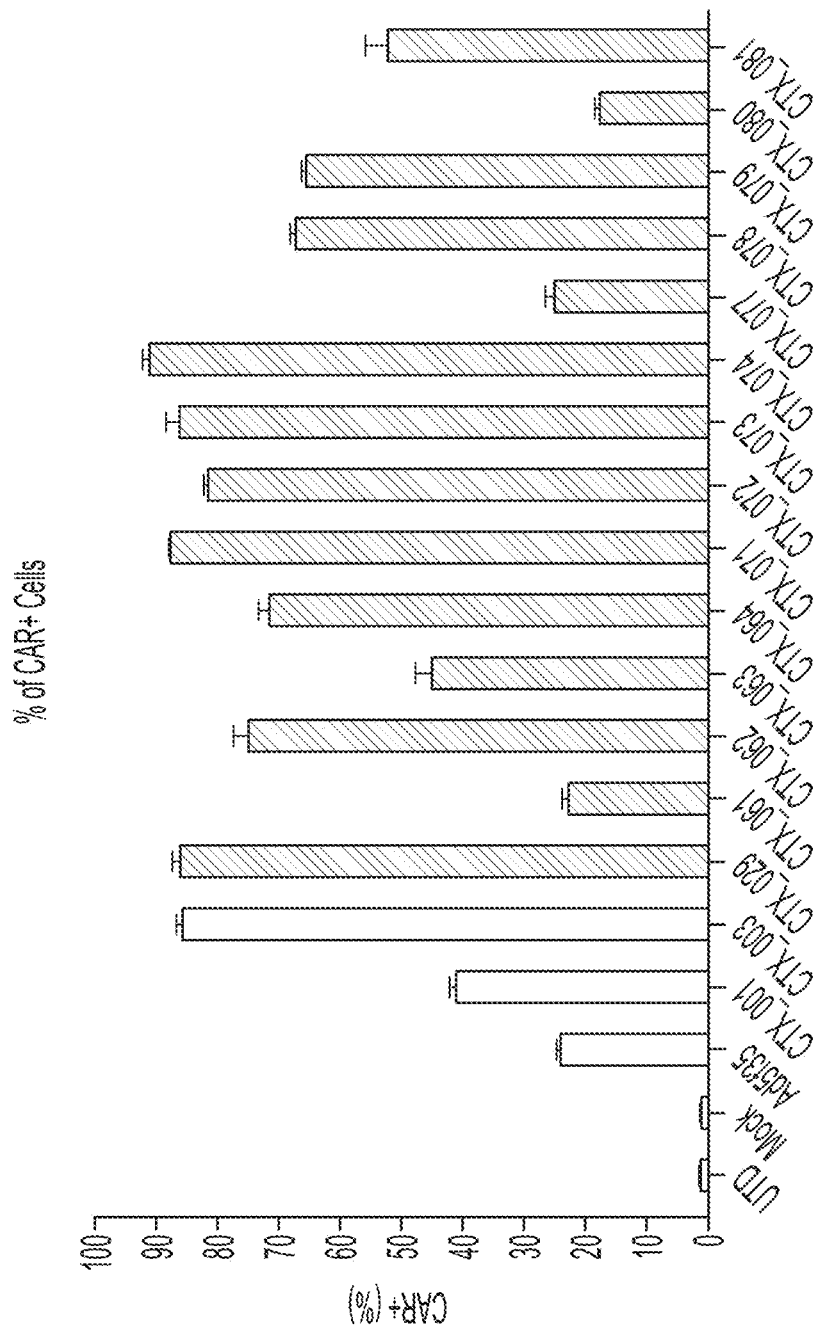
FIG. 119 is a graph showing percentage of CAR expression for macrophages transfected with CAR029, CAR061, CAR062, CAR063, CAR064, CAR071, CAR072, CAR074, CAR074, CAR077, CAR078, CAR079, CAR080, and CAR081.
Figure 120:
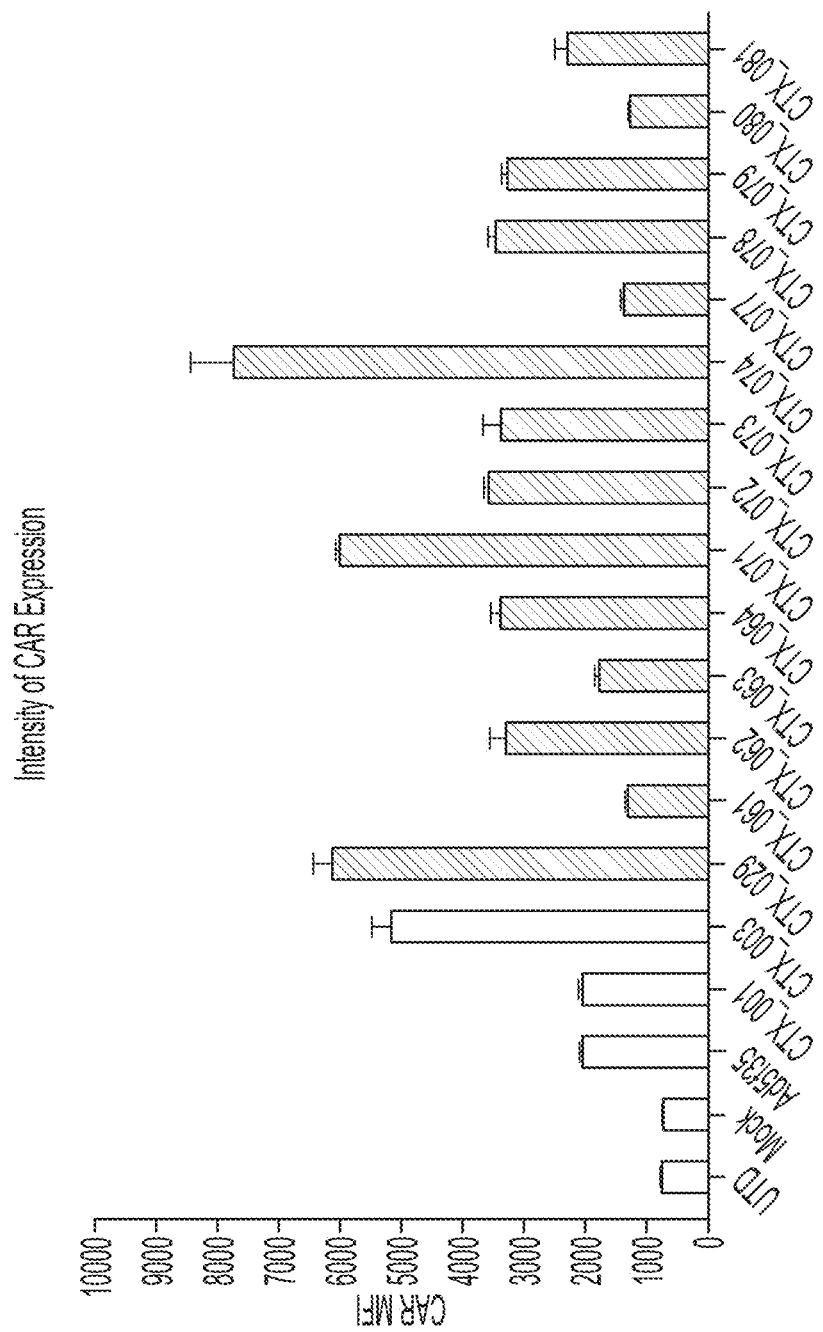
FIG. 120 is a graph showing the intensity (MFI) of CAR expression for macrophages transfected with CAR029, CAR061, CAR062, CAR063, CAR064, CAR071, CAR072, CAR074, CAR074, CAR077, CAR078, CAR079, CAR080, and CAR081.

Expression and CAR+ percentage were variable across CAR constructs (FIGS. 3A and B and 119 and 120). mRNA electroporation did not appear to influence live percentage (FIGS. 3C and 118). No CFR or TAR constructs appeared to have an effect in tumor cell killing. Constructs CAR001 (CAR comprising a CD8 leader, HER2 scFv, CD8 hinge, CD8 TM, and CD3z IC), CAR003 (CAR comprising a CD8 leader, HER2 scFv, CD8 hinge, and CD8 TM), CAR007 (CAR comprising a CD8 leader, 4D5 scFv, IgG4 hinge, CD8 TM, and CD3z IC), CAR013 (CAR comprising a CD8 leader, HER2 scFv, CD8 hinge, CD64 TM, and CD64 ICD), CAR017 (CAR comprising a CD8 leader, HER2 scFv, CD8 hinge, CD64 TM, CD64 ICD, P2A, and FCER1G), and CAR039 (CAR comprising a CD8 leader, HER2 scFv, CD8 hinge, TLR4 TM, and TLR4 ICD) were expressed in primary human macrophages and demonstrated killing function (FIG. 3D).

Figure 4A:
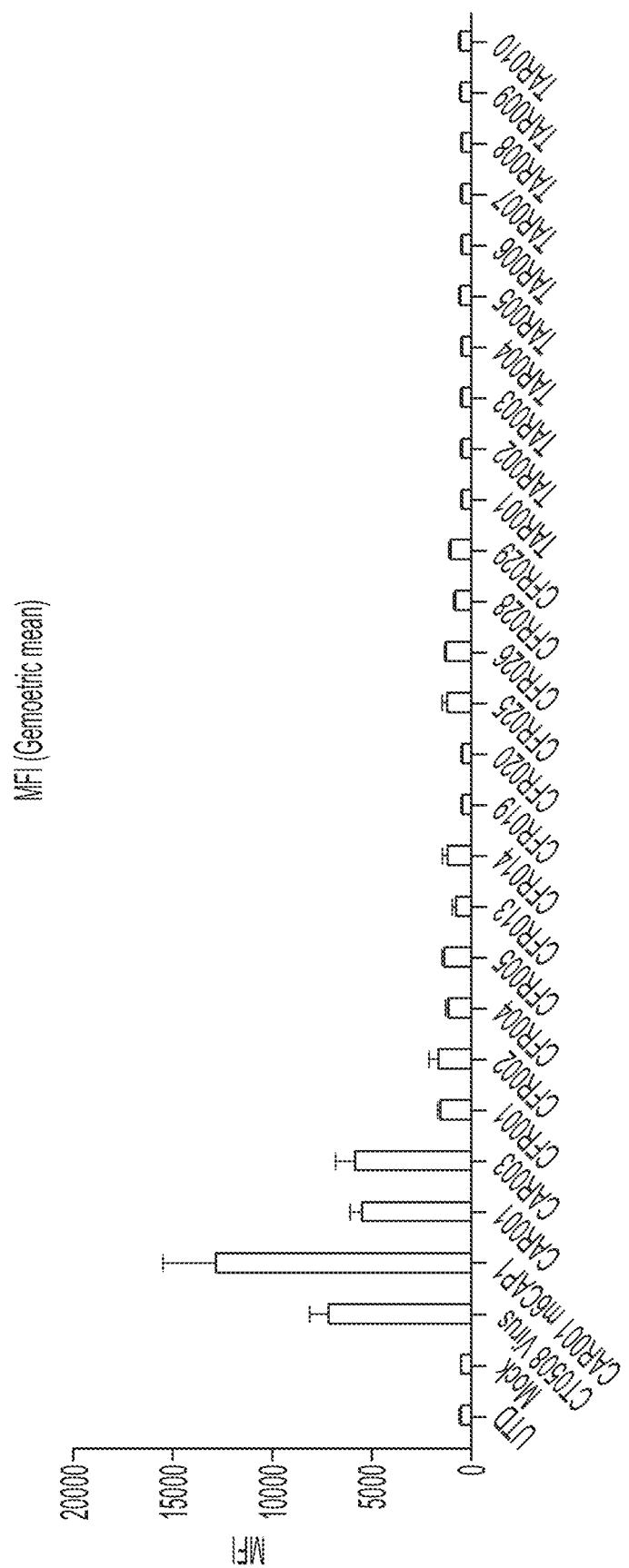
FIGS. 4A-4C are graphs showing Chimeric FcR (CFR) and Toll-Like Antigen Receptor (TAR) expression, CFR+ and TAR+ percentage, and live percentage of CFR and TAR macrophages.
Figure 4B:
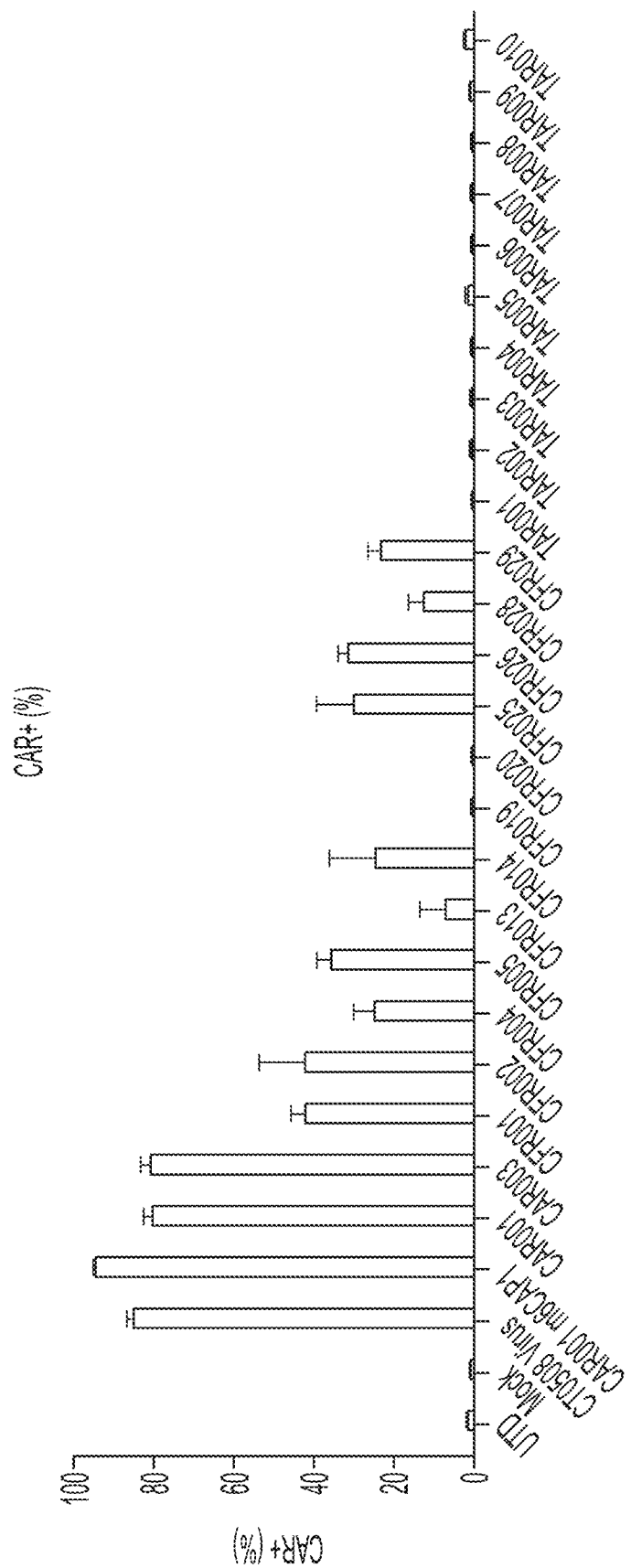
Figure 4C:
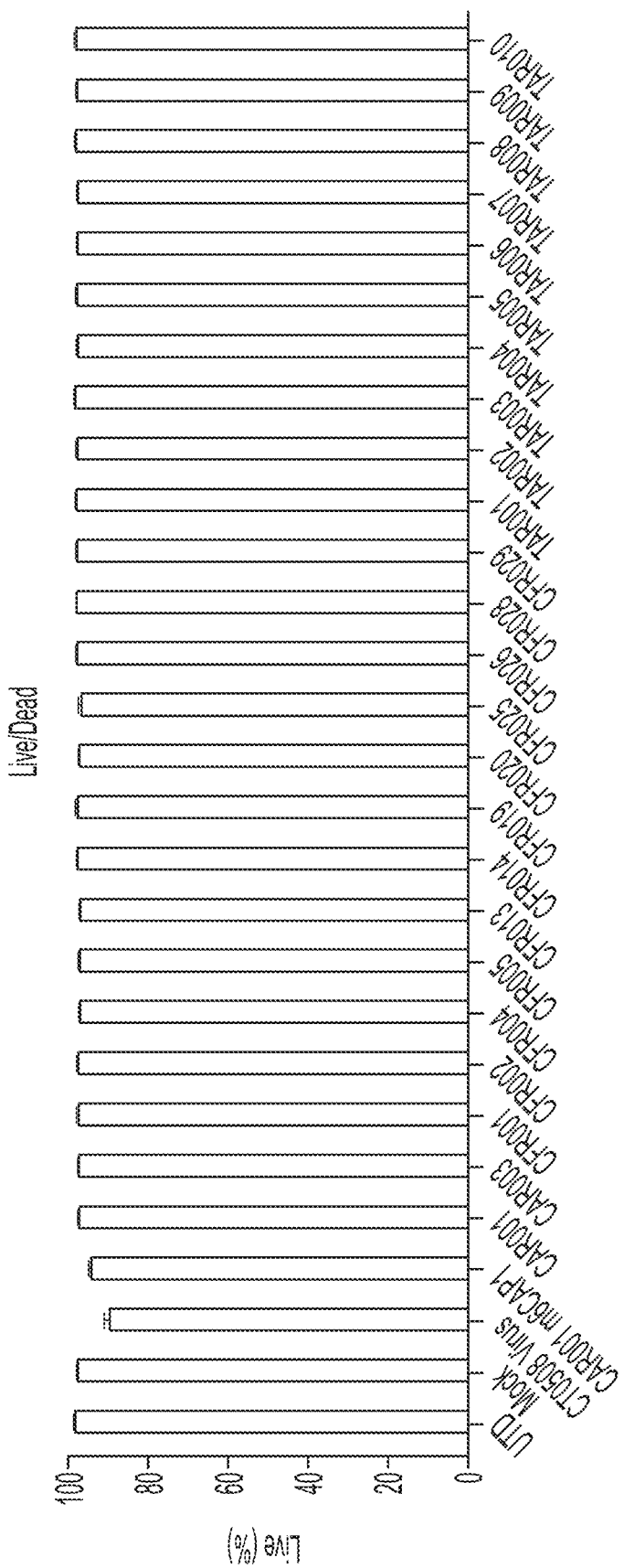

Expression and CFR and TAR+ percentage were variable across constructs (FIGS. 4A and B). mRNA electroporation did not appear to influence live percentage (FIG. 4C).

Example 5: Assessments of CAR Expression

Duration of CAR expression can be assessed by flow cytometry. CAR macrophages can be plated into the wells of a 96 well plate. In order to measure anti-Her2 CAR expression, His-tagged recombinant Her2 protein, along with a buffer such as PBS supplemented with BSA, is added to the cells and allowed to incubate for 15 minutes. The cells are then spun down at 300×g for 5 minutes and the supernatant removed. Fc-receptors are then blocked using an Fc blocking solution, such as Human TruStain FcX (BioLegend, Cat 422302) for five minutes in PBS. Following Fc blocking, staining for cell viability and other surface markers can be accomplished. For example, cell viability can be determined using LIVE/DEAD™ Fixable Aqua Dead Cell Stain Kit (Invitrogen, Cat L34957). In addition, anti-His antibodies, such as His Tag APC-conjugated Antibody (R&D Systems, Cat IC050A) are added. Expression of the CAR is determined through flow cytometry, first gating on a single cell population, followed by selection of live cells, and finally measuring the APC fluorescence of the cells. Cells expressing the CAR will be brighter in the APC channel than control cells which have not been exposed to the anti-His antibody. The brightness of the CAR-positive cells determines the extent of expression, while repeated measures over time allow for tracking the expression of the CAR over time.

For immunofluorescence, cells can be cultured as appropriate on a glass slide. Media is then removed and the cells washed three times with PBS. Cells can then be fixed using 4% paraformaldehyde or methanol. The exact time of incubation in the fixative will depend on its identity. Once the correct amount of time has pass, the fixative is removed and the cells washed again three times with PBS. If intracellular staining is desired, cells are now incubated in 1% Triton X-100 (ThermoFisher, Cat BP151-100) in PBS and then washed three times in PBS. Blocking solution, such as BSA in PBS, is now added to the cells and allowed to block for 60 minutes. The blocking solution is then removed and the cells washed. Fluorochrome conjugated antibodies are diluted according to the manufacturer's instructions and allowed to bind to the cells overnight. The antibody solution is then removed and the cells are washed. Finally, a mounting solution, such as ProLong™ Diamond Antifade Mountant with DAPI (Invitrogen, Cat P36966), is applied to the cells and the coverslip placed on top. This is allowed to dry for 24 hours before imaging. Imaging is performed via fluorescence microscopy. Cells expressing CAR with be brighter than cells not expressing the CAR in the appropriate channel for the fluorophore.

For RTPCR, macrophages can be lysed and the RNA collected through the use of a 1 step kit RTPCR kit (SuperScript™ III Platinum™ One-Step qRT-PCR Kit, Invitrogen Cat 11732-020) by following the manufacturer's instructions. Primers specific to the CAR will be used in the assay. Macrophages with mRNA for the CAR will show a signal in the RTPCR assay, whereas untransduced macrophages will not show the signal.

Example 6: Assessment of CAR Functionality

For a flow phagocytosis assay of cells, target positive and target negative tumor cells are labeled with CellTrace™ CFSE Cell Proliferation Kit (Invitrogen, Cat C34554)

according to the manufacturer's instructions or the cells have been engineered to express a fluorescent protein like GFP. CAR-expressing and control macrophages are then plated in a U-bottom 96 well plate at a 1:1 macrophage: tumor cell ratio and cultured for 4 hours. At the end of the incubation, the cells are removed from the wells and stained for flow cytometry. The panel includes a viability dye and a macrophage specific marker, such as CD11b. Upon gating for live cells, cells that are CD11b/CFSE double positive are macrophages presumed to have phagocytosed a cell. CAR macrophages should have an increased percentage of double positive cells when cultured with the target positive tumor cells compared to macrophages without the CAR. In addition, the specificity of the phagocytosis is shown by no significant change in the amount of phagocytosis when the macrophages are cultured with target negative cells.

For a flow phagocytosis assay using beads, polystyrene beads can be functionalized with the target of the CAR or an irrelevant protein. In addition, these beads are labeled with pHrodo™ Red, SE (Invitrogen, Cat P36600), which is a pH-reactive dye. Upon acidification, the dye increases its level of fluorescence. The beads are then cultured with CAR and untransduced macrophages. After a period of time, the macrophages can be removed and stained for flow cytometry using a viability dye and a macrophage specific marker, such as CD11b. Upon gating for live cells, cells that are CD11b/pHrodo double positive are macrophages presumed to have phagocytosed a bead. CAR macrophages should have an increased percentage of double positive cells when cultured with the target positive beads compared to macrophages without the CAR. In addition, the specificity of the phagocytosis is shown by no significant change in the amount of phagocytosis when the macrophages are cultured with target negative beads.

For Incucyte® analysis of cells, target-positive tumor cells expressing a fluorescent protein like GFP are cultured with CAR and untransduced macrophages in a 96 well plate. The ratio between the effector macrophages and target tumor cells is varied from 10:1 E:T to 1:10 E:T, along with a 0:1 E:T target cell only control. The number of macrophages is kept constant at 10e3 macrophages per well. The change in fluorescence over time, measured every four hours, can be measured to determine the amount of tumor cell killing occurring in the culture. In addition, image analysis techniques can be used to determine the location of macrophages in the culture and determine the number of macrophages that have also phagocytosed a tumor cell. CAR macrophages should show increased colocalization of macrophages and tumor cells, along with increased killing, compared to untransduced macrophage or tumor cell only controls.

For Incucyte® analysis of beads, pHrodo functionalized beads bearing the protein target for the CAR are added to both CAR and untransduced macrophages in the wells of a 96 well plate. The macrophages are plated at a concentration of 20e3 per well and the beads are added at a 5:1 bead to macrophage ratio. The fluorescence of the pHrodo is measured for five hours, with measurements every 30 minutes. The ratio of increase in fluorescence between the initial time point and the 1 hour time point is used to determine the amount of phagocytosis occurring. The CAR macrophages are expected to have a higher change in fluorescence than the untransduced controls.

For antigen processing and presentation post-phagocytosis, T cell expansion, IL2 release, IFNg release, TNFα release, and/or CD69 upregulation can be analyzed. T cell clones known to be responsive to a particular antigen (e.g., ovalbumin) can be obtained and cultured. Often, these clones are murine cells. Murine CAR macrophages, which have been MHC matched to the T cells, are cultured with cancer cells express both the CAR-targeted receptor and the known antigen. The macrophages can then be isolated and co-cultured with the T cells. Upon antigen presentation by the macrophages, the T cells will secrete IL2 (which can be measured through cytokine measurement techniques) and proliferate (which can be measured through counting cell numbers or CFSE dilution). In addition, activated T cells can be checked for cytotoxic function through co-culture of the T cells with an antigen-expressing cell line. CAR macrophages are expected to cause more proliferation and increased cytokine production in the T cells compared to untransduced macrophage controls.

Tumor killing in other ways than phagocytosis can also be assessed. In conditioned media, CAR macrophages and target-positive cells can be co-cultured together for a period of time (ex 24 hours) to allow for the macrophage to sense and response to the target cells. The ratio between numbers of tumor cells can be varied depending on the level of expression of the target protein on the tumor cells. After the desired amount of time has passed, the supernatant is removed from the CAR macrophages and any cells remaining in the supernatant are removed through filtration through a 0.22 micron filter or centrifugation. The filtered supernatant is then placed onto other cancer cells which have not been cultured with CAR macrophages. The resulting change in tumor cell viability and proliferation can be measured via cell counting, flow cytometry, MTT/XTT assay, or microscopy. CAR macrophages should cause either the death of the tumor cells cultured with the supernatant or a reduction in the rate of growth when compared to supernatant from untransduced macrophages cultured with the same target positive cell line.

For co-culture of target+/target−/CAR macs, CAR macrophages, target positive cells, and target negative cells are co-cultured together. There must be some way to distinguish between target positive and target negative cells, for example the expression of different fluorescent proteins. Over time, the relative numbers of the different cell types can be determined, either through microscopy or flow cytometry. Comparing the growth of target negative cells with CAR macrophages with and without target positive cells lends some insight into tumor cell killing not using phagocytosis. It would be expected that the CAR macrophages would show either increased death or a reduction in the growth rate of the target negative cell line compared to untransduced macrophages. In addition, there is expected to be a difference between the target negative cells cultured with CAR macrophages depending on the presence of the target positive cells as well.

For production of favorable cytokines by flow cytometry, CAR macrophages can be co-cultured with either target positive cells or target positive beads, along with a target negative control. After a specific amount of time, the supernatant of the culture can be harvested and stray cells removed through filtration or centrifugation. Desired cytokines can be measured through the use of a flow cytometry-based cytokine bead assay, which measures the concentration of various cytokines in the supernatant. The beads are stained according to the manufacturer's instructions. One example of such a system is the BioLegend LEGENDplex system. In addition, CAR macrophages from the culture system can be harvested and stained for cytokine production through the use of intracellular cytokine staining using flow cytometry. Cells can be fixed, permeabilized, and stained according to the manufacturer's directions, such as for Fixation/Permeabilization Solution Kit (BD, Cat 554714). CAR macrophages cultured with target positive cells or beads should show higher levels of pro-inflammatory cytokines compared to untransduced macrophages or CAR macrophages not stimulated with the target protein.

For ELISA/MSD analysis, CAR macrophages can be co-cultured with either target positive cells or target positive beads, along with a target negative control. After a specific amount of time, the supernatant of the culture can be harvested and stray cells removed through filtration or centrifugation. One example would be an 8:1 macrophage to target ratio for 24 hours. After the culture period, the supernatant is removed and the amount of cytokine present in the solution can be measured using an ELISA cytokine kit (ex IL-1 beta Human Instant ELISA™ Kit, Invitrogen Cat BMS224INST) following the manufacturer's direction. In addition, the cytokines can be measured through the use of the MesoScaleDiscovery QuickPlex system by following the manufacturer's directions. It is expected that CAR macrophages cultured with target positive cells or beads should show higher levels of pro-inflammatory cytokines compared to untransduced macrophages or CAR macrophages not stimulated with the target protein.

For Production of ROS by flow cytometry, CAR macrophages can be co-cultured with either target positive cells or target positive beads, along with a target negative control. Untransduced macrophages can be cultured under the same conditions. Measurement of the production of reactive oxygen species (ROS) can be measured through the use of flow cytometry-based kits, such as Total Reactive Oxygen Species (ROS) Assay Kit 520 nm (Invitrogen, Cat 88-5930-74). The cells can be prepared according to the manufacturer's instructions. It is expected that CAR macrophages cultured with target positive cells or bead would show higher levels of ROS than CAR macrophages cultured with target negative cells or beads and untransduced macrophages cultured with either target positive or negative cells or beads. Additional methods are described in Dikalov & Harrison. *Antioxid Redox Signal.* 2014; 20(2):372-382, which is hereby incorporated by reference in its entirety.

For resistance to phagocytic checkpoints, CAR macrophages can be co-cultured with target positive beads or cells which have varying levels of CD47 or other anti-phagocytic ligands. Beads can easily have altered levels of CD47 or other anti-phagocytic ligands through differences in the amount of protein used to functionalize them. Altering levels of anti-phagocytic ligands on cells requires genetic engineering, such as the use of shRNA or CRISPR/Cas9 systems. The amount of phagocytosis can be quantified through either microscopy or flow cytometry, as outlined in the above sections. Both CAR and untransduced macrophages are expected to show less phagocytosis as the amount of CD47 or other anti-phagocytic ligands increased. Macrophages engineered to express dominant negative receptors (such as a truncated SIRPα) should show increased levels of phagocytosis compared to macrophages lacking such dominant negative receptors, for both CAR and untransduced types.

For comparison to CD47 blockade, the action of CD47 can be blocked though the use of blocking antibodies, such as the murine clone B6H12. Altering the amount of CD47 on the surface of a target positive or negative cell will allow for different levels of phagocytosis. A dose-titration curve of CD47 blocking antibody can be determined by culturing target positive and target negative cells with varying amounts of the blocking antibody. Phagocytosis assays using both CAR and untransduced macrophages should show that Car macrophages are less sensitive to CD47 by showing a lower level of inhibition at a given level of CD47 blockade compared to untransduced cells. In contrast, target negative cells will not show a difference between CAR and untransduced macrophages.

For expression of chemokine receptors to aid in trafficking, expression of chemokine receptors can be measured through the binding of specific antibodies to the CAR macrophages, which can then be measured using a flow cytometer. It is expected that the CAR macrophages will show a higher level and wider variety of chemokine receptors compared to untransduced macropahges.

CAR and untransduced macrophages can be lysed and the RNA harvested for the technique of RNA sequencing. A comparison of the expressed RNA transcripts within a cell can allow for the determination of what receptors are expressed on the cell. It is expected that the CAR macrophages will show a higher level and wider variety of chemokine receptors compared to untransduced macrophages.

For Western blotting, CAR and untransduced macrophages can be cultured, lysed, and the total protein collected. This protein is then fractionated by size through its mobility through a gel in an electric field, and then transferred onto a membrane. The membrane can be stained using antibodies specific for a certain protein and the presence or absence of a protein can be determined through this staining. It is expected that the CAR macrophages will show a higher level and wider variety of chemokine receptors compared to untransduced macropahges.

For expression of chemokines to recruit other immune cells, CAR macrophages can be co-cultured with either target positive cells or target positive beads, along with a target negative control. After a specific amount of time, the supernatant of the culture can be harvested and stray cells removed through filtration or centrifugation. Desired cytokines can be measured through the use of a flow cytometry-based cytokine bead assay, which measures the concentration of various cytokines in the supernatant. The beads are stained according to the manufacturer's instructions. One example of such a system is the BioLegend LEGENDplex system. In addition, CAR macrophages from the culture system can be harvested and stained for cytokine production through the use of intracellular cytokine staining using flow cytometry. Cells can be fixed, permeabilized, and stained according to the manufacturer's directions, such as for Fixation/Permeabilization Solution Kit (BD, Cat 554714). CAR macrophages cultured with target positive cells or beads should show higher levels of pro-inflammatory cytokines compared to untransduced macrophages or CAR macrophages not stimulated with the target protein.

For ELISA/MSD, CAR macrophages can be co-cultured with either target positive cells or target positive beads, along with a target negative control. After a specific amount of time, the supernatant of the culture can be harvested and stray cells removed through filtration or centrifugation. One example would be an 8:1 macrophage to target ratio for 24 hours. After the culture period, the supernatant is removed and the amount of cytokine present in the solution can be measured using an ELISA cytokine kit (ex IL-1 beta Human Instant ELISA™ Kit, Invitrogen Cat BMS224INST) following the manufacturer's direction. In addition, the cytokines can be measured through the use of the MesoScaleDiscovery QuickPlex system by following the manufacturer's directions. It is expected that CAR macrophages cultured with target positive cells or beads should show higher levels of pro-inflammatory cytokines compared to untransduced macrophages or CAR macrophages not stimulated with the target protein.

For a transwell assay, CAR macrophages can be co-cultured with either target positive cells or target positive beads, along with a target negative control. In addition, the macrophages and target cells can be cultured separately as a control. After a sufficient incubation, for example 48 hours, the supernatant can be harvested and remaining cells removed via filtration. A purified subpopulation of immune cells, such as CD3 positive T cell, can be labeled with CFSE according to the manufacturer's instruction. The transwell inserts (for example, HTS Transwell®-96 Permeable Support with 3.0 µm Pore Polycarbonate Membrane, Corning Cat. 3386) ca be functionalized with a extracellular matrix protein, such as fibronectin or collagen. The matrix protein is made into a solution and applied to the membranes for 30 minutes at 37 C. The remaining solution is then removed and the membrane washed with PBS. The CFSE labeled cells are then resuspended in serum-free media and placed onto the top face of the insert. These cells are allowed to settle and adhere for 20 minutes. The insert is then transferred so that the bottom face of the membrane is exposed to the collected supernatant. The cells are allowed to migrate for at least 2 hours. After the incubation period, the insert is removed and the fluorescence of the wells in the bottom plate containing the supernatant is measured. It is expected that the CAR macrophages will exhibit a higher degree of recruitment compared to the untransduced controls. In addition, CAR macrophages cultured with target positive cells are expected to better recruit the labeled immune cells better than CAR macrophages cultured with target negative cells.

For proliferation by CFSE dilution, macrophages can be labeled with CFSE stain according the manufacturer's directions. These labeled macrophages can then be cultured for an appropriate period of time. The level of CFSE dilution within the cells can be used to determine the extent of proliferation of the macrophages.

For MTT/XTT assay, cells are plated and the assay run using the manufacturer's instructions for MTT (ThermoFisher, Cat V13154) or XTT (ThermoFisher, Cat X12223) assays.

For production of macrophages from induced pluripotent stem cells (iPSCs), methods can be used as described in Ackermann et al. Nat Commun. 2018; 9(1):5088; Zhang et al. Circ Res. 2015; 117(1):17-28; Mucci et al. Stem Cell Reports. 2018; 11(3):696-710; Shi et al. Curr Protoc Stem Cell Biol. 2019; 48(1):e74; and Takata et al. 2017; 47(1): 183-198.e6; Cao et al. Stem Cell Reports. 2019; 12(6):1282-1297, each of which is hereby incorporated by reference in its entirety. For preparing IPSCs, transduction with lentivirus can be done prior to differentiation.

Example 7: Priming of Macrophages

To generate Her2-Zeta CAR expressing macrophages, primary human macrophages were suspended in EP buffer (MaxCyte) containing 300 nM mRNA (TriLink) at a concentration of $90 \times 10^6$ cells/mL. 100 µL of cell mixture was added to an electroporation cassette (OC100×2; MaxCyte) and electroporated using the Experimental T cell 1 setting. Cells were removed from the cassette, plated in 3 mL of TexMACS media (Miltenyi Biotech) containing 20% FBS (Gibco) on UpCell plates (Thermo Scientific), and incubated overnight at 37 C and 5% $CO_2$.

Recombinant CD40 ligand (Peprotech), 4-1BB ligand (Enzo Life Sciences), and 4-1BB receptor (Peprotech) were resuspended in molecular grade water to a stock concentration of 100 µg/mL. Stock solution was then used to create working solutions in PBS ranging from 2-0.002 µg/mL. 100 uL of working solution was added to wells in a 96-well plate and left at room temperature for 4 h.

Plates were removed from the incubator and left at room temperature for 30 min. Cells were detached from plate, counted using the NC-200 automated cell counter (Chemomtech), and re-suspended in TexMACS media with 10% FBS. Protein coated plates were washed 2× with PBS, followed by addition of macrophages in a final volume of 100 uL TexMACS media with 10% FBS. Plates were incubated for 3 h at 37 C and 5% CO2. After 3 h, 10,000 CRL-2351 cells expressing nuclear GFP were added to each well. Final concentration of GM-CSF was 10 ng/mL in all wells. Cell lysis was detected using Incucyte® analysis (Essen Bioscience). Tumor cell death was calculated by integrated GFP intensity per well relative to time 0.

For detection of cell surface proteins, macrophages were plated onto wells coated with agonist molecules in a final volume of 200 uL TexMACS media+10% FBS+10 ng/mL GM-CSF and incubated for 3 days at 37 C and 5% CO2. Cells were incubated in 300 µL Accutase (Sigma) for 30 min and transferred to 96-well round bottom plate for staining. Cells were incubated in FACS buffer containing 20 µg/mL Her2-His for 20 min at RT, followed by incubation in Human TruStain FcX for 10 min at RT. Surface protein staining was done using the following panel: CD80-FITC, CD86-PE, CD163-APC-Cy7, CD206-BV421, anti-His-APC, Aqua Live/Dead. Detection of surface protein expression was completed using the Attune N×T flow cytometer (Thermo Fischer).

Figure 5A:
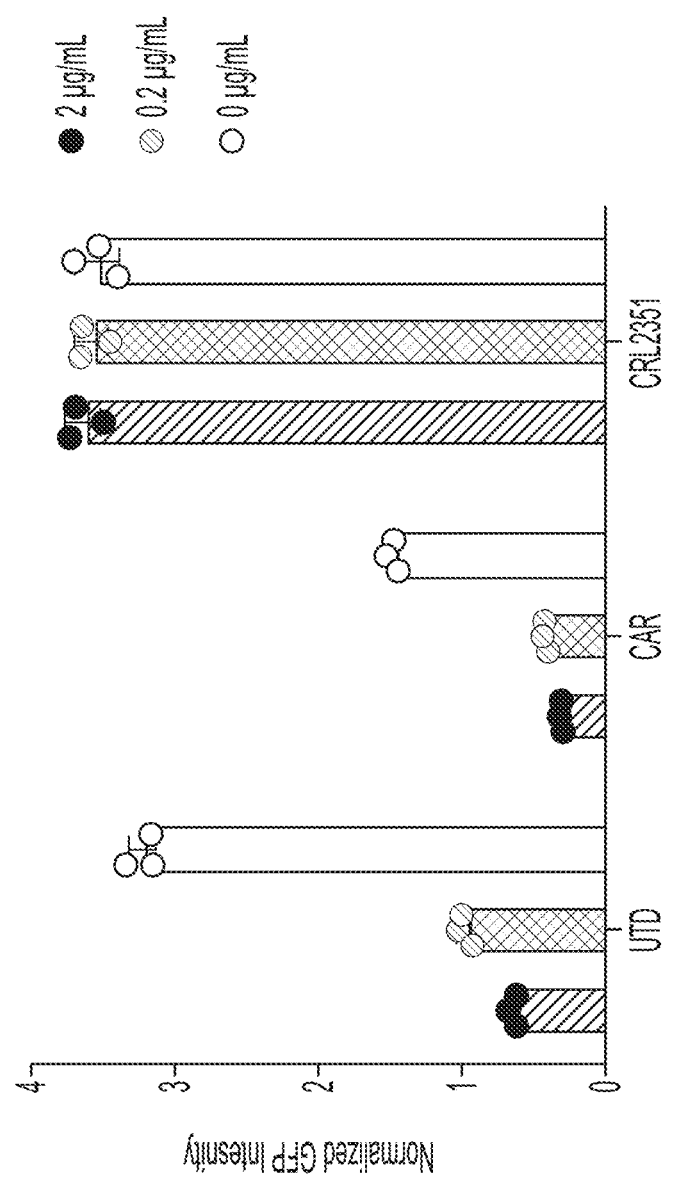
FIGS. 5A-5B are graphs showing tumor killing ability (FIG. 5A) and induction of expression of M1 and M2 markers (FIG. 5B) after incubation of macrophages and CAR macrophages with CD40 ligand (CD40L).
Figure 5B:
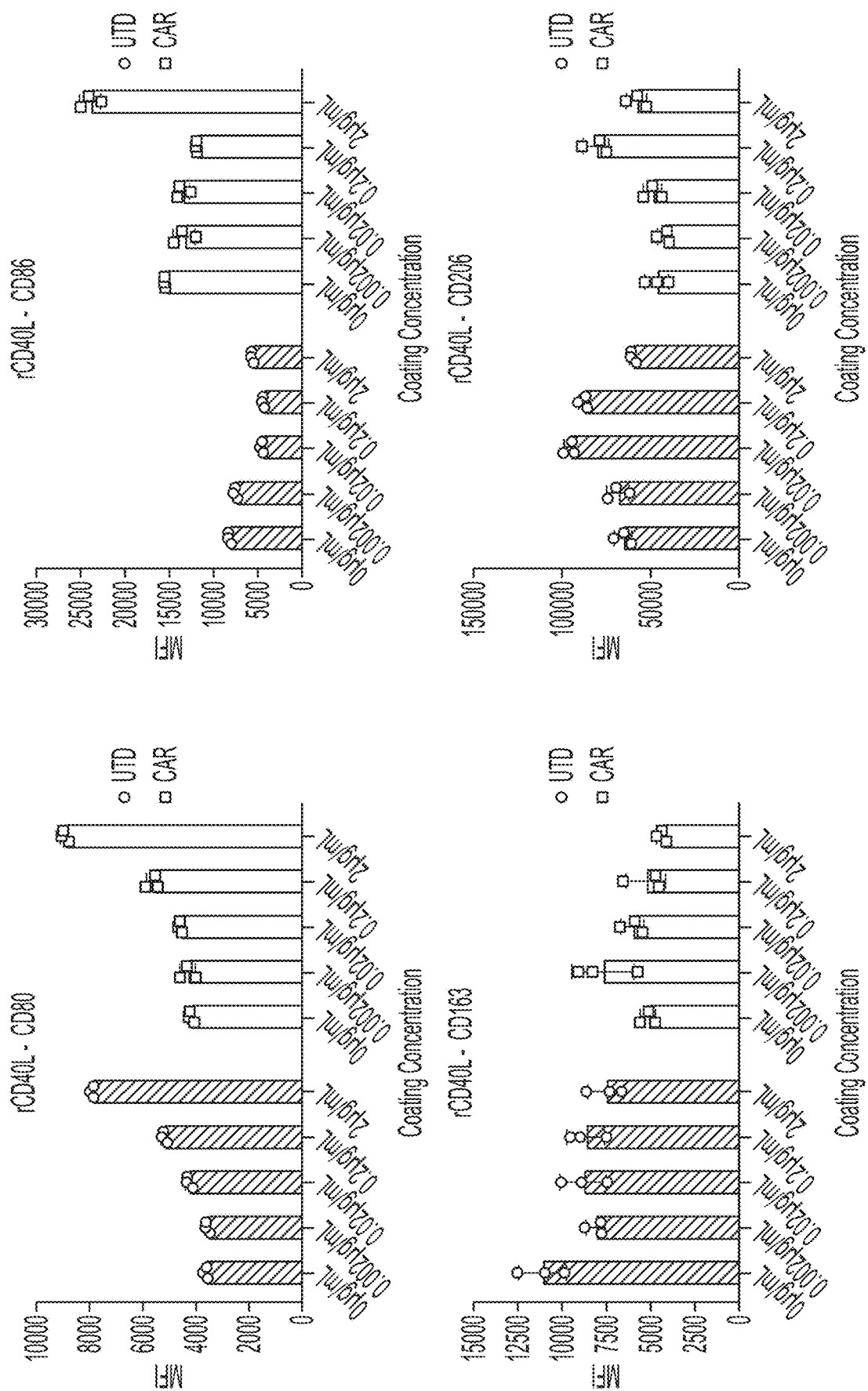
Figure 6B:
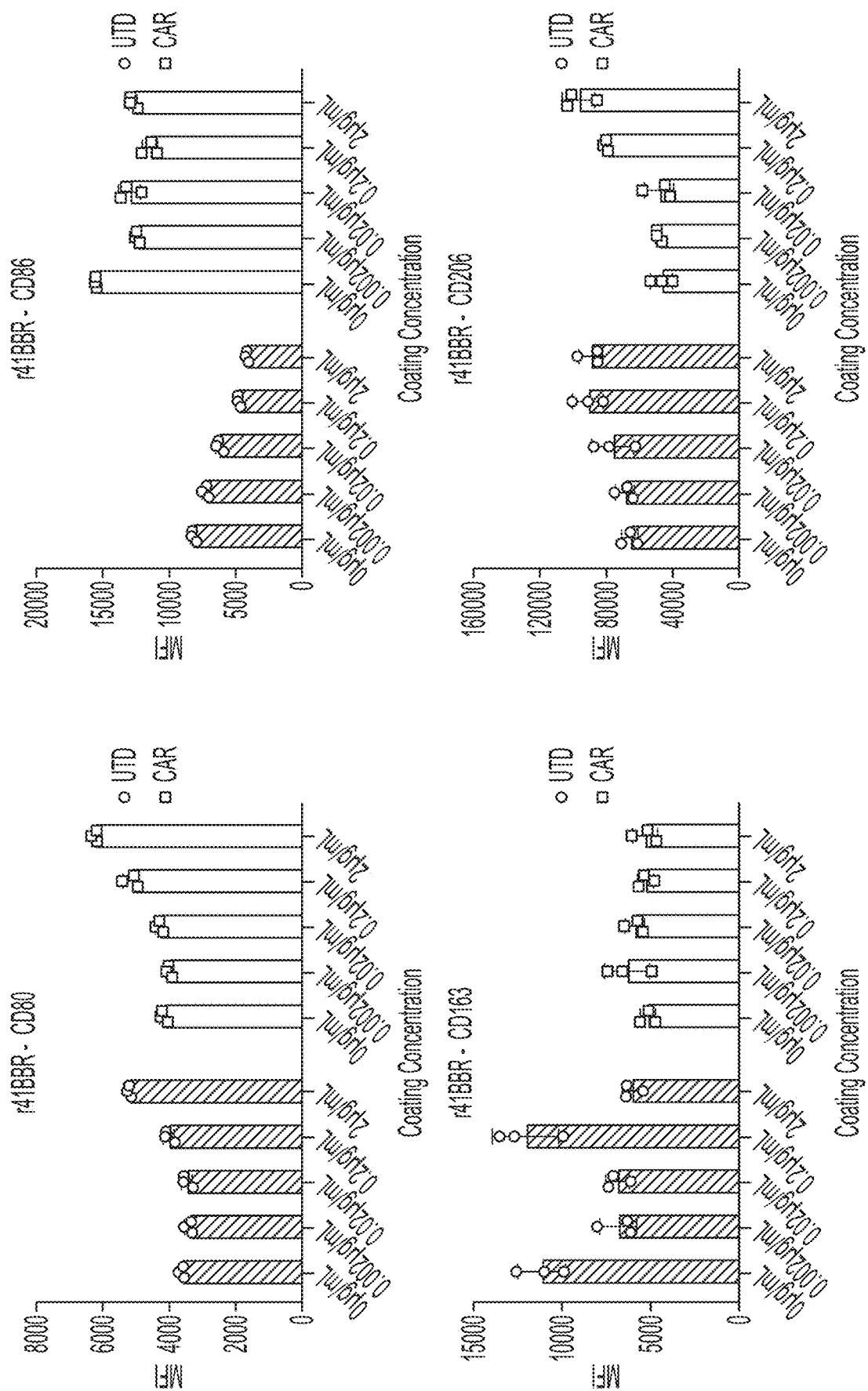
Figure 7A:
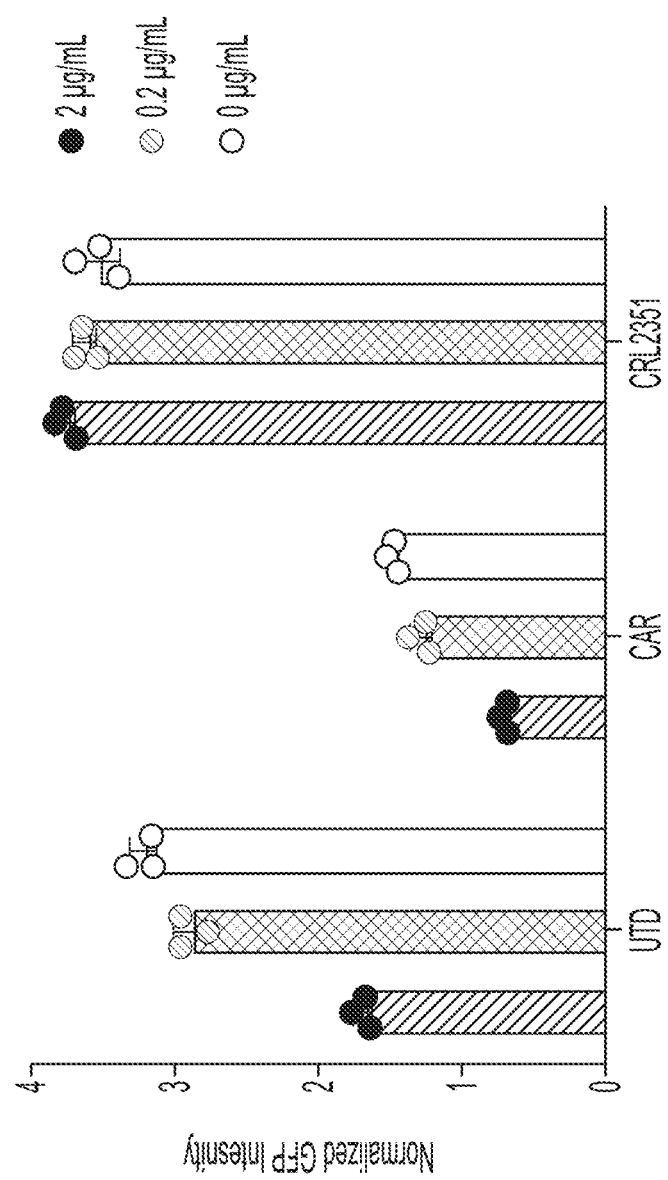
FIGS. 7A-7B are graphs showing killing ability (FIG. 7A) and induction of expression of M1 and M2 markers (FIG. 7B) after incubation of macrophages and CAR macrophages with 4-1BB ligand (4-1BBL).
Figure 7B:
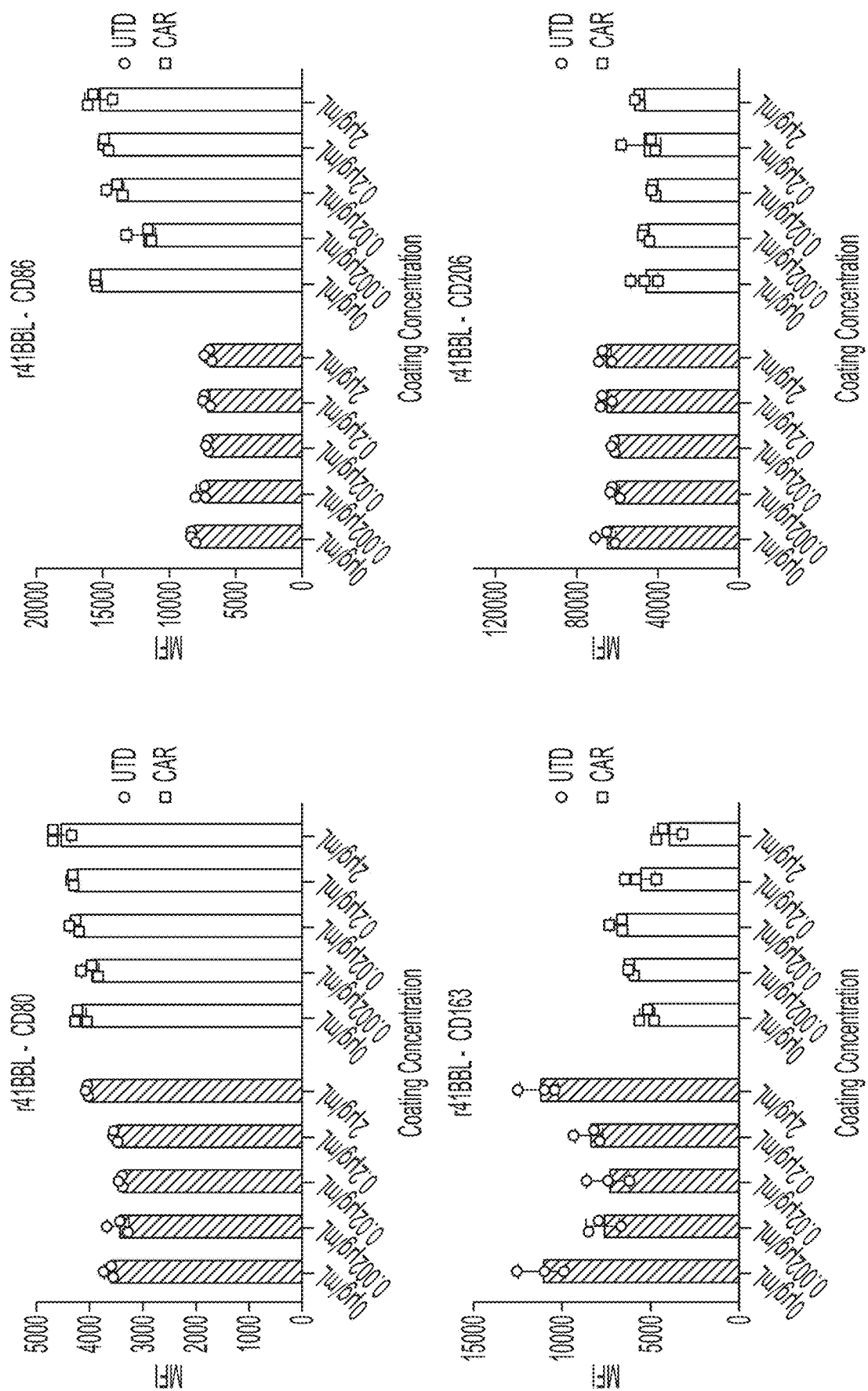

Treatment of CAR macrophages with CD40L significantly improved the tumor killing ability of macrophages and CAR macrophages (FIG. 5A). Priming with CD40L also induced an M1 phenotype in mRNA transduced CAR macrophages (FIG. 5B). Treatment with 4-1BB and 4-1BBL caused similar results, although less potent than CD40L (FIGS. 6A-6B and 7A-7B). These results indicate that pre-treatment or priming of CAR macrophages with CD40 agonists, such as CD40L, may result in increased efficacy and that a combination therapy comprising CAR macrophages with CD40 agonists may have increased efficacy.

Example 8: M1 Polarization Enhances mRNA Persistence and Macrophage/CAR-Macrophage Function Human macrophages were electroporated with HER2 CAR mRNA comprising m6AGCap1 and PsU modifications. Cells were cultured with cytokines that induce an M1 phenotype such as IFN-alpha, IFN-beta, IFN-gamma, IFN-gamma plus lipopolysaccharide (LPS), TNF-alpha, IL-6 or a STING ligand (STING-L) for up to 48 hours and then cytokines were washed off and fresh media was added. CAR expression and M1 marker expression were measured on days 2 and 7 after transfection. Fluorescent labeled HER2+ breast cancer cells (CRL2351) were co-cultured with HER2 CAR macrophages two days after the macrophages were transfected. Cancer cell growth was monitored via its fluorescence on an Incucyte® live imaging microscope every four hours. The Effector (CAR macrophage) to Target (cancer cell) ratio was 5:1.

Figure 121A:
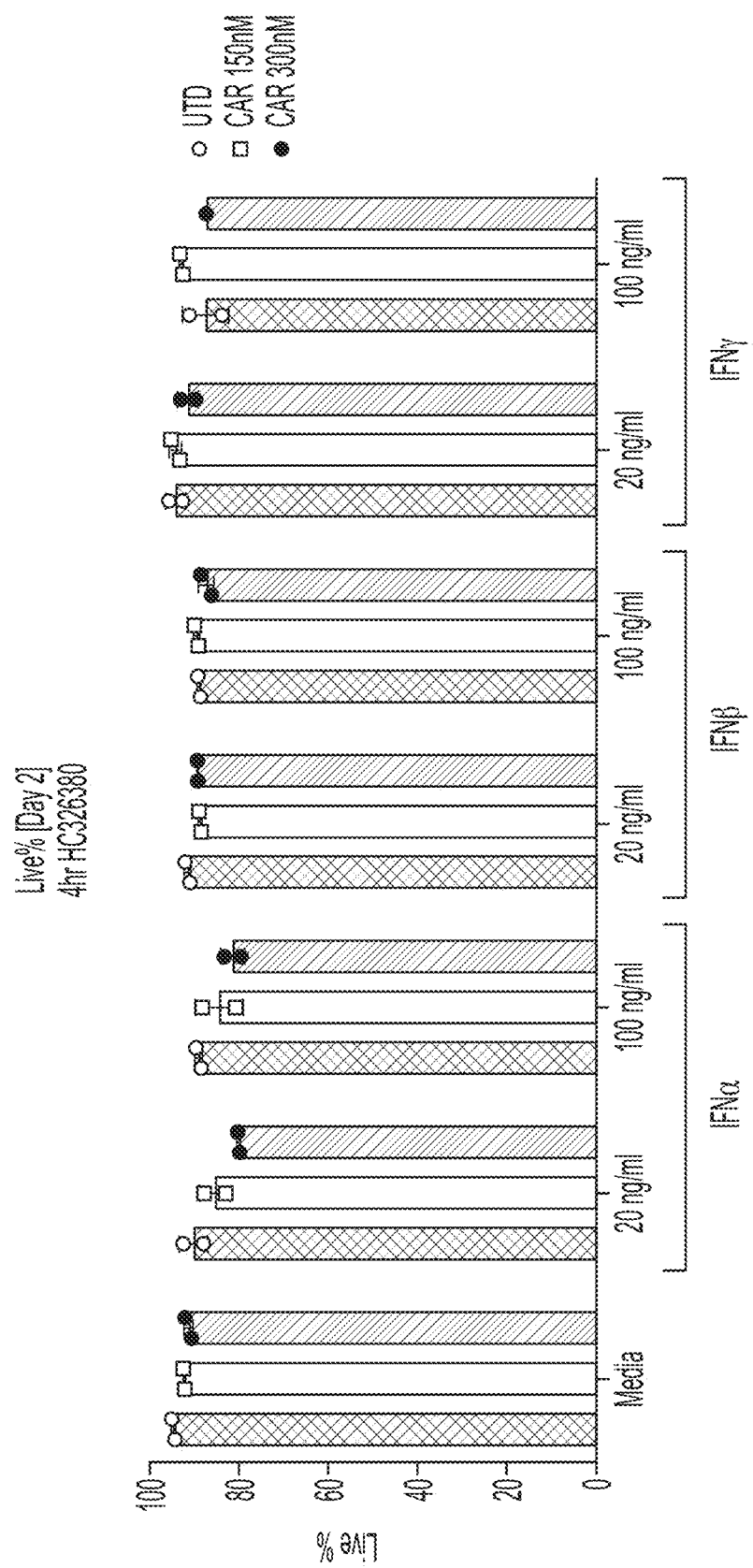
FIGS. 121A-121F show exemplary graphs illustrating CAR macrophage viability (FIG. 121A and FIG. 121C), indicated surface marker mean fluorescent intensity (FIG. 121B, FIG. 121D, FIG. 121E, and FIG. 121F) after treatment with cytokines.
Figure 121B:
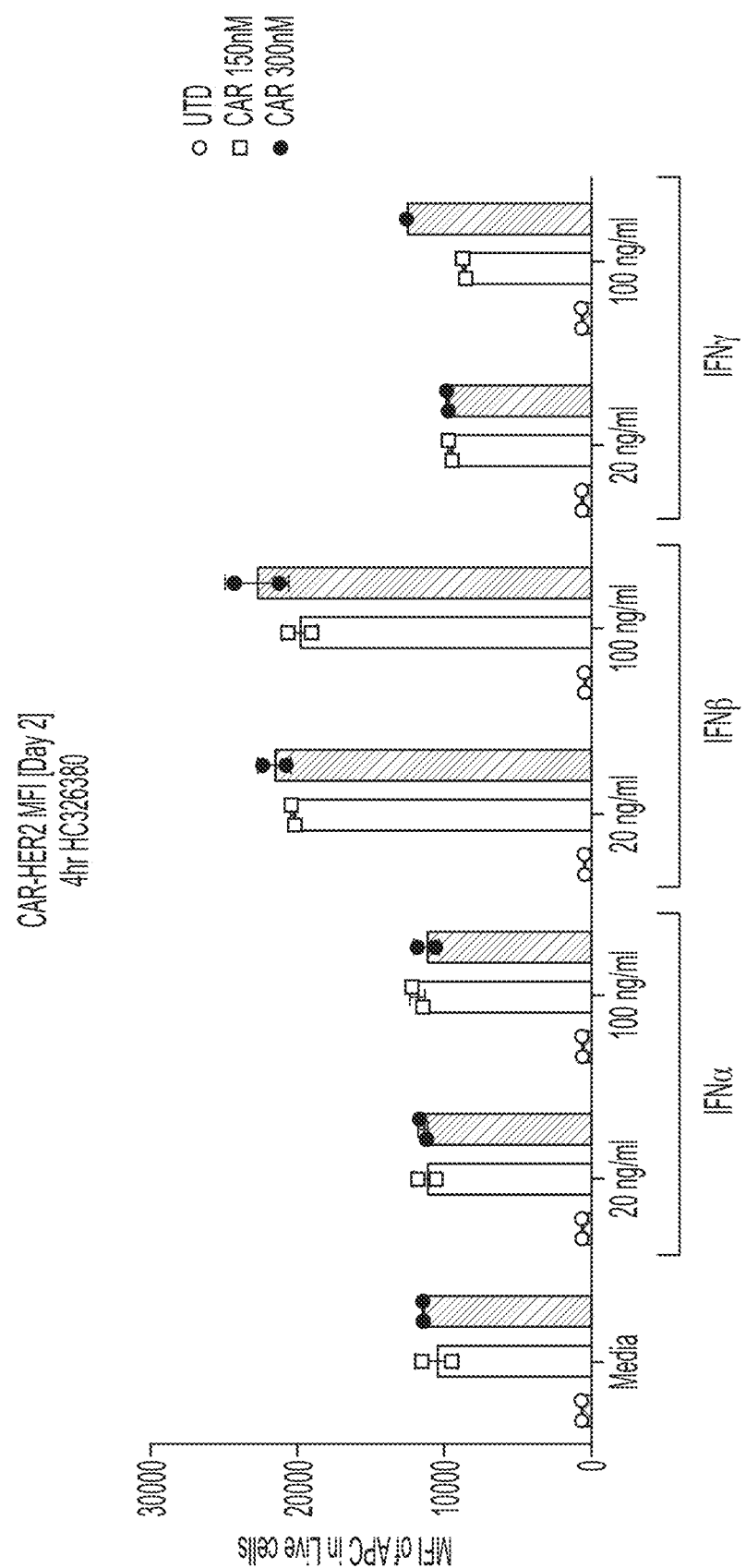
Figure 121C:
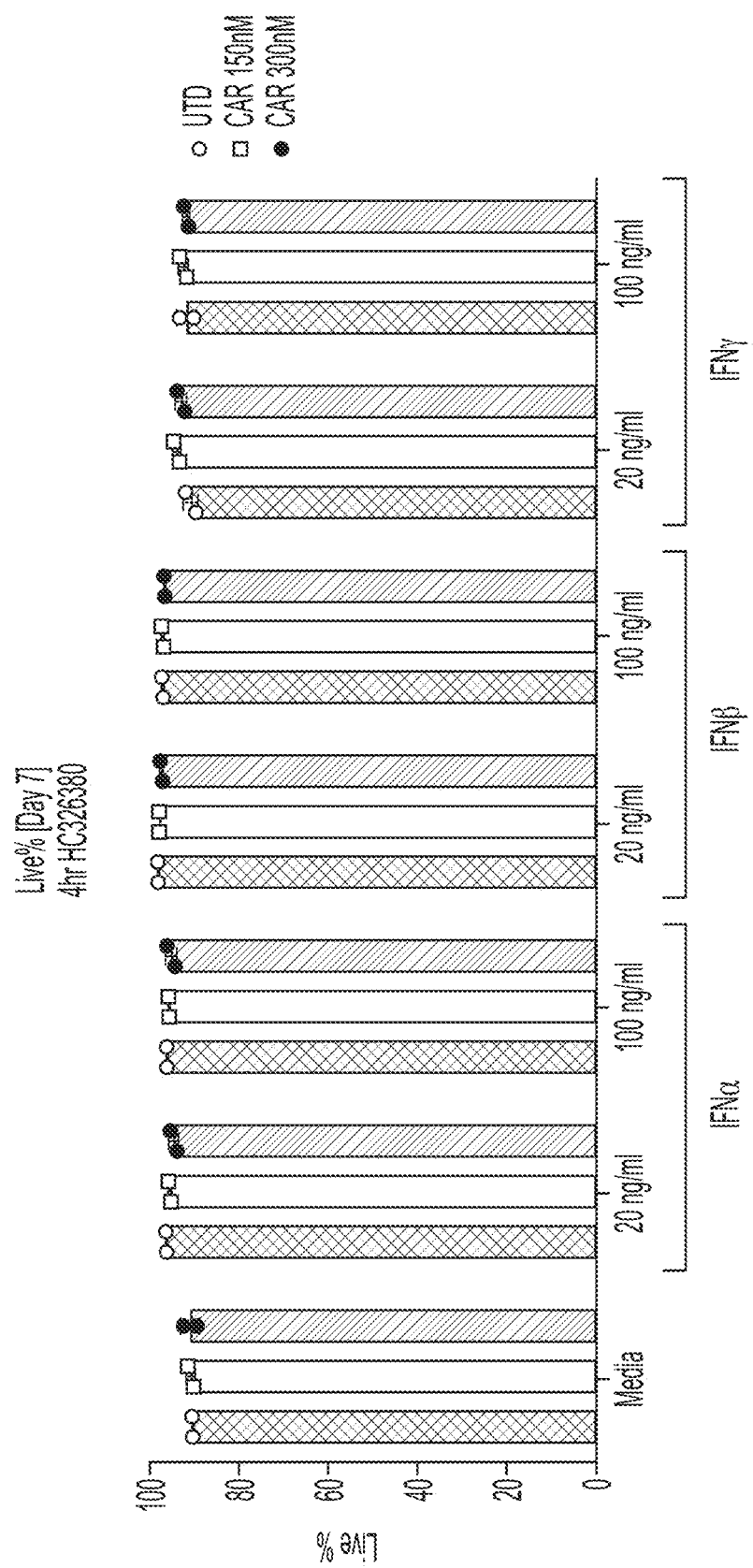
Figure 121D:
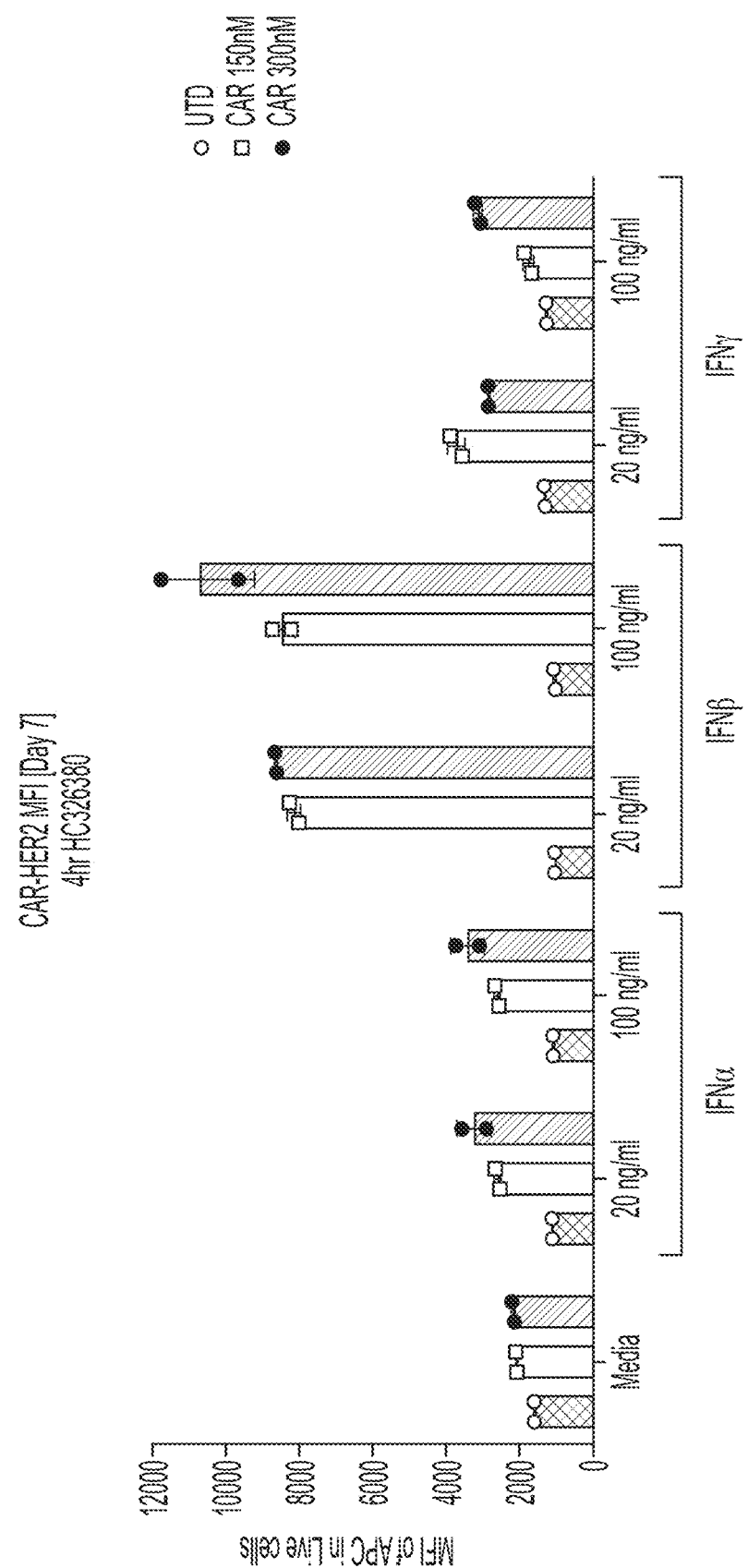
Figure 121E:
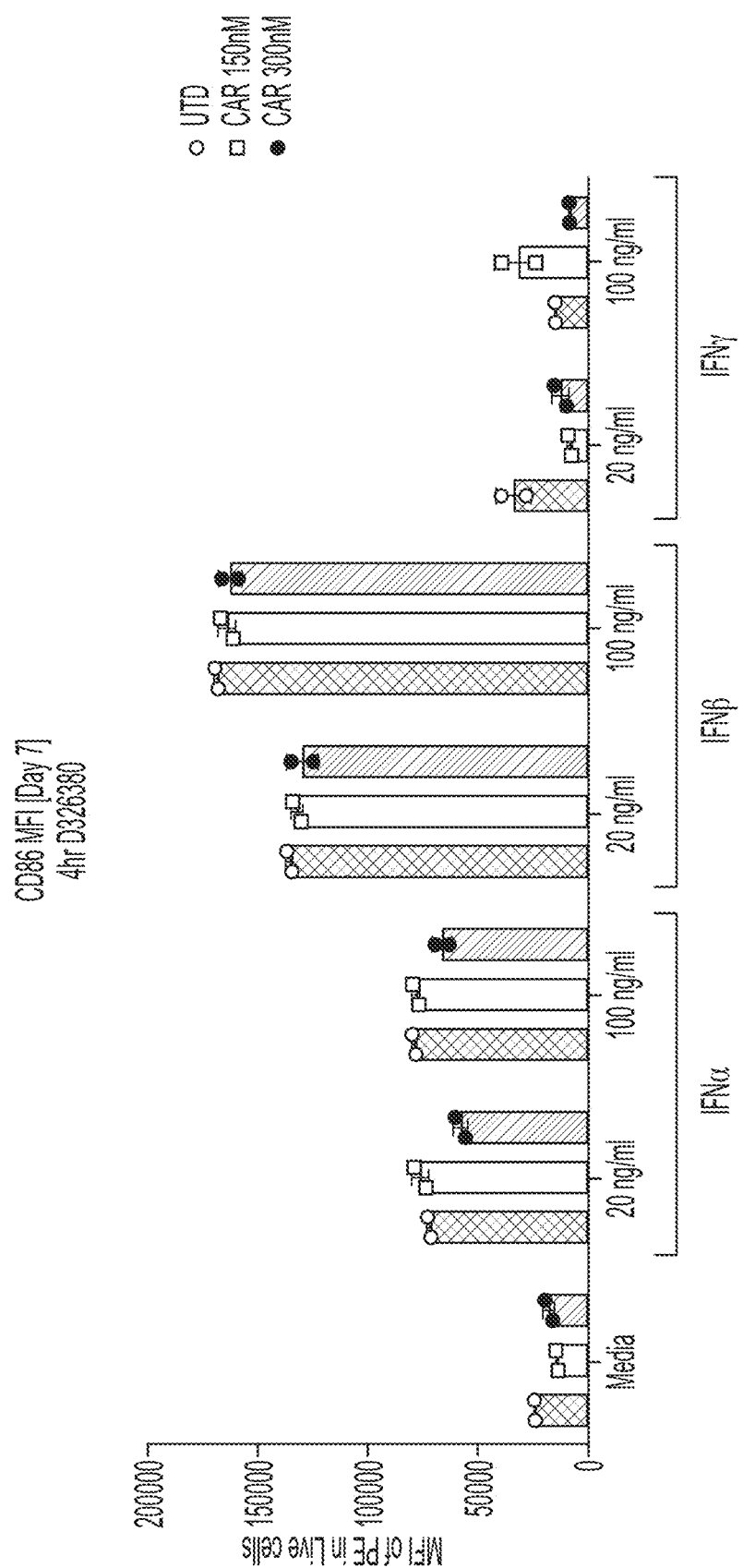
Figure 121F:
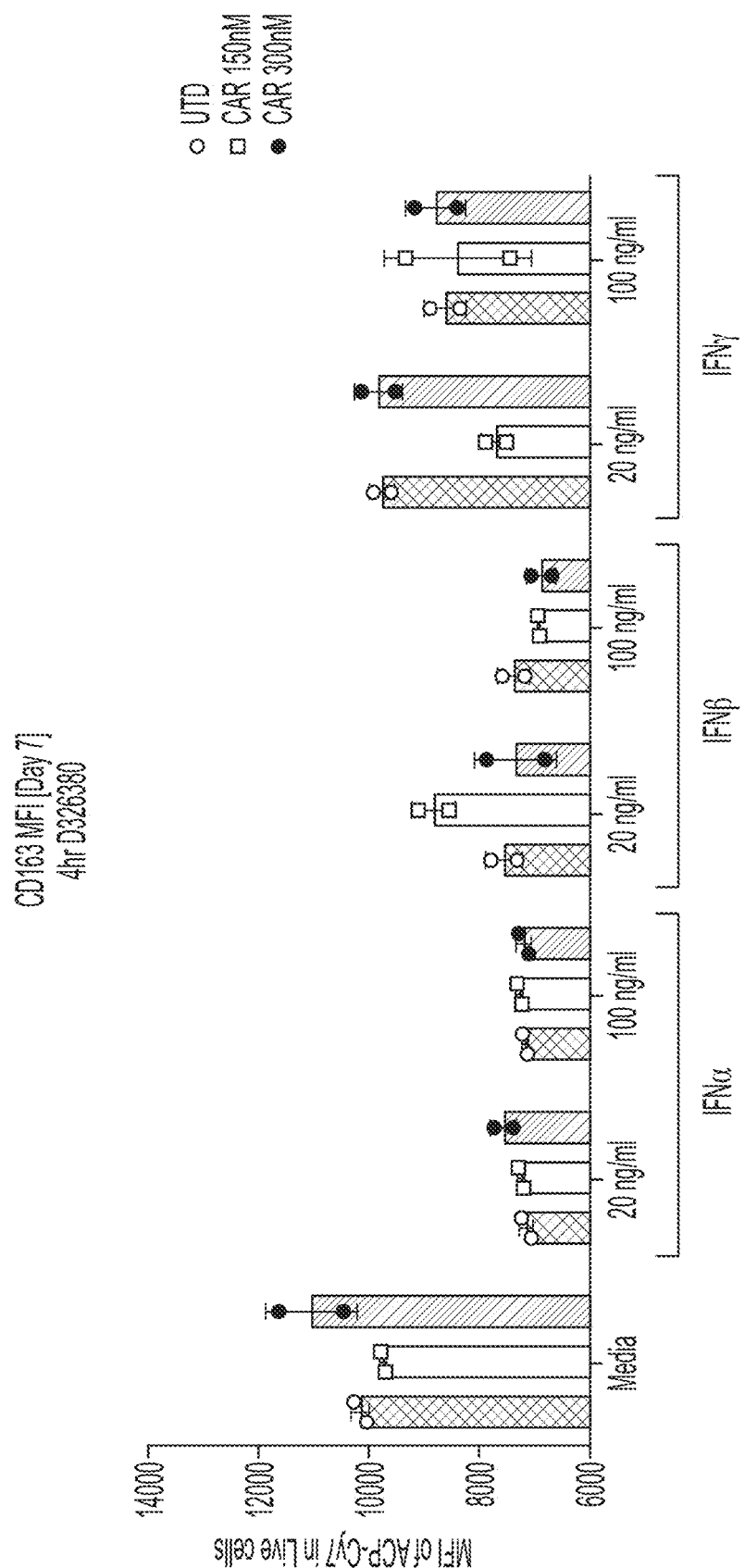

As shown in FIG. 121A, the interferon cytokines tested did not lead to lowered viability of CAR transfected macrophages on day 2. Surprisingly, macrophages treated with IFN-β demonstrated higher CAR expression than macrophages treated with control media, IFN-α or IFN-γ (FIG. 121B). As shown in FIG. 121C, treatment of macrophages with the interferon cytokines did not lead to lowered viability of CAR transfected macrophages on Day 7. Surprisingly, macrophages treated with IFN-β demonstrated higher CAR expression than macrophages treated with control media, IFN-α, or IFN-γ-demonstrating that IFN-β improves the duration of expression of mRNA encoded transgenes, such as a CAR, in human macrophages (FIG. 121D). Additionally, treatment of mRNA transfected CAR macrophages with IFN-α, IFN-β, or IFN-γ led to induction of an M1 phenotype (based on CD86 expression; FIG. 121E) and reduction of M2 markers (based on CD163 expression; FIG. 121F). IFN-β led to the strongest M1 phenotype of the interferons evaluated, and the M1 phenotype persisted for at least 7 days post treatment (FIG. 121E).

Example 9: Effect of IFN Treatment on CAR Expression, CAR Macrophage Function, M1 Phenotype Markers and Cytokine Production Five different mRNA modifications were also tested to determine if interferon treatment differentially affected macrophages transfected with mRNA comprising different modifications. Human macrophages were electroporated with HER2 CAR mRNA comprising different mRNA modifications. CAR expression and M1 markers were detected by Flow Cytometry (Attune) on day four after electroporation. Day 4 CAR macrophage cells were then co-cultured with a Nuc-Light labeled, HER2+ breast cancer cell line (CRL2351) at an Effector (CAR macrophage) to Target (cancer cell) ratio of 5:1. Cancer cell growth was monitored via its fluorescence on an Incucyte® live imaging microscope every four hours.

Figure 122:
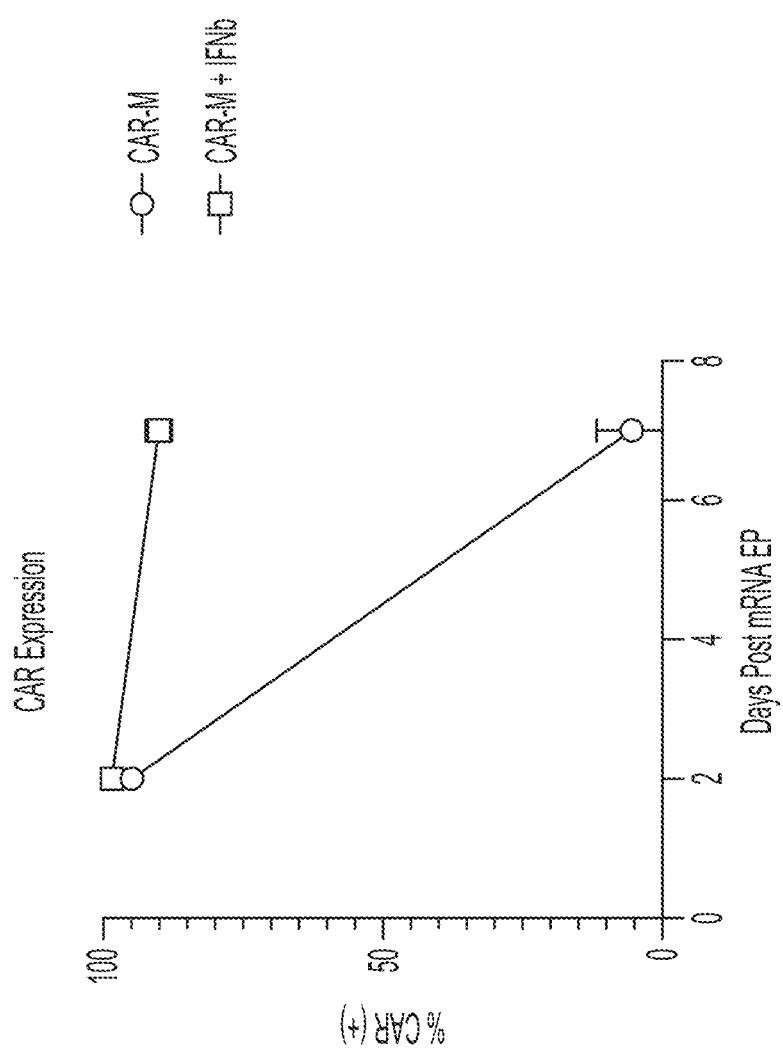
FIG. 122 shows an exemplary graph illustrating persistence of CAR expression in macrophages treated with an interferon cytokine.

To further evaluate the impact of IFN-β on CAR persistence, human macrophages electroporated with m6AGCap1/PsU mRNA encoding a HER2 CAR were evaluated on day 2 and day 7. IFN-β treatment led to a significantly improved CAR expression rate on day 7 as compared to CAR macrophages not treated with IFN-β (FIG. 122).

Figure 123A:
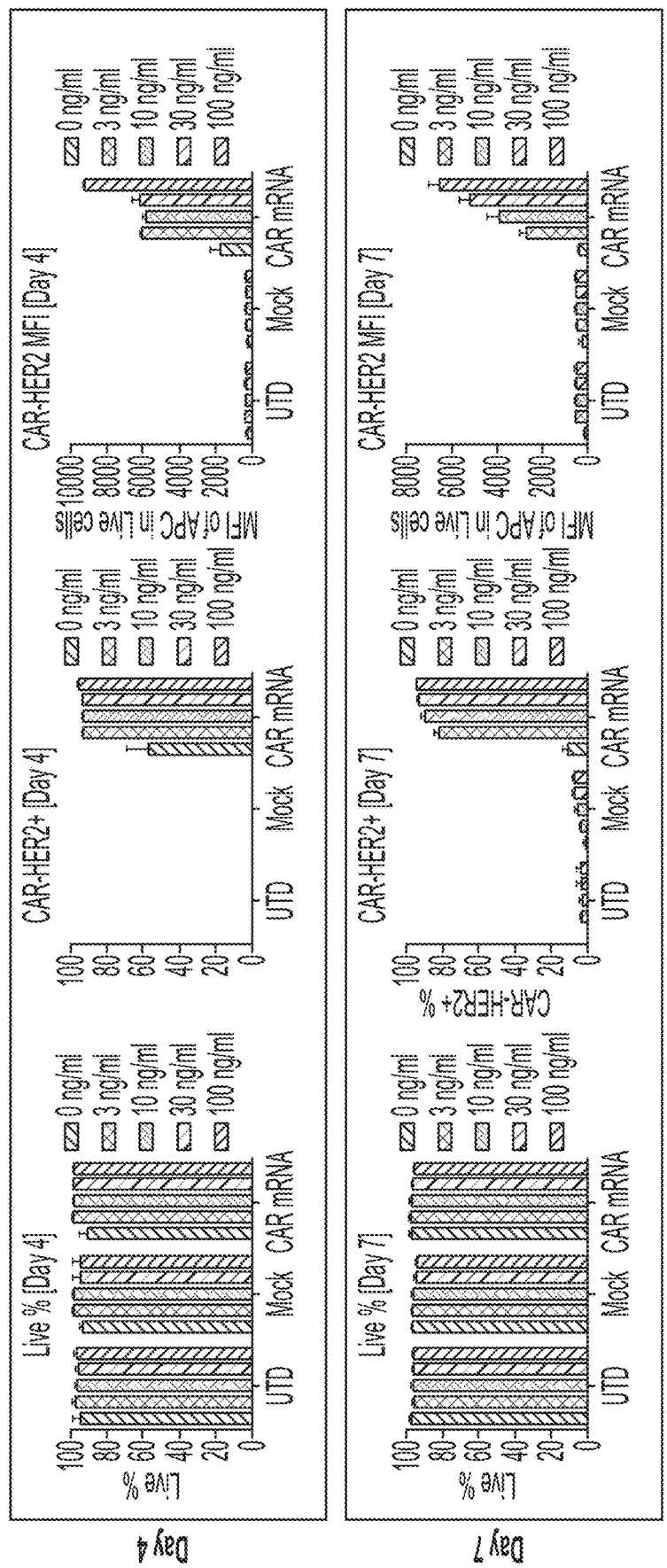
FIGS. 123A and 123B show exemplary graphs illustrating CAR macrophage viability, CAR expression and mean fluorescent intensity (FIG. 123A) and induction of M1 markers (FIG. 123B) after transfection with CAR mRNA and treatment with a variety of IFN-concentrations.
Figure 123B:
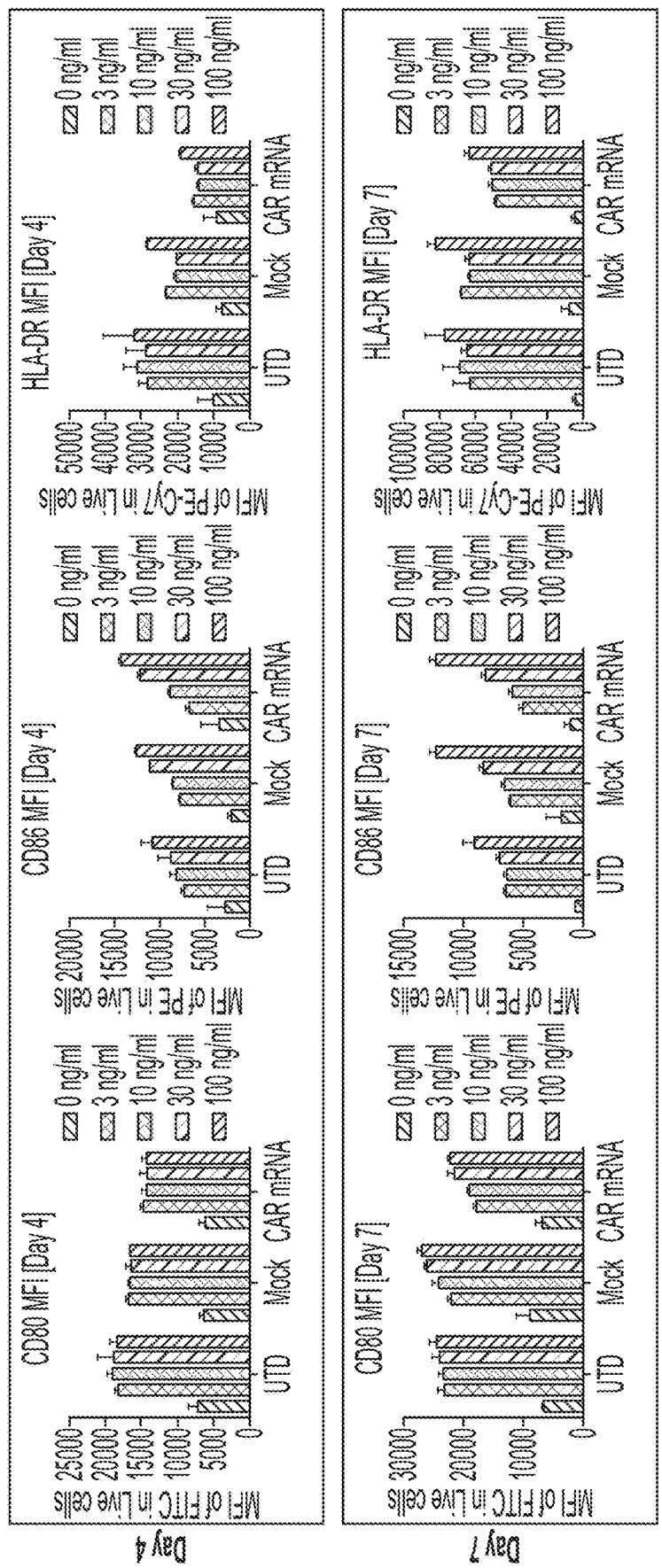

In order to validate the effect of IFN-β treatment on improved CAR expression, and to optimize the IFN-β concentration, macrophages transfected with M6AGCap1/PsU modified mRNA were treated with 0, 3, 10, 30, or 100 ng/mL IFN-β for 4 hours and the viability, CAR percentage, and CAR MFI were evaluated on day 4 and day 7 post electroporation. A dose-dependent effect of IFN-β on CAR expression by human macrophages was observed (FIG. 123A). As described in Example 4, treatment of CAR macrophages with IFN-β induced an M1 phenotype, so further experiments were performed to determine if the effect was dose dependent. As shown in FIG. 123B, induction of M1 markers CD80, CD86, and HLA-DR was IFN-β dose-dependent.

Figure 124A:
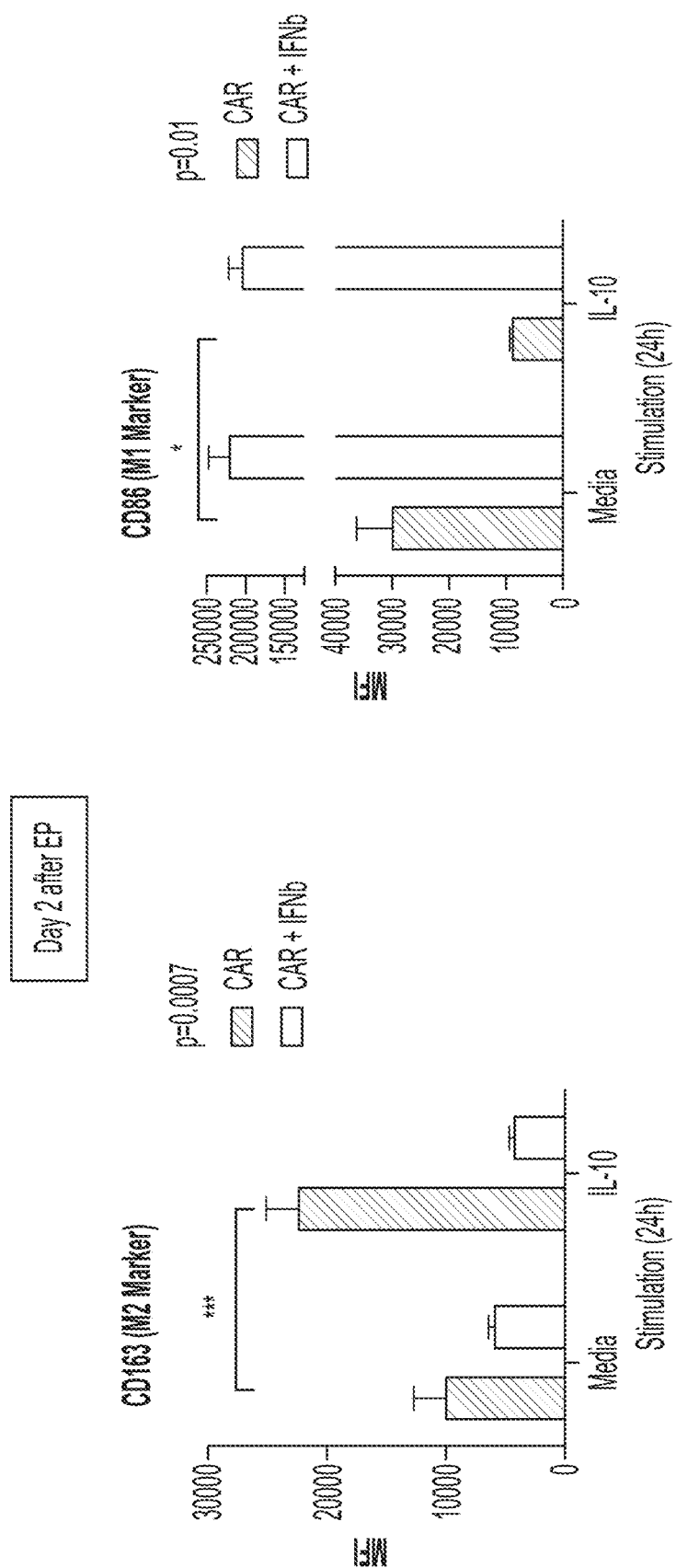
FIGS. 124A and 124B show exemplary graphs illustrating CAR macrophage M2 and M1 marker mean fluorescent intensity two days (FIG. 124A) or seven days (FIG. 124B) after electroporation with CAR mRNA and treatment with IFN-β.
Figure 124B:
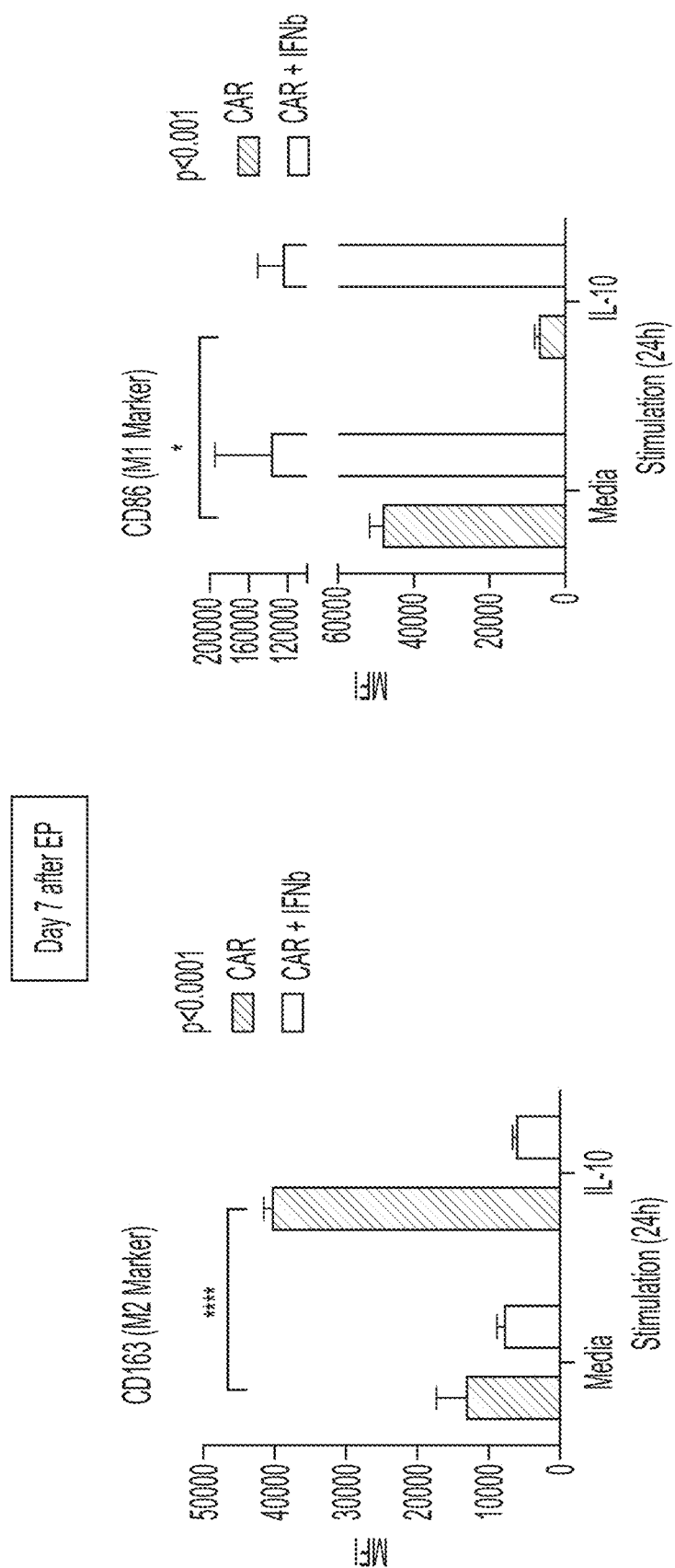

Given that macrophage phenotype is considered plastic, and immunosuppressive cytokines such as IL-10 are known to induce an M2 phenotype, the impact of IL-10 treatment on IFN-β treated or untreated HER2 CAR mRNA transfected macrophages was evaluated. IFN-β treated CAR macrophages resisted the effects of IL-10 and did not express the M2 marker CD163, while instead retaining expression of the M1 marker CD86 48 hours post-treatment (FIG. 124A) and 7 days post-treatment with IL-10 (FIG. 124B). IFN-β primed CAR macrophages resisted other M2 inducing factors as well.

Figure 125A:
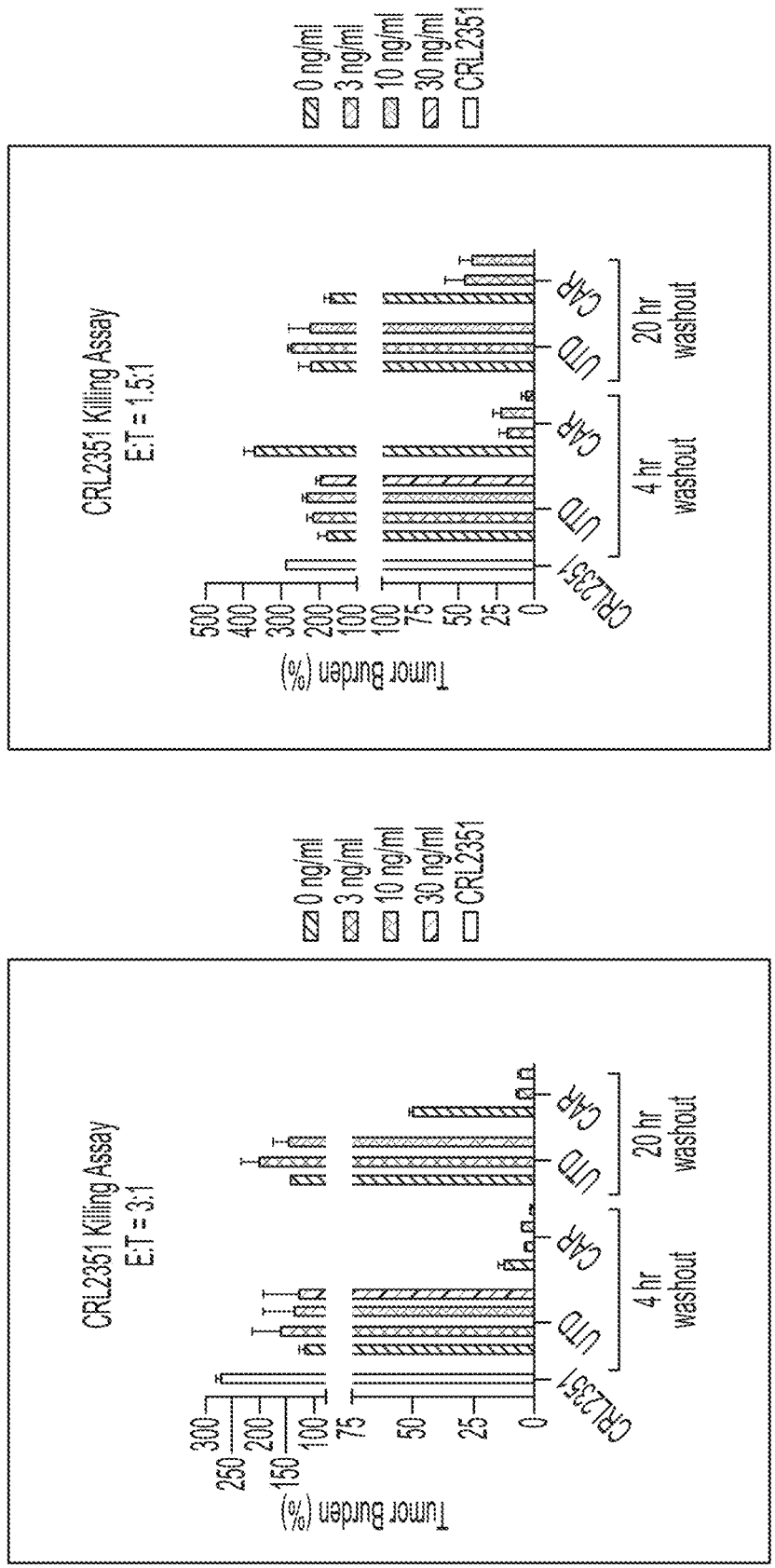
FIGS. 125A-125C show exemplary graphs illustrating anti-tumor function of CAR macrophages.
Figure 125B:
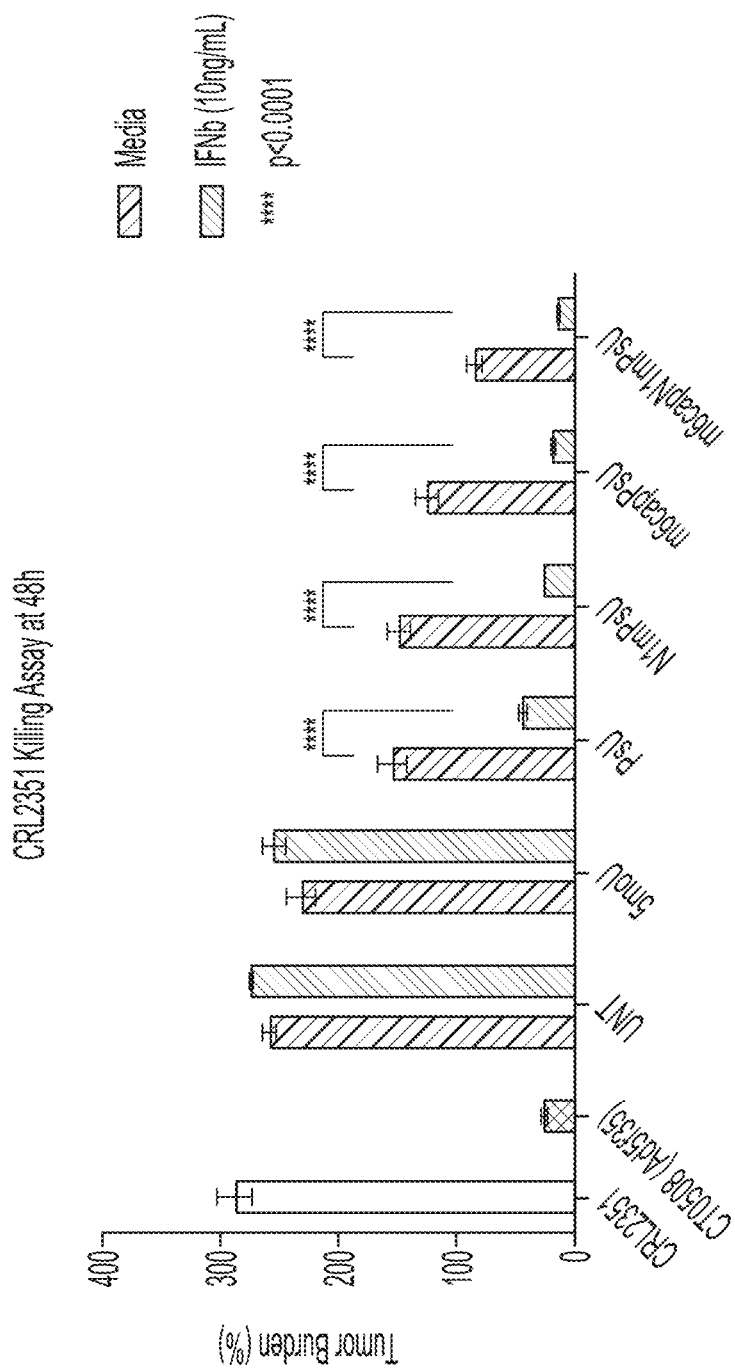
Figure 125C:
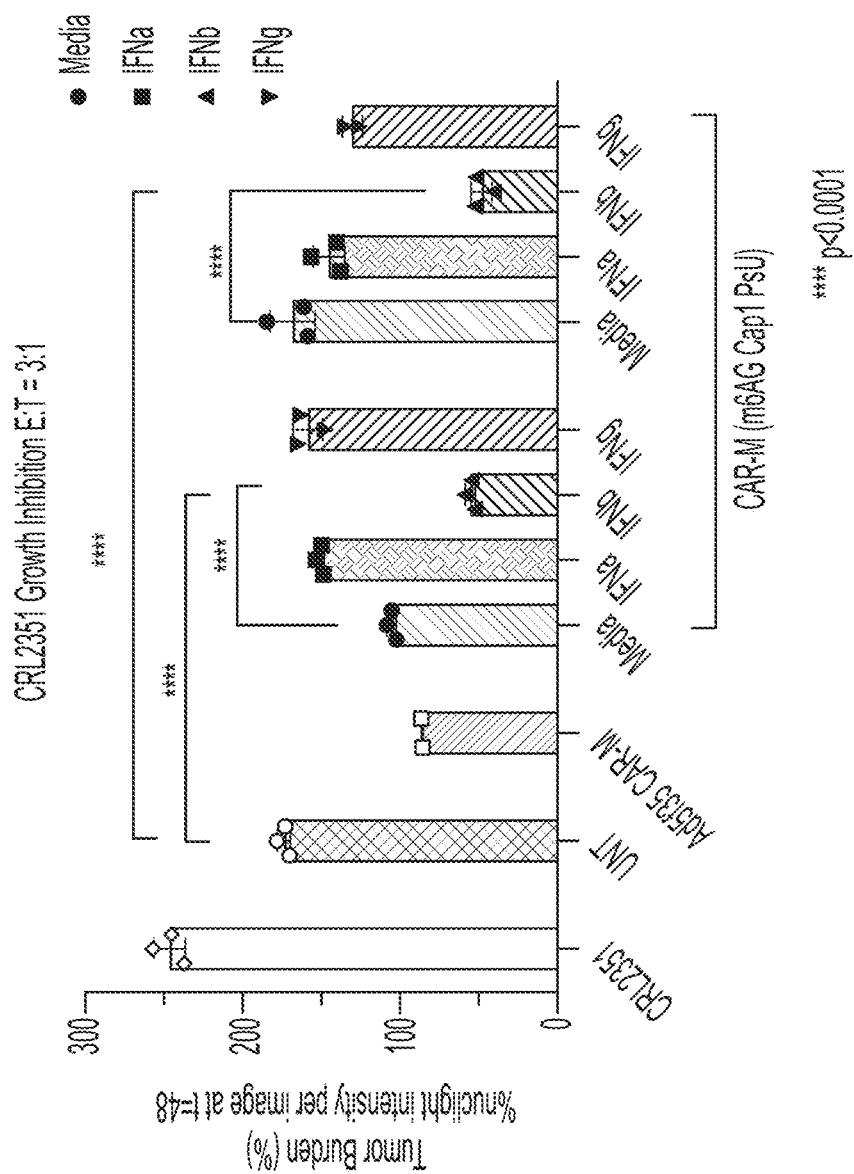

To evaluate the anti-tumor function of macrophages transfected with mRNA encoding a HER2 CAR with or without priming with IFN-β, untransduced (UTD) or CAR macrophages were primed with 0, 3, 10, 30, or 100 ng/mL IFN-β for 4 hours or 20 hours. These effector cells were then co-cultured with the HER2+ breast cancer cell line CRL2351-GFP at an effector to target ratio of 3:1 or 1.5:1 and anti-tumor activity was measured based on GFP expression using an Incucyte® live imaging microscope. IFN-β priming led to an improved ability for CAR macrophages to kill cancer cells (FIG. 125A). To evaluate whether IFN-β treatment improved CAR macrophage anti-tumor activity with mRNAs comprising modifications, the anti-tumor activity of macrophages electroporated with mRNA comprising unique modifications with or without IFN-β treatment was evaluated. IFN-β treatment led to improved anti-tumor activity for all CAR macrophages except those transfected with 5moU mRNA (FIG. 125B). To evaluate whether the improved mRNA-transfected CAR macrophage anti-tumor effect was universal to all interferons or only interferon beta, macrophages electroporated with M6AGCap1/PsU mRNA were treated with IFN-alpha, beta, or gamma and evaluated for their cancer cell killing ability. CAR macrophages treated with IFN-β led to the best cancer cell killing, with a greater effect than IFN-α or IFN-γ (FIG. 125C).

Figure 126:
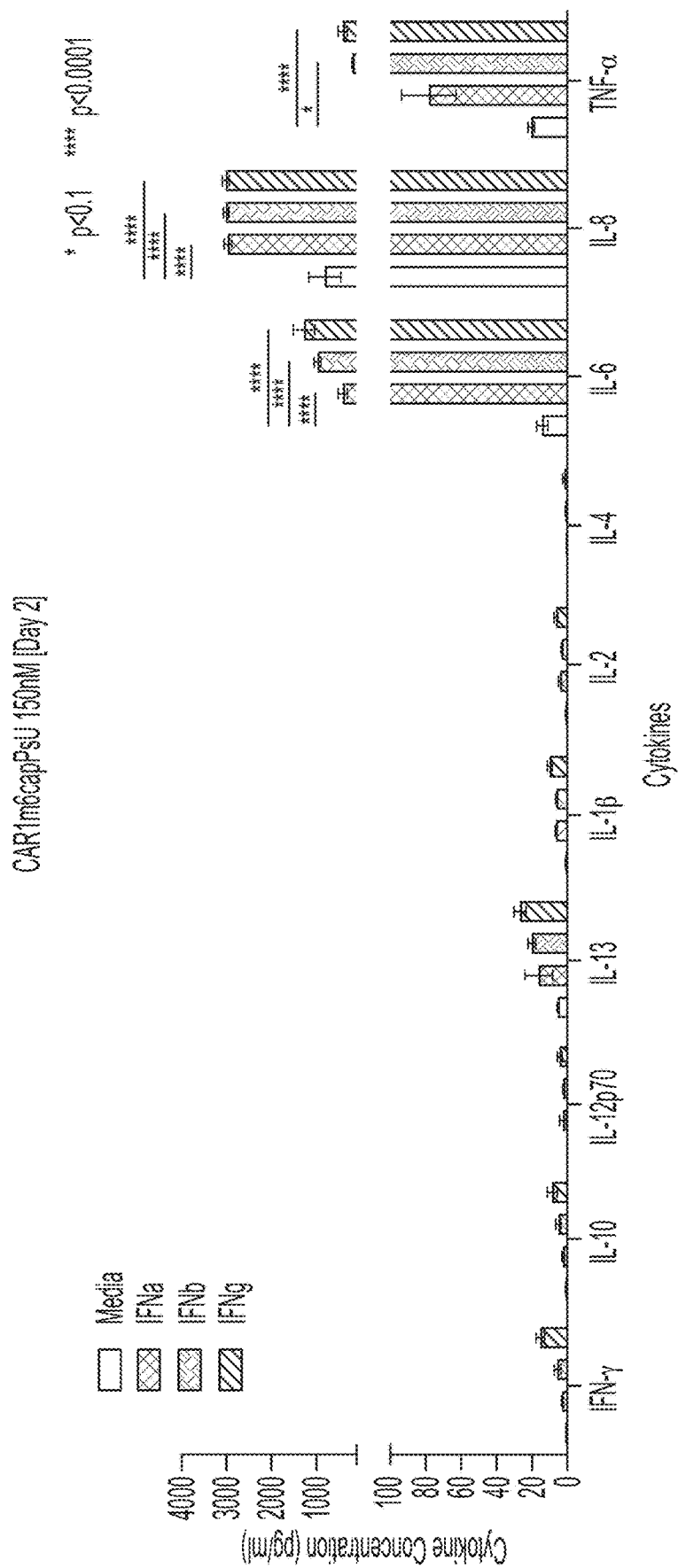
FIG. 126 shows an exemplary graph illustrating an effect of treating CAR macrophages with interferons on cytokine secretion.

To evaluate whether interferon treatment of macrophages improved other anti-tumor functions, the cytokine secretion of interferon treated or untreated mRNA transfected HER2 CAR macrophages after co-culture with HER2+ breast cancer cells was evaluated. Human macrophages were electroporated with 150 nM HER2 CAR mRNA comprising m6AGCap1 and PsU modifications. HER2+ breast cancer cells (CRL2351) were co-cultured with CAR macrophages after the macrophages were transfected with the CAR mRNA at an Effector (CAR macrophage) to Target (cancer cell) ratio of 3:1. Supernatant was collected 48 hours after the cancer cells and macrophages were co-cultured and cytokine levels were measured using a Meso Scale Discovery (MSD) instrument. As shown in FIG. 126, treatment of macrophages with IFN-α, IFN-0, or IFN-γ led to increased secretion of the cytokines IL-6, IL-8 and TNFα from the macrophages.

Additional studies were performed to determine if treatment with interferons could further improve CAR mRNA persistence in macrophages and if CAR macrophage functionality could be extended. Human macrophages were electroporated with 300 nM CAR mRNA comprising m6AGCap1 and PsU modifications. Cells were cultured with 20 ng/mL IFNs for 24 hours and then the cells were washed to remove cytokines. CAR expression was detected by Flow Cytometry (Attune) on day 2 after transfection. Cells were then co-cultured with a Nuc-Light labeled, HER2+ breast cancer cell line (CRL2351) at the Effector to Target ratio of 3:1. Cancer cell growth was monitored via its fluorescence on an Incucyte® live imaging microscope. CAR expression and M1 markers in macrophages were detected by Flow Cytometry (Attune) on day 7 after transfection.

Figure 127A:
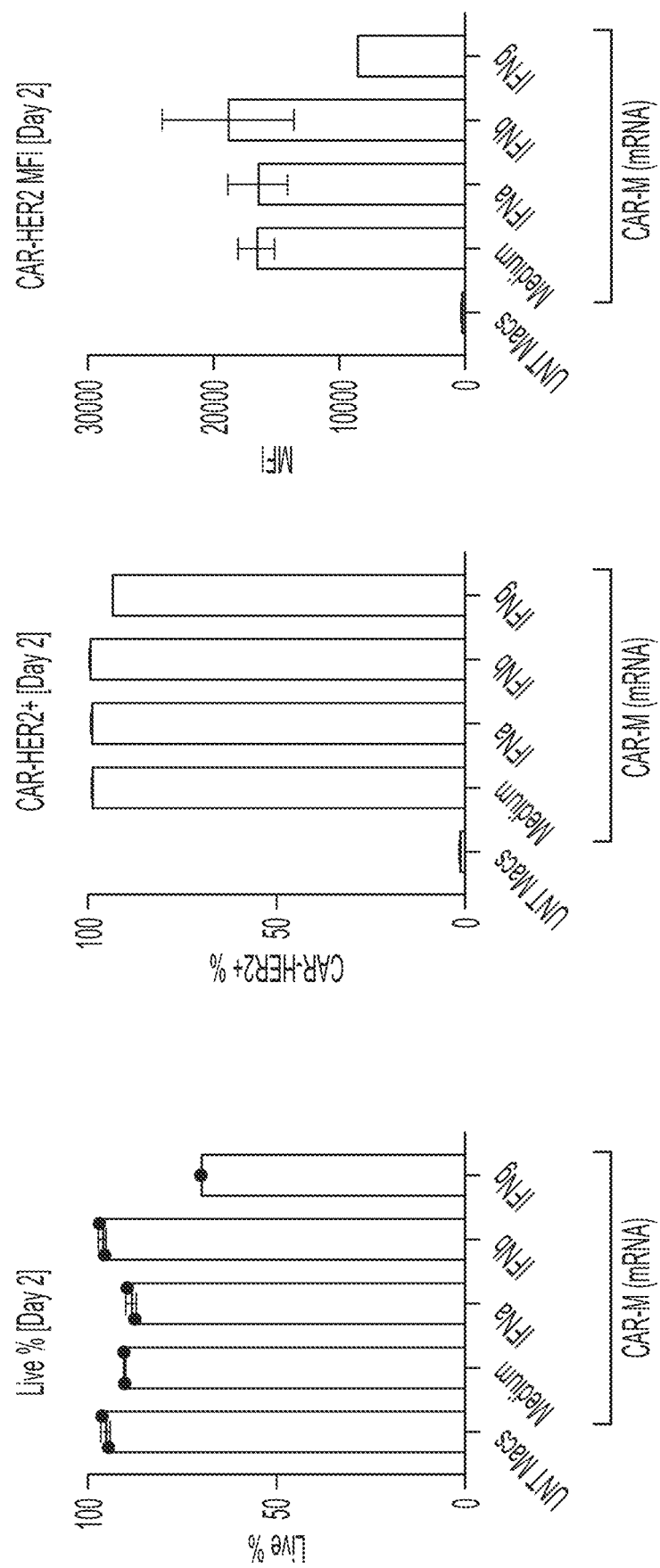
FIGS. 127A-127C show exemplary graphs illustrating an effect of treatment with interferons on CAR mRNA persistence in macrophages and duration of CAR macrophage functionality.
Figure 127B:
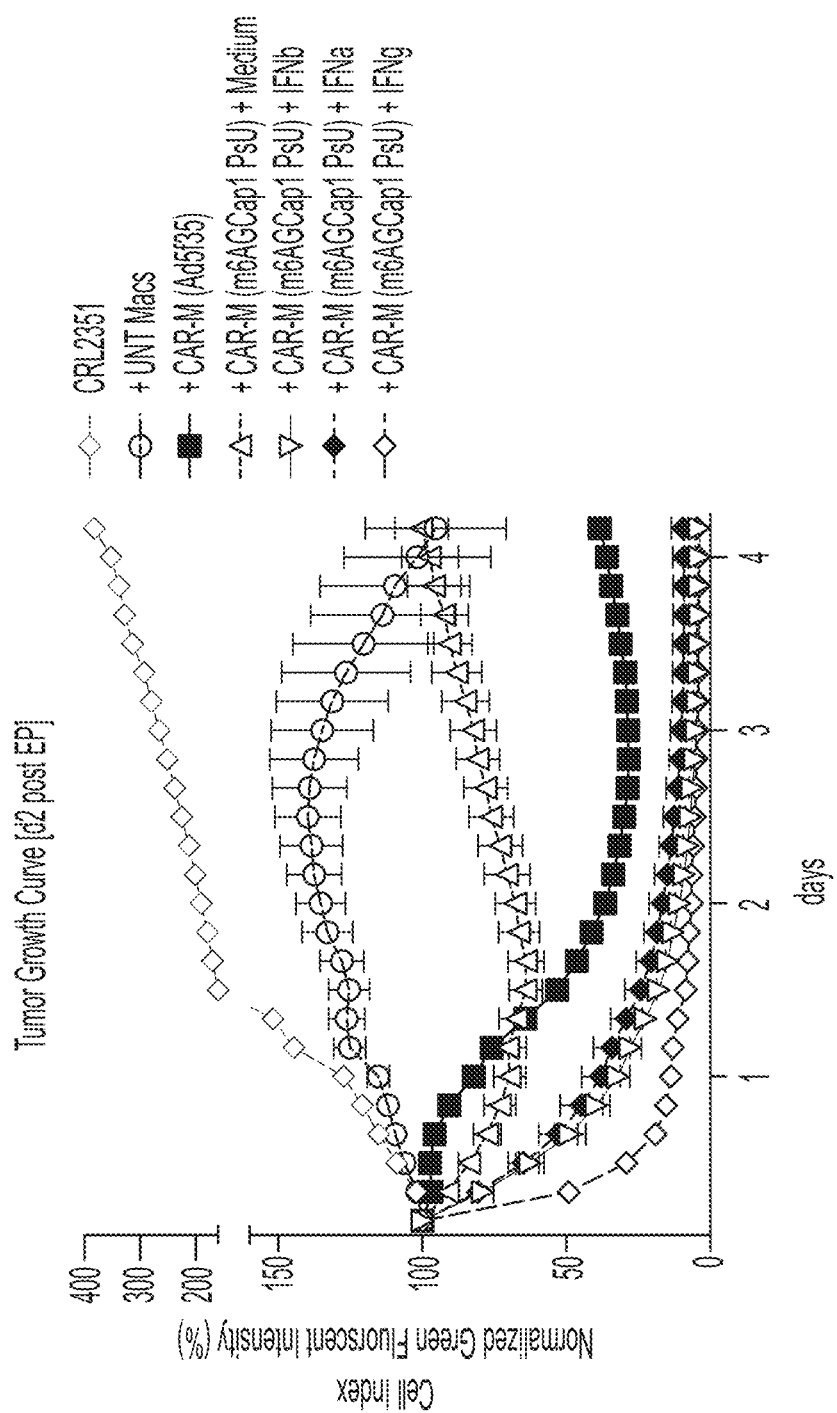
Figure 127C:
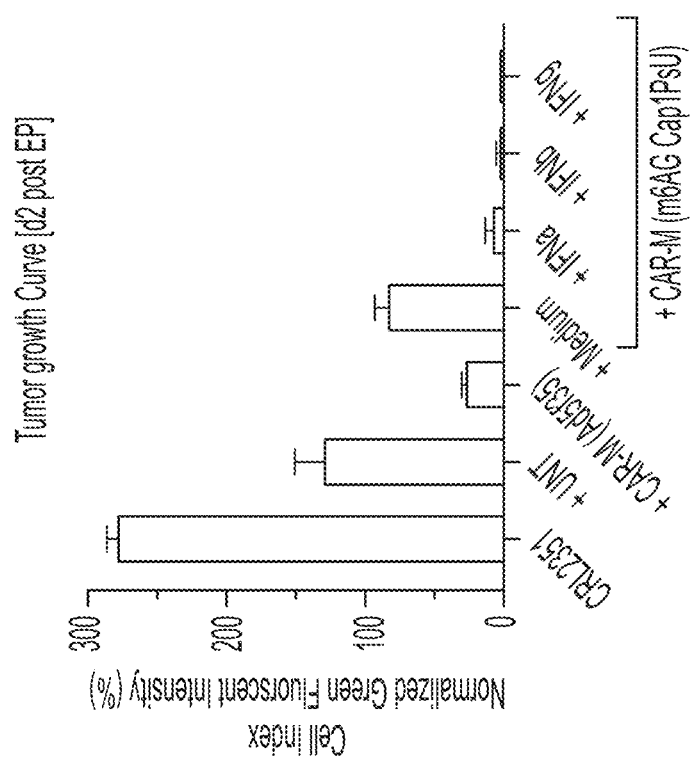

As shown in FIG. 127A, two days after transfection with CAR mRNA, CAR macrophage viability and CAR expression were very high except in macrophages that had been treated with IFN-γ. Additionally, as shown in FIG. 127B and FIG. 127C, IFN treatment enhanced the target cell killing activity of CAR macrophages. FIG. 127C shows target cell killing after cancer cells and macrophages had been co-cultured for 72 hours. Treatment with IFN also impacted macrophage viability, CAR expression, M1 marker expression, and CAR macrophage functionality. As shown in FIG.

Figure 128A:
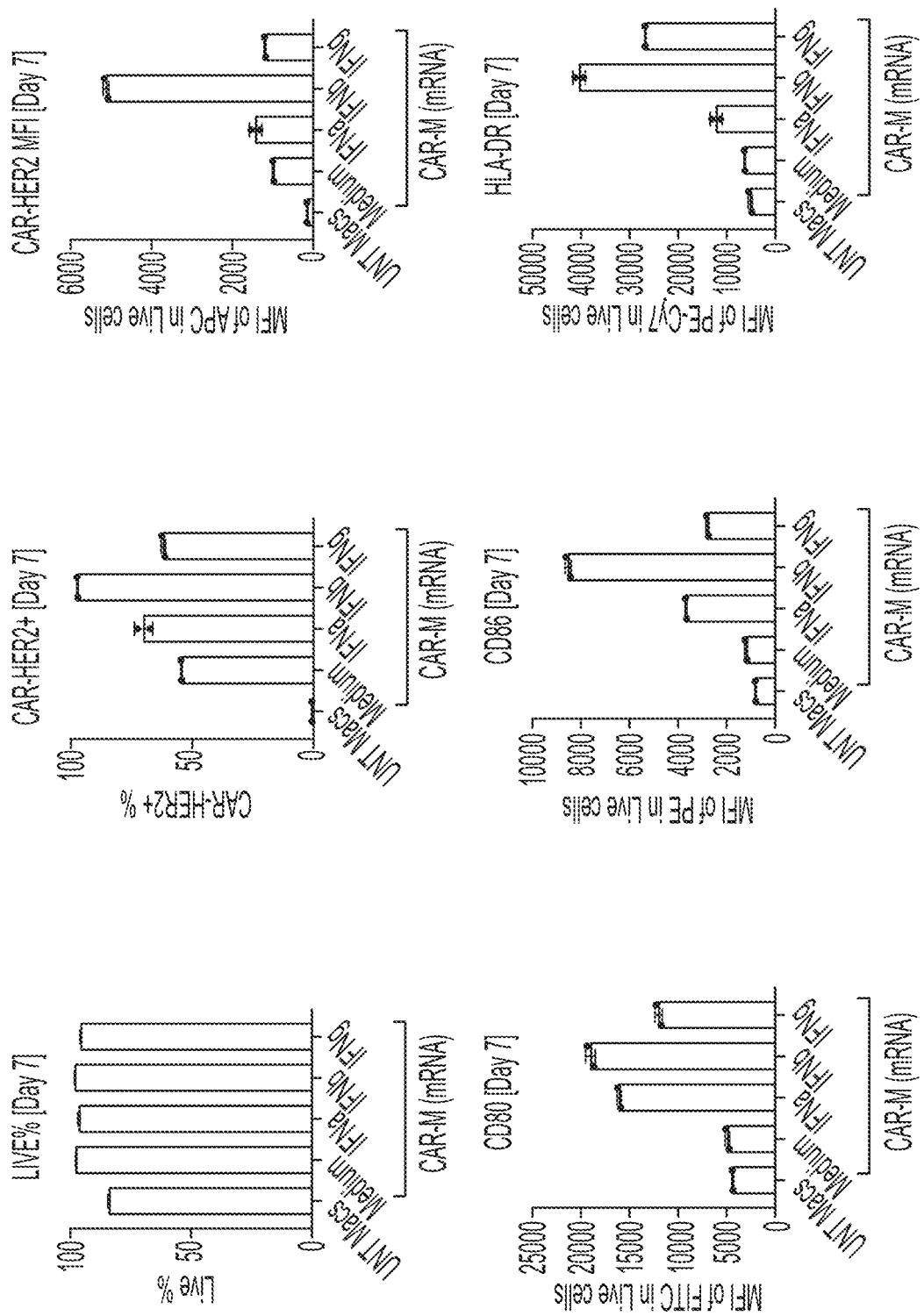
FIGS. 128A-128C show exemplary graphs illustrating an effect of treatment with interferons on macrophage viability, CAR expression, M1 marker expression, and CAR macrophage functionality.
Figure 128B:
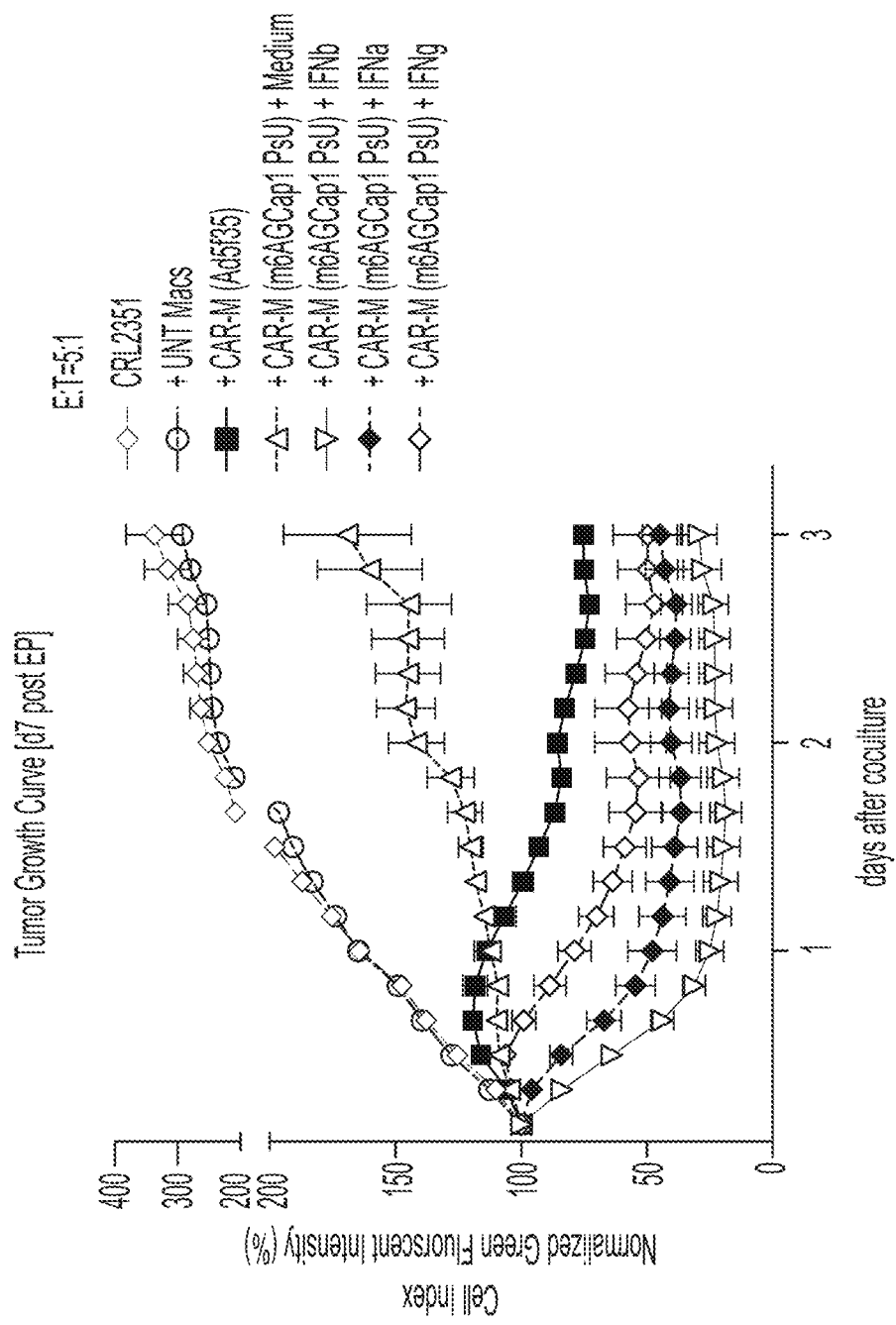
Figure 128C:
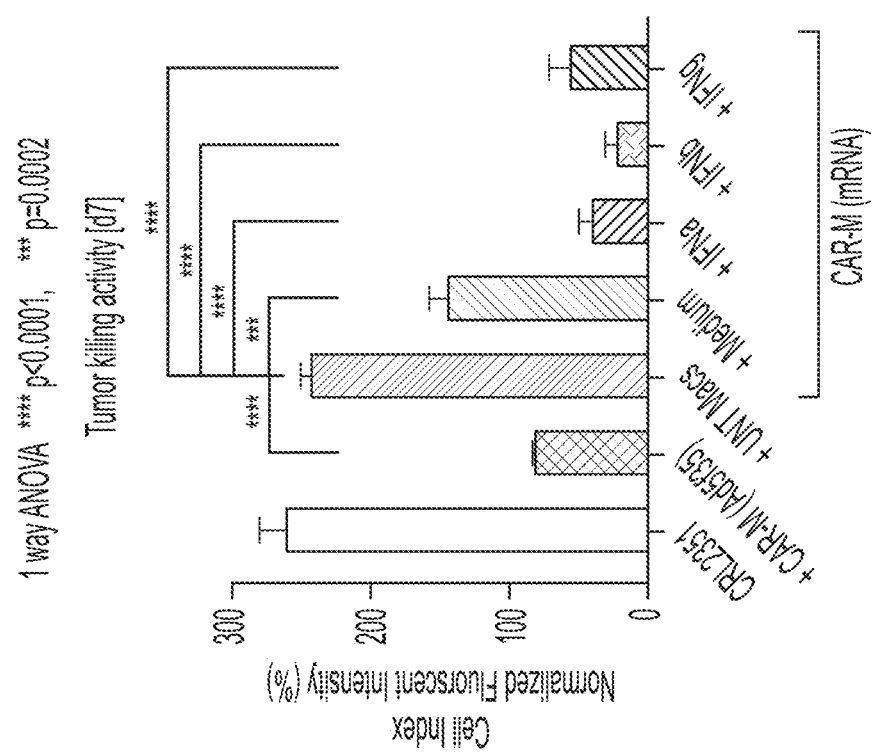

128A, treatment of transfected macrophages with IFN-β lead to increased cell viability, HER2 CAR expression and expression of M1 markers CD80, CD86 and HLA-DR relative to macrophages that hadn't been treated with an interferon at the later day 7 timepoint. FIG. 128A shows that all macrophages had high viability at day 7, but IFN-β treated macrophages expressed the highest level of CAR by a significant margin. FIG. 128B shows that out of all CAR macrophages that were tested in a cancer cell killing assay 7 days post-electroporation, those treated with IFN-β led to the highest level of cancer killing (greatest decrease in tumor growth). Seven days after macrophages were electroporated, they were co-cultured with target cancer cells for 72 hours. As shown in FIG. 128C, all interferons improved the cancer cell killing activity of CAR macrophages compared to CAR macrophages that weren't treated with an interferon.

Example 10: Transfected Macrophages are Sensitive to IFNγ

Figure 129:
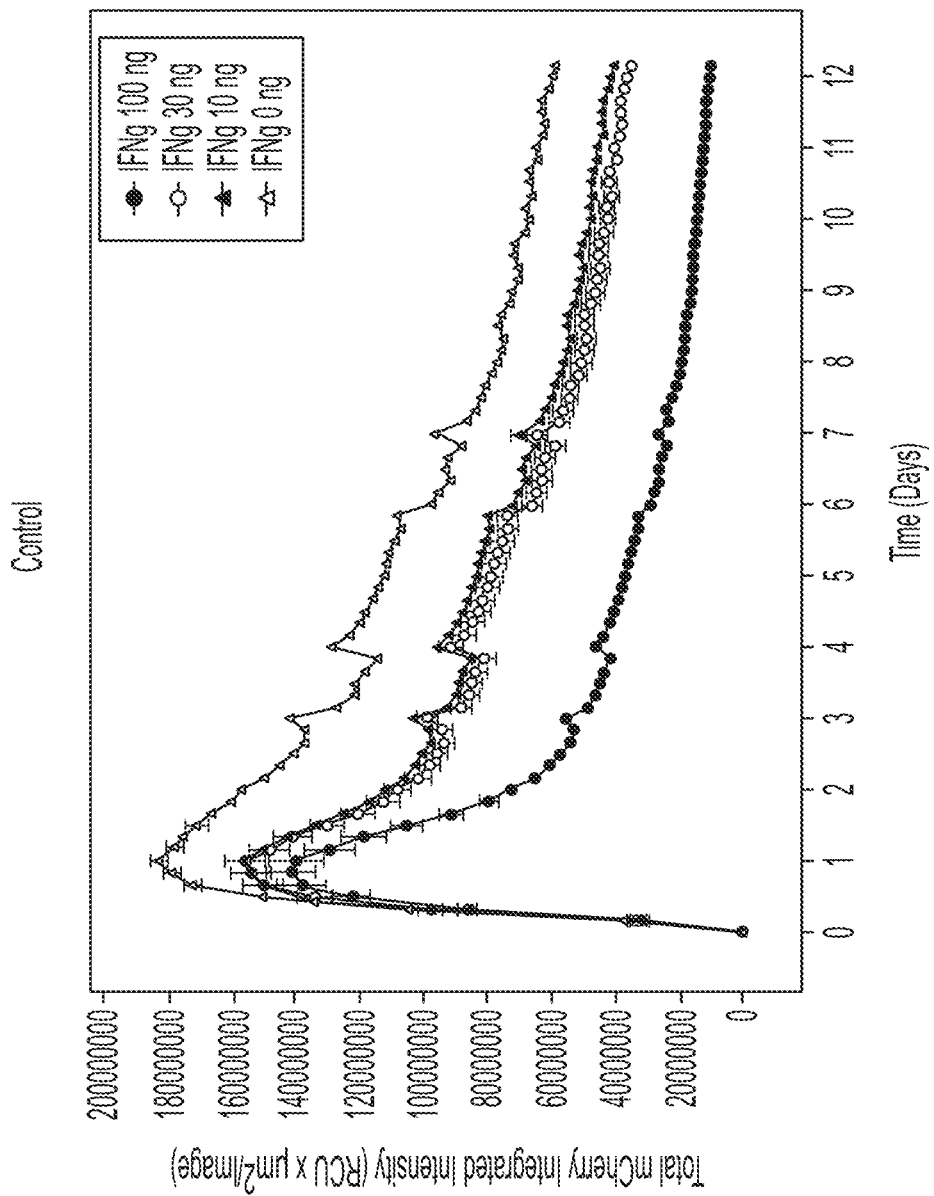
FIG. 129 shows an exemplary graph illustrating an effect of IFN-γ on transfected macrophages.

Human macrophages were transfected with mCherry mRNA comprising m6AGCap1 and PsU or N1mPsU modifications and were then cultured for one day with different doses of IFN-γ. mCherry expression was monitored on an Incucyte® live imaging microscope. As shown in FIG. 129, IFN-γ reduced mCherry mRNA expression when macrophages were transfected with mRNA.

It has been previously shown that in vitro transcribed mRNA is recognized by various endosomal innate immune receptors (e.g., Toll-like receptor (TLR) 3, TLR7 and TLR8) and cytoplasmic innate immune receptors (protein kinase RNA-activated (PKR), retinoic acid-inducible gene I protein (RIG-I), melanoma differentiation-associated protein 5 (MDA5) and 2'-5'-oligoadenylate synthase (OAS)). Signaling through these different pathways results in inflammation associated with type 1 interferon (IFN), tumor necrosis factor (TNF), interleukin-6 (IL-6), IL-12 and the activation of cascades of transcriptional programs. Overall, these create a pro-inflammatory microenvironment poised for inducing specific immune responses. Moreover, downstream effects such as decreased translation by eukaryotic translation initiation factor 2a (eIF2a) phosphorylation, enhanced RNA degradation by ribonuclease L (RNaseL), overexpression and inhibition of self-amplifying mRNA replication are all of relevance for the pharmacokinetics and pharmacodynamics of IVT mRNA.

Activation of IFN-γ via the TLR pathways can activate 2'-5'-oligoadenylate synthase (OAS), which produces 2'-5'-oligoadenylate (2-5A), which in turn can activate RNaseL, leading to RNA degradation and apoptosis.

Figure 130A:
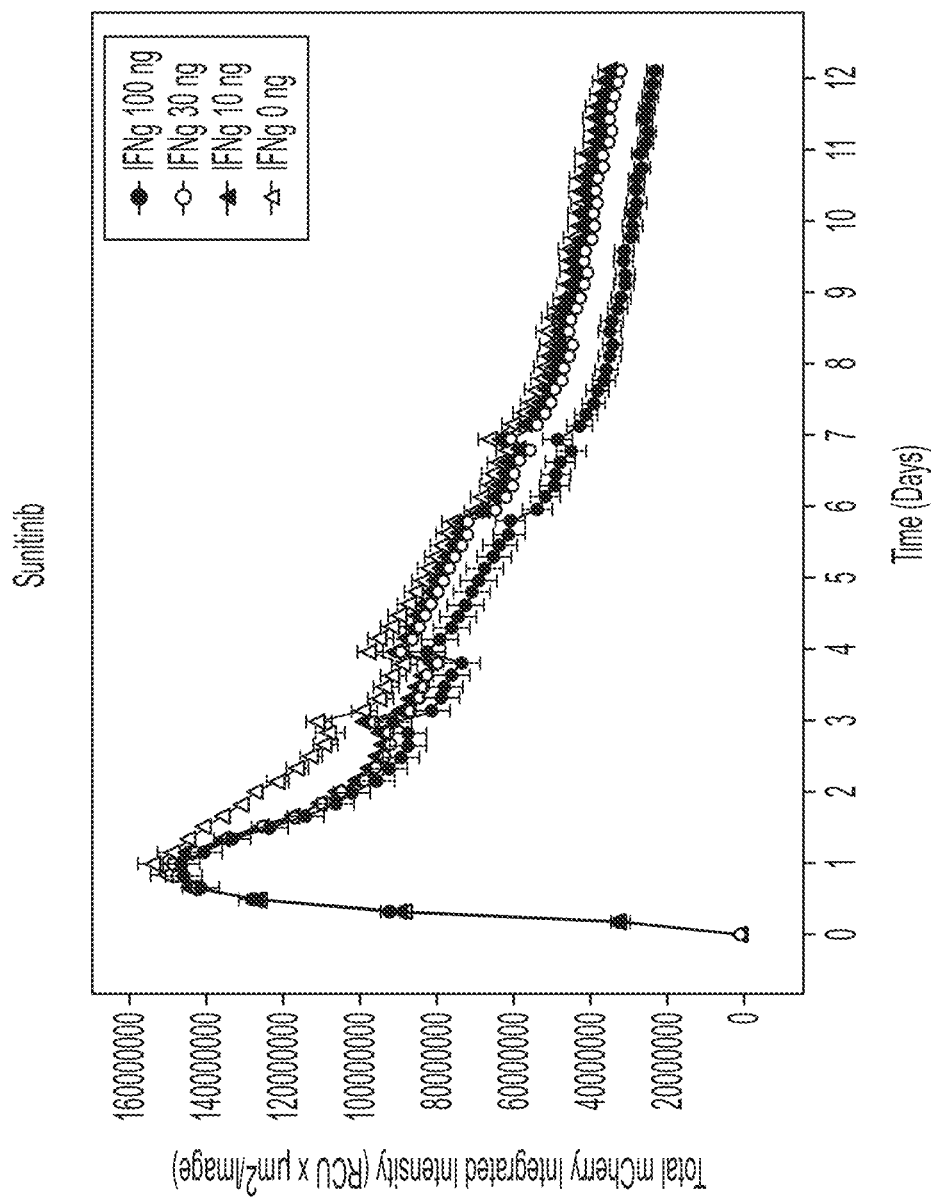
FIGS. 130A-130C show exemplary graphs illustrating an effect of RNaseL inhibitors on CAR macrophages.

Example 11: Effect of RNaseL Inhibitors, Sunitinib and ABCE1, on CAR Macrophages In order to determine whether an RNaseL inhibitor could rescue IFN-γ-induced instability of transfected mRNA, human macrophages were treated with 1 µM sunitinib (an RNaseL inhibitor) two hours prior to the transfection of mCherry mRNA comprising m6AGCap1 and PsU modifications. Transfected cells were then cultured for one day with different dosages of IFN-γ. mCherry expression was monitored on an Incucyte® live imaging microscope. As shown in FIG. 130A, sunitinib rescued the IFN-γ-induced degradation of mRNA.

Figure 130B:
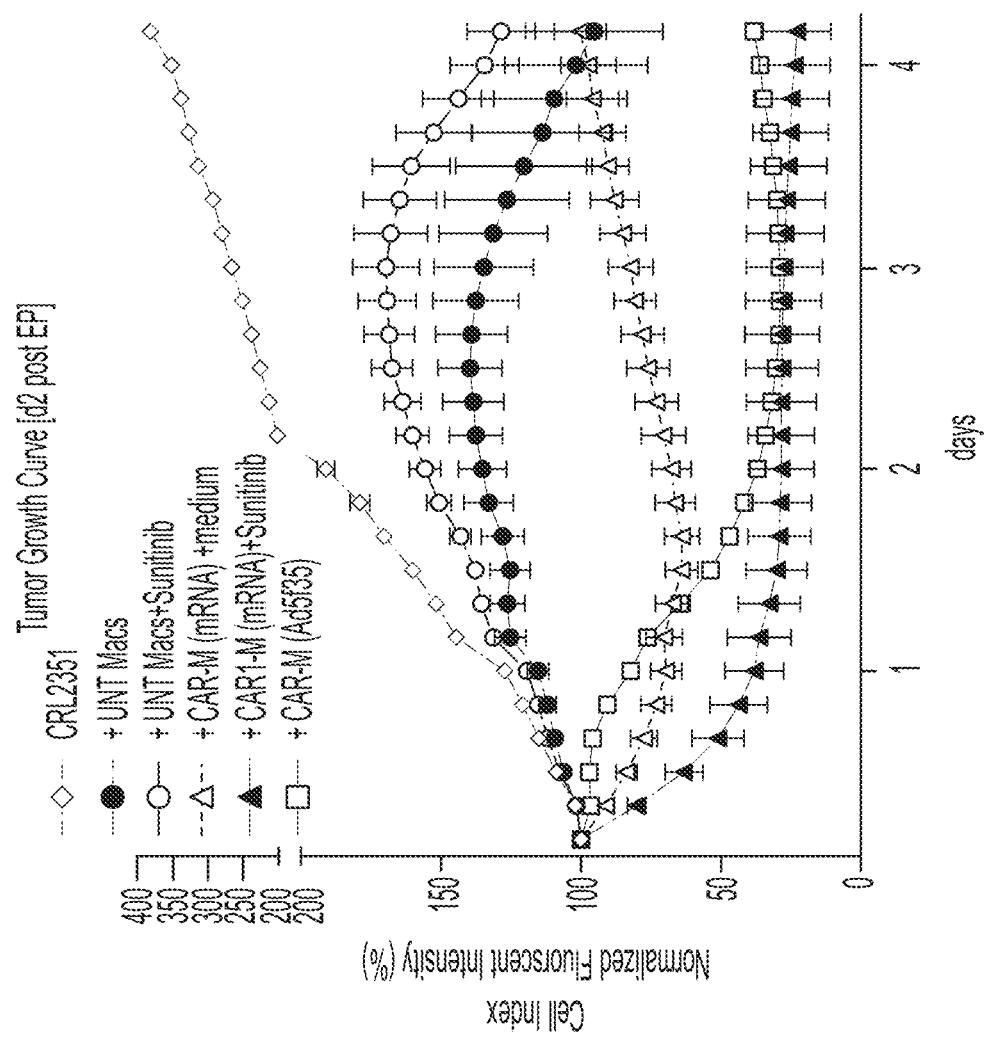
Figure 130C:
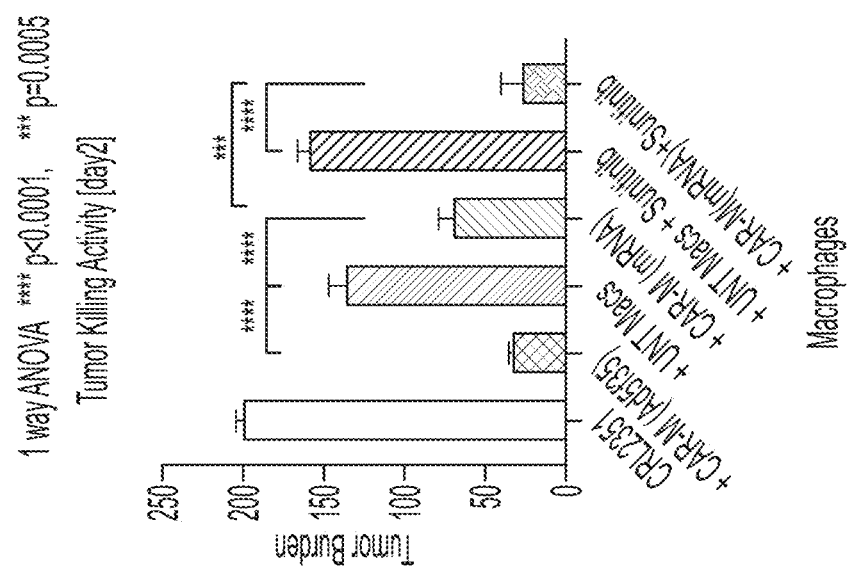

In order to evaluate if RNAse L inhibition can improve the anti-tumor function of mRNA-transfected CAR macrophages, macrophages were transfected with mRNA comprising modifications and pre-treated with sunitinib prior to being evaluated as effector cells in a cancer cell killing assay. CAR macrophage pre-treated with 1 nM sunitinib led to higher cancer cell killing than CAR macrophages not pre-treated with sunitinib or the untransfected control macrophages that were treated or untreated with sunitinib (FIG. 130B). The improved cancer killing ability of sunitinib-primed CAR macrophages in a 48 hour CRL2351 breast cancer cell killing assay is shown in FIG. 130C.

The effect of another RNaseL inhibitor (RLI or ABCE1) was also tested to further validate the concept. Human macrophages were co-transfected with mRNA encoding mCherry comprising m6AGCap 1 and PsU modifications and with mRNA encoding ABCE1.

Figure 131:
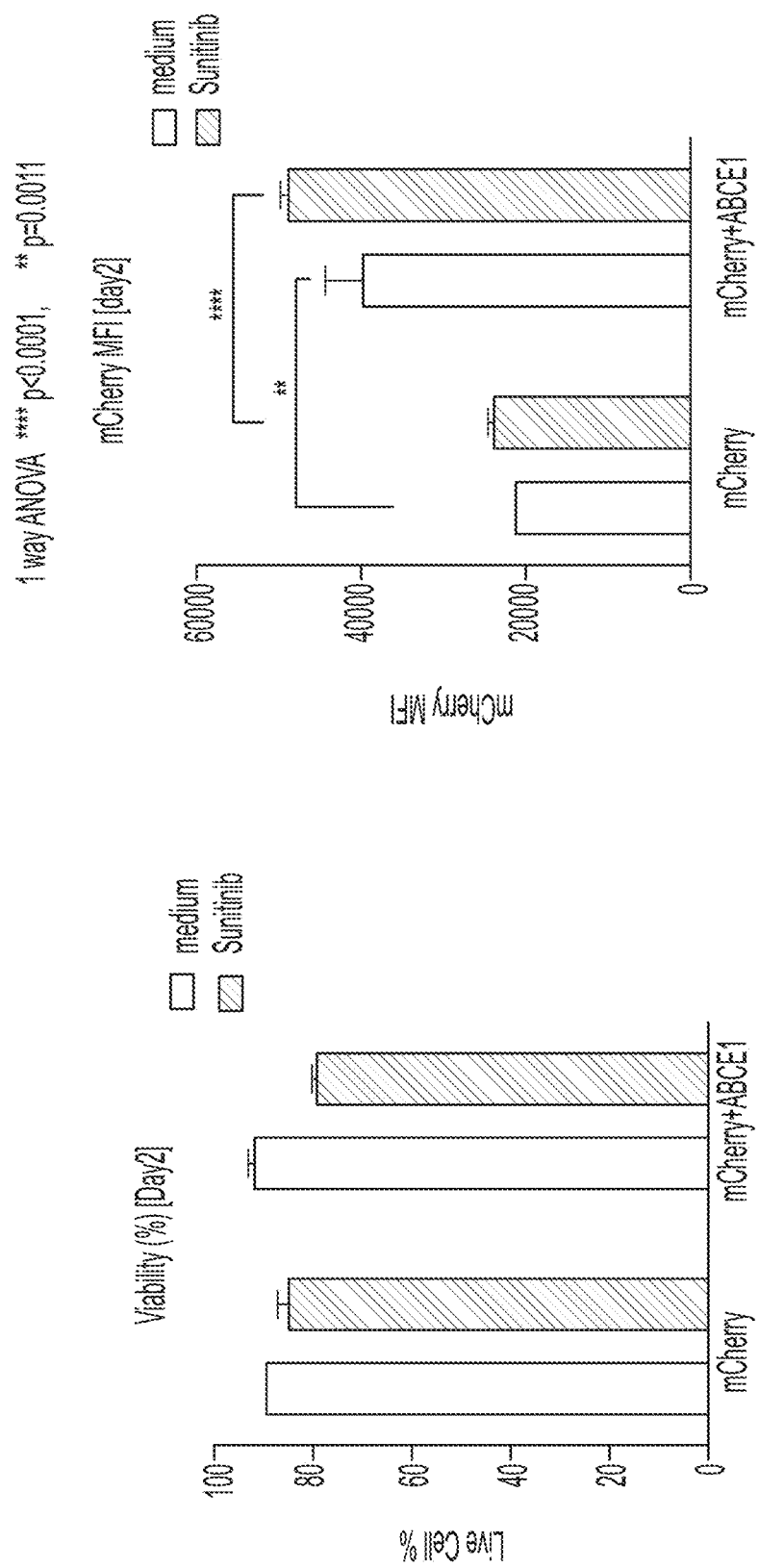
FIG. 131 shows exemplary graphs illustrating macrophage viability and mCherry expression of macrophages co-transfected with mRNA encoding mCherry and with mRNA encoding the RNaseL inhibitor ABCE1.

As shown in FIG. 131, ABCE1 co-expression significantly improved the expression of the mRNA-encoded transgene of interest 48 hours post-electroporation. The viability of macrophages co-transfected with ABCE1 was not impacted and remained high. ABCE1 co-transfection increased mCherry expression by roughly 2-fold, and pre-treating with sunitinib further enhanced this effect.

Figure 132:
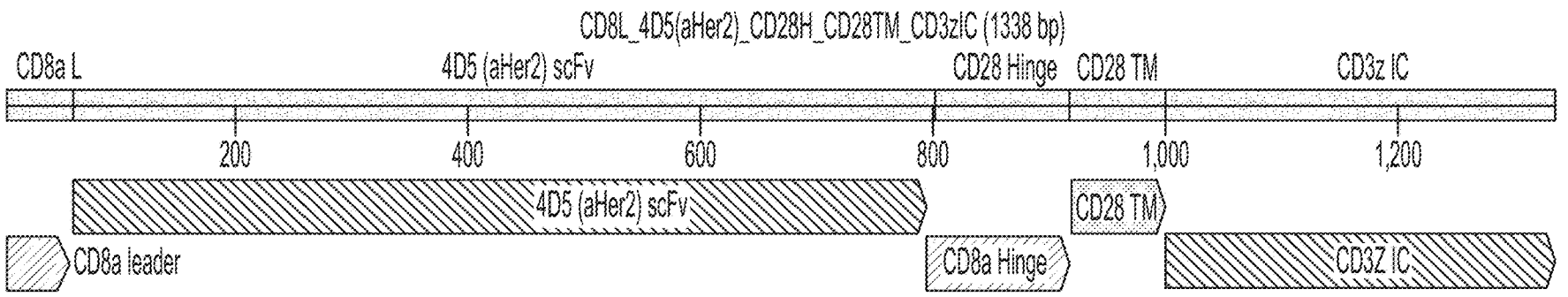
FIG. 132 is a schematic of an exemplary CAR construct comprising a CD28 hinge domain.

Example 12: Receptor Expression and Tumor Cell Killing of CAR Macrophages Comprising a CD28 Hinge Domain In this Example, a CAR construct comprising a CD8 leader, 4D5 scFv, CD28 hinge domain, CD28 transmembrane domain, and CD3 zeta intracellular signaling domain (CTX_219) was generated (FIG. 132). Expression of CTX_219 was then compared to an identical CAR construct with a CD8 hinge domain and CD8 transmembrane domain instead of a CD28 hinge domain and CD28 transmembrane domain (CTX_001; FIG. 8). Tumor killing ability of CTX_219 was compared to CTX_001 and also a CAR construct identical to CTX_001, but lacking an intracellular signaling domain (CTX_003).

Primary human macrophages were suspended in EP buffer containing 50-500 nM mRNA at a concentration of $1.0 \times 10^5$ to $1.0 \times 10^9$ cells/mL and electroporated. Cells were removed from the cassette, plated and incubated overnight at 37° C. and 5% CO2. CAR expression MFI, and percentage were detected after 24 hours with rHER2 binding by flow cytometry. Live percentage was detected using Live/Dead Aqua after 24 hours. For killing, macrophages were co-cultured with Her2+ CRL2351-NucGFP tumor cells at a 2:1 E:T ratio or a 1:1 E:T ratio and monitored via Incucyte® for 72 hours. Tumor cell death was calculated by integrated GFP intensity per well relative to time 0.

Figure 133A:
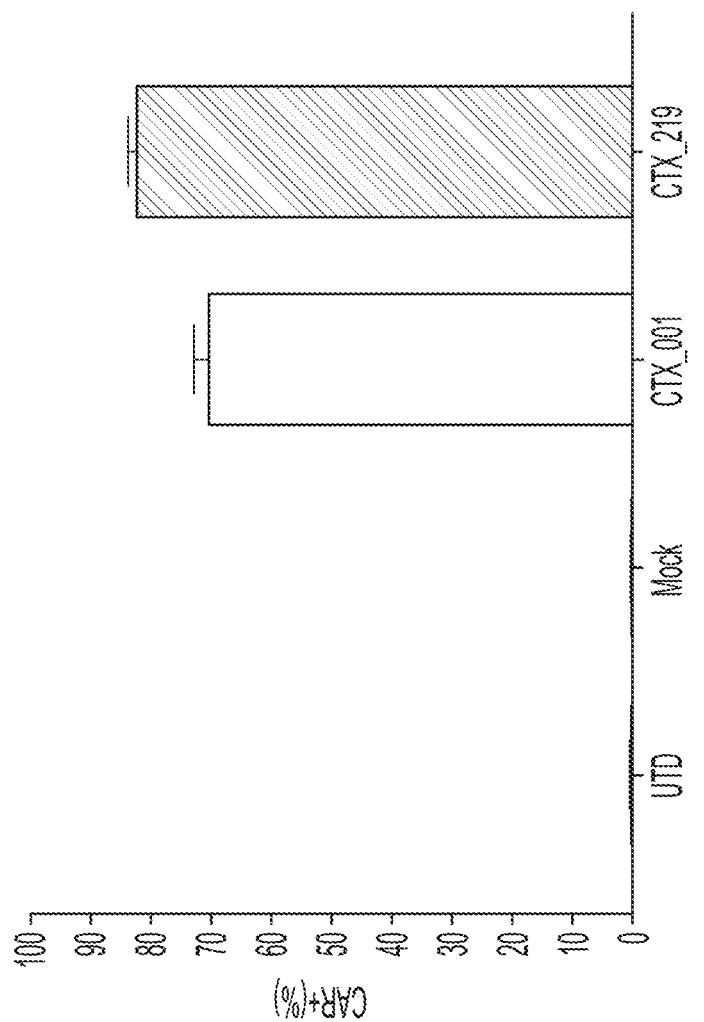
FIGS. 133A-133E are graphs showing CAR+ percentage, CAR expression, live percentage, and tumor killing ability of CAR macrophages.
Figure 133B:
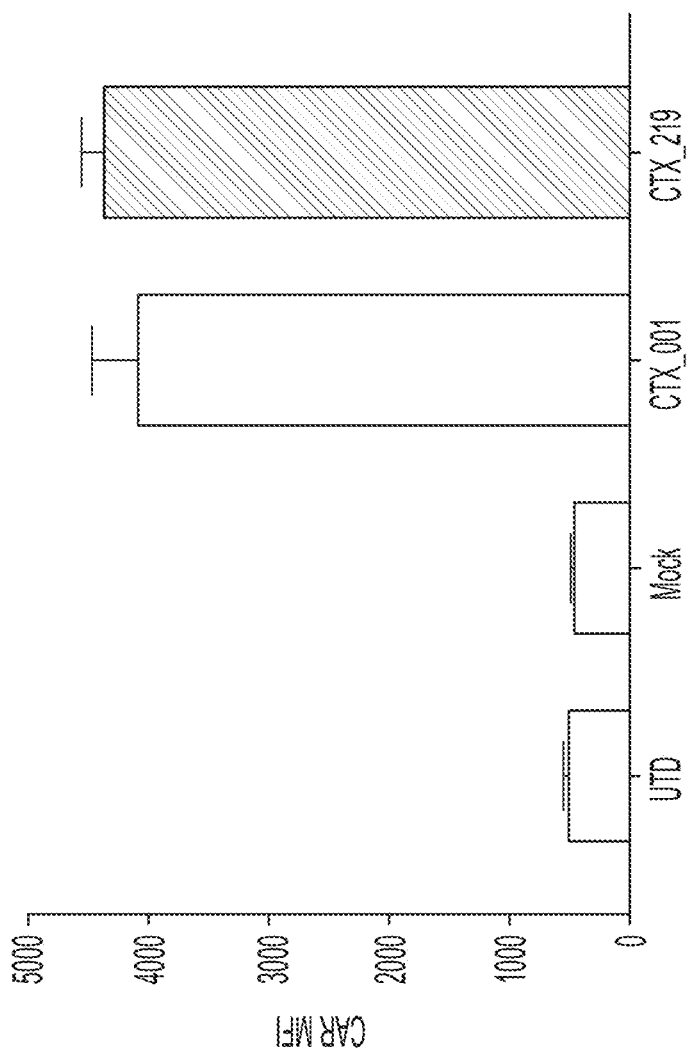
Figure 133C:
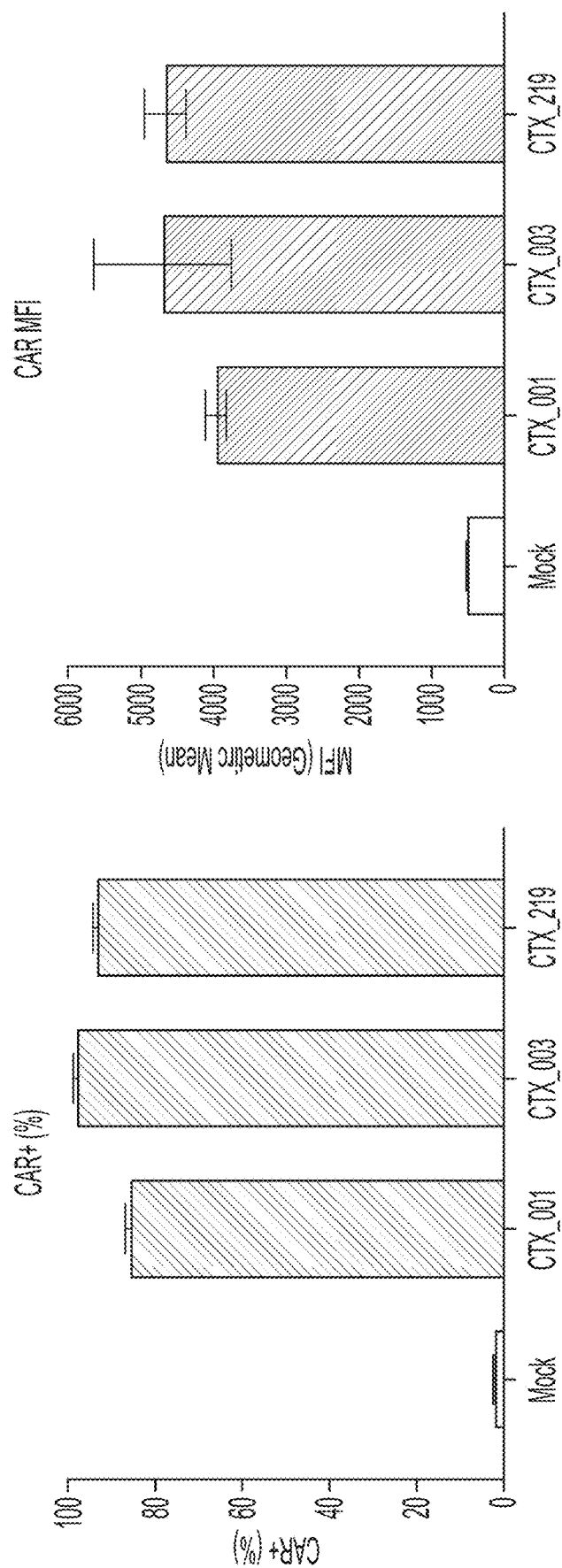
Figure 133D:
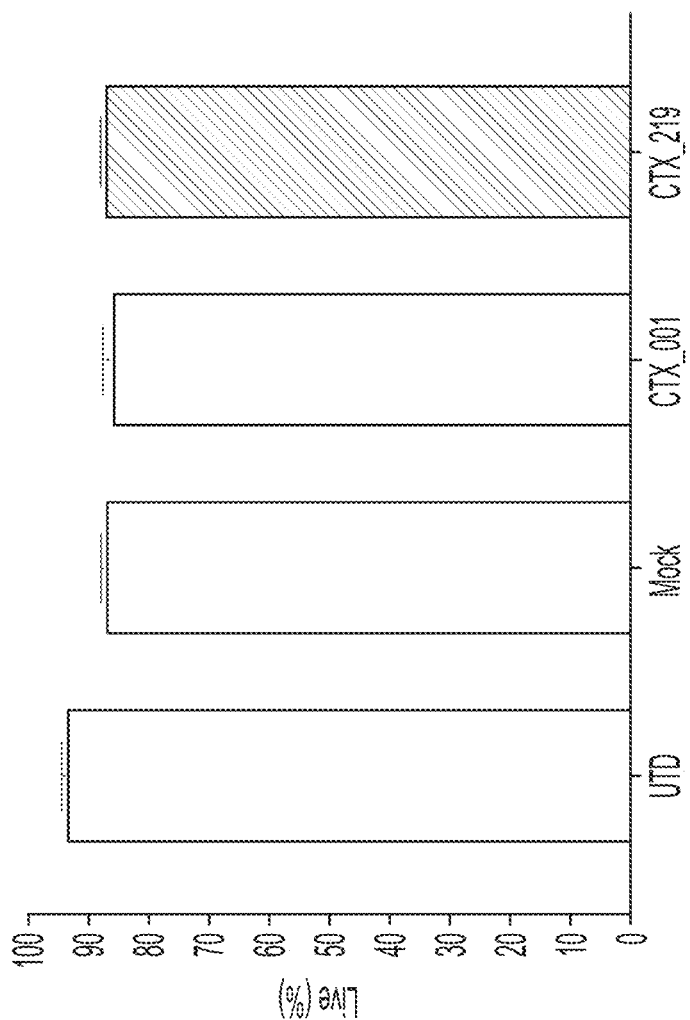
Figure 133E:
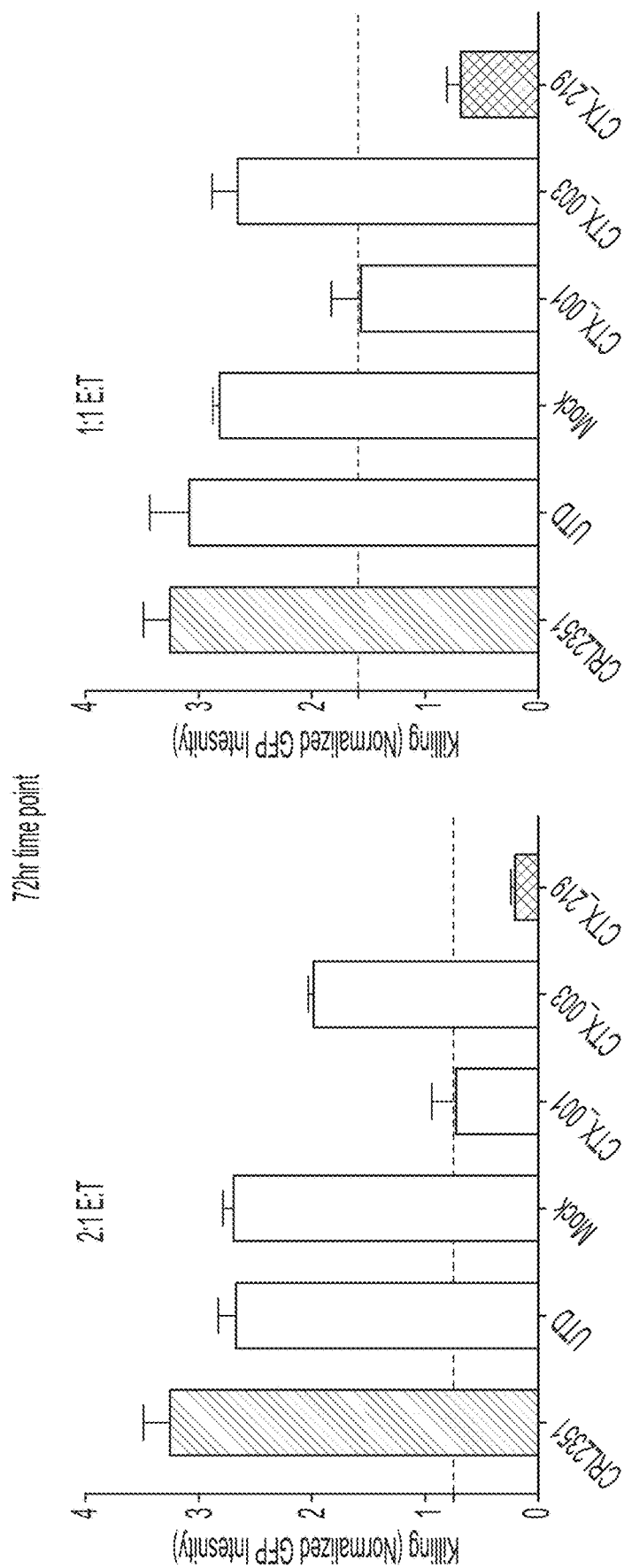

Expression and CAR+ percentage were comparable for the CAR construct comprising a CD28 hinge domain (CTX_219), the CAR construct comprising a CD8 hinge domain (CTX_001), and the CAR construct lacking an intracellular signaling domain (CTX_003; see FIGS. 133A-133C). Live percentage was also comparable for CTX_219 and CTX_001 (FIG. 133D). Surprisingly, the CAR construct comprising a CD28 hinge domain (CTX_219) demonstrated enhanced killing function relative to CTX_001 and CTX_003 control (FIG. 133E). These data show that a CAR construct comprising a CD28 hinge domain resulted in improved tumor cell killing by macrophages relative to a CAR construct comprising a CD8 hinge domain.

Figure 134:
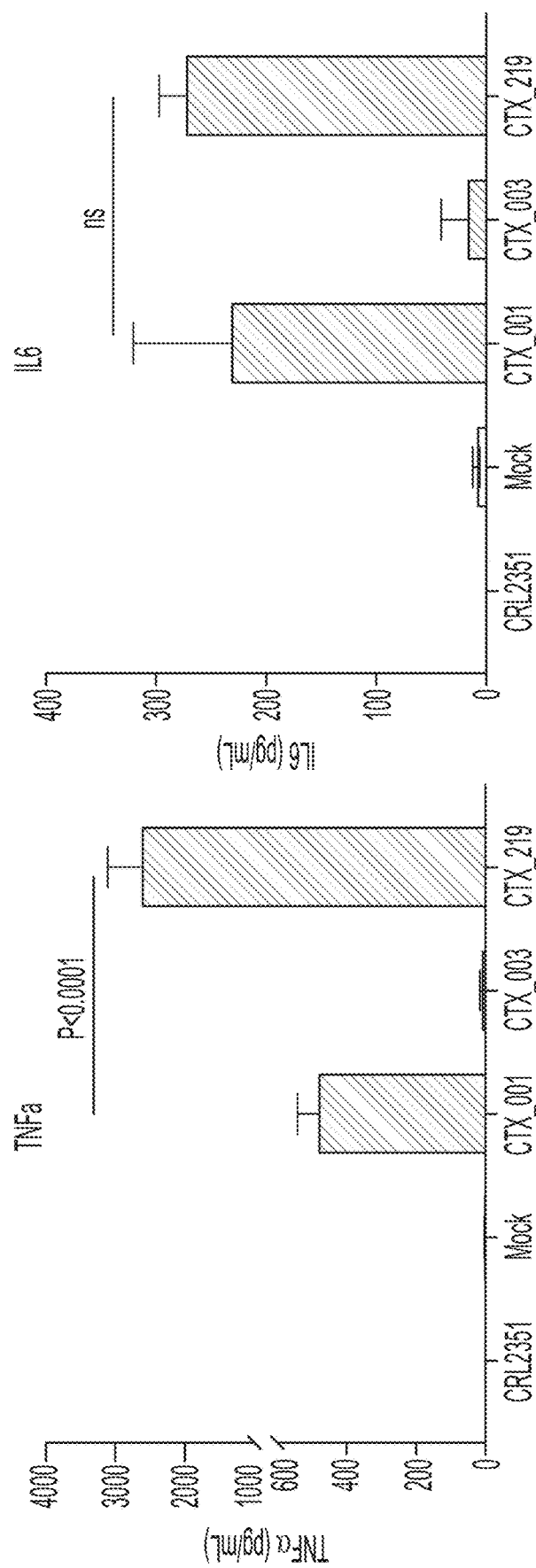
FIG. 134 is a graph showing TNFα and IL6 secretion by CAR macrophages.

TNFα and IL6 secretion by macrophages comprising CTX_219 relative to CTX_001 and CTX_003 was determined. Effector cells were co-cultured with HER2+ target cells for 24 hours at an E:T ratio of 1:1. Supernatant was harvested and TNFα and IL6 concentrations were measured using the MSD Pro-Inflammatory Panel 1 (Meso Scale Discovery) per the manufacturer's instructions. Surprisingly, the CAR construct comprising a CD28 hinge domain (CTX_219) demonstrated significantly increased TNFα secretion (~5× higher than CTX_001), without further increasing IL6 production (FIG. 134). These data show that a CAR construct comprising a CD28 hinge domain resulted in improved secretion of the tumor killing cytokine TNFα relative to a CAR construct comprising a CD8 hinge domain without increasing production of the inflammatory cytokine IL6.

Example 13: VPX-Mediated Lentiviral Transduction of Macrophages Comprising a CAR For lentiviral transduction of macrophages for CAR expression, macrophages were thawed and plated at a density of 5-10e6 cells per 10 cm in plates in 10 mL complete media (CM). After 2-3 hours rest, VPX lentivirus particles were diluted into CM and added to macrophages at specified MOIs. Media was fully exchanged 24 hrs post-lentivirus addition.

For harvesting of macrophages for experiments described herein, 10 cm plates were removed from incubator and placed at 4 C for 30 min. Cells were removed from plate, pelleted, and resuspended in CM. Cell counts were taken, and macrophages were either used for experiments or re-plated for later time points.

Functional Assays for Assessment of CAR Macrophages

For killing assays, macrophages were plated in a 96 well plate in 100 uL of CM at defined densities to achieve specific macrophage to target ratios (E:T). After 1-2 hr rest time, 10,000 tumor cells expressing nucLight GFP were resuspended in 100 uL CM and added to each well. Plates were placed in Incucyte® and imaged every 4 hours, starting ~1 hr after tumor cell addition. Killing was defined as integrated GFP intensity relative to time 0 scan. Tumor cells used in these assays were AU565 HER2+ breast cancer and SKOV3 ovarian carcinoma cells.

For cytokine secretion studies, soluble Her2-His was dissolved in molecular grade water at a concentration of 0.2 ug/uL. Her2-His was then diluted into PBS at specified concentrations. 100 uL of Her2-His dilution were added to wells in a 96 well plate. The plate was stored at 4 C overnight and subsequently washed 2× with PBS. 50,000 macrophages were added to each well in a final volume of 200 uL CM. Supernatant was harvested ~24 hours post macrophage addition and stored at −20 C for further assessment. Cytokine detection was done using a MSD U-Plex kit.

For detection of cell surface proteins and CAR expression, cells were incubated in FACS buffer containing Human TruStain FcX for 10 min at RT. Surface protein staining was done using the following panel: CD80-FITC, CD86-PE, CD163-APC-Cy7, CD206-BV421, anti-trastuzumab-APC, and Aqua Live/Dead. Detection of surface protein expression was completed using the Attune NxT flow cytometer (Thermo Fischer) and analyzed in FlowJo.

For detection of CAR expression comparing VPX and non-VPX lentivirus, cells were incubated in FACS buffer containing 20 μg/mL Her2-His for 20 min at RT, followed by incubation in Human TruStain FcX for 10 min at RT. Surface protein staining was done using the following panel: CD80-FITC, CD86-PE, CD163-APC-Cy7, CD206-BV421, anti-His-APC, Aqua Live/Dead. Detection of surface protein expression was completed using the Attune NxT flow cytometer (Thermo Fischer) and analyzed in FlowJo.

Results of Lentiviral Transduction using VPX of CAR Macrophages

Figure 136:
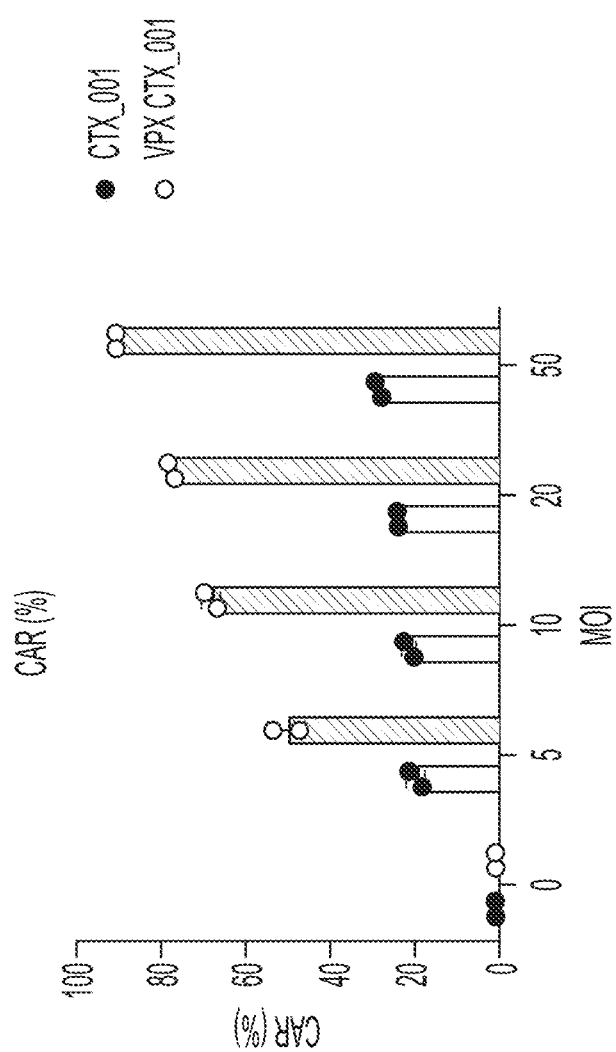
FIG. 136 is a graph showing expression of a CAR construct (CTX_001 comprising an anti-HER2 scFv, CD8 hinge, CD8 transmembrane domain, and CD3-zeta signaling domain.

VPX addition resulted in significantly increased expression of a CAR construct (CTX_001) in macrophages (FIG. 136). CTX_001 comprises an anti-HER2 scFv, CD8 hinge, CD8 transmembrane domain, and CD3-zeta intracellular signaling domain (FIG. 8). VPX-based transduction increased CAR (%) to over 40% at a MOI of 5, over 60% at a MOI of 10, over 80% at a MOI of 50, and over 90% at a MOI of 50 relative to the same CAR (CTX_001) transduced without VPX with ~20% CAR (%) at MOI of 5-50.

Figure 137:
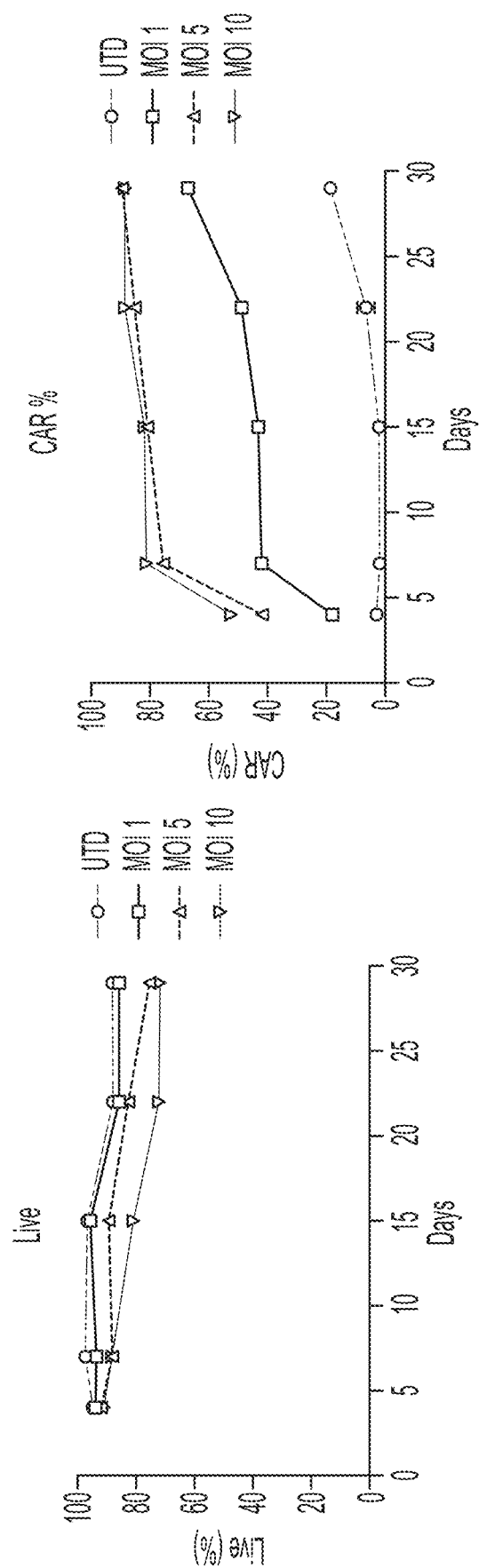
FIG. 137 is a series of graphs showing viability (live %) and CAR expression (CAR %) of CTX_001 in macrophages transduced with VPX lentivirus over 30 days at MOI of 1, MOI of 5, and MOI of 10. UTD macrophages were used as control.

Next, viability and CAR expression were assessed over time for VPX-lentiviral transduction with a MOI titration. CAR-M transduced with VPX-lentivirus were shown to be highly viable and to express CTX-001 over 30 days (FIG. 137). CAR-M transduced with VPX-lentivirus at MOI of 1, 5, and 10 were viable over a time period of about 30 days with a % live ranging from about 80% to about 100%. CAR % expression increased from MOI of 1 to MOI of 5 and 10. Untransduced (UTD) macrophages were used as control.

Figure 138:
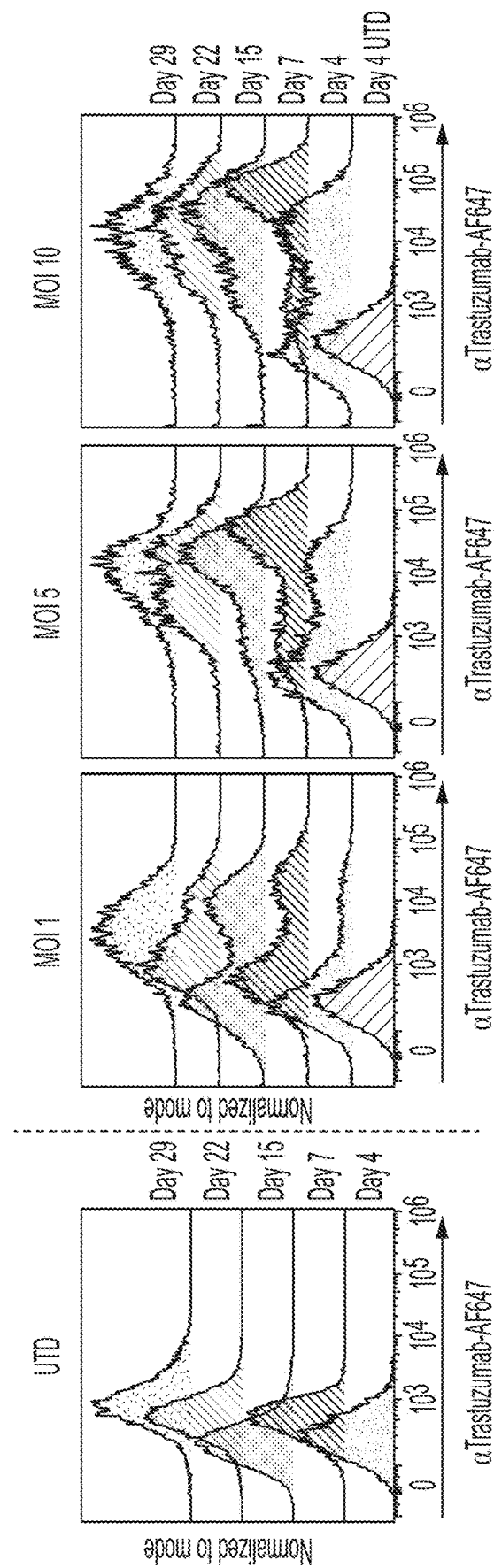
FIG. 138 is a series of graphs showing surface protein expression of CTX_001 using αTrastuzumab-A F647 in macrophages transduced with VPX lentivirus at MOI of 1, MOI of 5, and MOI of 10 at Days 4, 7, 15, 22, and 29 after transduction. UTD macrophages were used as control.

CAR expression was also assessed for CTX_001 in macrophages transduced with VPX-lentivirus using αTrastuzumab-A F647 for analysis of surface protein over time. CAR cell surface expression was shown at MOI of 1, MOI of 5, and MOI of 10 with increased expression at MOI of 5 and 10 for Days 4, 7, 15, 22, and 29 (FIG. 138). UTD macrophages were used as control.

Figure 139:
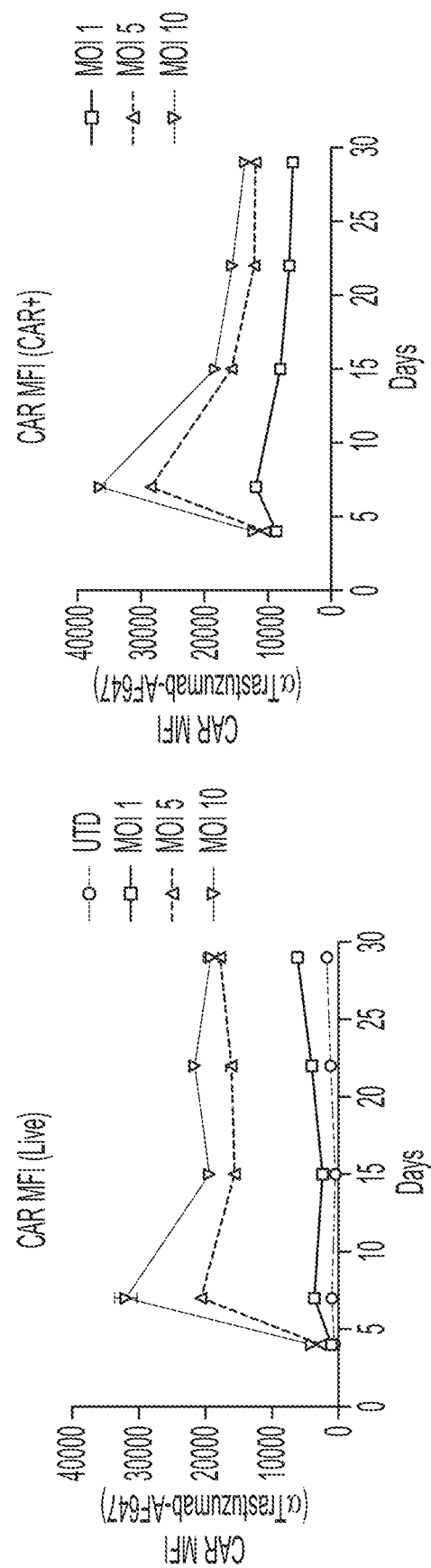
FIG. 139 is a series of graphs showing Mean Fluorescence Intensity (MFI) of viability (live) and CAR expression (CAR+) of CTX_001 in macrophages transduced with VPX lentivirus over 30 days at MOI of 1, MOI of 5, and MOI of 10. UTD macrophages were used as control.

The Mean Fluorescence Intensity (MFI) of CAR expression was also assessed for CTX_001 in macrophages transduced with VPX-lentivirus using αTrastuzumab-A F647 for analysis of surface protein over time. CAR macrophages transduced with VPX-lentivirus were shown to be highly viable and to express CTX-001 over a 30 day time period (FIG. 139). Thus, CAR macrophages transduced with VPX-lentivirus maintained CAR expression for at least 29 days.

Figure 140:
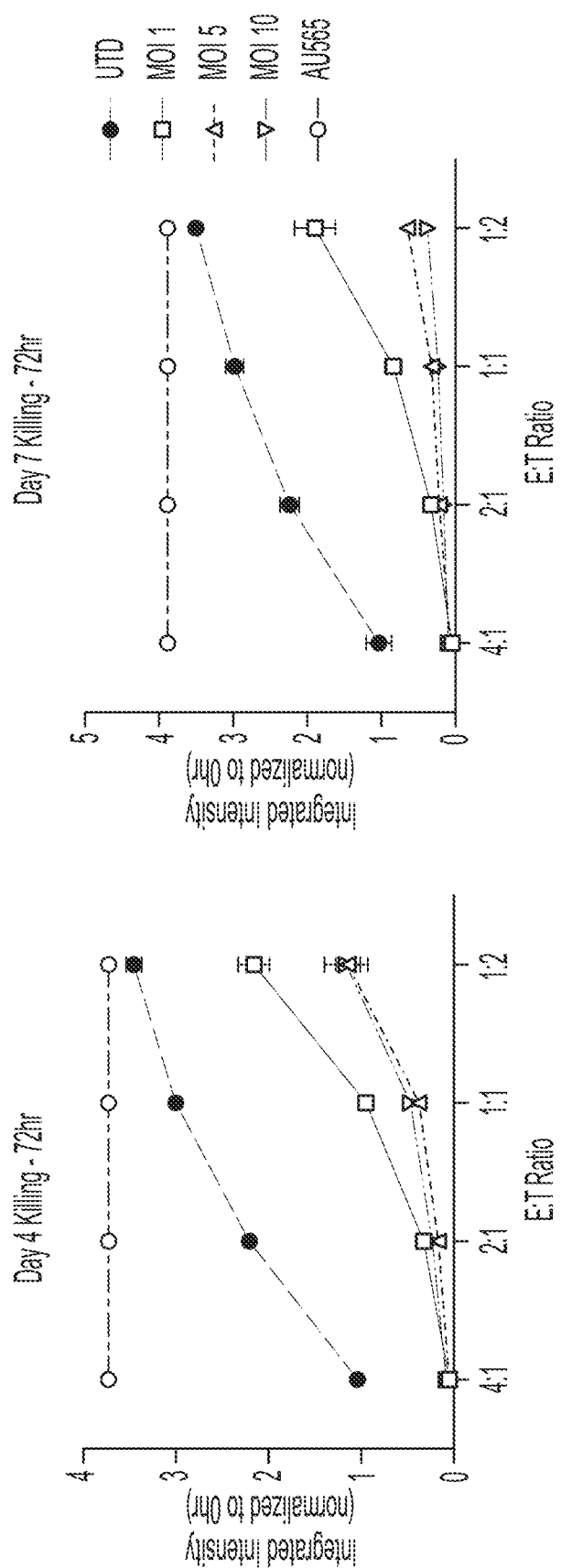
FIG. 140 is a series of graphs showing killing function of CTX_001 in macrophages transduced with VPX lentivirus at MOI of 1, MOI of 5, and MOI of 10 after 4 and 7 days. Different ratios of effector macrophages to target tumor cells (E:T) were 4:1, 2:1, 1:1, and 1:2. Integrated intensity is indicative of tumor burden. The results after 72 hours of tumor cell and macrophage co-culture are graphed. UTD macrophages and AU565 HER2+ breast cancer cells without macrophages were controls.

Killing function of CTX_001 macrophages transduced with VPX lentivirus was also assessed. Ratios of effector macrophages to target tumor cells (E:T) were 4:1, 2:1, 1:1, and 1:2. Integrated intensity is indicative of tumor burden. UTD macrophages and AU565 cells (HER2+ breast cancer cell line) without macrophages were used as controls. Killing function was evident for CTX_001 macrophages at all E:T ratios and at MOIs of 1, 5, and 10 after 4 days, which was sustained after 7 days (FIG. 140). Notably, CTX_001 macrophages at MOI 5 and MOI 10 exhibited similar levels of killing function at all E:T ratios. Anti-tumor activity at 72 hours post co-culture was plotted.

Figure 10:
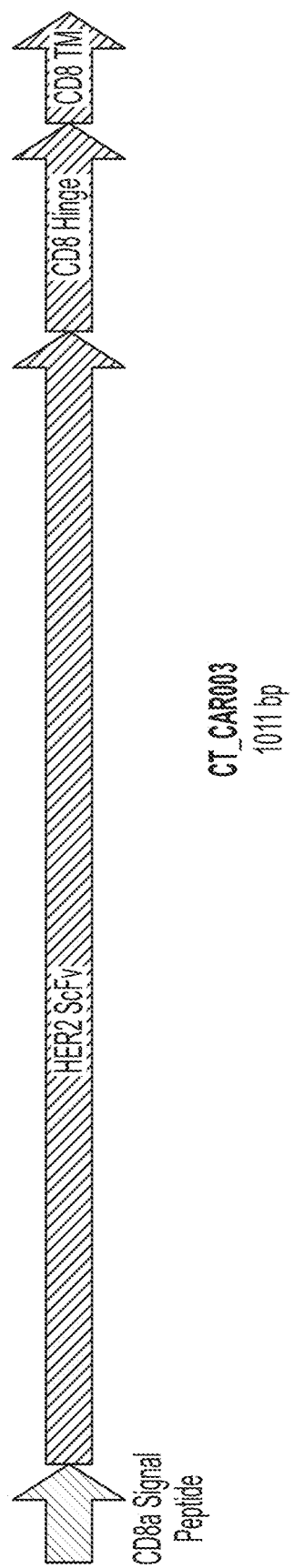
FIG. 10) as assessed using αTrastuzumab-A F647 in macrophages transduced with VPX lentivirus at MOI of 2 and MOI of 5 (FIG. 141A) and showing viability (live %) and CAR expression (CAR %) of CTX_001 and CTX_003 in macrophages transduced with VPX lentivirus at MOI of 2 and MOI of 5 (FIG. 141B). UTD macrophages were used as control.
Figure 11:
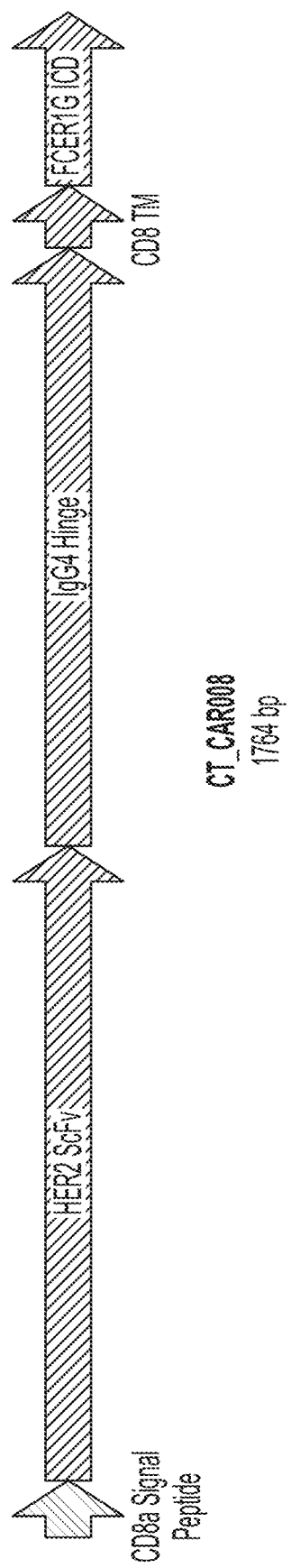
Figure 12:
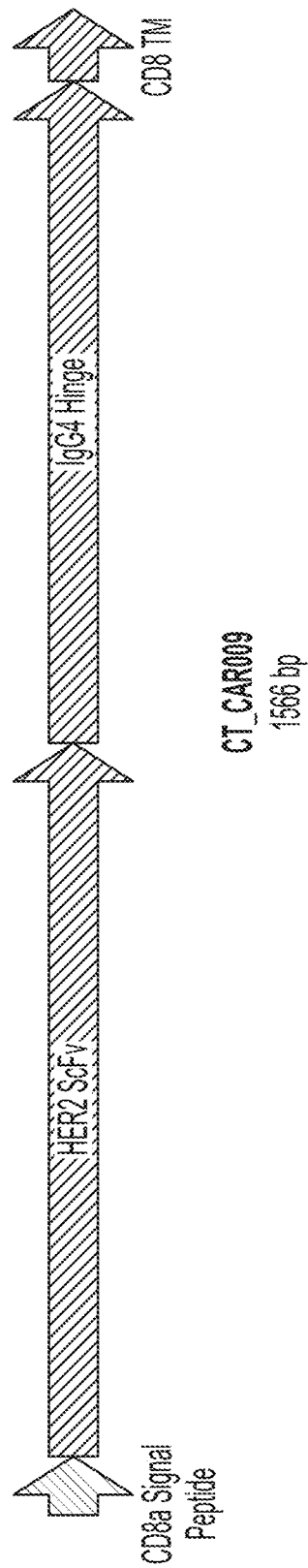
Figure 13:
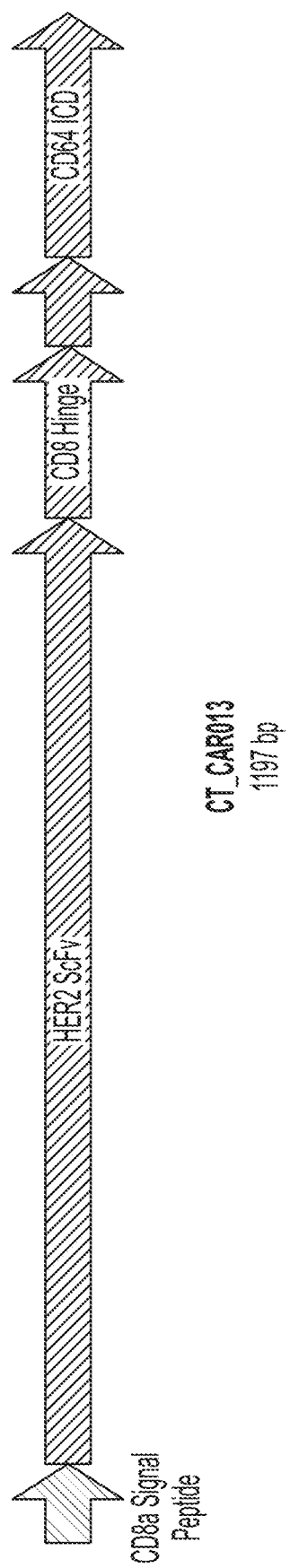
Figure 14:
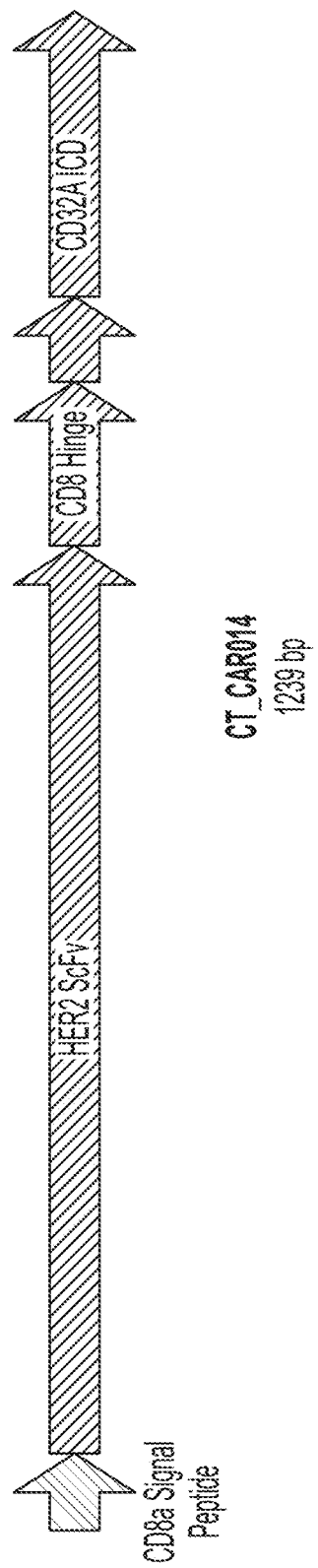
Figure 15:
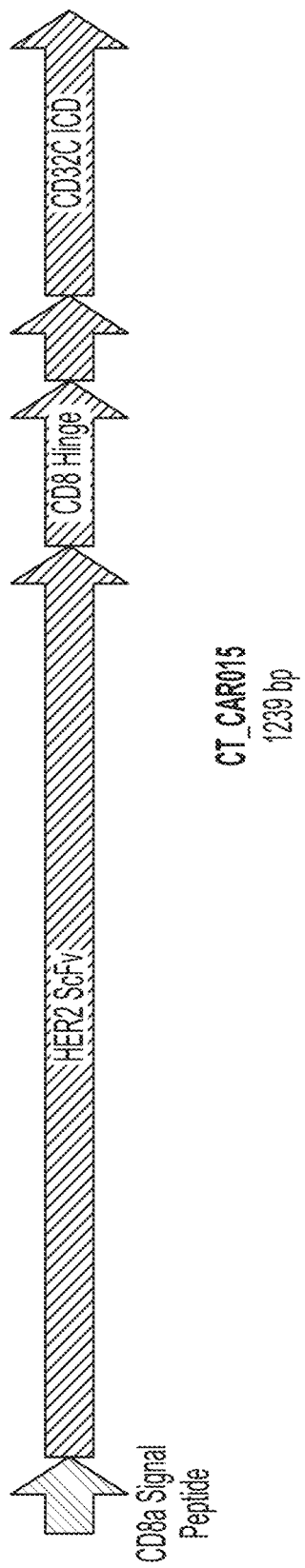
Figure 16:
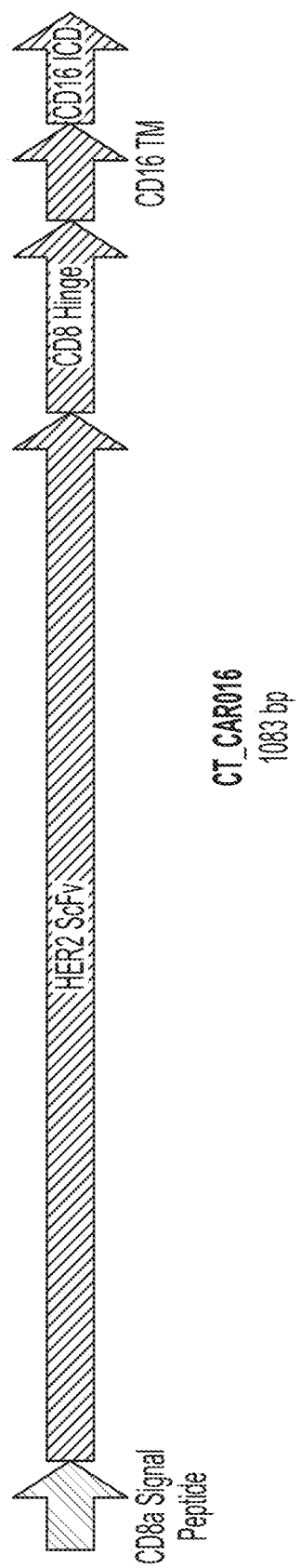
Figure 17:
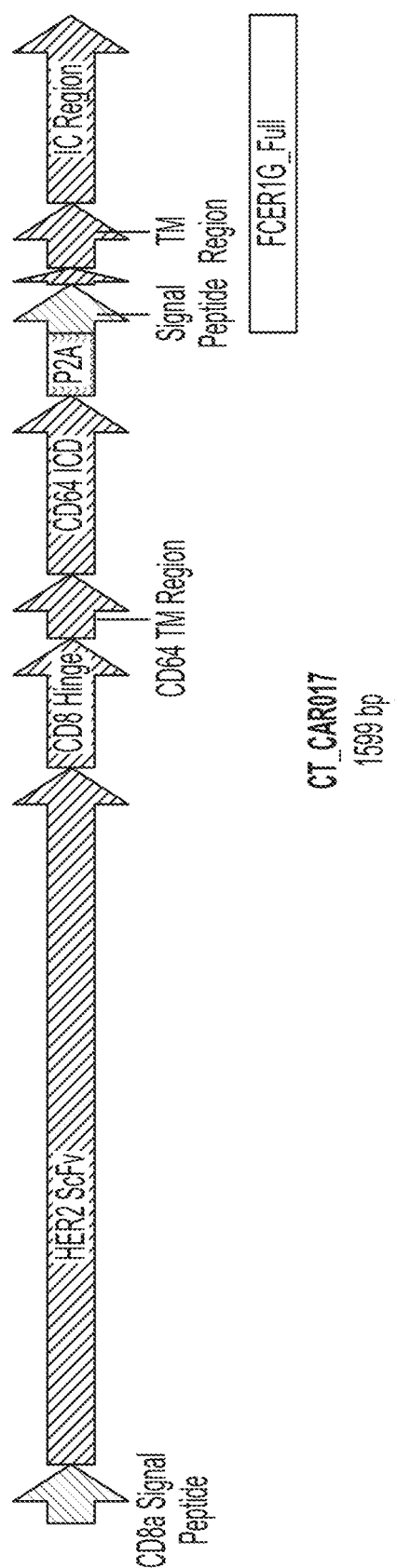
Figure 18:
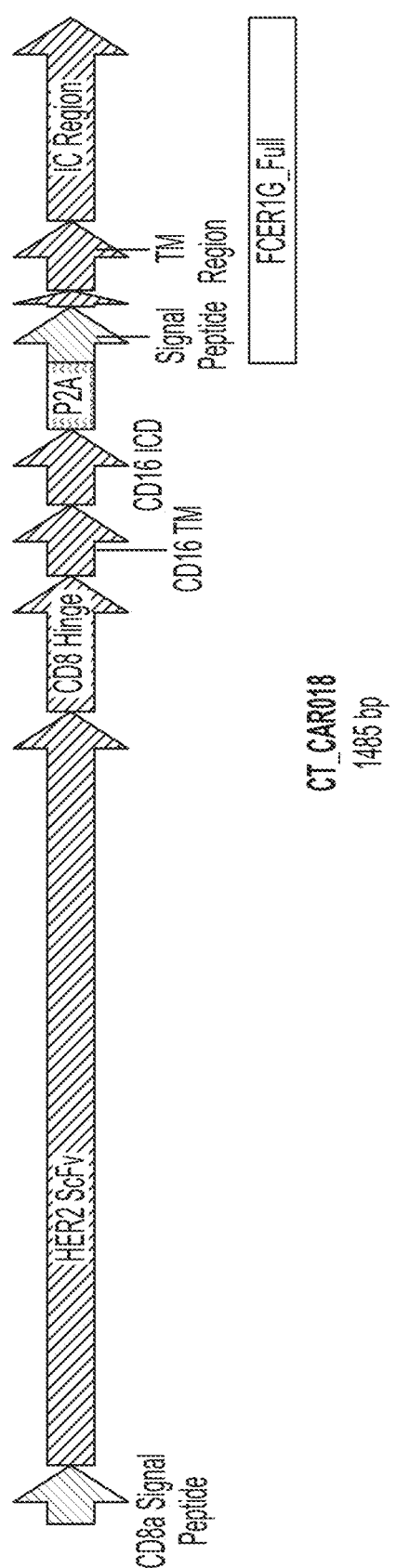
Figure 19:
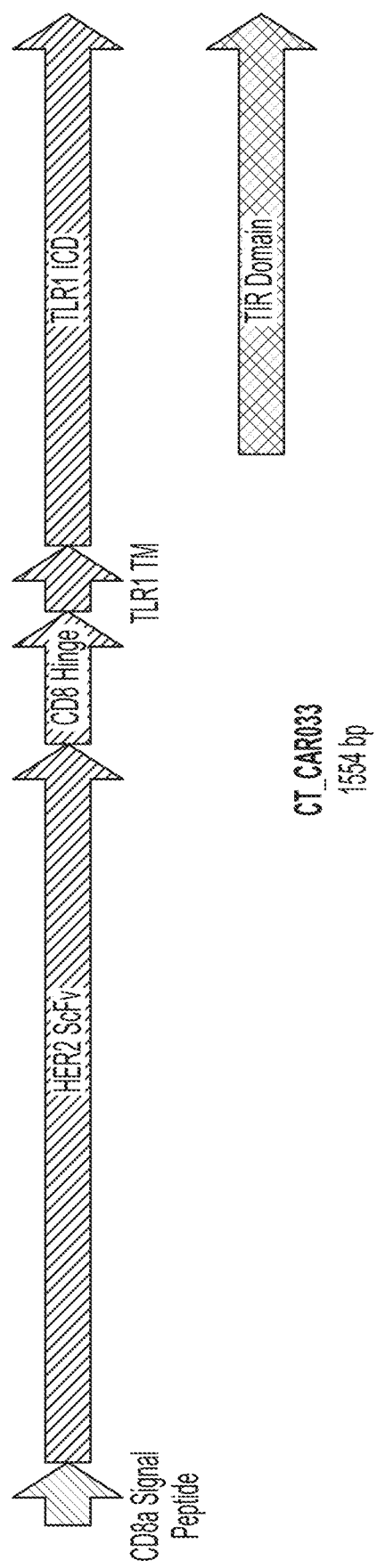
Figure 20:
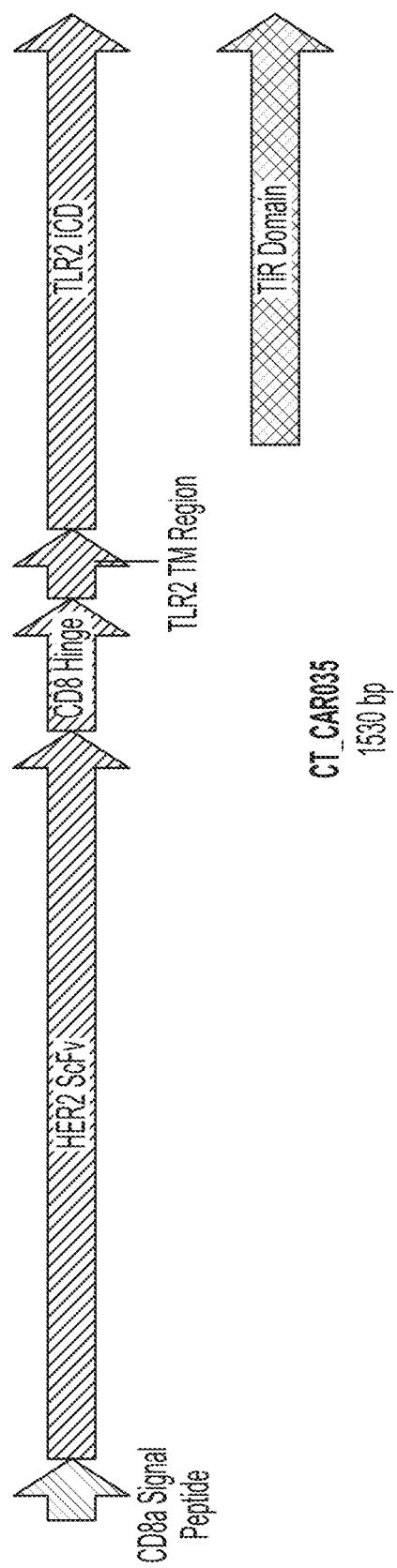
Figure 21:
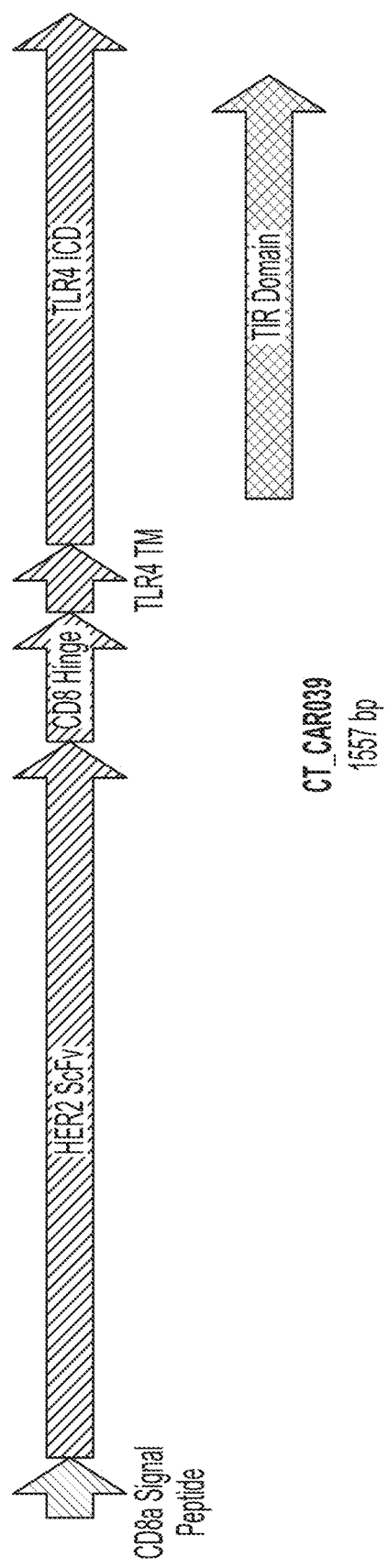
Figure 22:
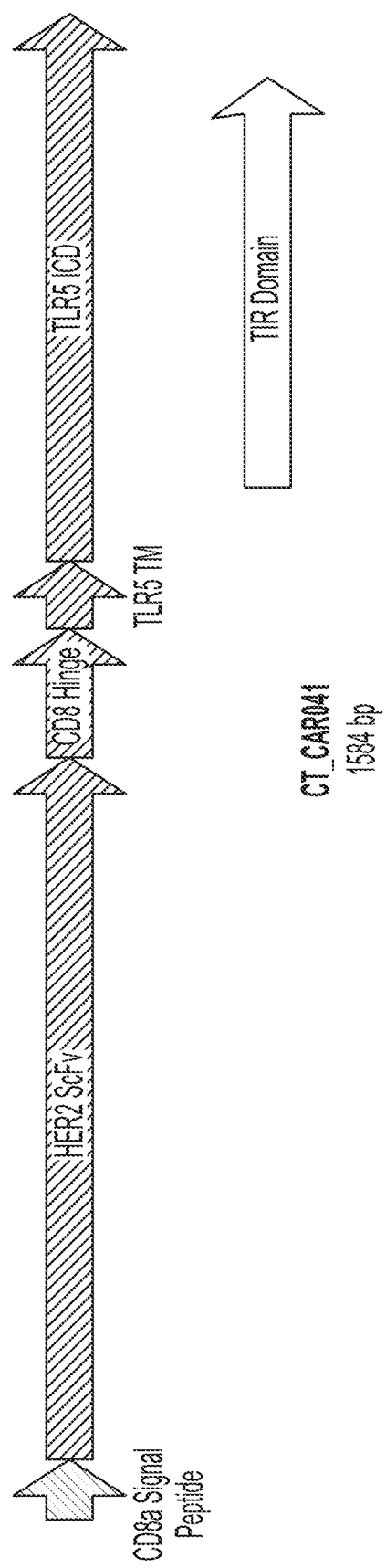
Figure 23:
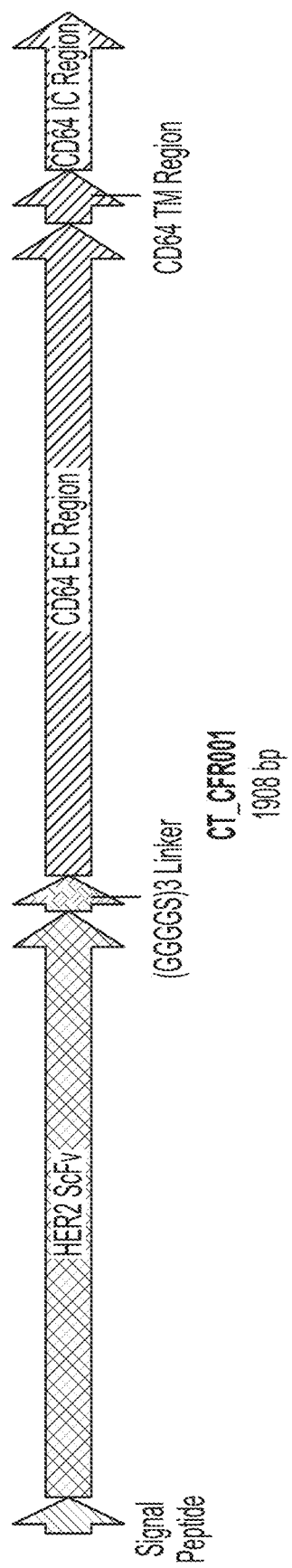
Figure 24:
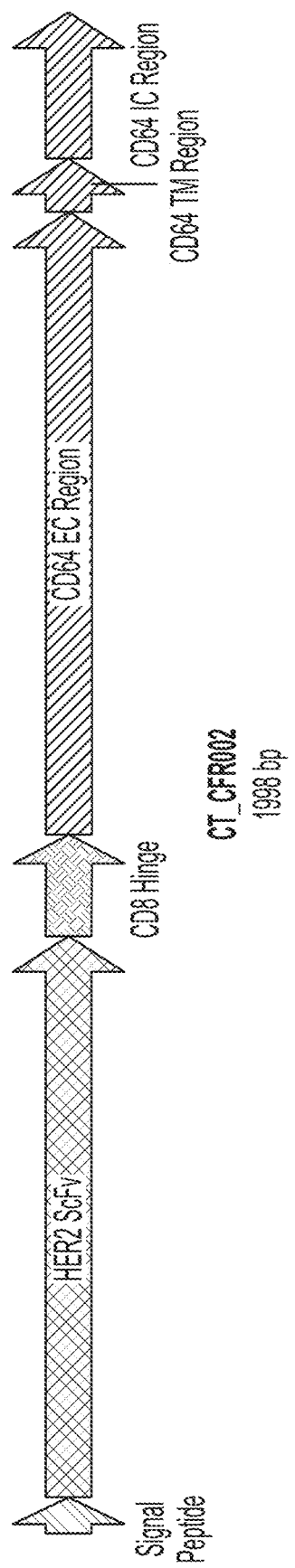
Figure 25:
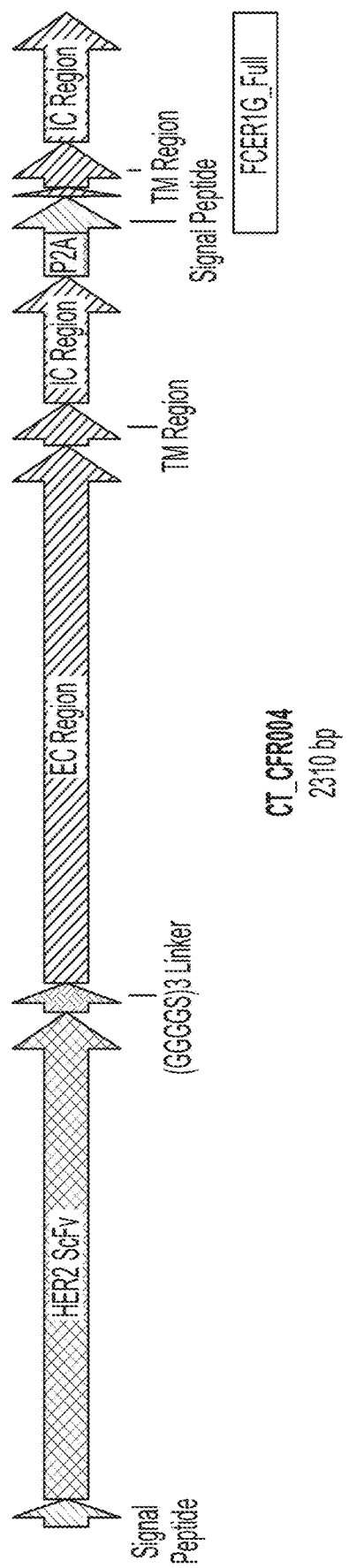
Figure 26:
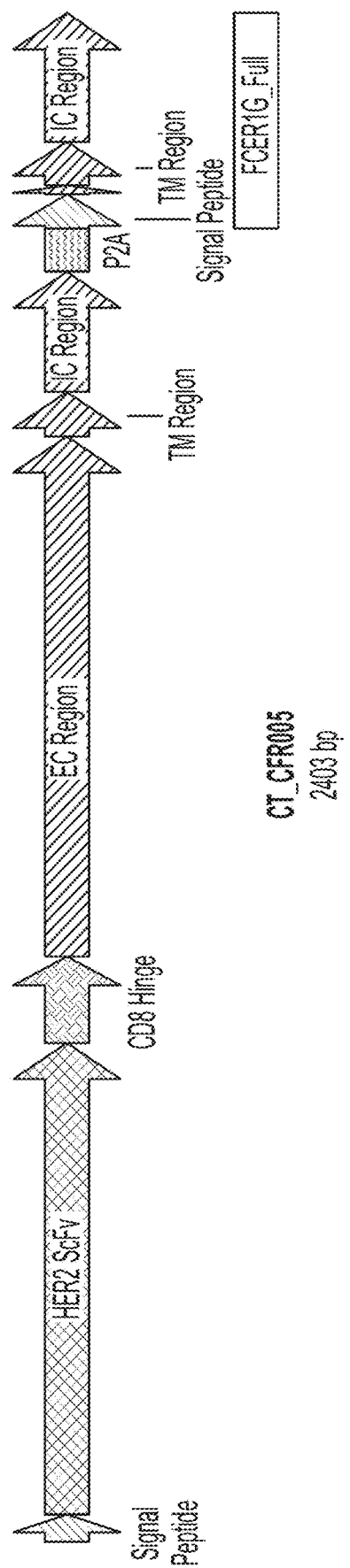
Figure 27:
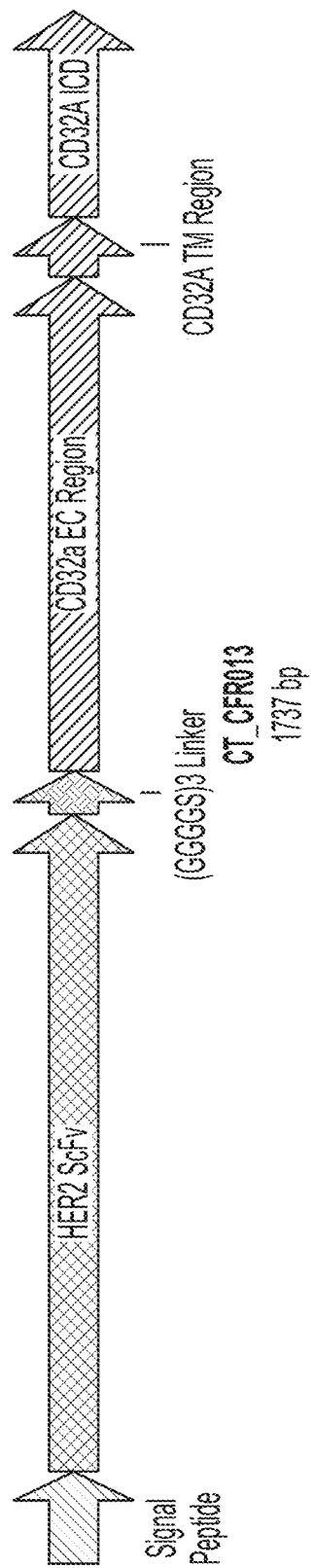
Figure 28:
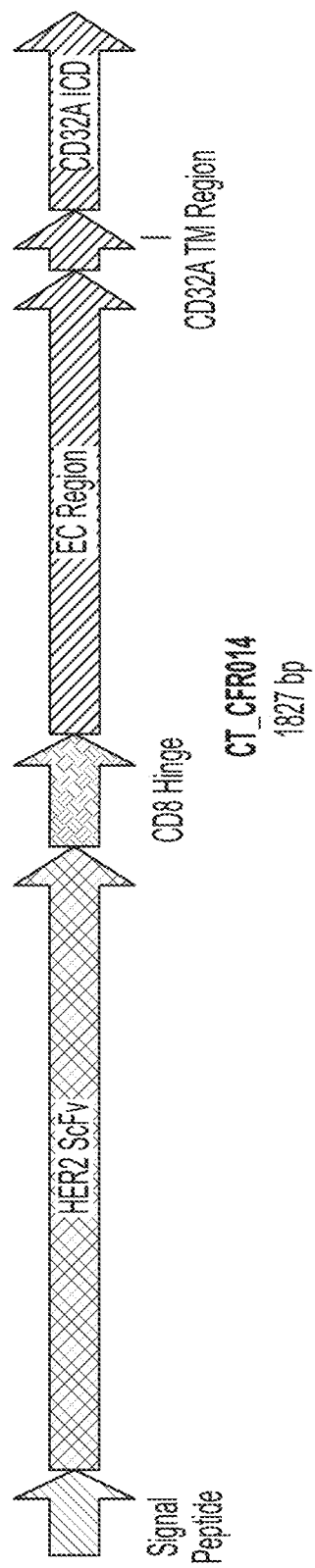
Figure 29:
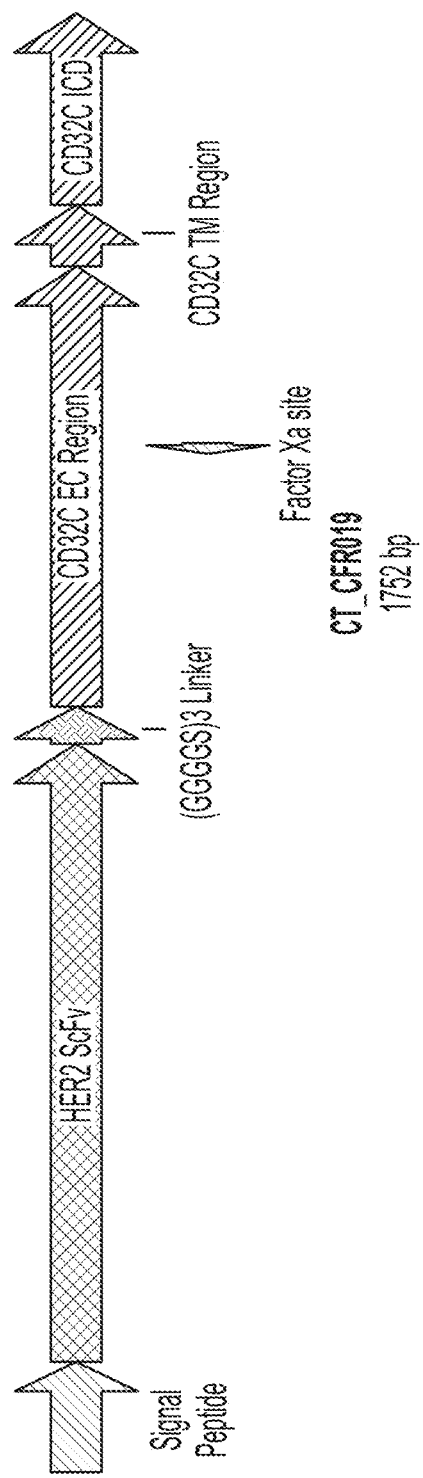
Figure 30:
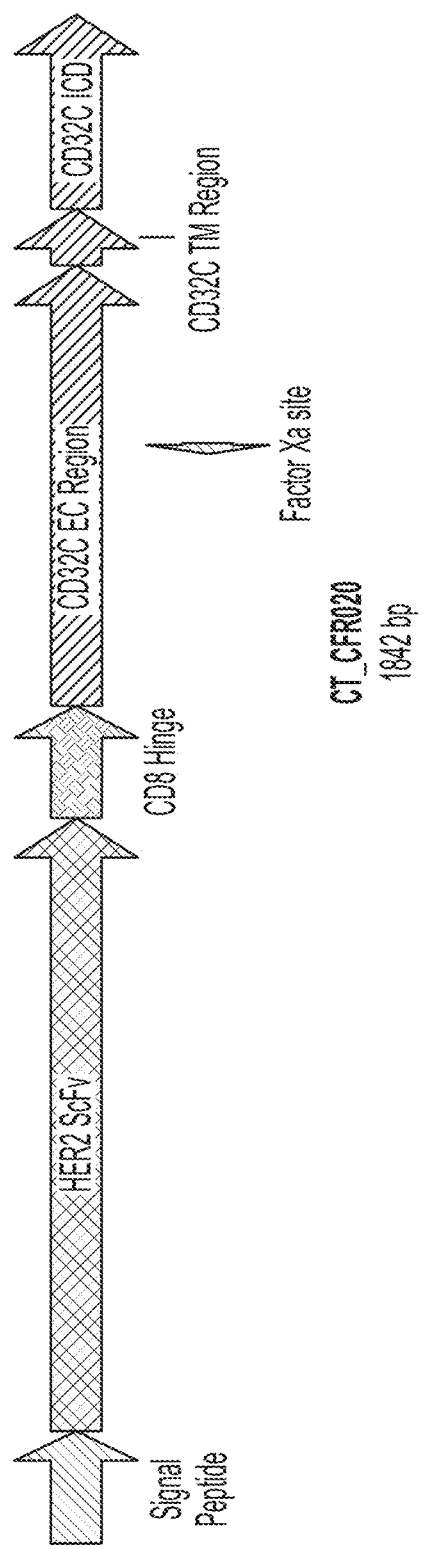
Figure 31:
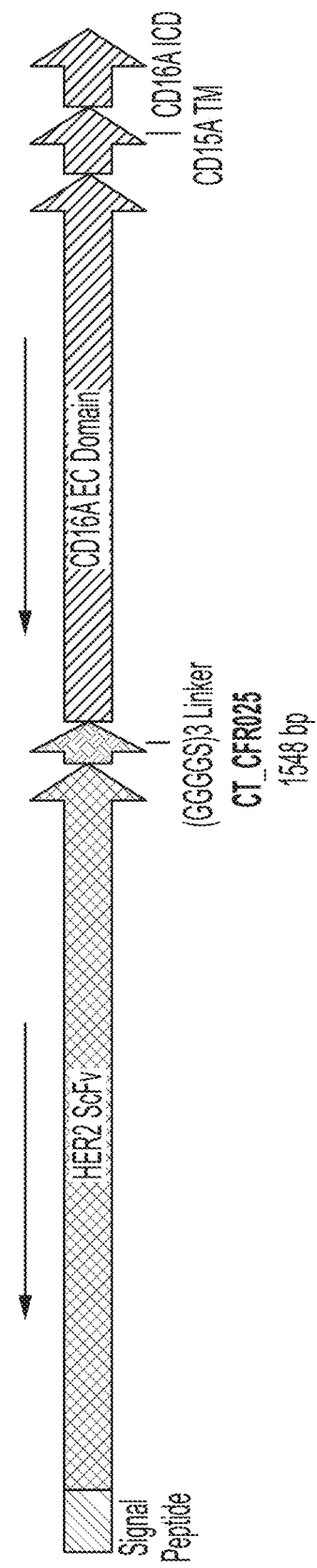
Figure 32:
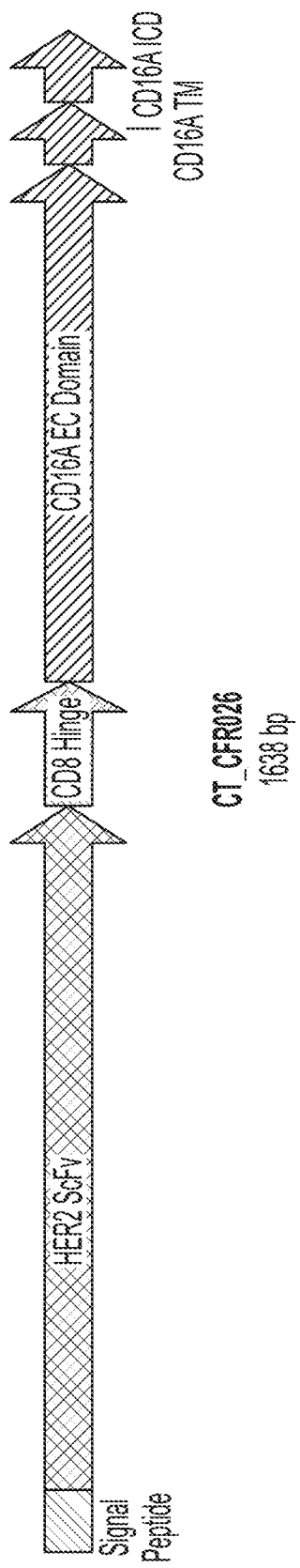
Figure 33:
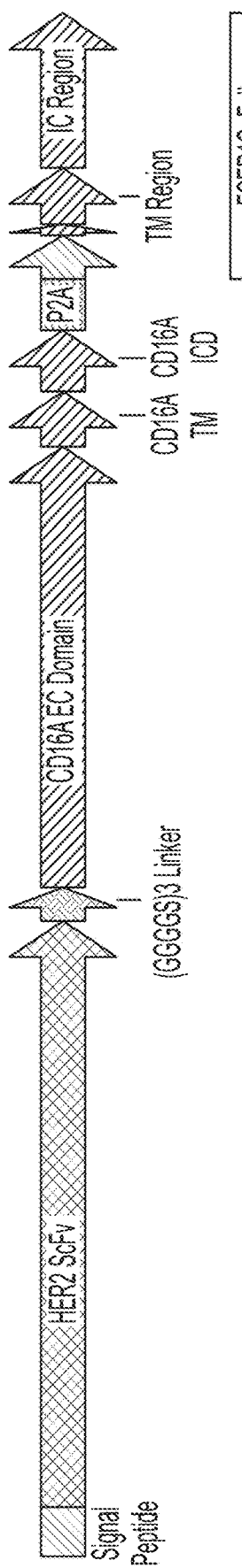
Figure 34:
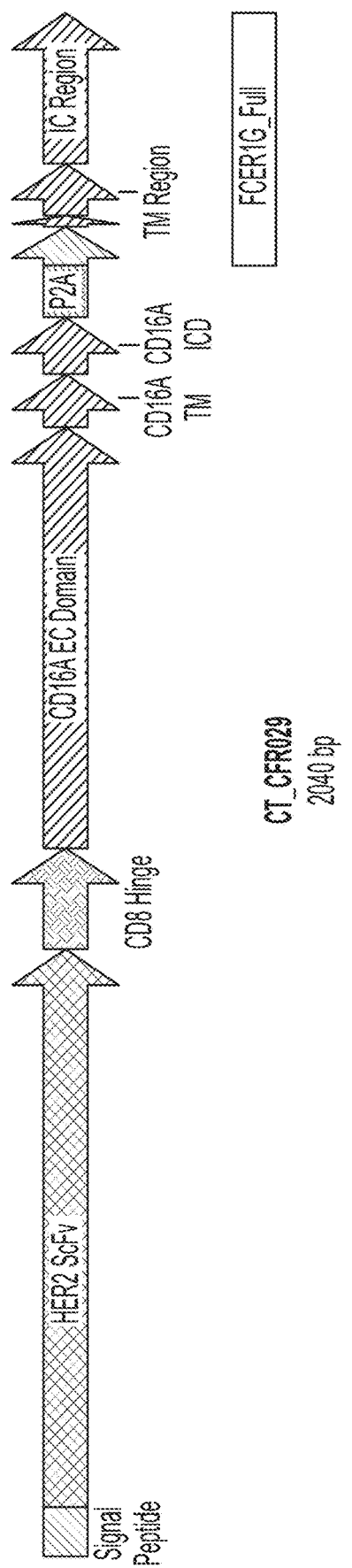
Figure 35:
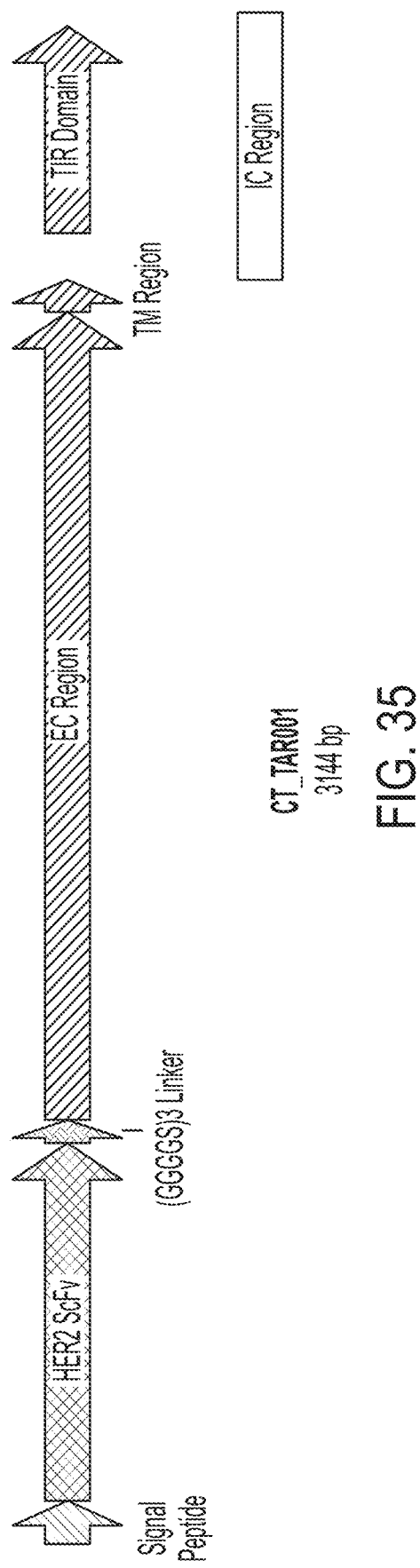
Figure 36:
Figure 37:
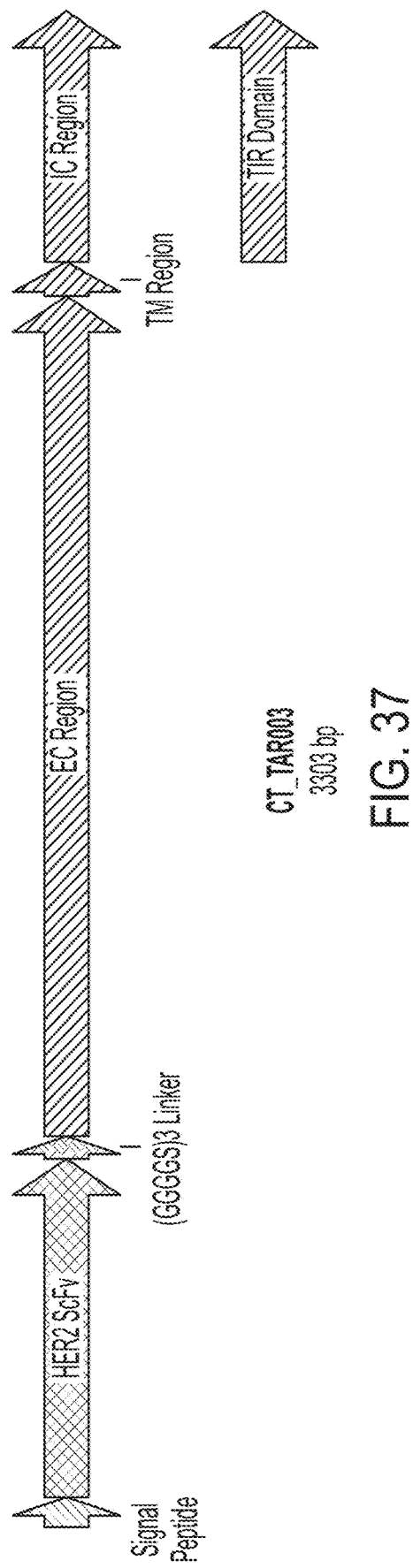
Figure 38:
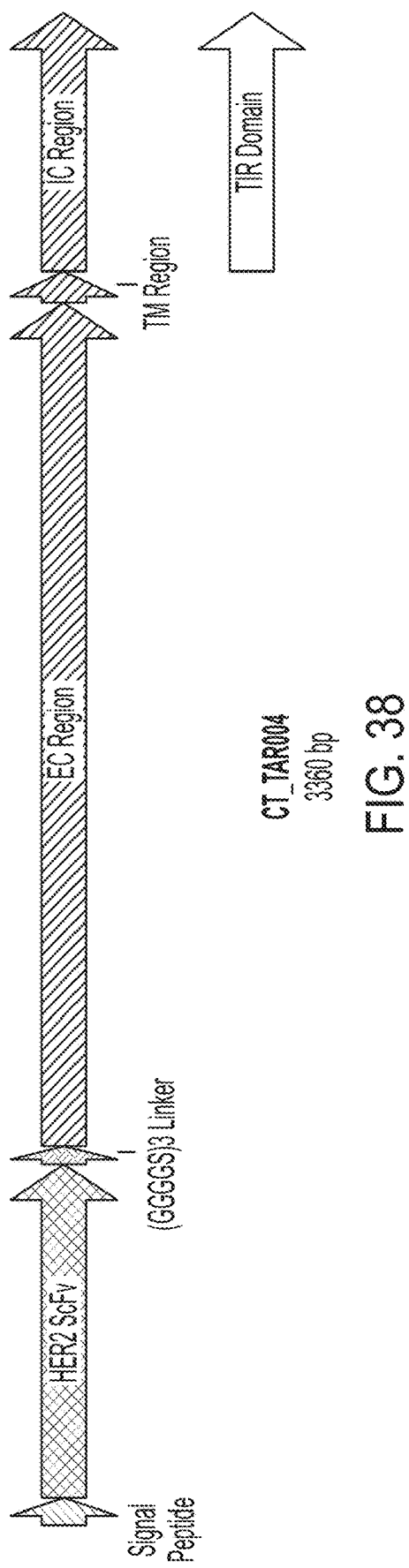
Figure 39:
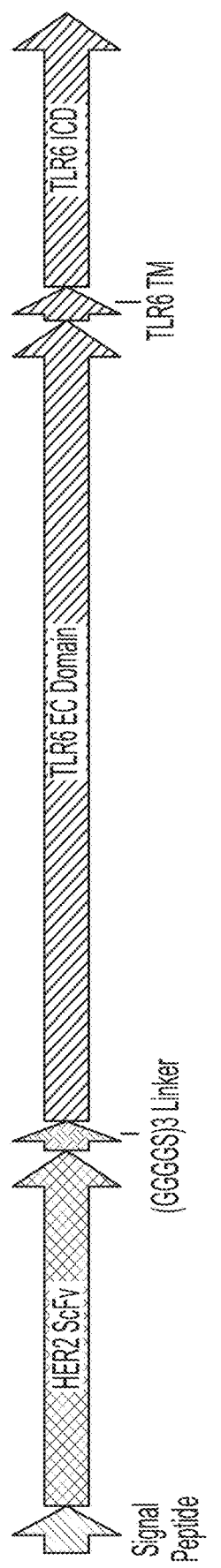
Figure 40:
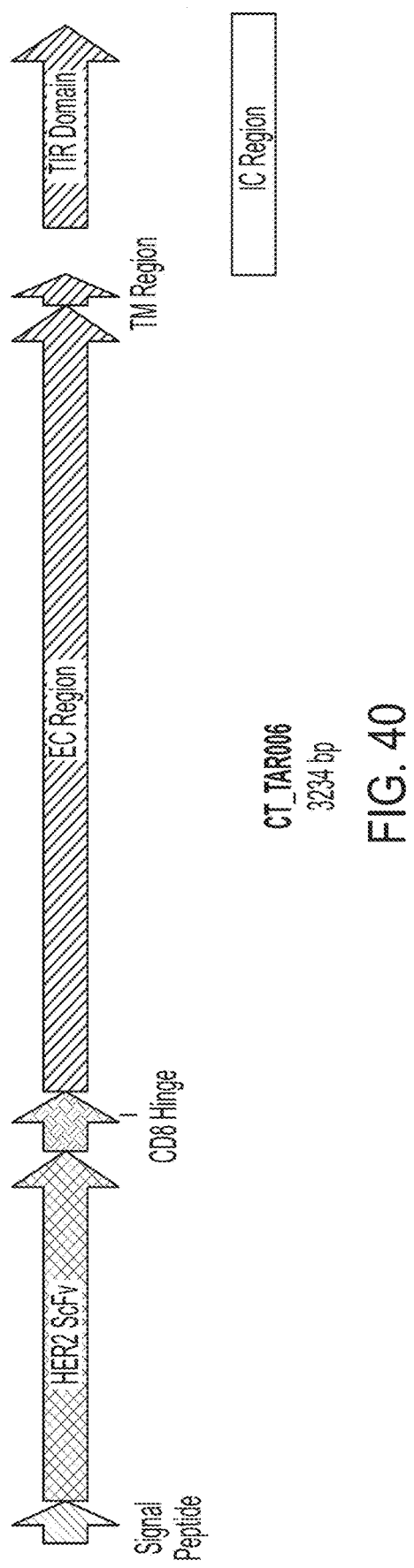
Figure 41:
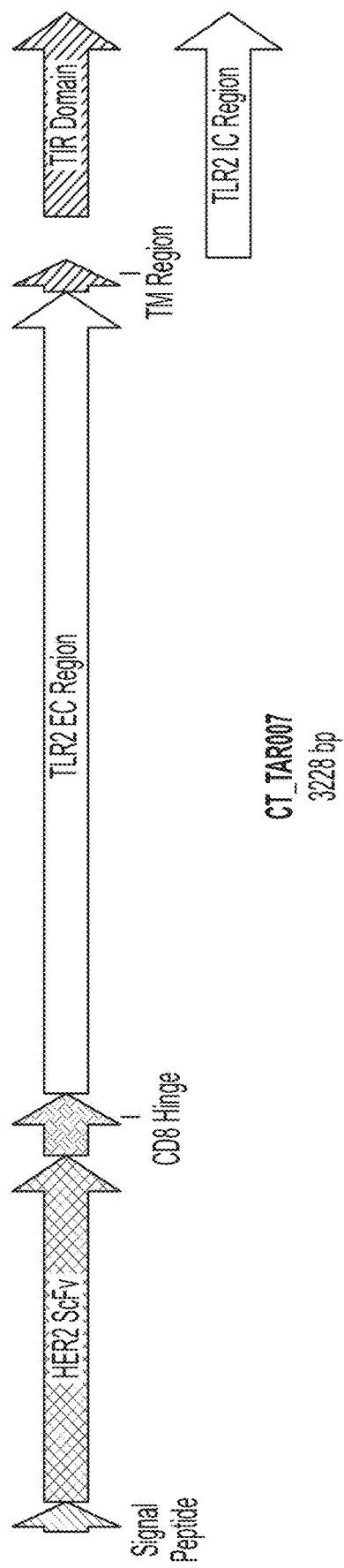
Figure 42:
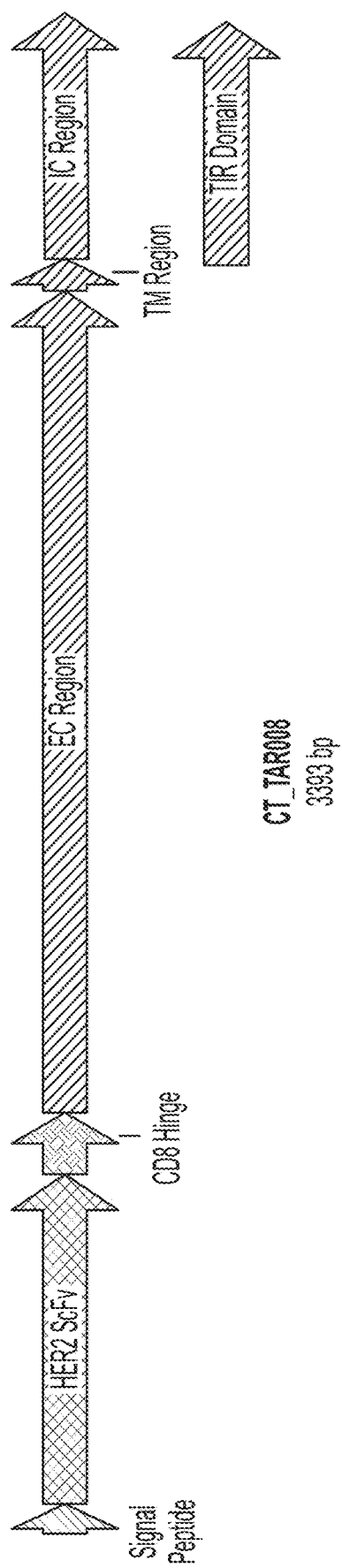
Figure 43:
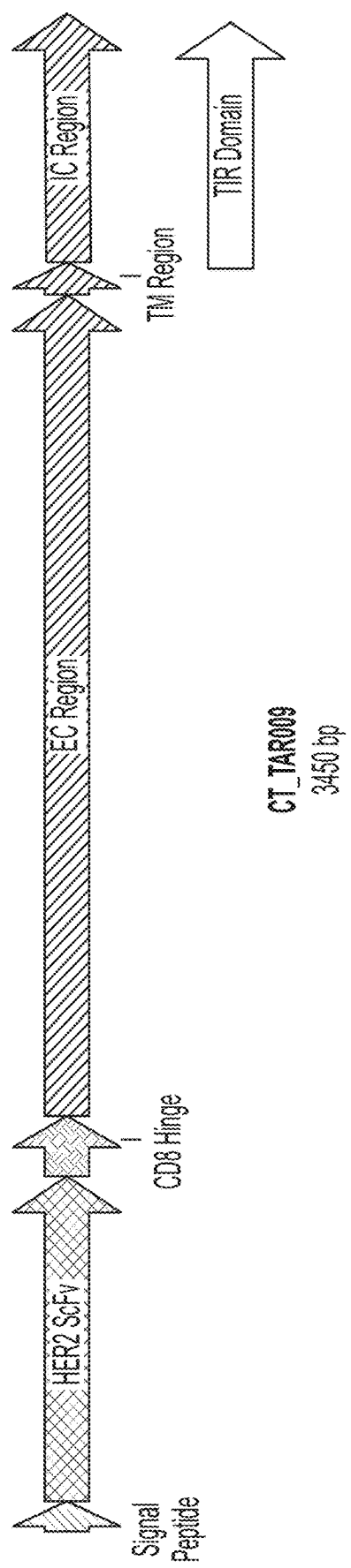
Figure 44:
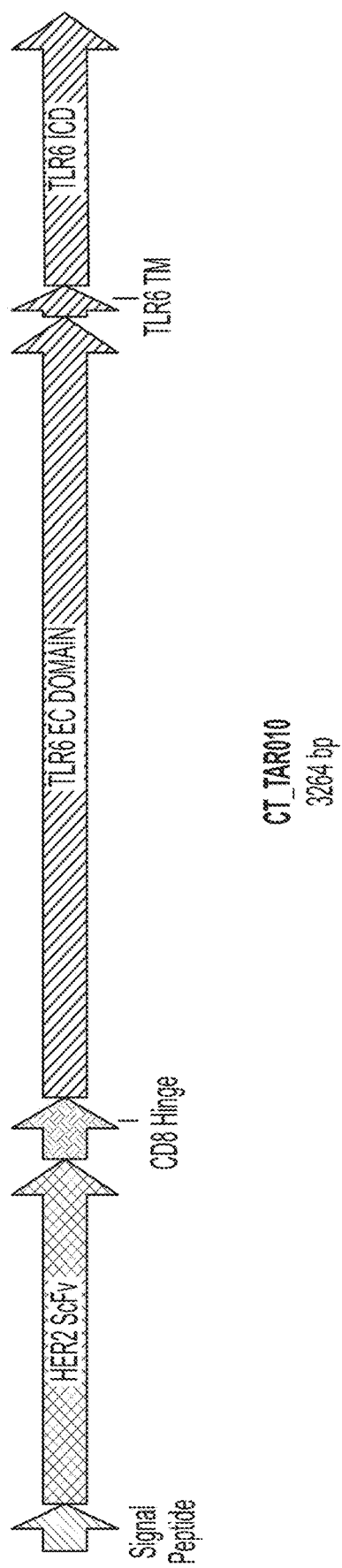
Figure 45:
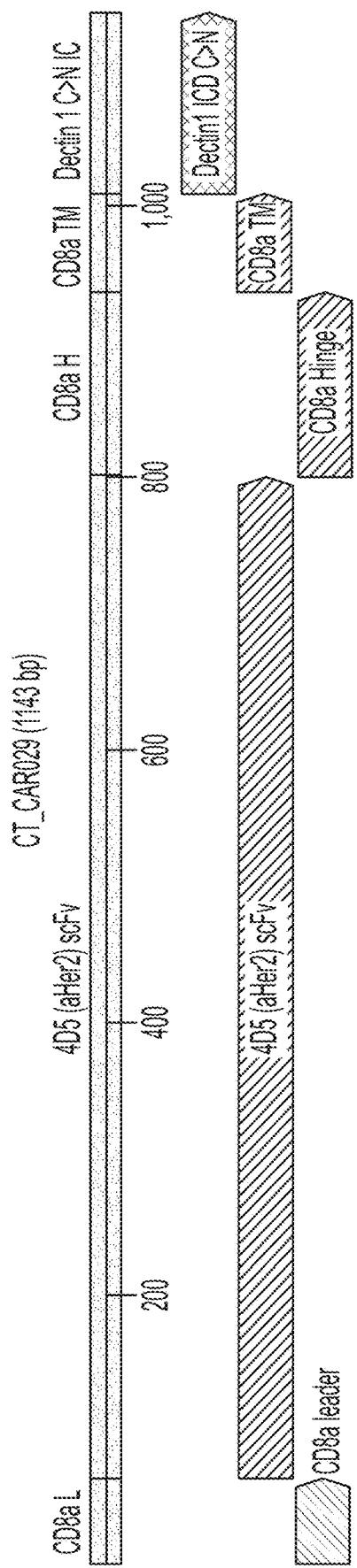
Figure 46:
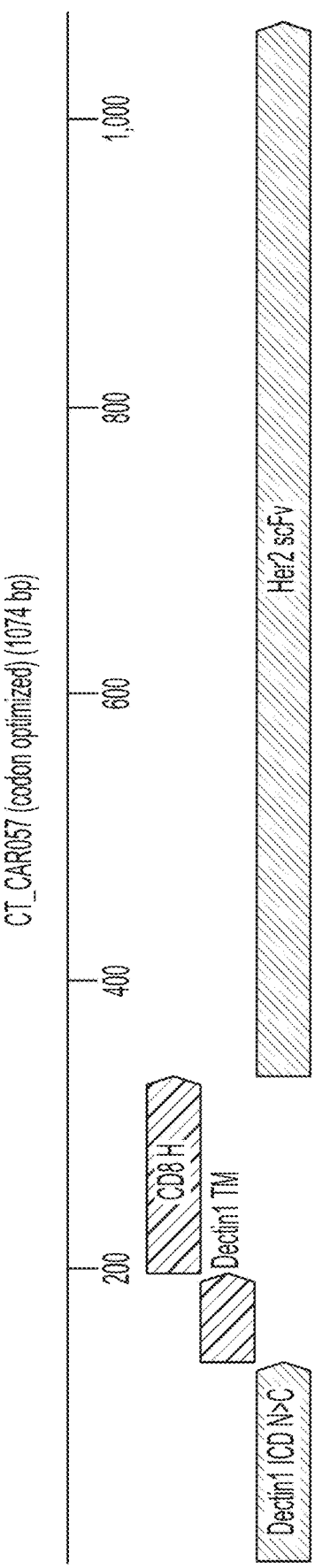
Figure 47:
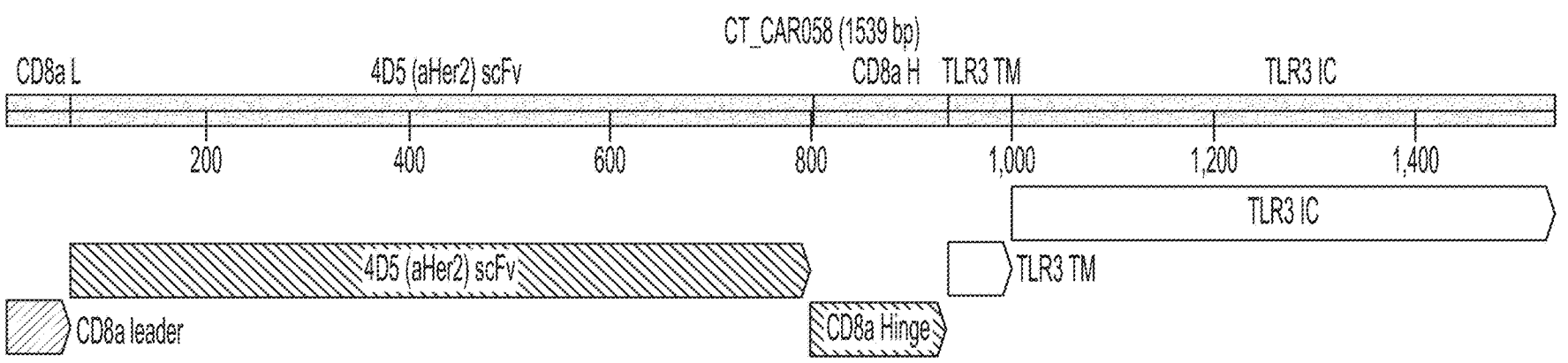
Figure 48:
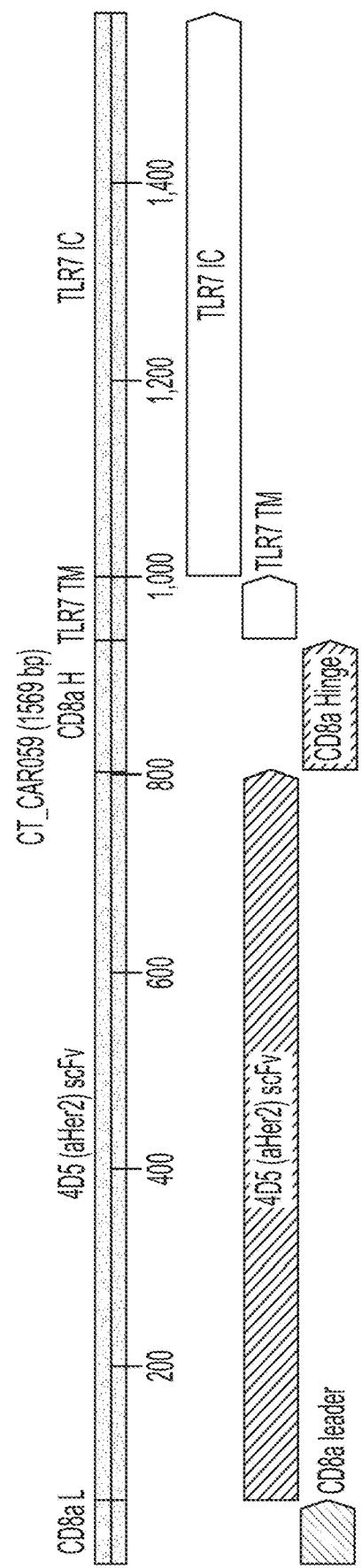
Figure 49:
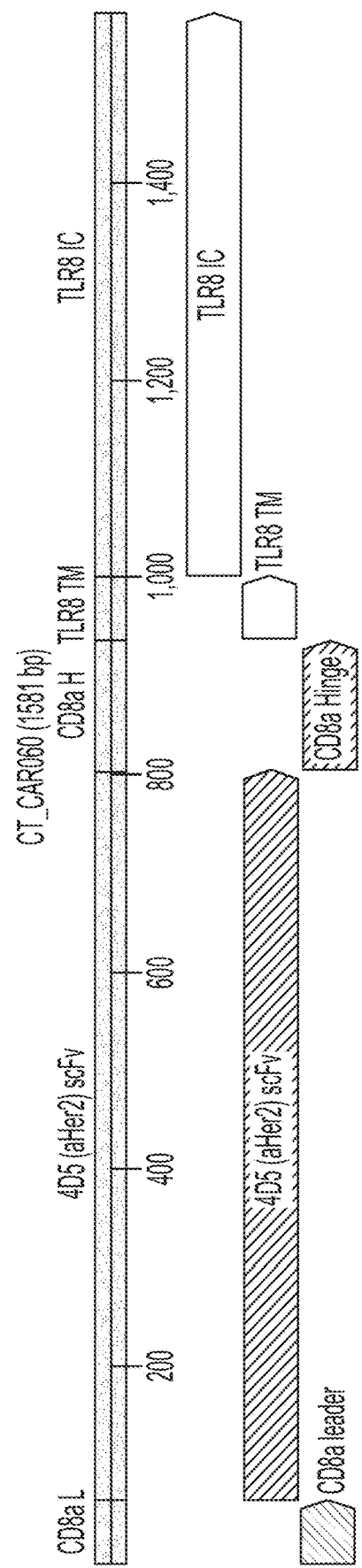
Figure 50:
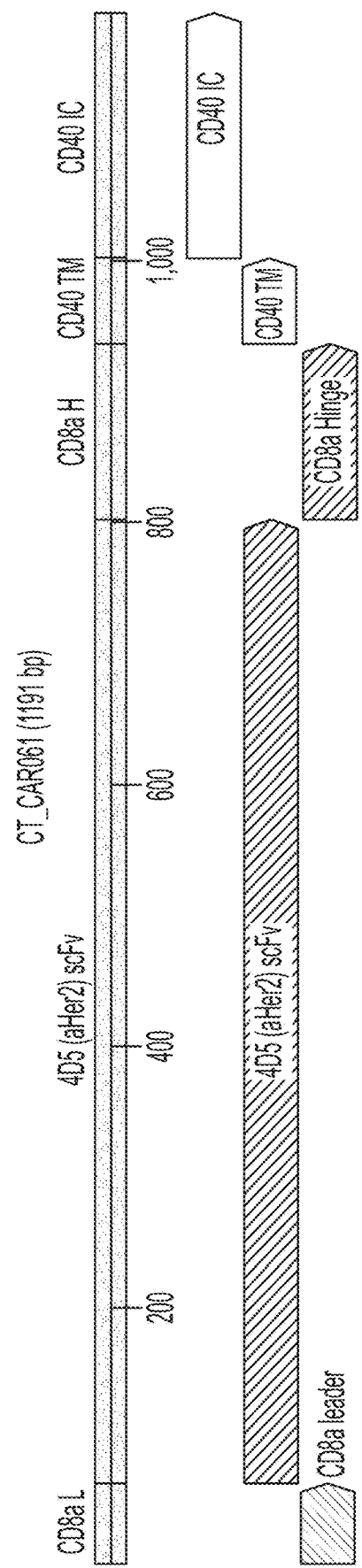
Figure 51:
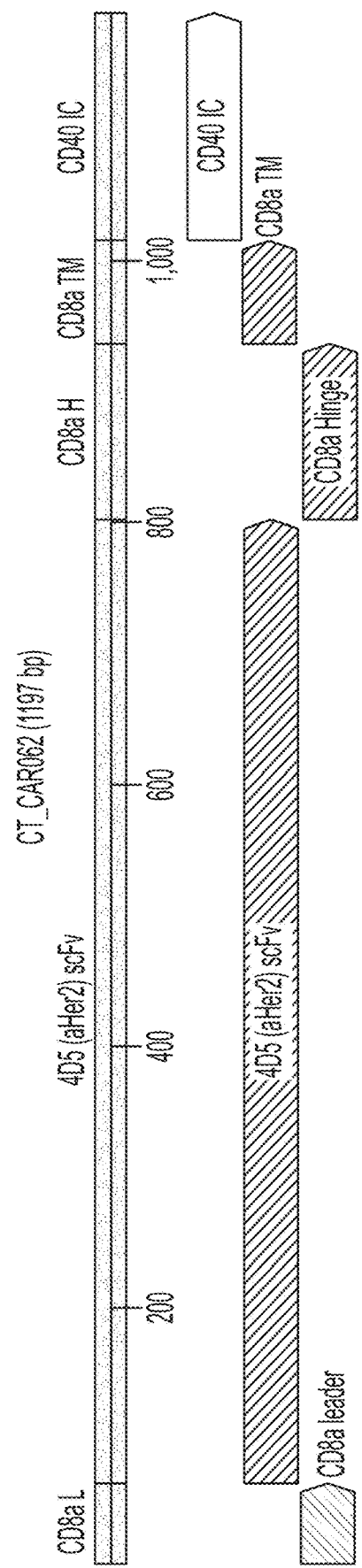
Figure 52:
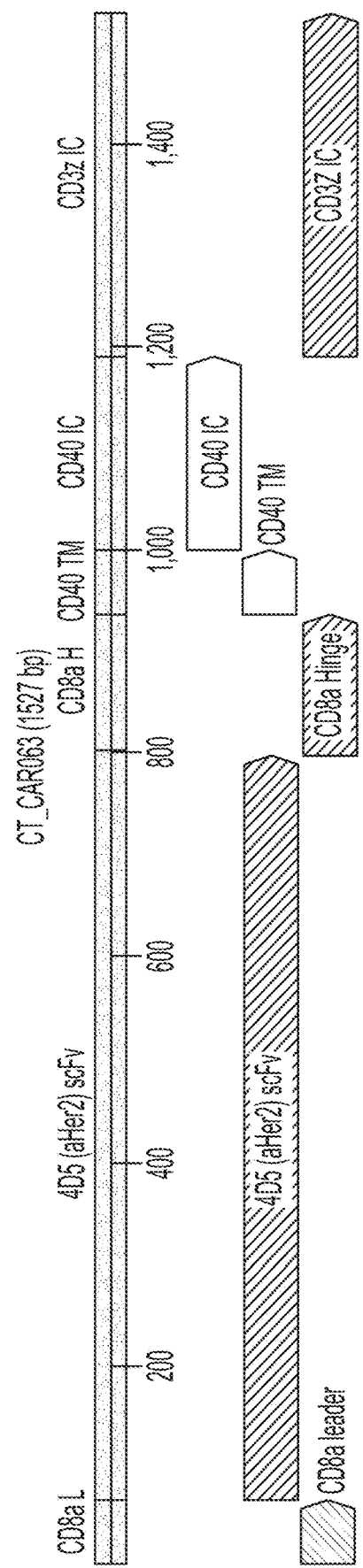
Figure 53:
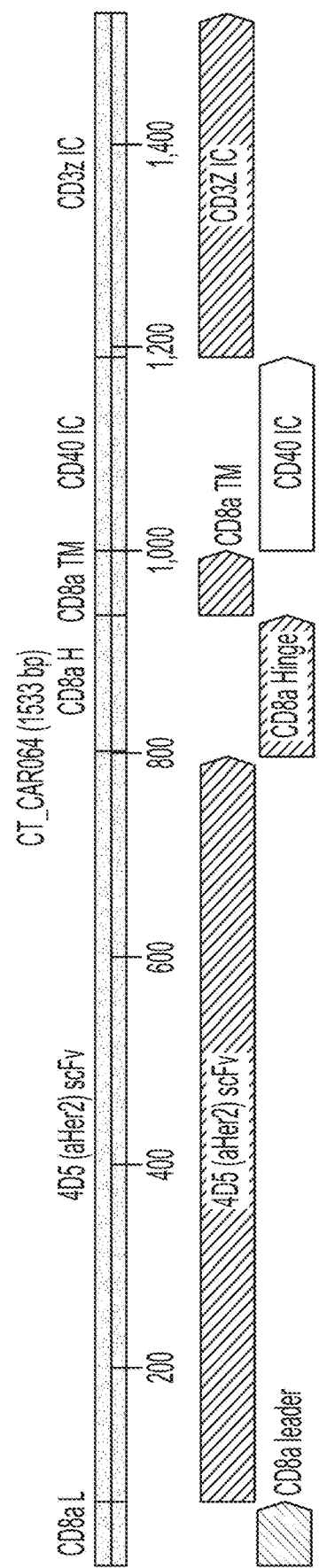
Figure 54:
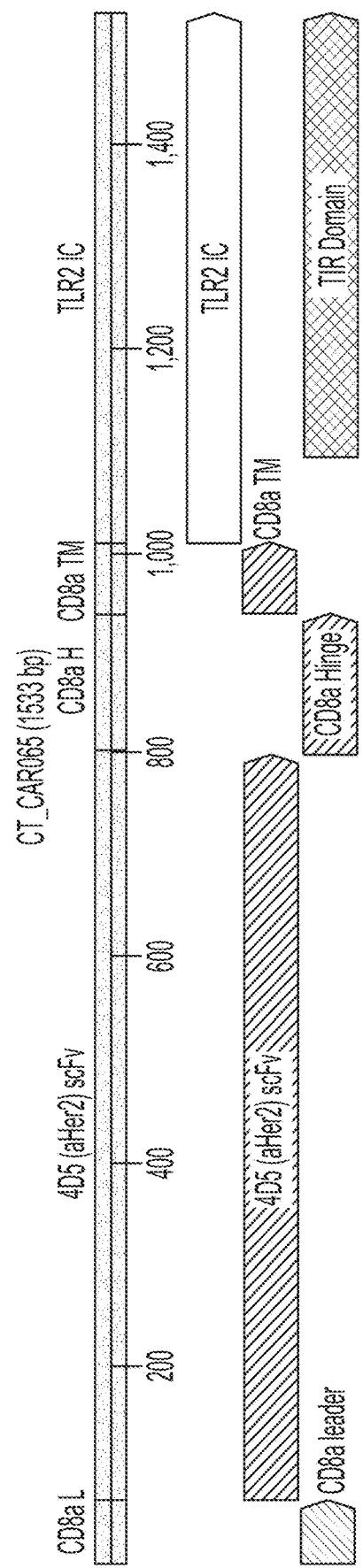
Figure 55:
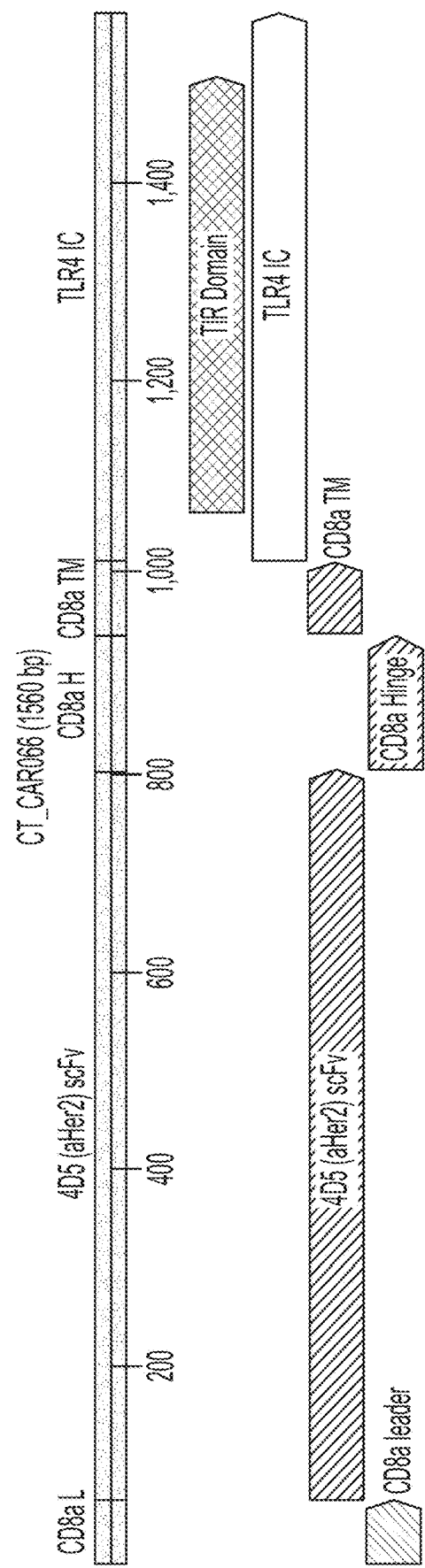
Figure 56:
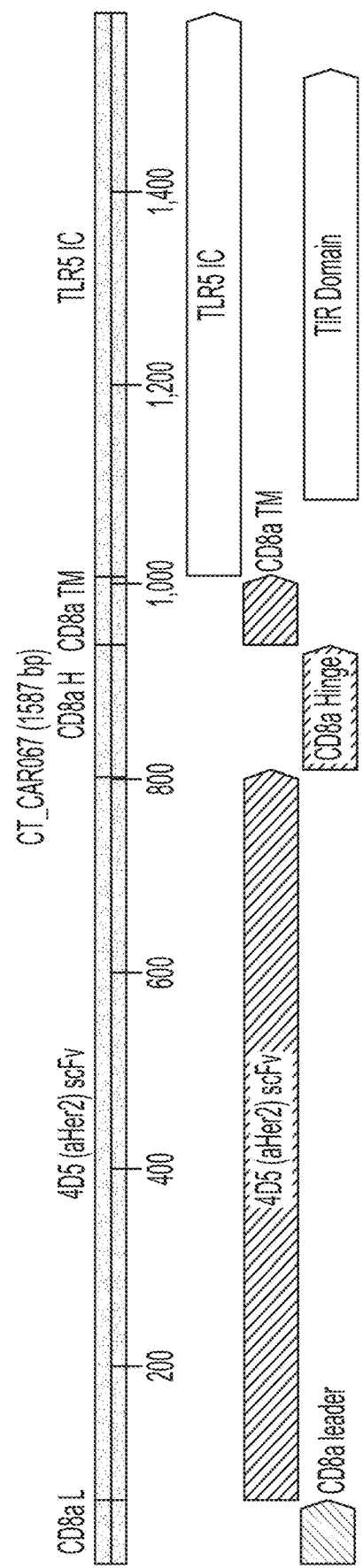
Figure 57:
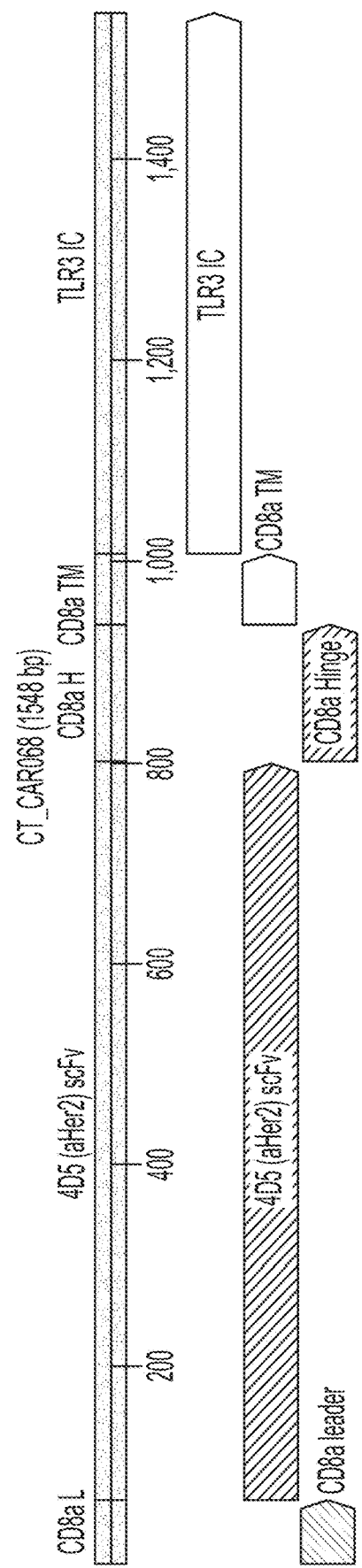
Figure 58:
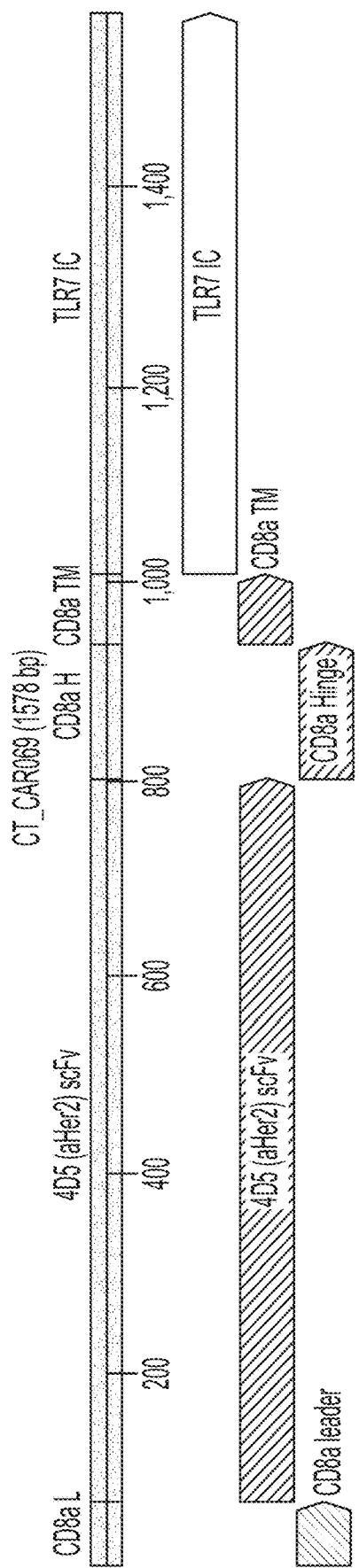
Figure 59:
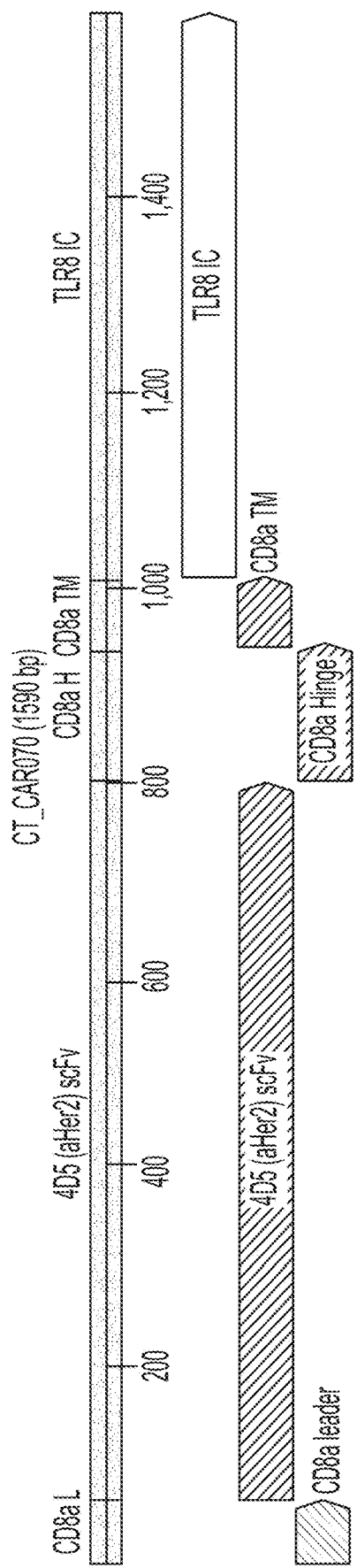
Figure 60:
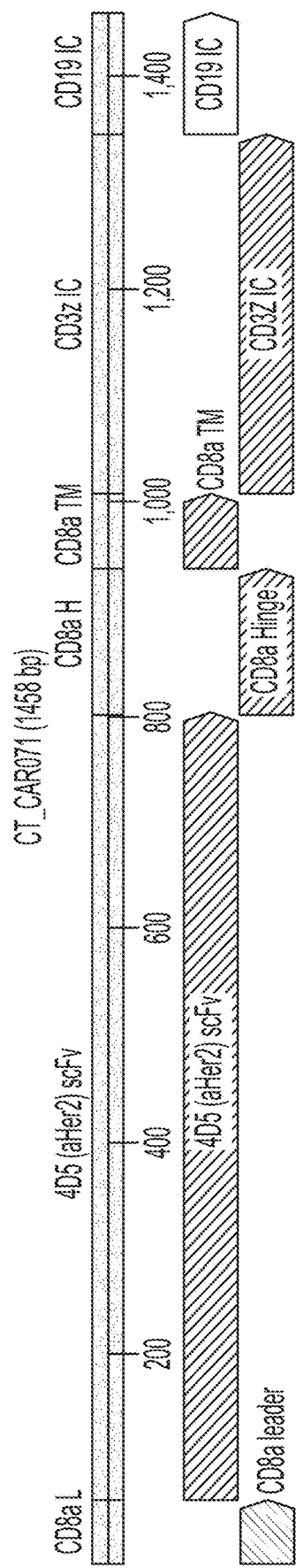
Figure 61:
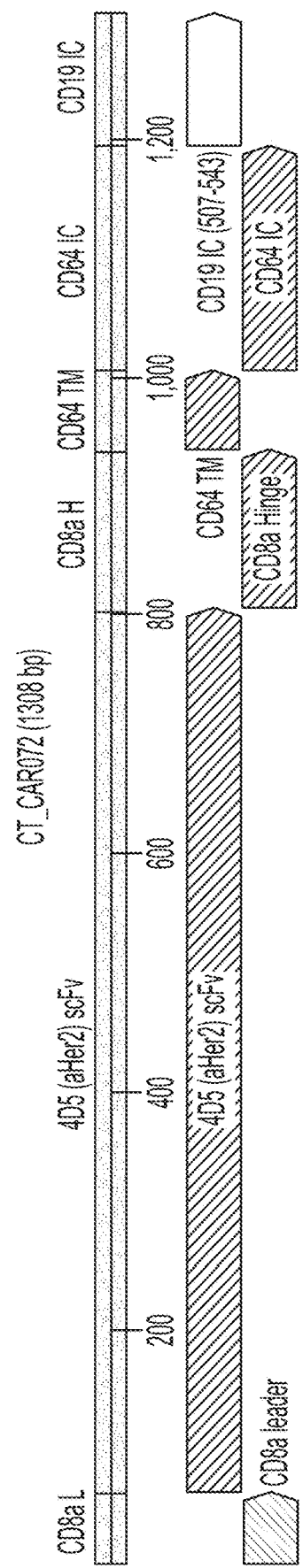
Figure 62:
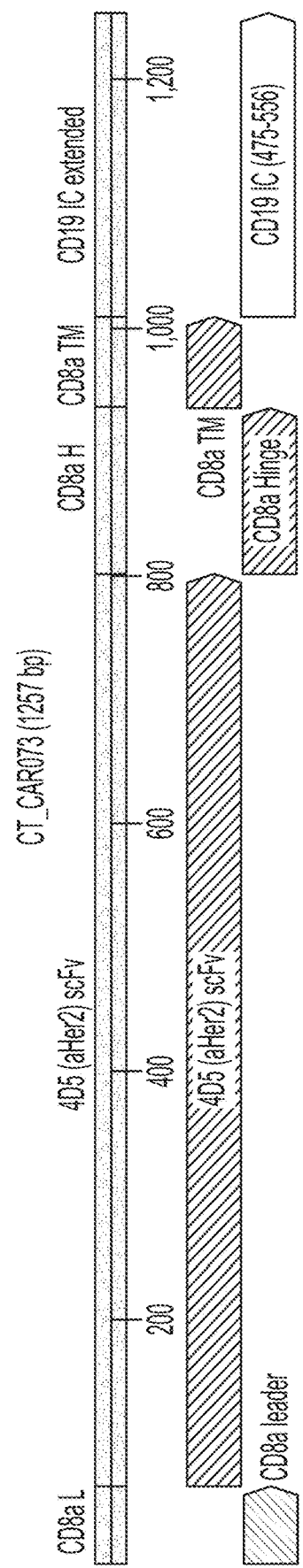
Figure 63:
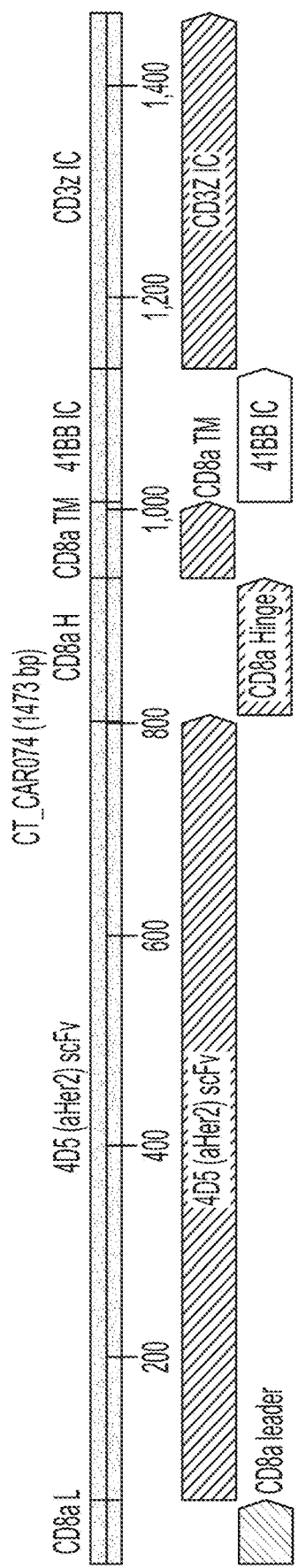
Figure 64:
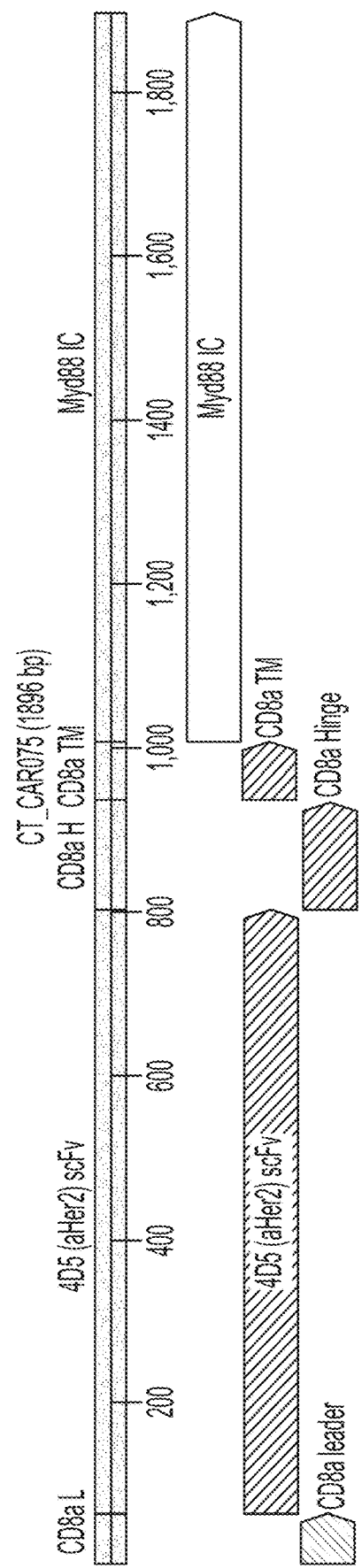
Figure 65:
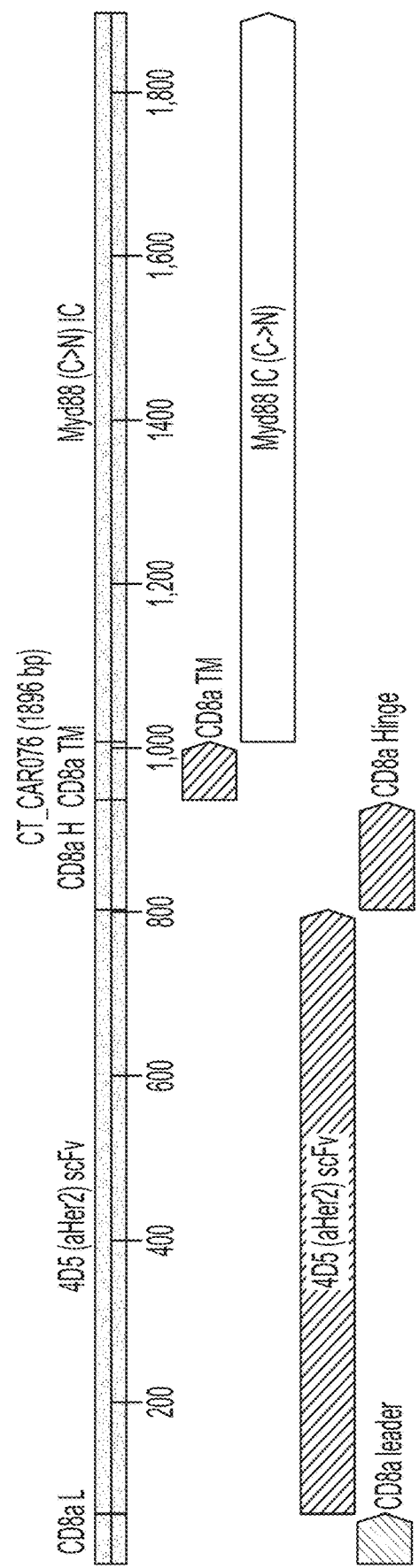
Figure 66:
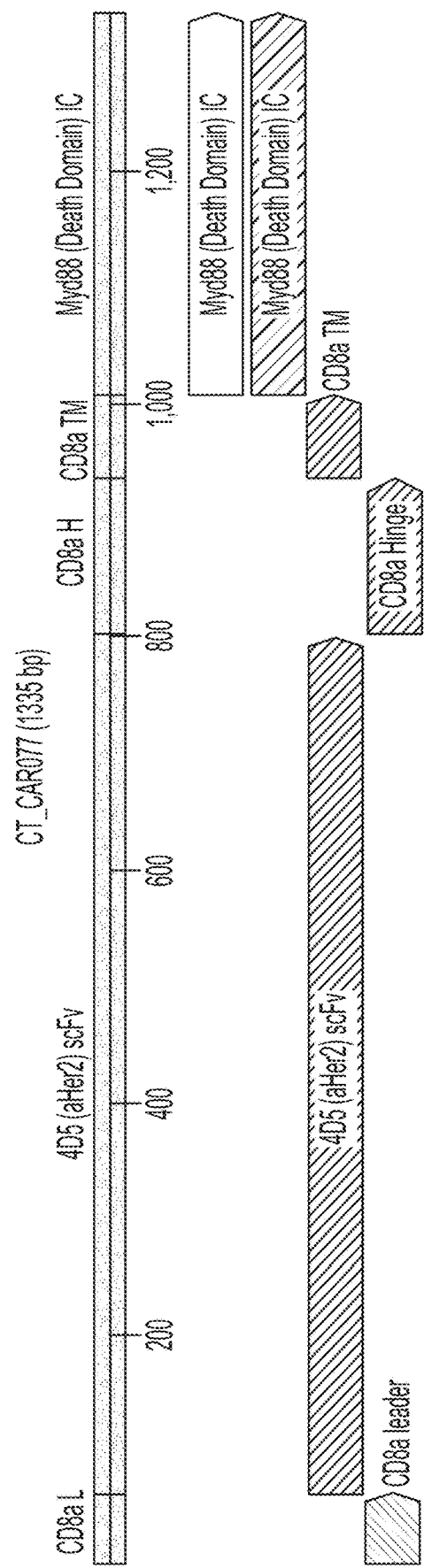
Figure 67:
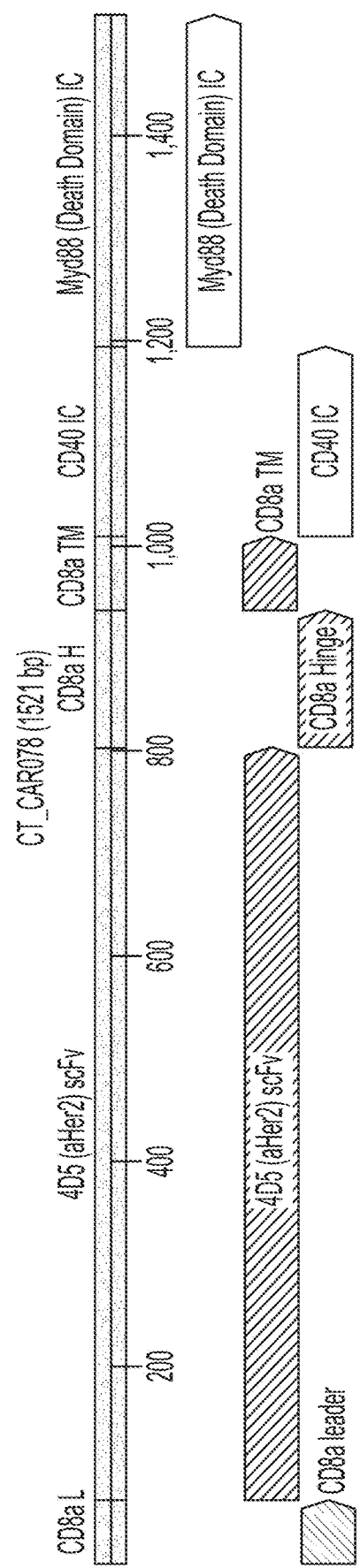
Figure 68:
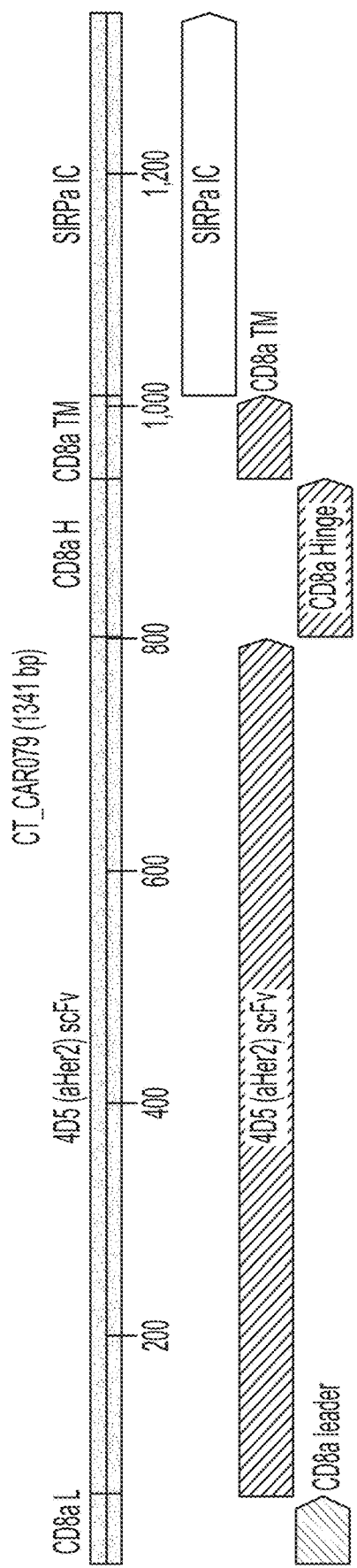
Figure 69:
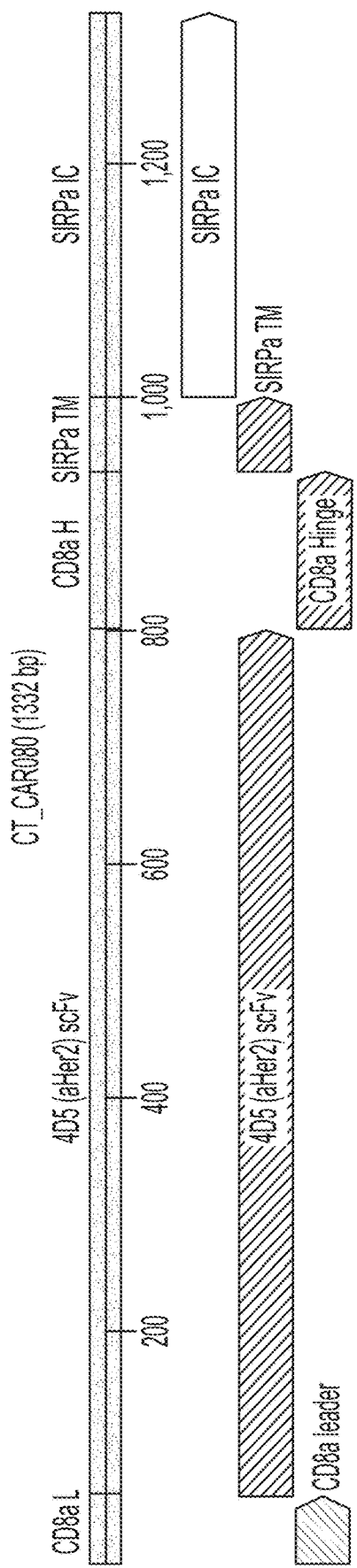
Figure 70:
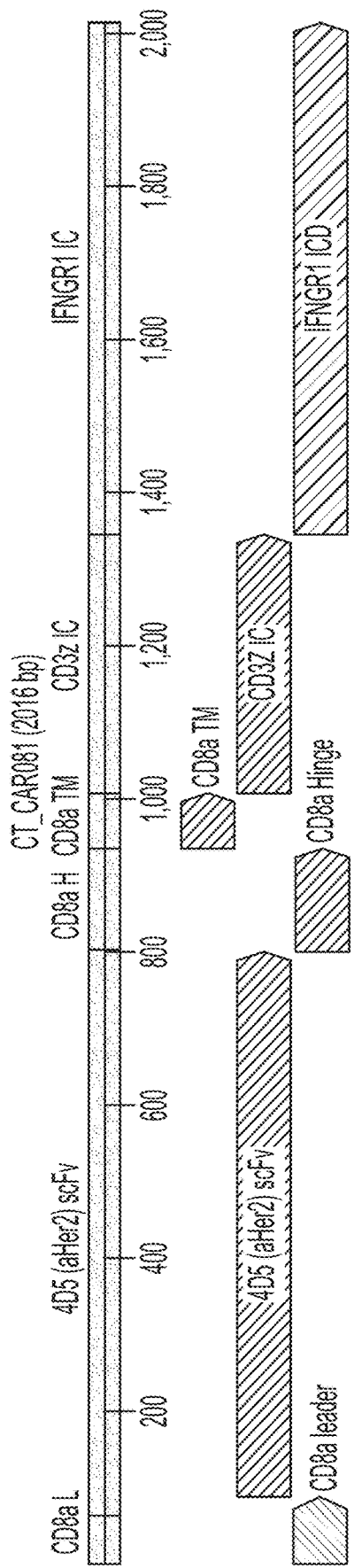
Figure 71:
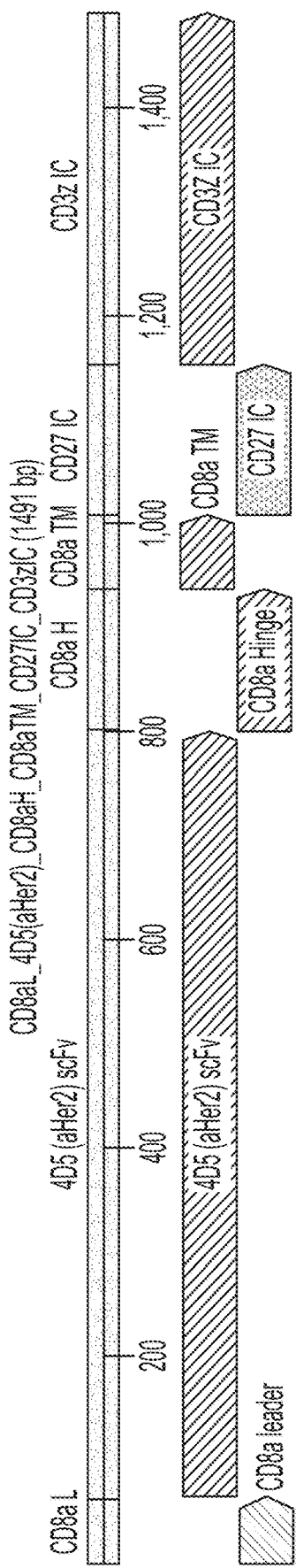
Figure 72:
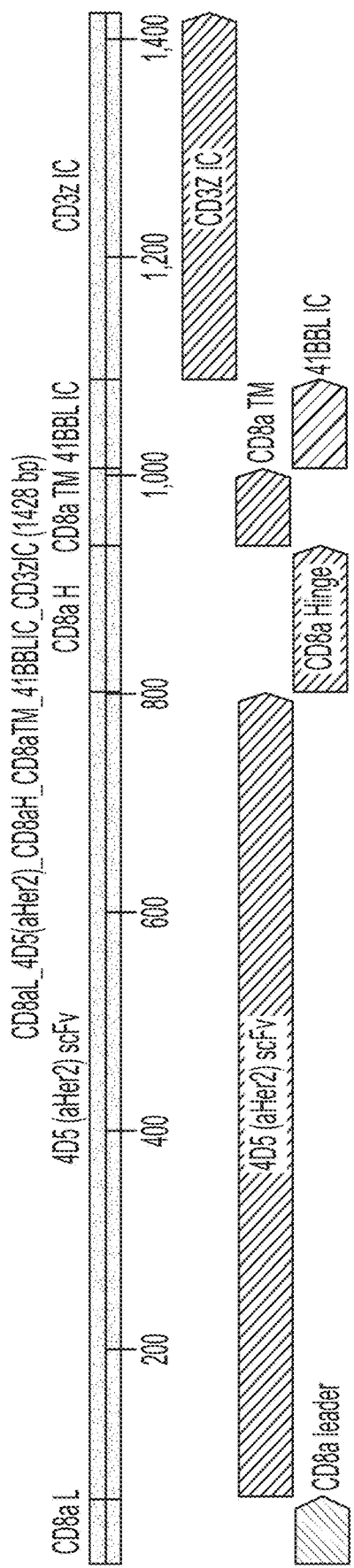
Figure 73:
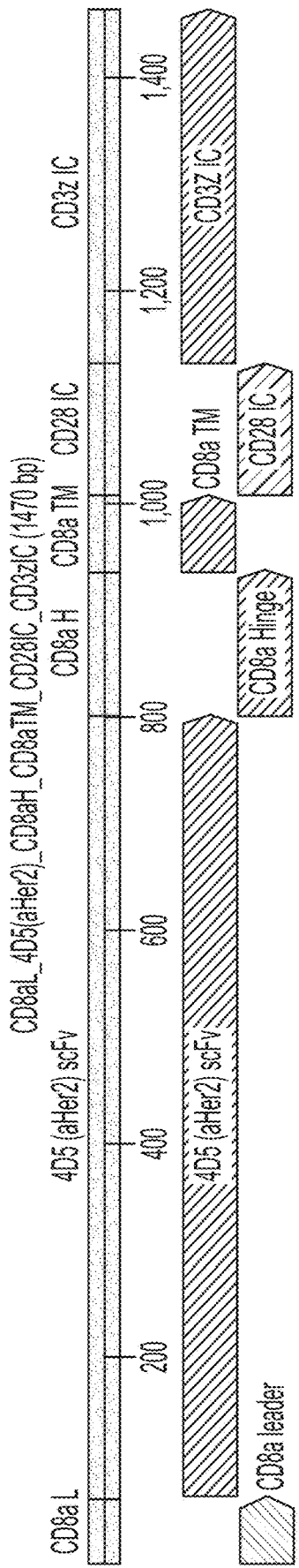
Figure 74:
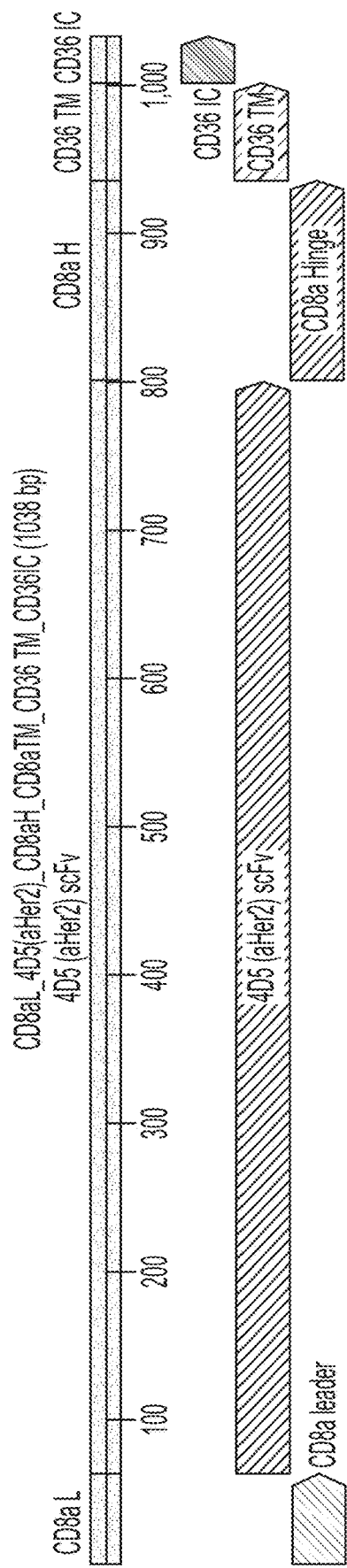
Figure 75:
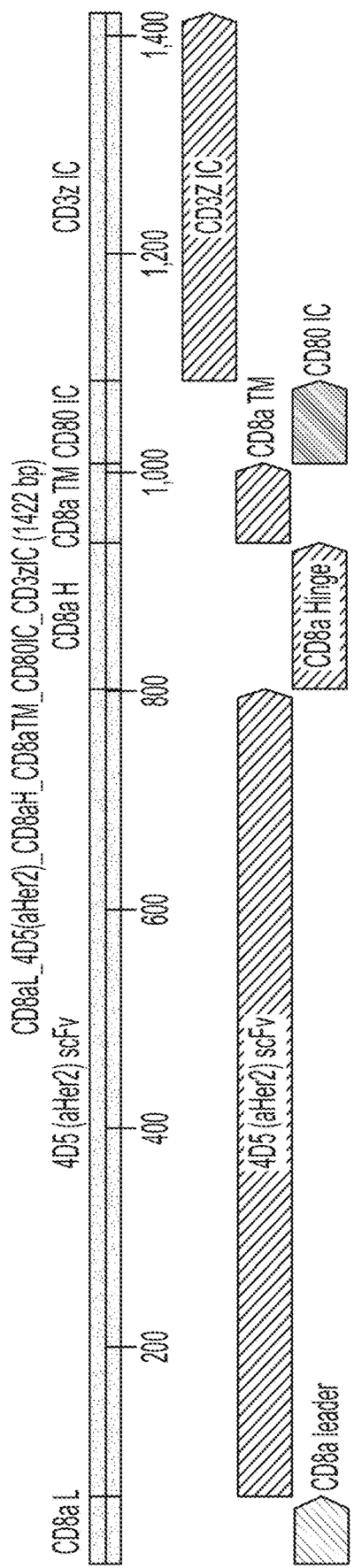
Figure 76:
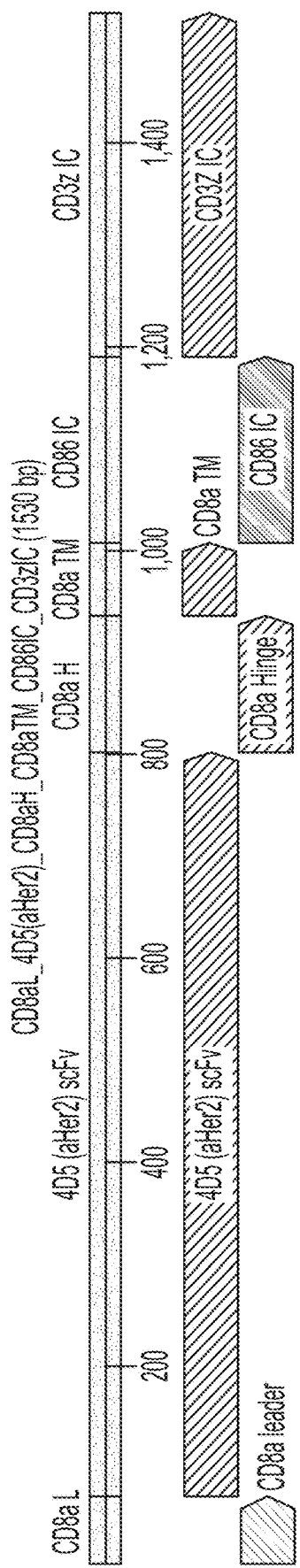
Figure 77:
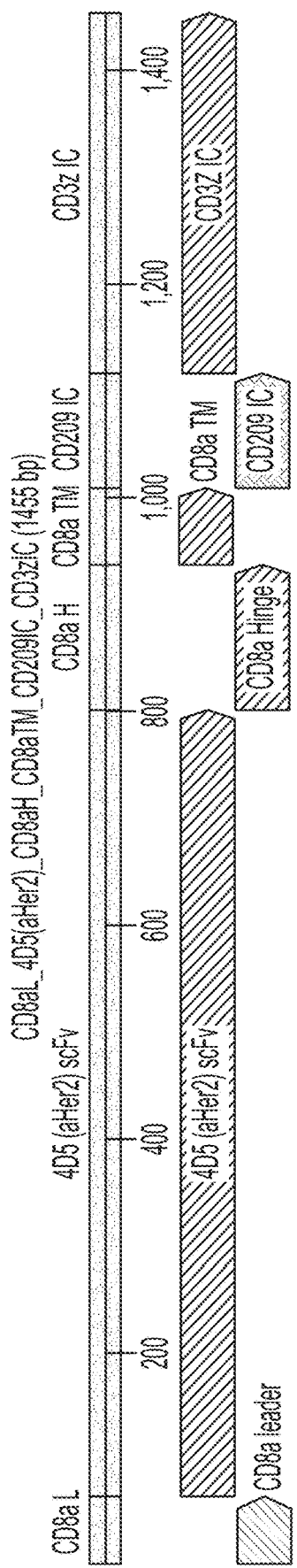
Figure 78:
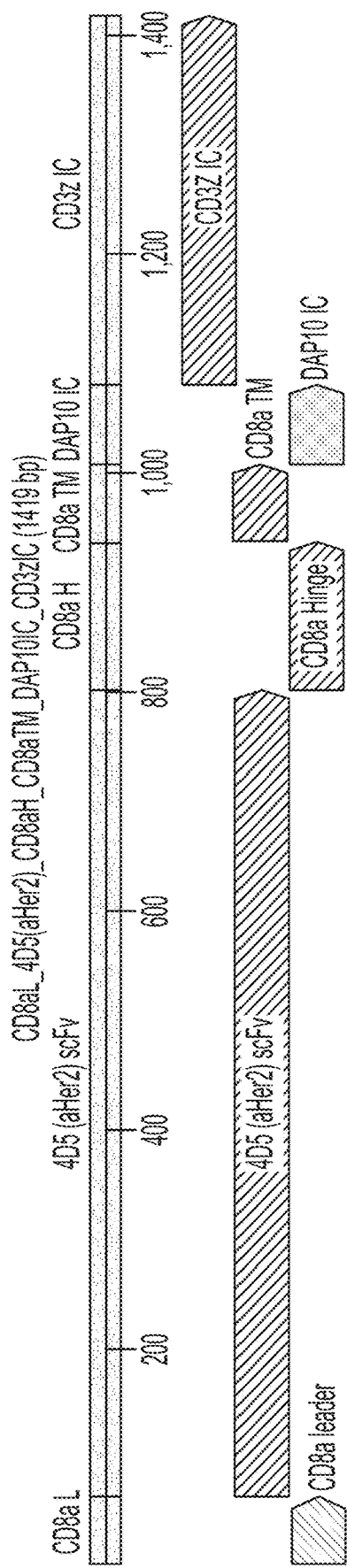
Figure 79:
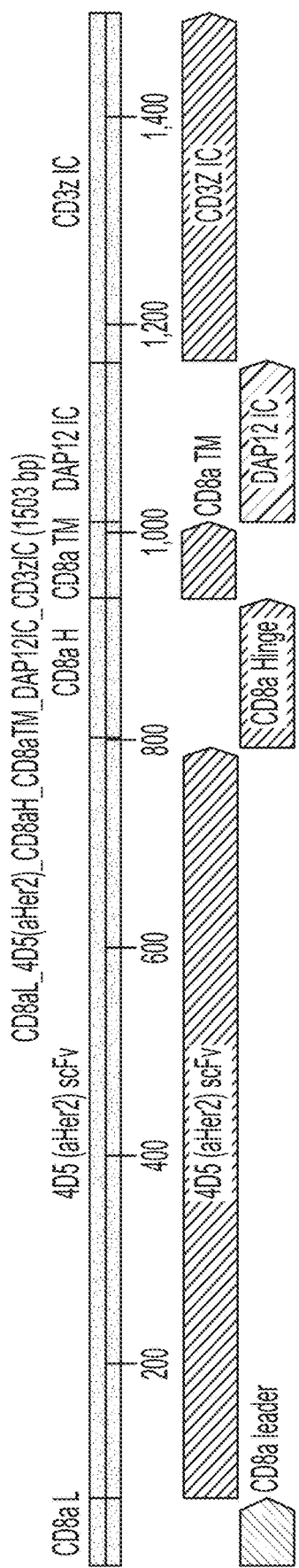
Figure 80:
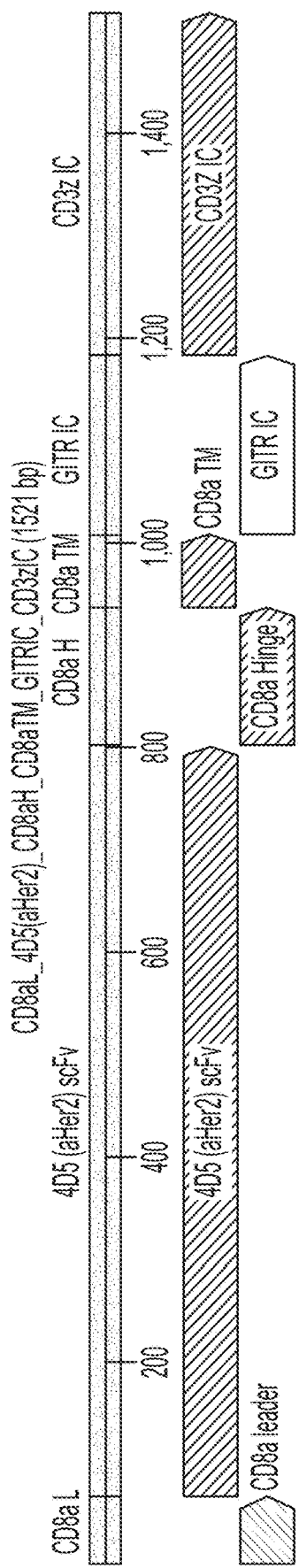
Figure 81:
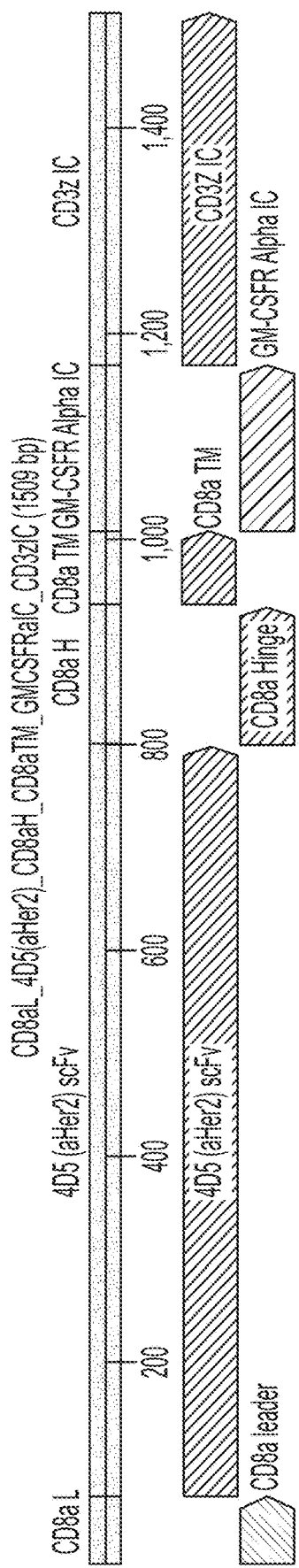
Figure 82:
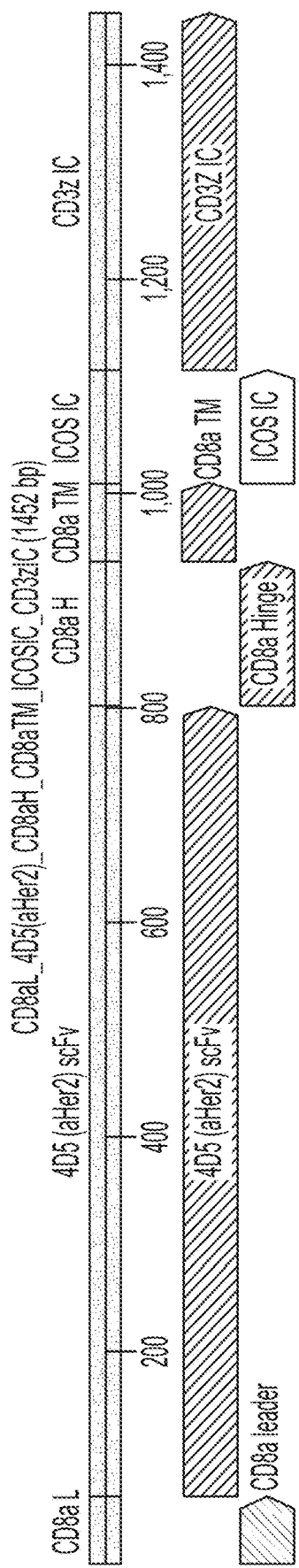
Figure 83:
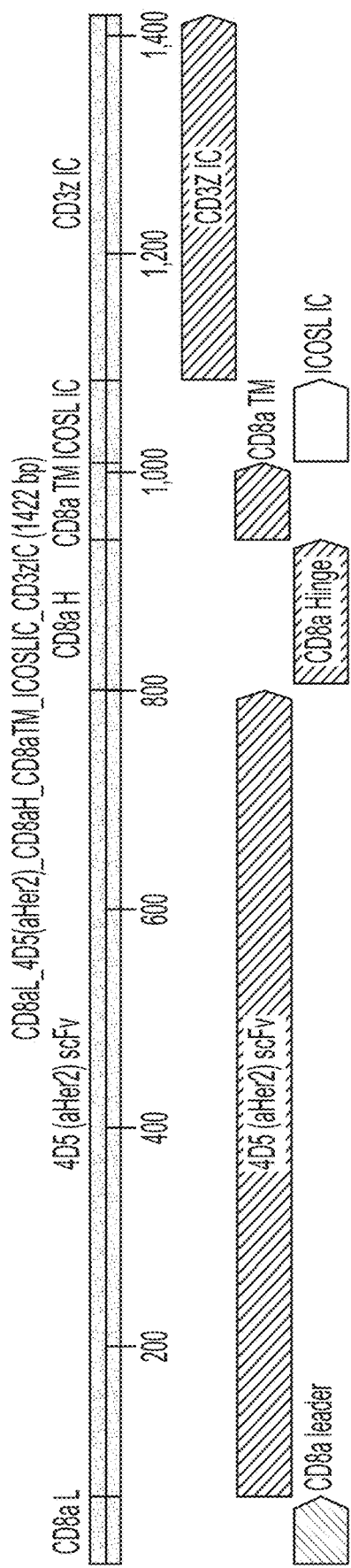
Figure 84:
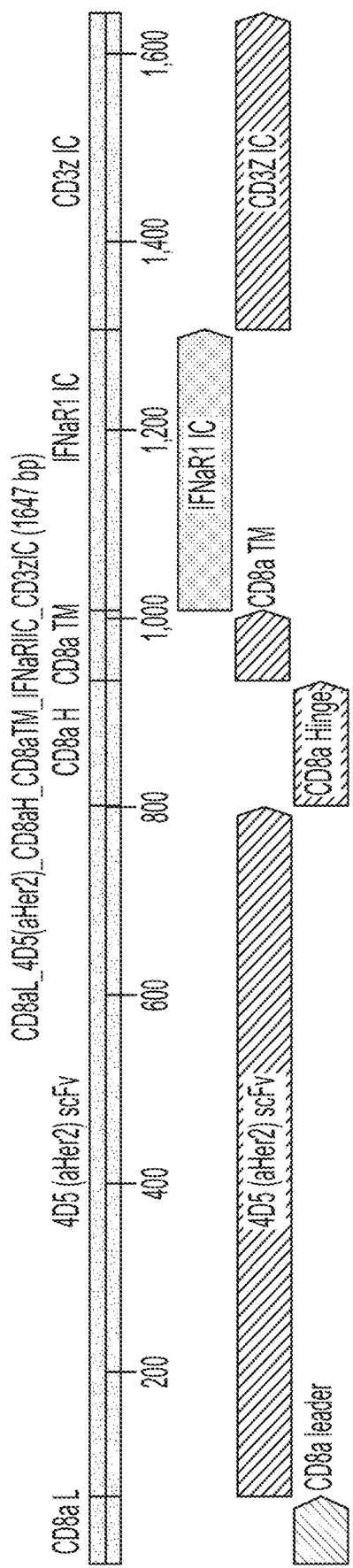
Figure 85:
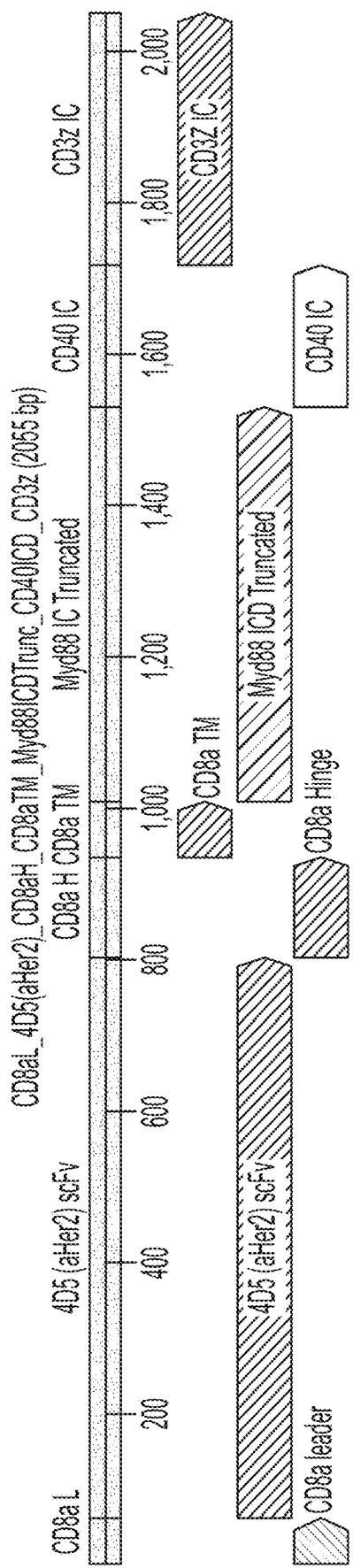
Figure 86:
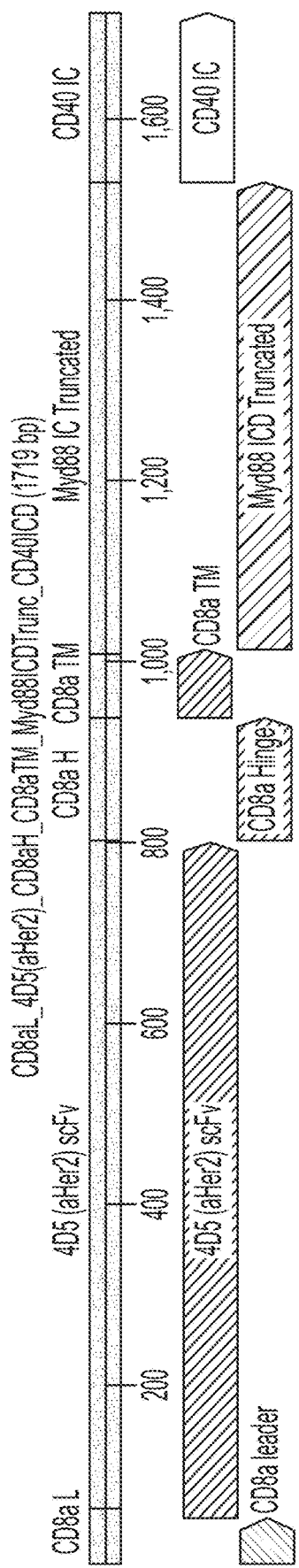
Figure 87:
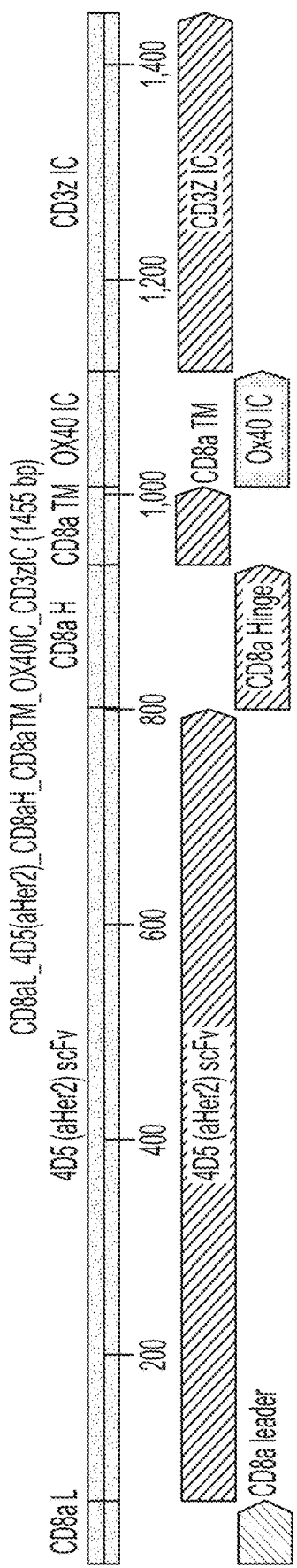
Figure 88:
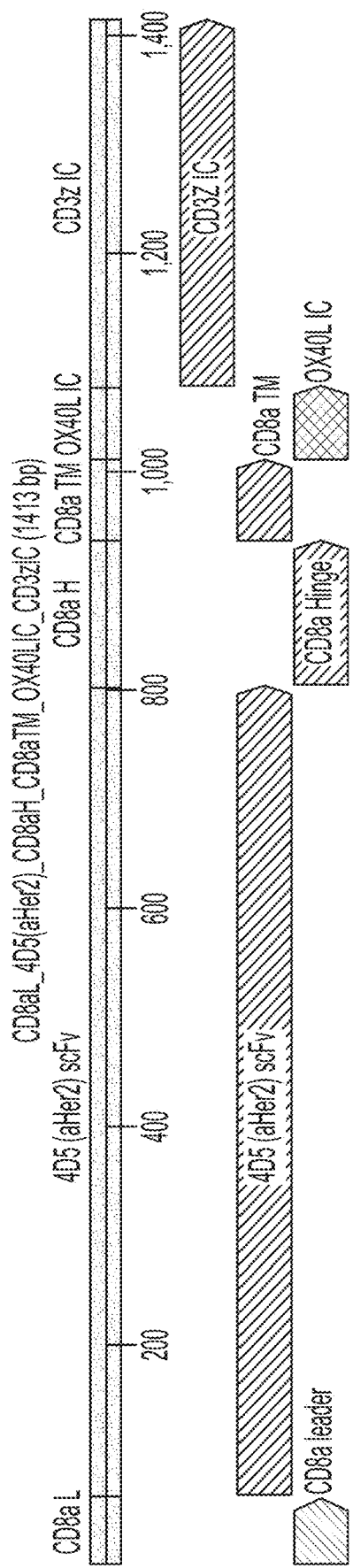
Figure 89:
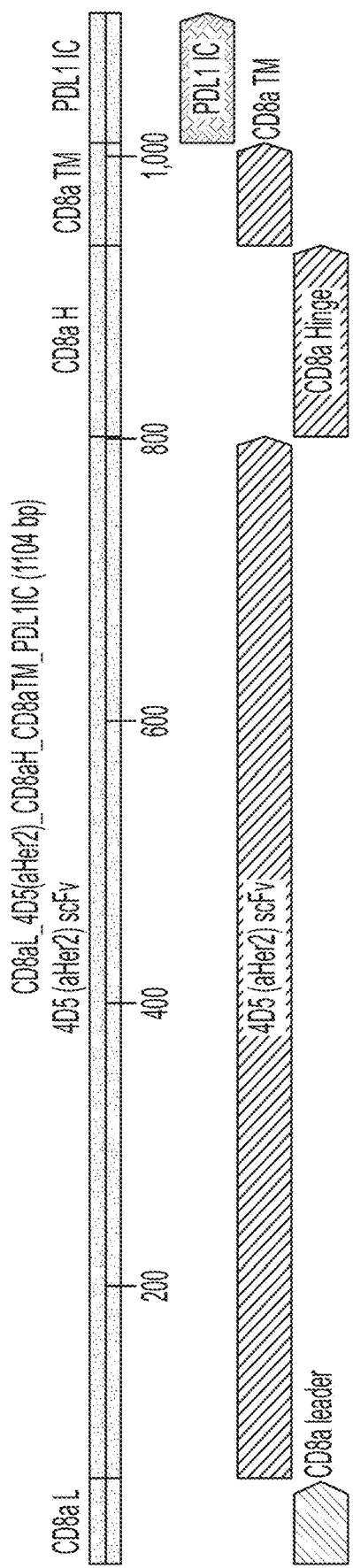
Figure 90:
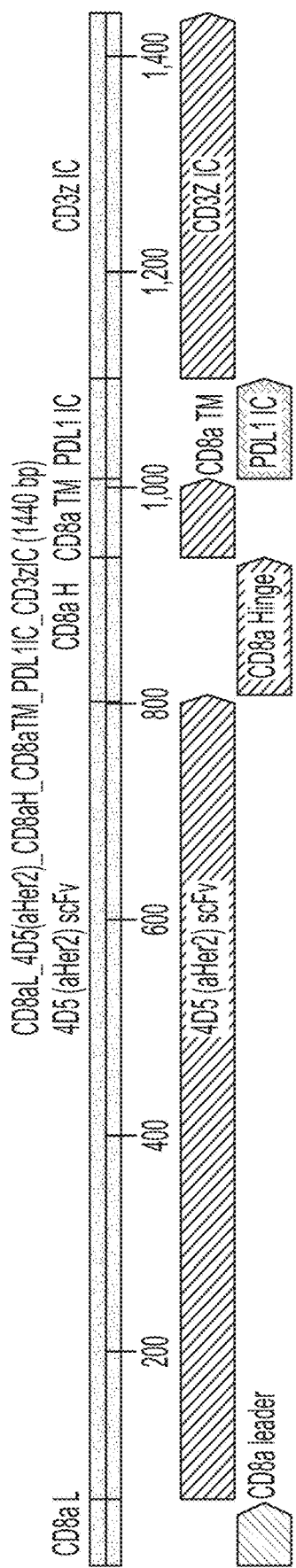
Figure 91:
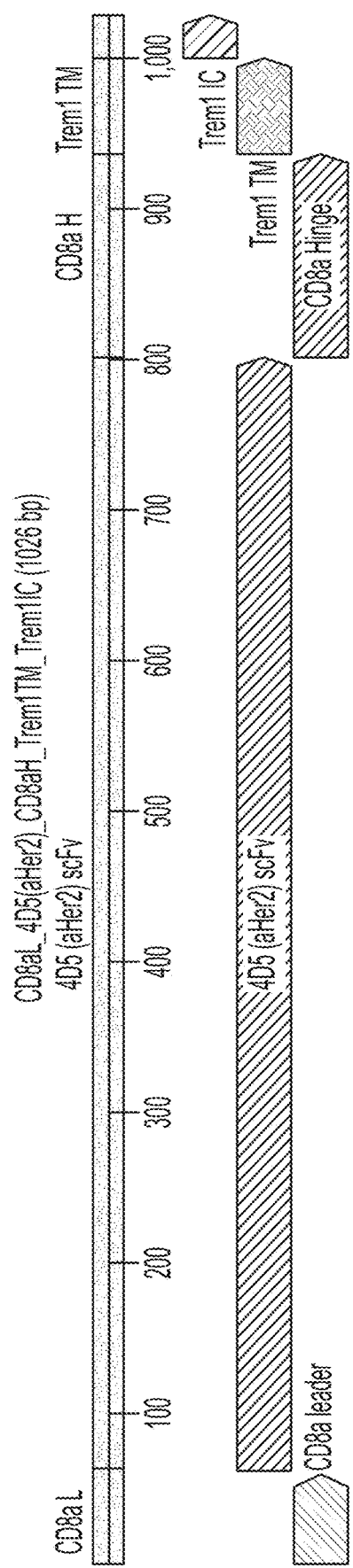
Figure 92:
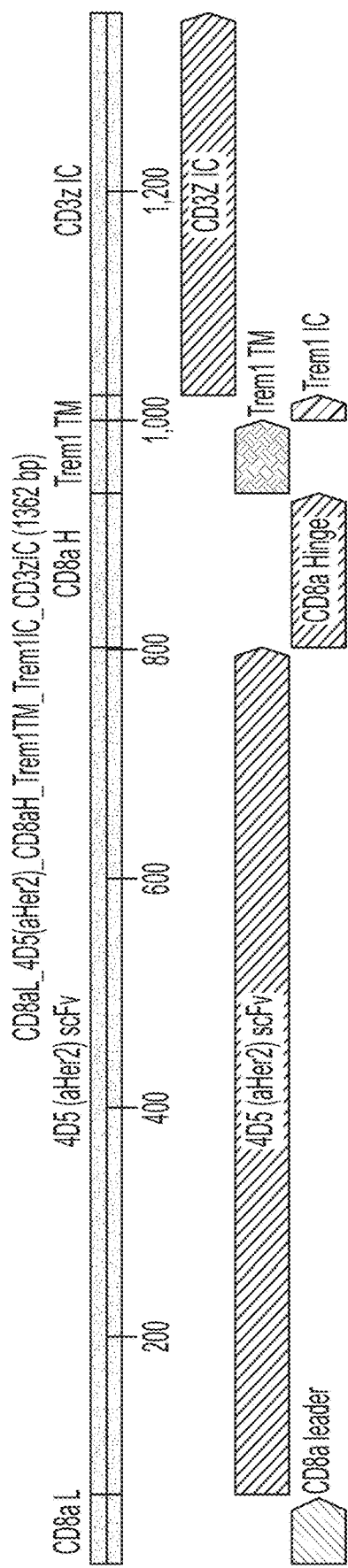
Figure 93:
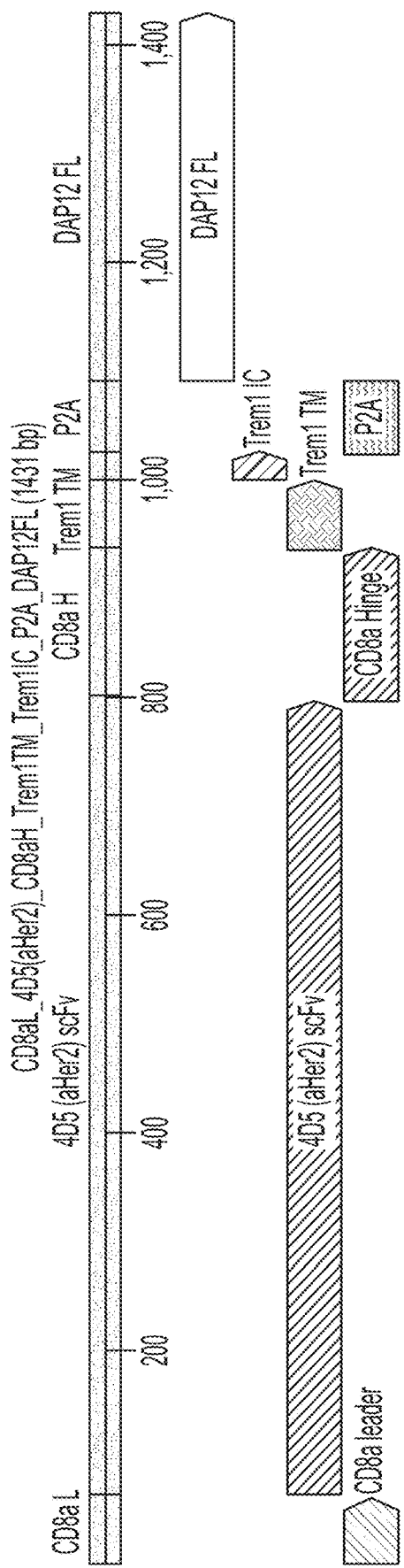
Figure 94:
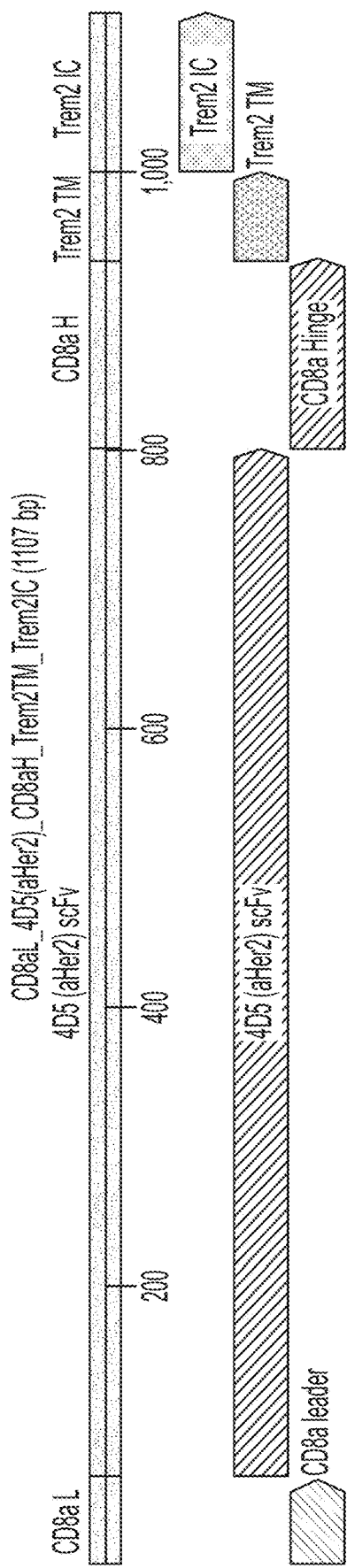
Figure 95:
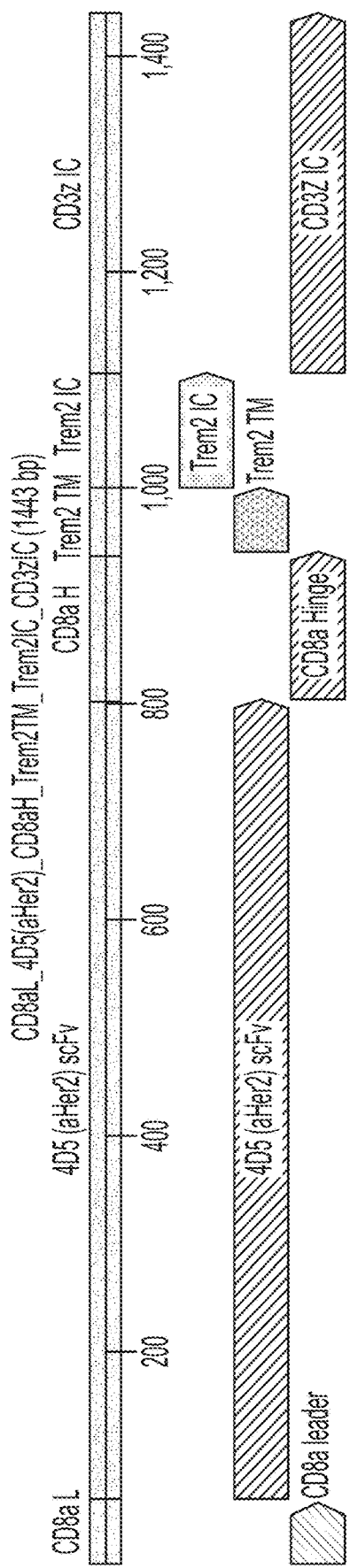
Figure 96:
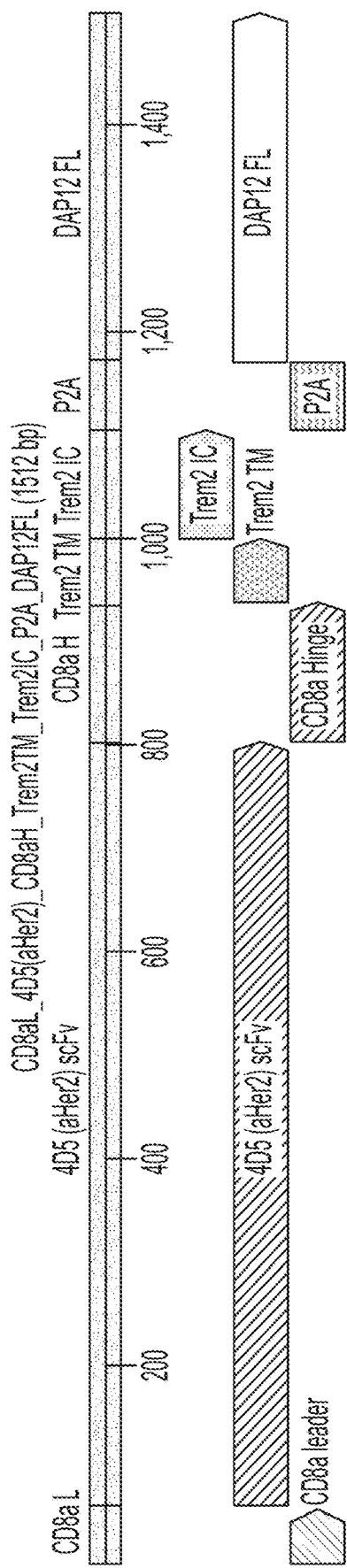
Figure 97:
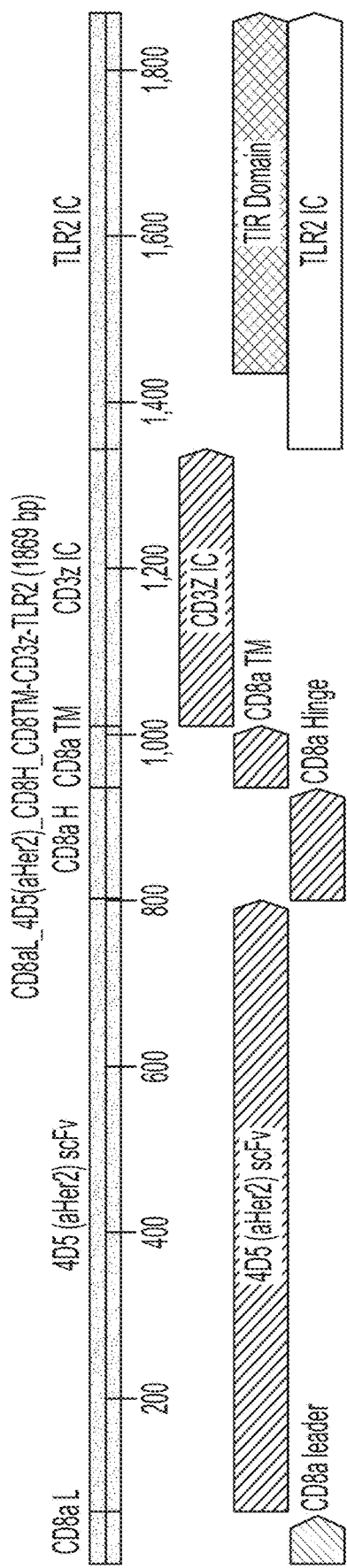
Figure 98:
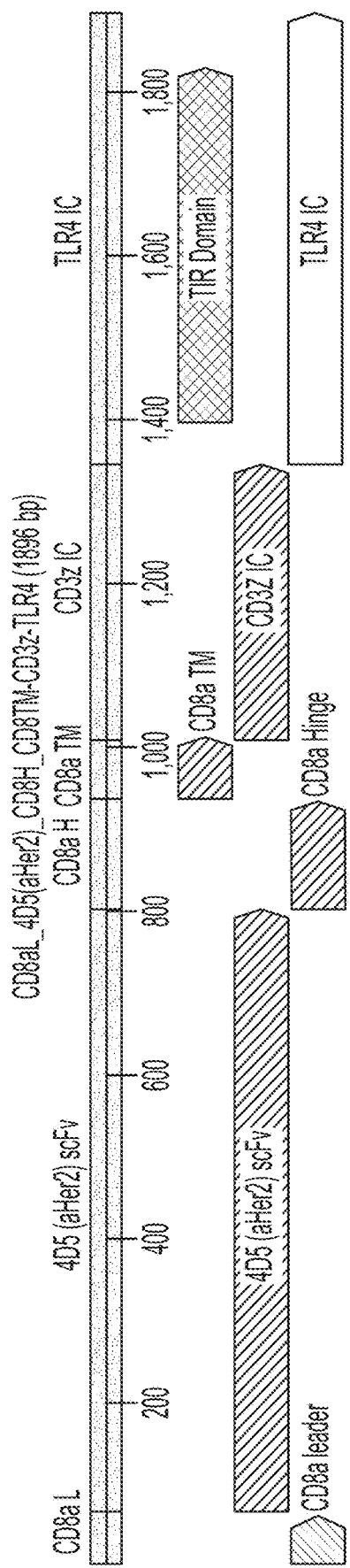
Figure 99:
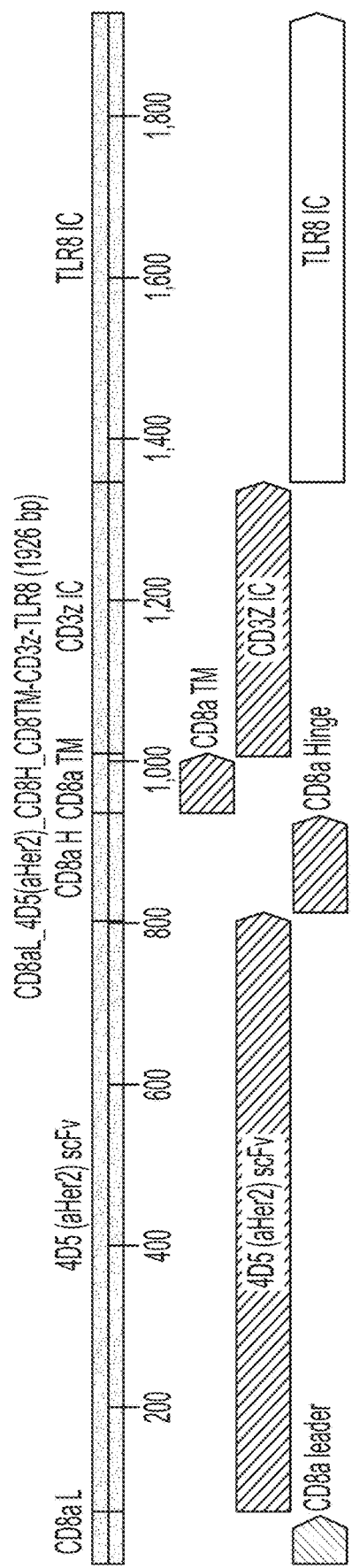
Figure 100:
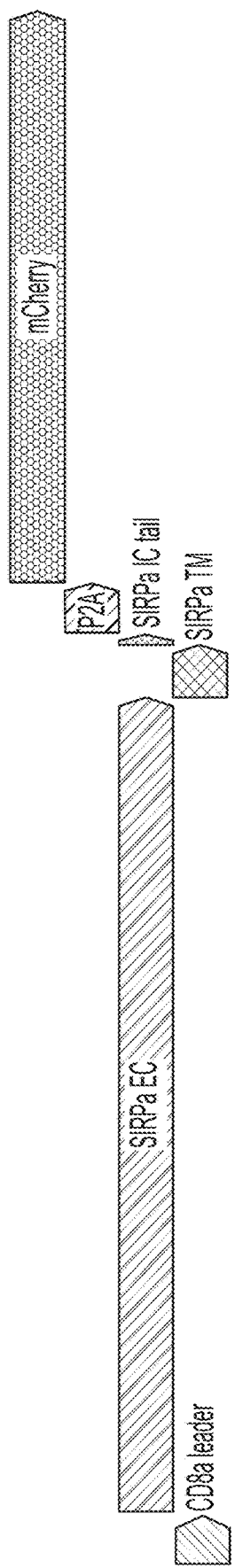
Figure 101:
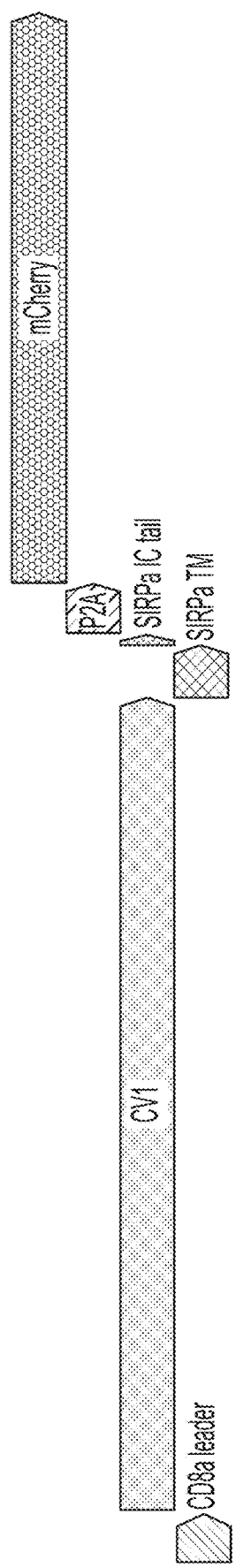
Figure 102:
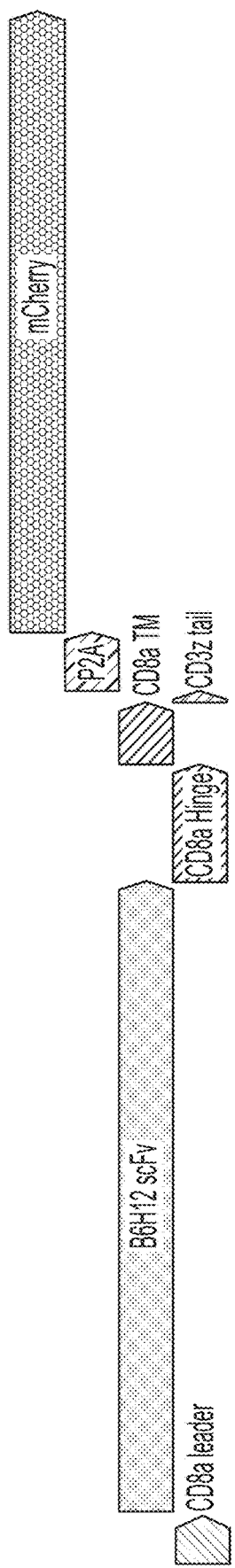
Figure 103:
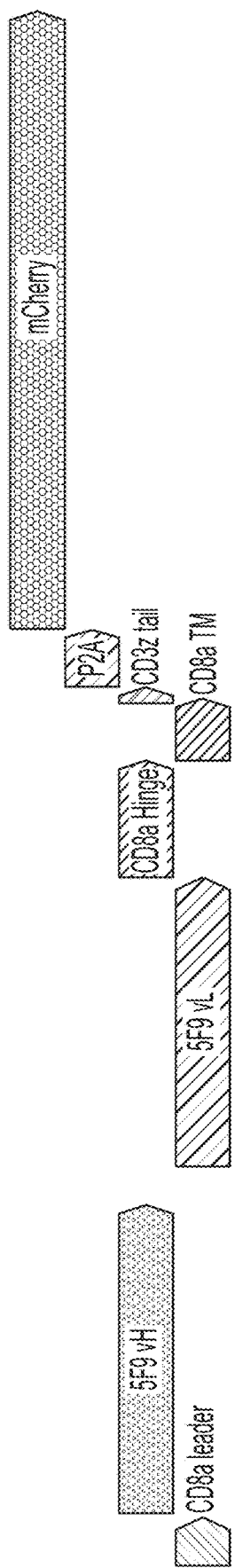
Figure 104:
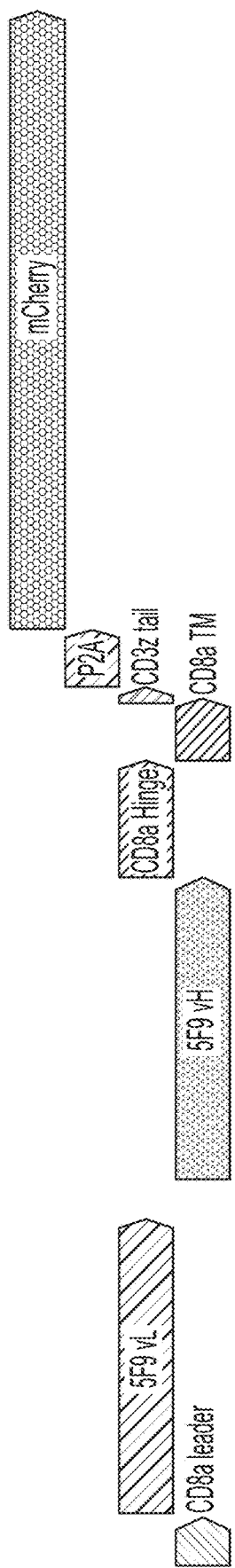
Figure 105:
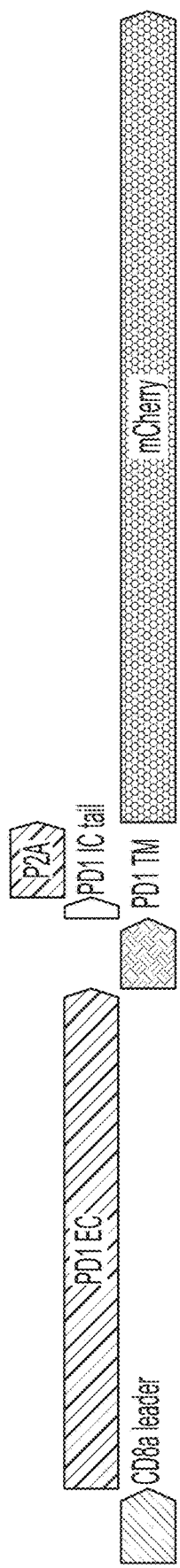
Figure 106:
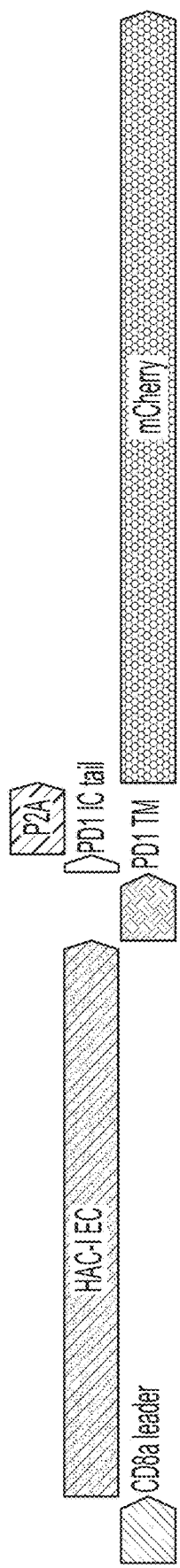
Figure 107:
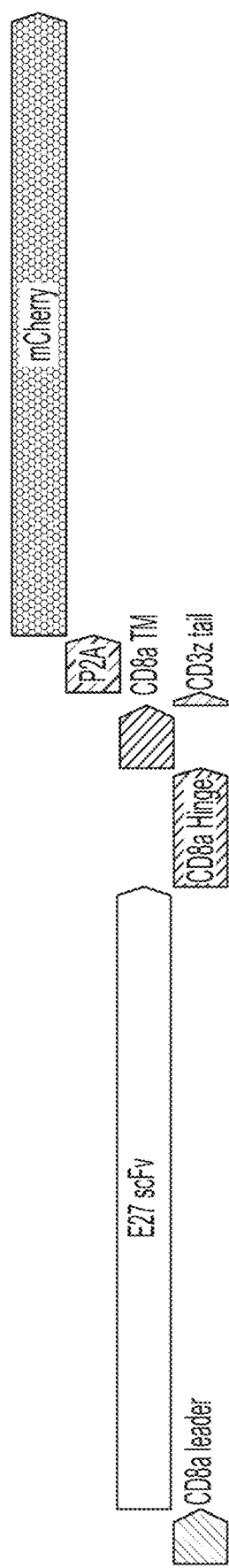
Figure 108:
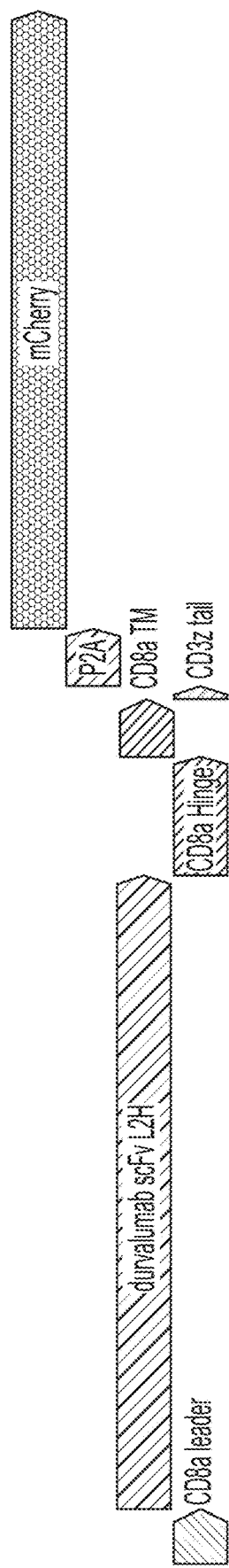
Figure 109:
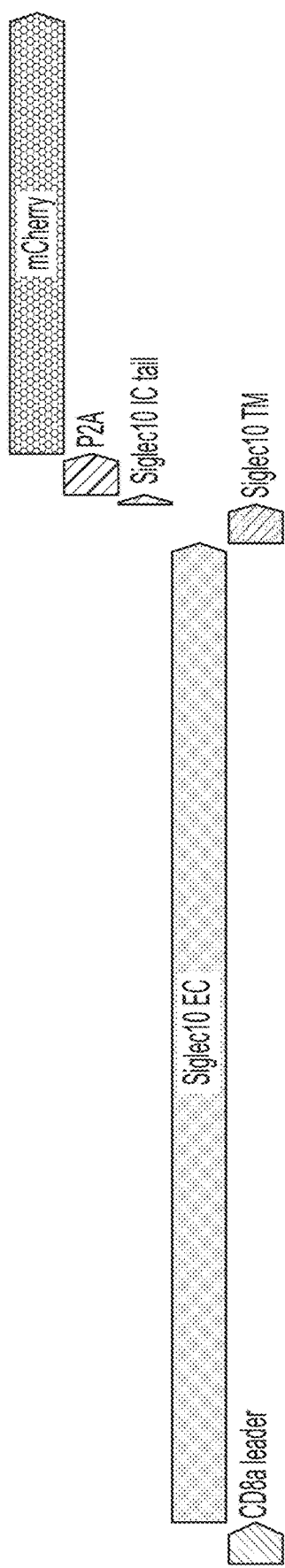
Figure 110:
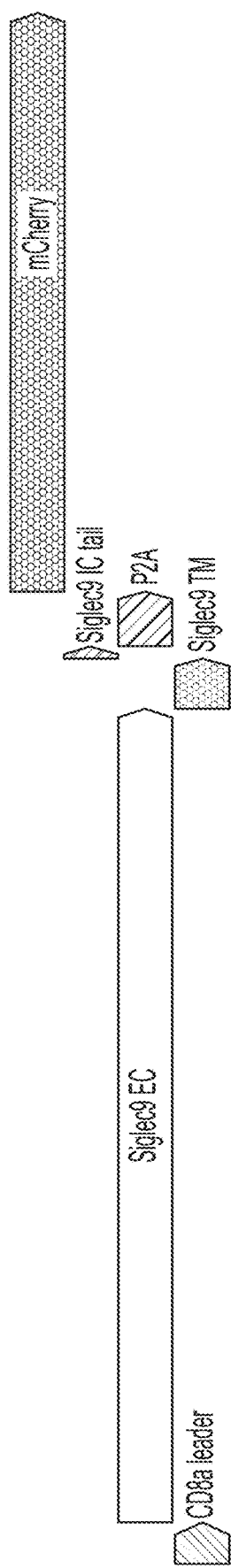
Figure 111:
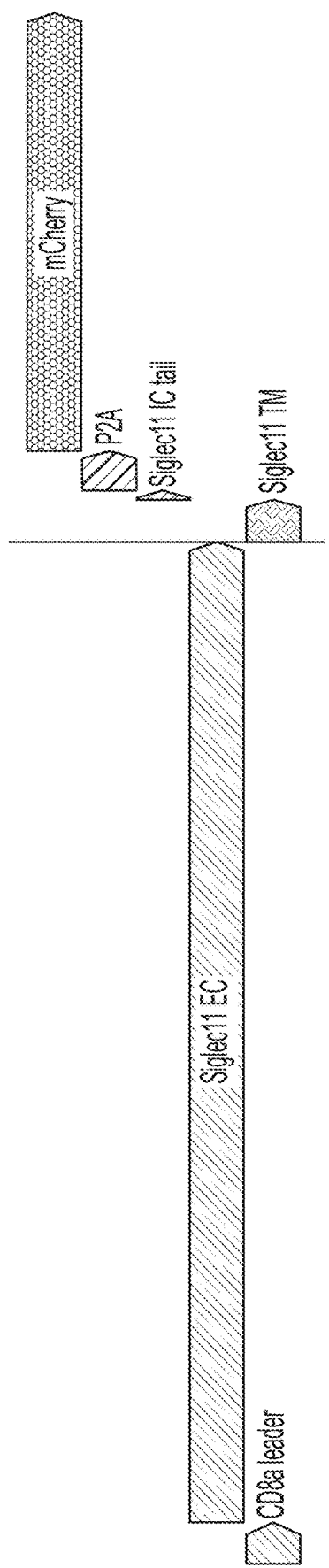
Figure 112:
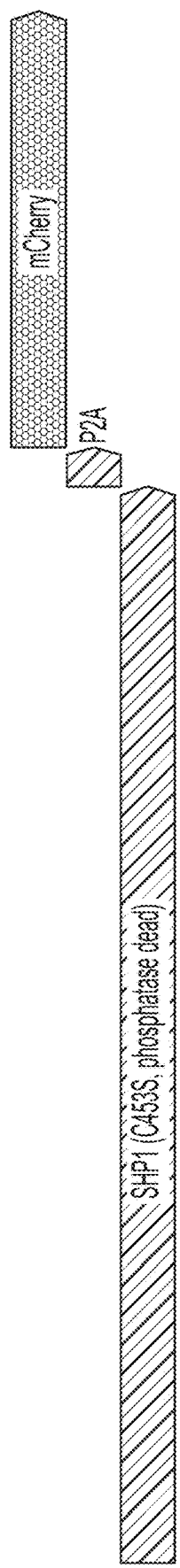
Figure 113:
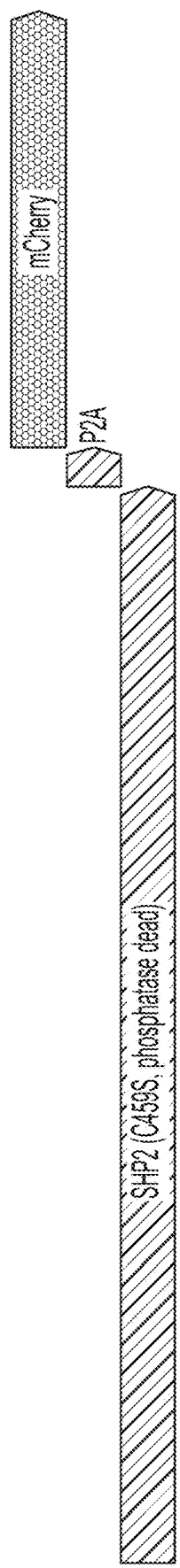
Figure 114:
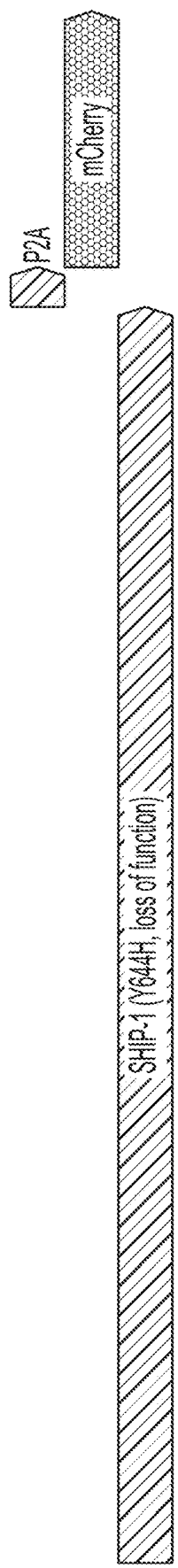
Figure 115:
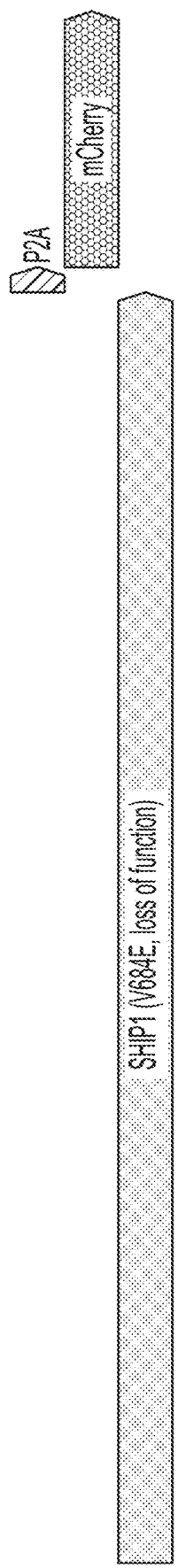
Figure 116:
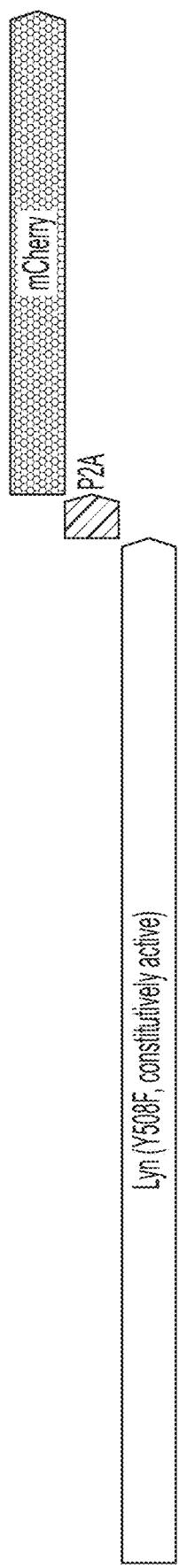
Figure 141A:
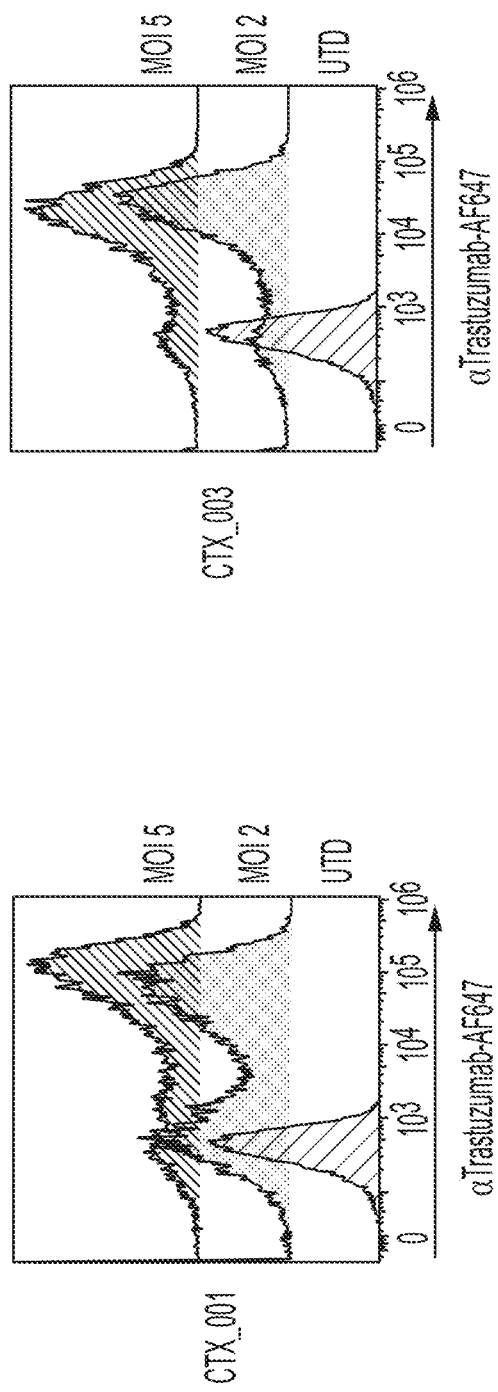
FIGS. 141A-141B are a series of graphs showing surface protein expression of CTX_001 and CTX_003 (CAR comprising an anti-HER2 scFv, CD8 hinge, and CD8 transmembrane domain.
Figure 141B:
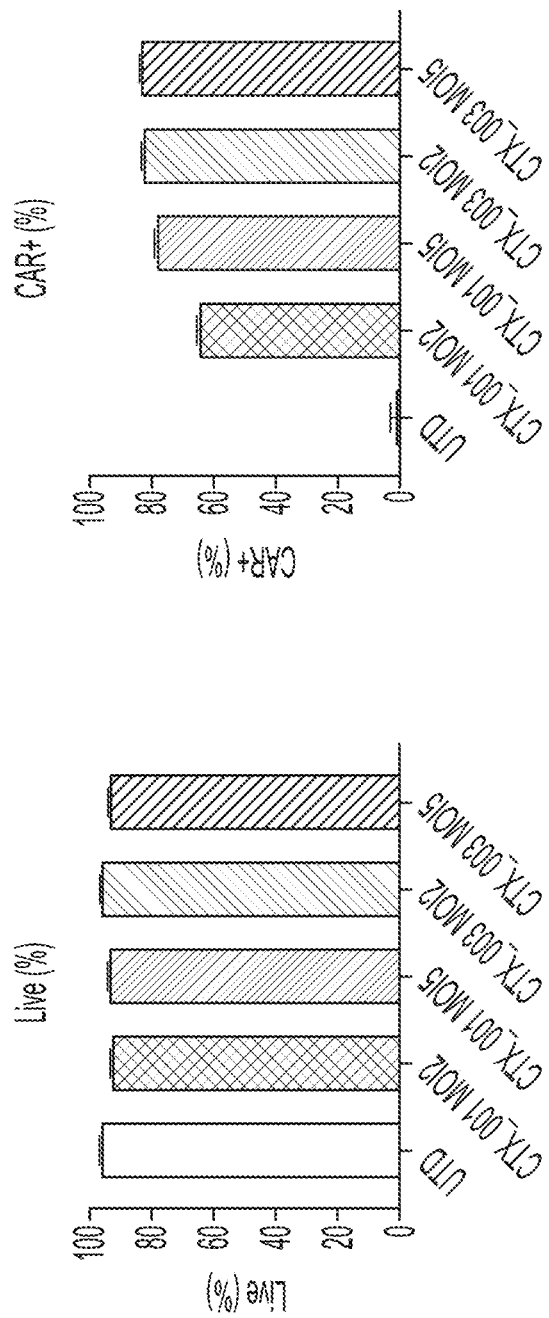

Next, MOI range for clinical transduction was investigated. CARs were investigated with a CD3-zeta domain (CTX_001) and without a CD3-zeta domain (CTX_003; CAR comprising an anti-HER2 scFv, CD8 hinge, and CD8 transmembrane domain; FIG. 10). MOI of 2 and MOI of 5 resulted in CAR cell surface expression of CTX_001 and CTX_003 in macrophages transduced with VPX lentivirus (FIG. 141A). CTX_001 and CTX_003 macrophages transduced with VPX-lentivirus were shown to be viable and to express each CAR relative to UTD macrophages (FIG. 141B). CTX_001 macrophages transduced with VPX-lentivirus were shown to express higher CAR levels at a MOI of 5 than at a MOI of 2 (FIG. 142). Transduction with VPX lentivirus also resulted in a moderate, dose-dependent M1 polarization of CTX_001 and CTX_003 macrophages based on CD80 and CD86 expression and reduction of CD163 and CD206 expression (FIG. 143).

Experiments were also performed to compare polarization of CTX_001 macrophages transduced with VPX-lentivirus relative to adeno-associated viral transduction with Ad5f35.

Figure 144:
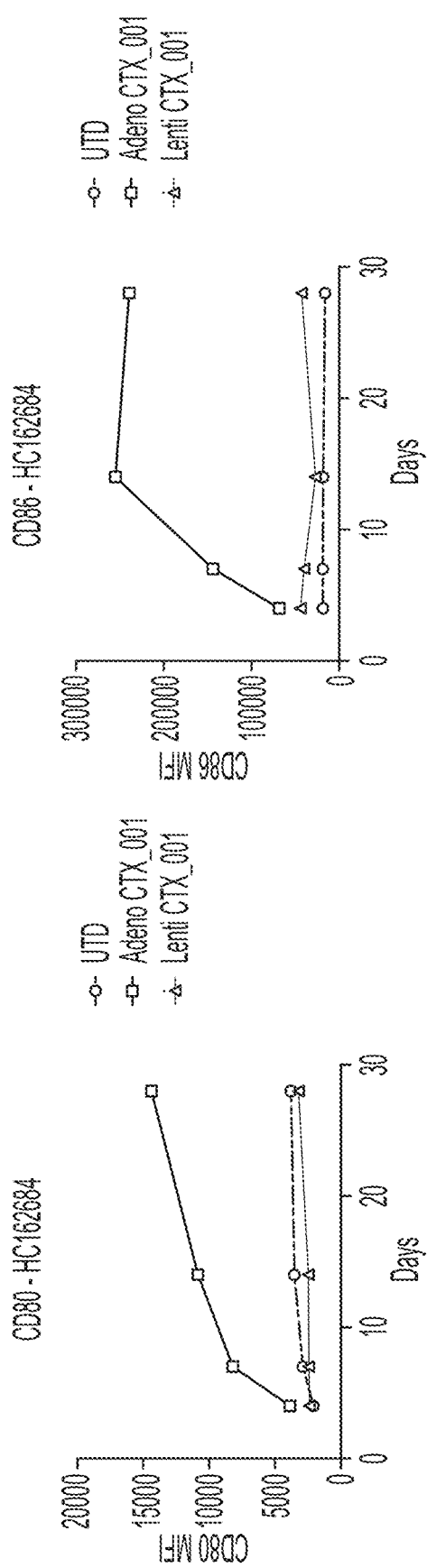
FIG. 144 is a series of graphs showing M1 polarization of CTX_001 macrophages transduced with VPX-lentivirus relative to transduction with Ad5f35 as assessed using CD80 and CD86. UTD macrophages were used as control.
Figure 145:
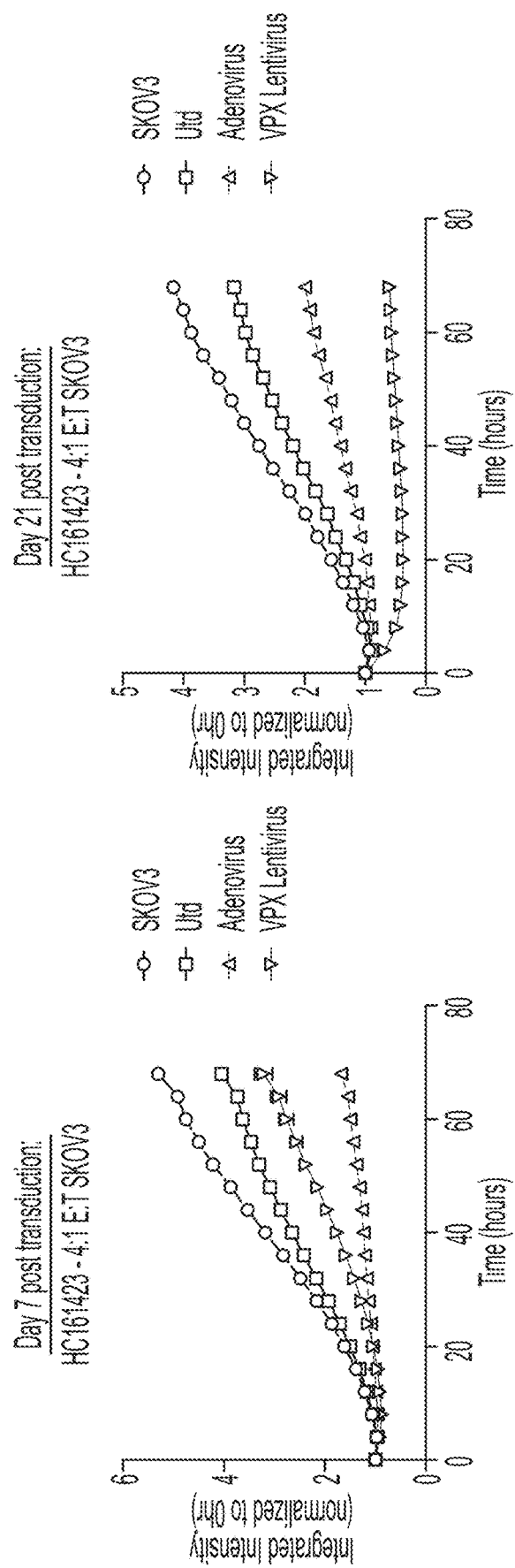
FIG. 145 is a series of graphs showing killing function of CTX_001 macrophages transduced with VPX lentivirus or Ad5f35 for SKOV3 ovarian carcinoma cells at 7 days post-transduction and 21 days post-transduction. Ratio of E:T was 4:1. UTD macrophages and SKOV3 cells without macrophages were used as control.

Transduction with Ad5f35, but not VPX-lentivirus, induced the M1 markers CD80 and CD86 (FIG. 144). VPX-lentivirus transduced CTX_001 macrophages also demonstrated more persistent anti-tumor activity relative to Ad5f35 transduced CTX_001 macrophages at 7 days post-transduction and 21 days post-transduction (FIG. 145). These results demonstrate that, in some instances, different viral vectors can be used for equivalent CAR expression in macrophages without M1 induction when VPX-lentivirus is used, which allows for maintenance of macrophage plasticity and subsequent control of phenotype. Thus, VPX-lentivirus can be used to make M0 CAR macrophages. Subsequently, Vpx-lentivirus derived M0 CAR macrophages can be polarized to M1 or M2 to make M1 or M2 polarized engineered macrophages or CAR macrophages. Such CAR macrophages could also encode signaling domains within the CAR construct to induce a phenotypic shift. Such CAR macrophages could be primed with M1 cytokines (e.g., IFNa, IFNb, IFNg, LPS, or TLR agonists) or M2 cytokines (e.g., IL4, IL10, IL13, or TGFb) cytokines to make a CAR macrophages with a chosen phenotype. Such CAR macrophages could be engineered with transcription factors, immune ligands, or secreted cytokines to induce an M1 or M2 phenotype.

Figure 146:
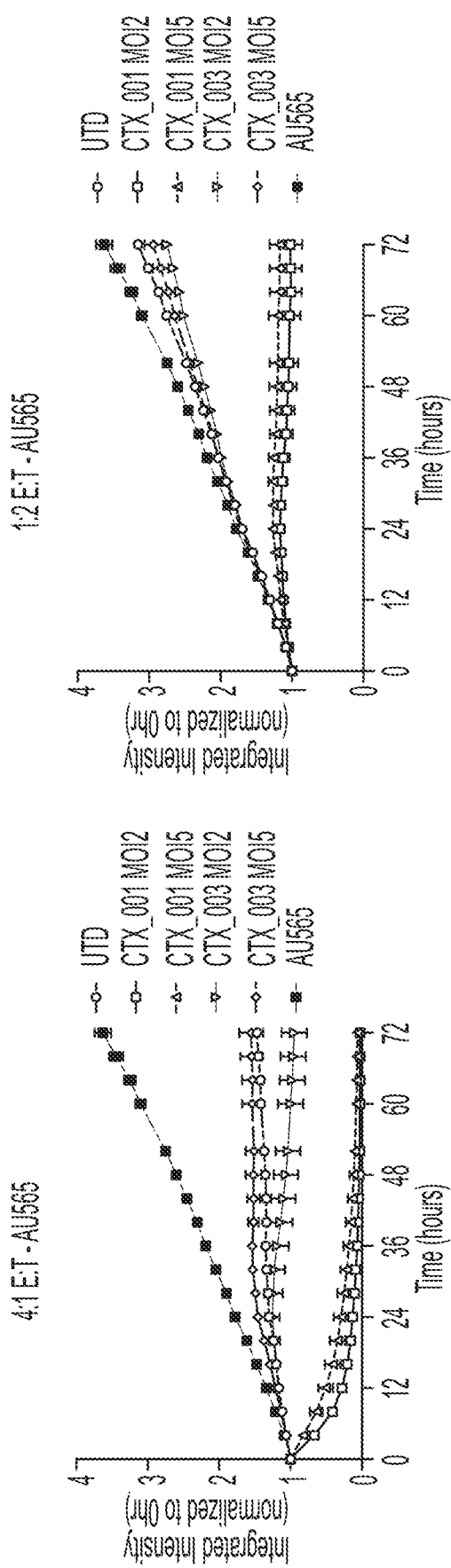
FIG. 146 is a series of graphs showing killing function of CTX_001 and CTX_003 macrophages transduced with VPX lentivirus at MOI of 2 and MOI of 5 for AU565 cells over 72 hours. Different ratios of E:T were 4:1 and 1:2. UTD macrophages and AU565 cells without macrophages were used as control.
Figure 147:
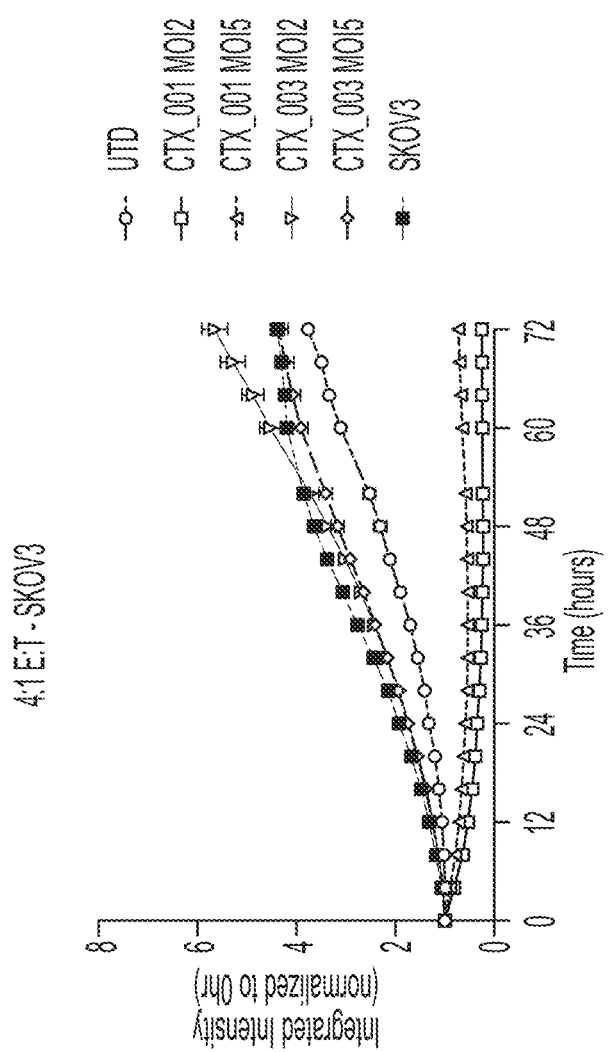
FIG. 147 is a series of graphs showing killing function of CTX_001 and CTX_003 macrophages transduced with VPX lentivirus at MOI of 2 and MOI of 5 for SKOV3 ovarian carcinoma cells. Ratio of E:T was 4:1. UTD macrophages and SKOV3 cells without macrophages were used as control.

Killing function of CTX_001 and CTX_003 macrophages transduced with VPX lentivirus was also assessed at MOI 2 and MOI 5 in AU565 and SKOV3 cells. Ratios of E:T were 4:1 and 1:2 for AU565. At 7 days after transduction with VPX lentivirus, MOI 2 and MOI 5 transduced CTX_001 macrophages demonstrated similar killing capacity at E:T ratios of 4:1 and 2:1 with UTD and AU565 cells as controls (FIG. 146). A ratio of E:T was 4:1 for SKOV3. At 7 days after transduction with VPX lentivirus, MOI 2 and MOI 5 transduced CTX_001 macrophages demonstrated similar killing capacity at an E:T ratio of 4:1 with UTD and SKOV3 cells as controls (FIG. 147).

Figure 148:
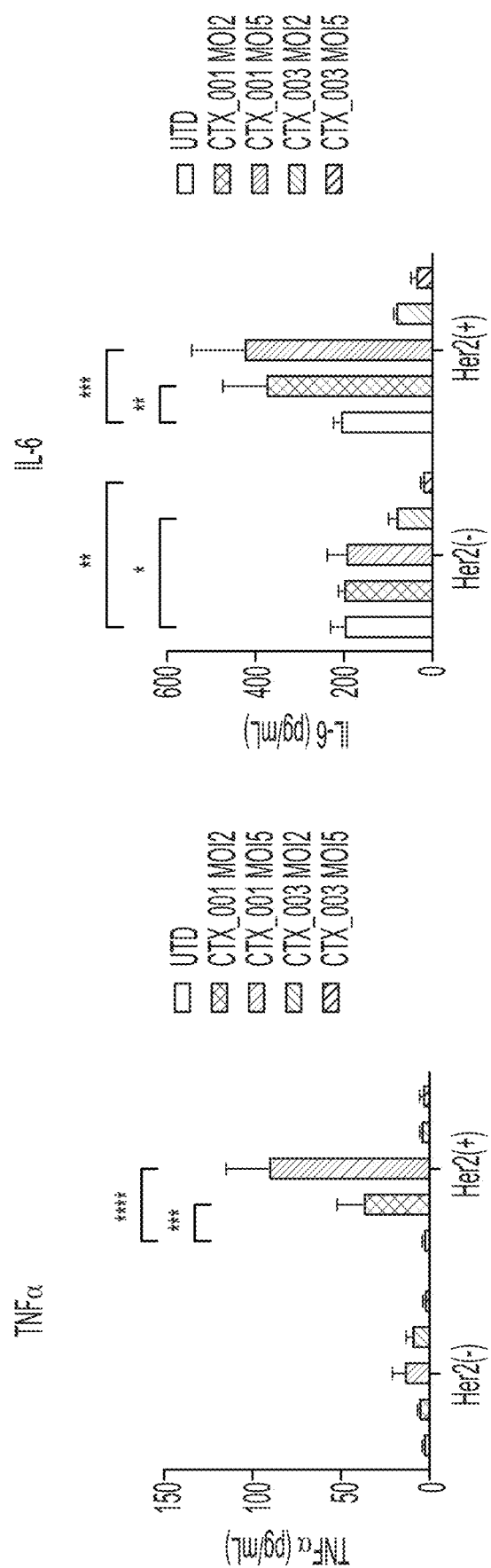
FIG. 148 is a series of graphs showing production of TNFα and IL-6 by CTX001 or CTX_003 macrophages transduced with VPX lentivirus at MOI of 2 and MOI of 5 and cultured with or without platebound HER2 for 24 hours. UTD macrophages were used as control.

Inflammatory cytokine production after transduction of CTX_001 and CTX_003 macrophages with VPX lentivirus was also investigated. CTX_001 and CTX_003 macrophages were transduced with VPX lentivirus and cultured with or without plate-bound HER2 for 24 hours. At 7 days after transduction with VPX lentivirus, MOI 2 and MOI 5 transduced CTX_001 macrophages showed differences in inflammatory cytokine secretion with increased TNFα and IL-6 production in the presence of HER2 (FIG. 148).

Figure 149:
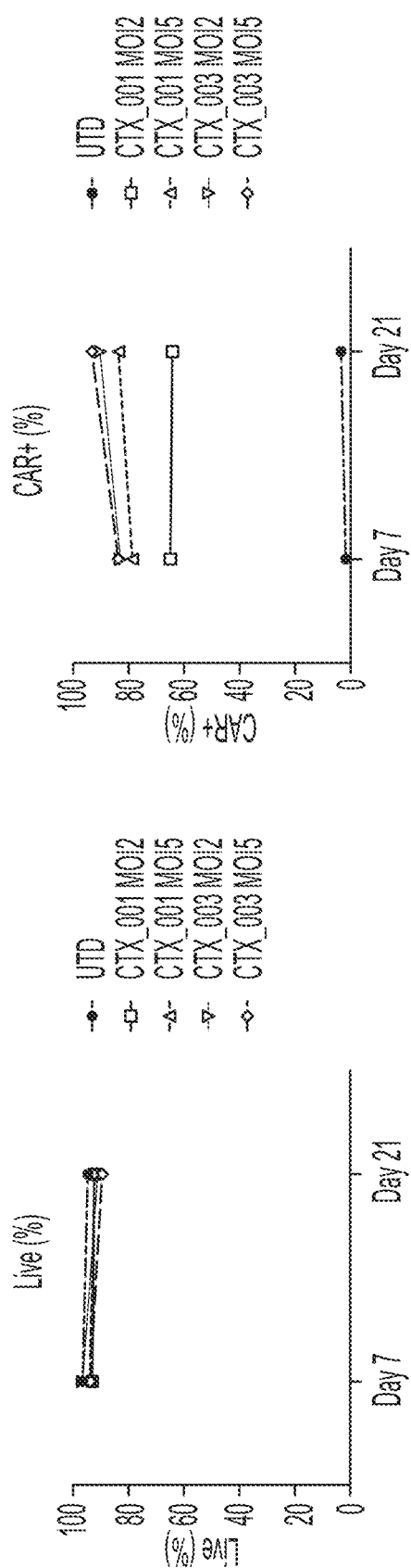
FIG. 149 is a series of graphs showing viability (live %) and CAR expression (CAR+%) of CTX_001 and CTX_003 in macrophages transduced with VPX lentivirus at MOI of 2 and MOI of 5 over 21 days. UTD macrophages were used as control.
Figure 150:
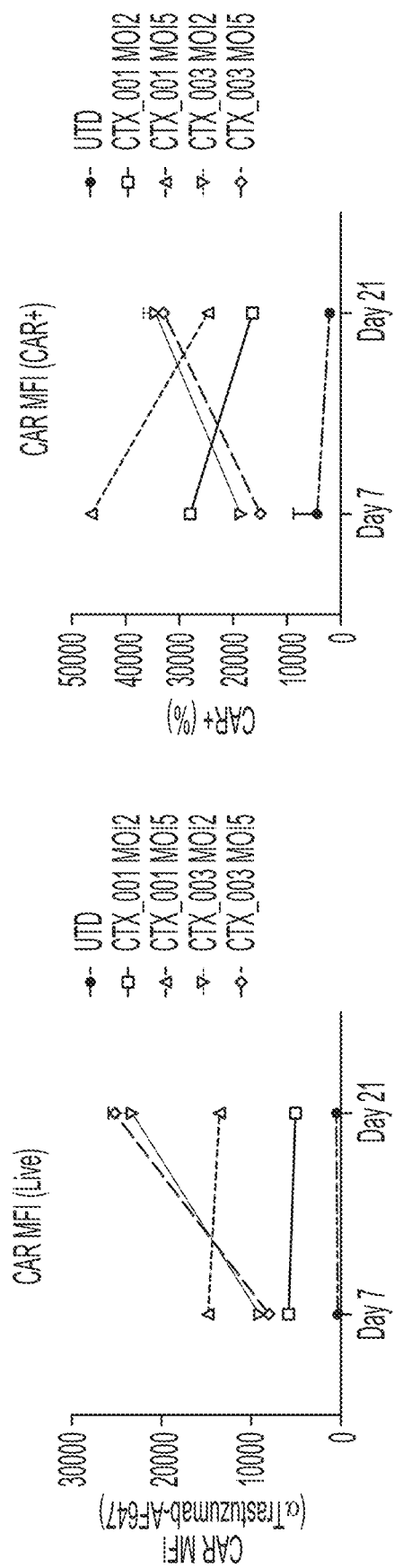
FIG. 150 is a series of graphs of MFI showing viability (live) and CAR expression (CAR+) of CTX_001 and CTX_003 in macrophages transduced with VPX lentivirus at MOI of 2 and MOI of 5 over 21 days as assessed using αTrastuzumab-A F647. UTD macrophages were used as control.

Next, viability and CAR expression were assessed over time for VPX-lentiviral transduction of CTX_001 and CTX_003 macrophages with MOI 2 and MOI 5. CTX_001 and CTX_003 macrophages transduced with VPX-lentivirus were shown to be highly viable and to express CTX-001 and CTX_003 for a 21 day time period (FIG. 149). UTD macrophages were used as control. The MFI of CTX-001 and CTX_003 CAR expression was also assessed for macrophages transduced with VPX-lentivirus using αTrastuzumab-A F647 for analysis of cell surface protein over time. CTX_001 and CTX_003 macrophages transduced with VPX-lentivirus were shown to be highly viable and to express CTX-001 and CTX-003 for a 21 day time period (FIG. 150).

Figure 151:
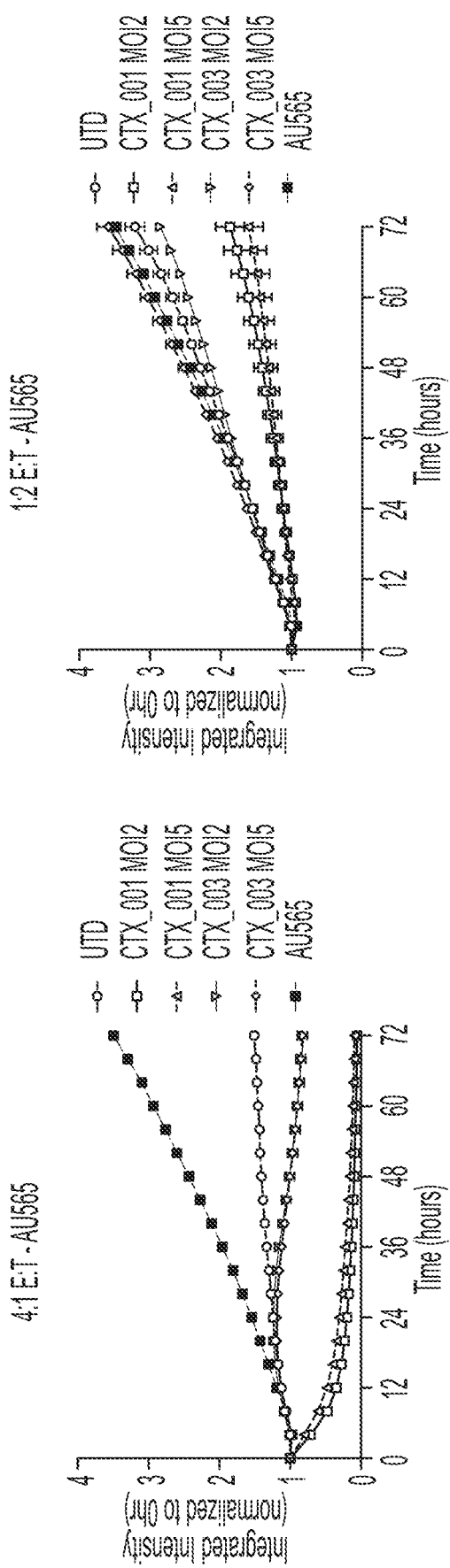
FIG. 151 is a series of graphs showing killing function of CTX_001 and CTX_003 macrophages transduced with VPX lentivirus at MOI of 2 and MOI of 5 for AU565 cells initiated at 21 days post-transduction and over 72 hours. Different ratios of E:T were 4:1 and 1:2. UTD macrophages were used as control.
Figure 152:
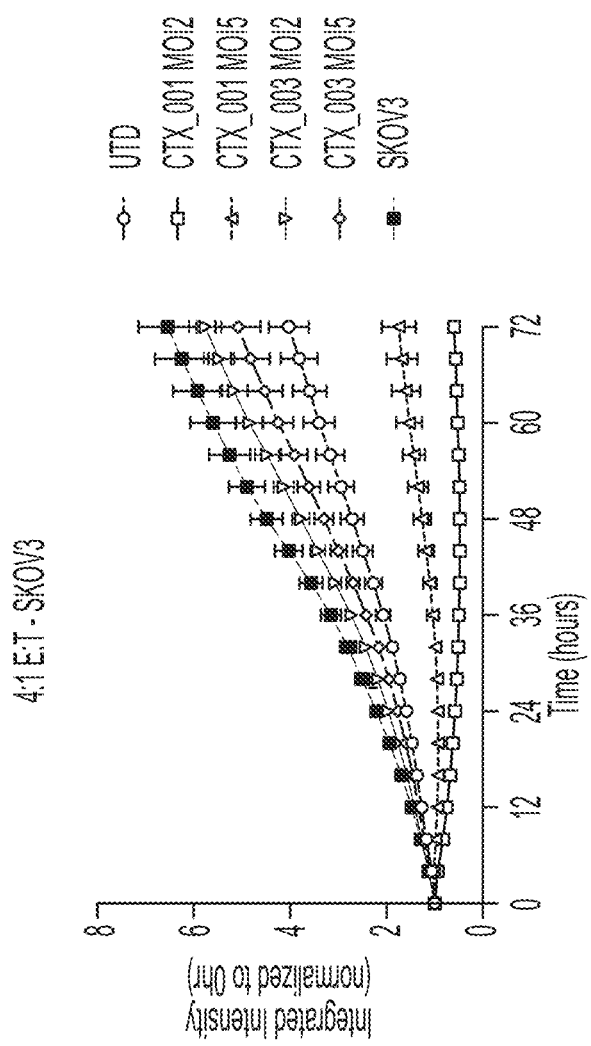
FIG. 152 is a series of graphs showing killing function of CTX_001 and CTX_003 macrophages transduced with VPX lentivirus at MOI of 2 and MOI of 5 for SKOV3 cells initiated at 21 days post-transduction and over 72 hours. Ratio of E:T was 4:1. UTD macrophages were used as control.

Killing function of CTX_001 and CTX_003 macrophages transduced with VPX lentivirus was also assessed at MOI 2 and MOI 5 in AU565 and SKOV3 cells over time. The killing assay was initiated at 21 days post-transduction. Ratios of E:T were 4:1 and 1:2 for AU565. At 21 days after transduction with VPX lentivirus, MOI 2 and MOI 5 transduced CTX_001 macrophages demonstrated similar killing capacity at E:T ratios of 4:1 and 2:1 over 72 hours with UTD and AU565 cells as controls (FIG. 151). A ratio of E:T was 4:1 for SKOV3. At 21 days after transduction with VPX lentivirus, MOI 2 and MOI 5 transduced CTX_001 macrophages demonstrated similar killing capacity at an E:T ratio of 4:1 with UTD and SKOV3 cells as controls (FIG. 152).

Figure 153A:
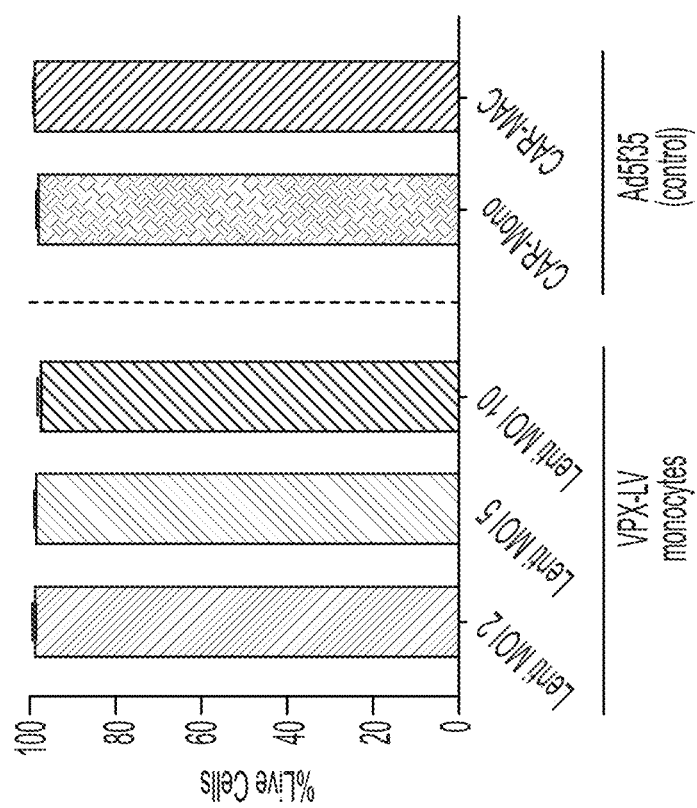
FIG. 153A-D are a series of graphs showing viability (FIG. 153A), percentage CAR expression (FIG. 153B), MFI of CAR expression (FIG. 153C), and CAR expression histograms (FIG. 153D) after transduction of CD14+ monocytes with CTX_001 using VPX lentivirus at MOI of 2, 5, or 10. Ad5f35 transduced CAR monocytes and CAR macrophages are shown as a comparator. UTD macrophages were also used as a control for CAR expression histograms.
Figure 153B:
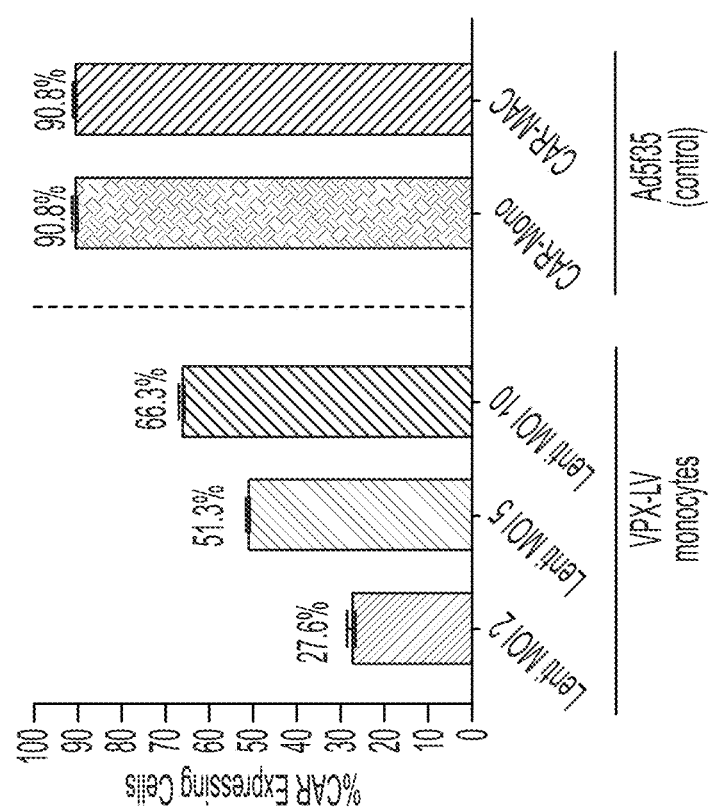
Figure 153C:
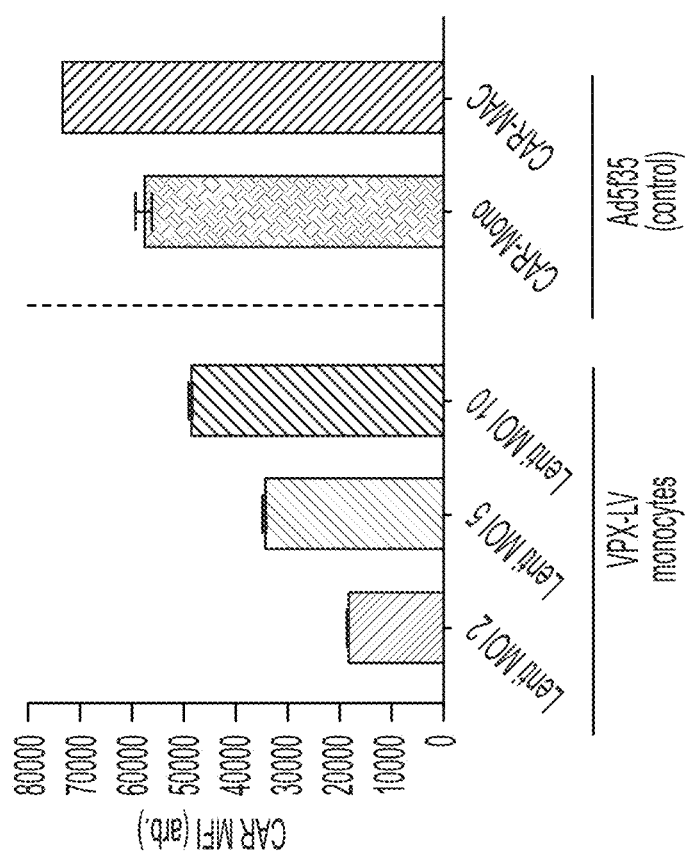
Figure 153D:
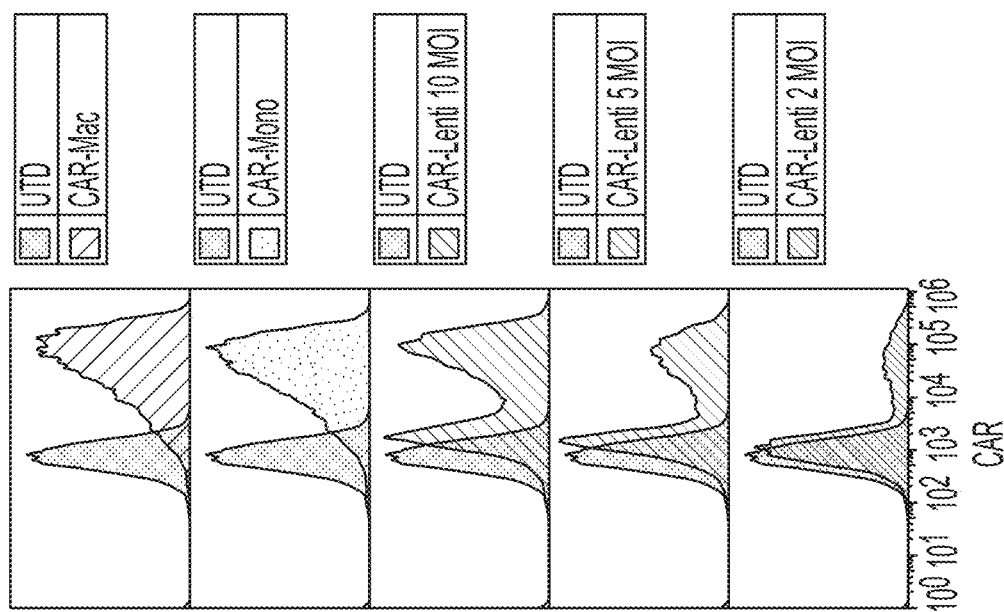

Expression of CTX_001 (FIG. 8) and viability in monocytes after VPX lentivirus transduction was also investigated. CD14+ human monocytes were thawed, washed and counted. Cells were plated in 6 well Upcell plate at 3e6 cells/well, UTD, or with addition of Lentivirus at appropriate MOI. Cells were fed at day 5, and harvested on day 7 for flow cytometry analysis. CAR macrophages and CAR monocytes transduced using Ad5f35 transduction were used as controls. CAR monocytes were viable after transduction with VPX lentivirus at MOI 2, 5, or 10 with Ad5f35 transduced CAR monocytes and CAR macrophages used as a comparator of viability (FIG. 153A). CAR monocytes transduced with VPX lentivirus at MOI 2, 5, and 10 showed an increasing percentage (%) of CAR expression with 27.6% at MOI 2, 51.3% at MOI 5, and 66.3% at MOI 10 with Ad5f35 transduced CAR monocytes and CAR macrophages used as a comparator of viability (FIG. 153B). CAR monocytes transduced with VPX lentivirus at MOI 2, 5, and 10 also showed an increasing mean fluorescent intensity (MFI) of CAR expression with increasing MOI with Ad5f35 transduced CAR monocytes and CAR macrophages used as a comparator (FIG. 153C). CAR expression histograms of CD14+ monocytes transduced with VPX lentivirus at MOI 2, 5, and 10 also showed increasing CAR expression with increasing MOI with Ad5f35 transduced CAR monocytes and CAR macrophages used as a comparator (FIG. 153D). UTD macrophages were also used as a control for CAR expression histograms. These results demonstrate that monocytes expressed CAR after VPX lentivirus transduction and indicate that monocytes would retain CAR expression in the macrophage stage.

Example 14: SIRPα Knockout for Enhanced Phagocytosis of CAR Macrophages

Interaction of immune checkpoints SIRPα and CD47 inhibit macrophage phagocytosis. Thus, macrophages expressing CAR receive conflicting pro- and anti-phagocytic signals from tumors. The results presented herein demonstrate that knockout of SIRPα improved CAR macrophage killing and phagocytosis.

Ribonucleoprotein (RNP) formation was performed and mixed with macrophages one day after thawing macrophages. Purified Cas9 protein was incubated with a cocktail of three gRNAs at room temp for 10-20 minutes. gRNA sequences used were from Synthego's "gene knockout kit" for human SIRPα (Table 2). A ratio of 1:3 of Cas9 to total gRNA (therefore 1:1 ratio of Cas9 to each individual gRNA in the cocktail) was used. RNP mixed with macrophages in EP buffer was at a final concentration of 2.5 µM Cas9 RNP for 3e7-8e7 cells/mL. Macrophages were electroporated in a MaxCyte electroporation cassette. Following recovery culture, cells were analyzed at least 3 days after electroporation to allow the gene knockout to take effect at the level of protein expression. SIRPα expression was then analyzed and functional assays were performed.

TABLE 2

Guide RNA Sequences for SIRPα KO.

| gRNA Name | RNA Sequence |
| --- | --- |
| SIRPa_gKOv2_1 | GAGCCCGCCGGCCCGGCCCC |
| SIRPa_gKOv2_2 | GUGCUUACCUGACCAGGCGC |
| SIRPa_gKOv2_3 | CGGGCTCAGGCCTCTCAGAC |

Figure 154A:
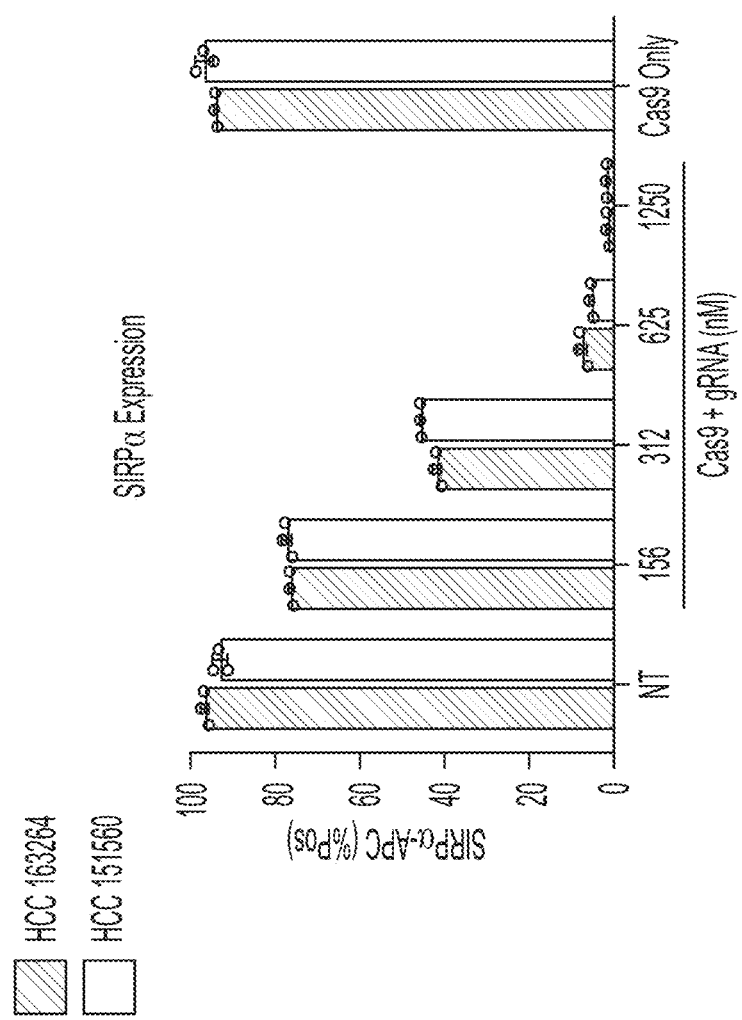
FIG. 154A-D are a series of graphs showing SIRPα knockout in CTX_001 macrophages in two donors as assessed by SIRPα-APC % POS (FIG. 154A) and MFI (FIG. 154B), flow cytometry (FIG. 154C), and cell viability (FIG. 154D). Ribonucleoprotein (RNP) concentrations were 165, 312, 625, and 1250 nM, except for flow cytometry (312 and 1250 nm). Nontreated (NT) CAR macrophages or Cas9 only were used as controls.
Figure 154B:
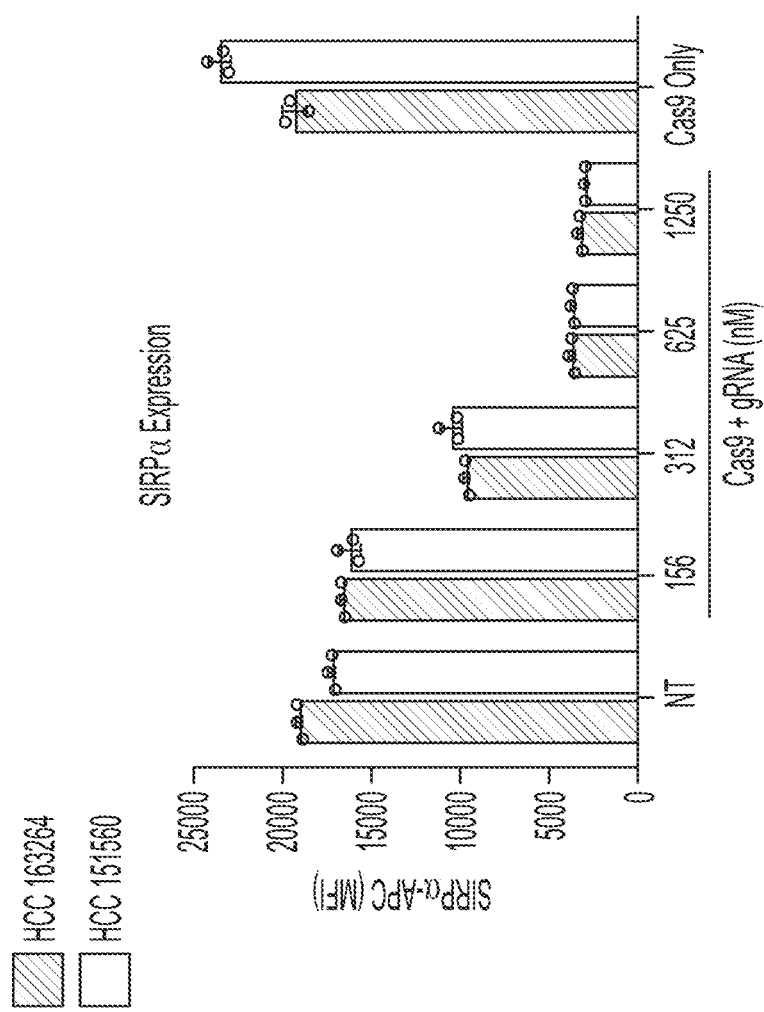
Figure 154C:
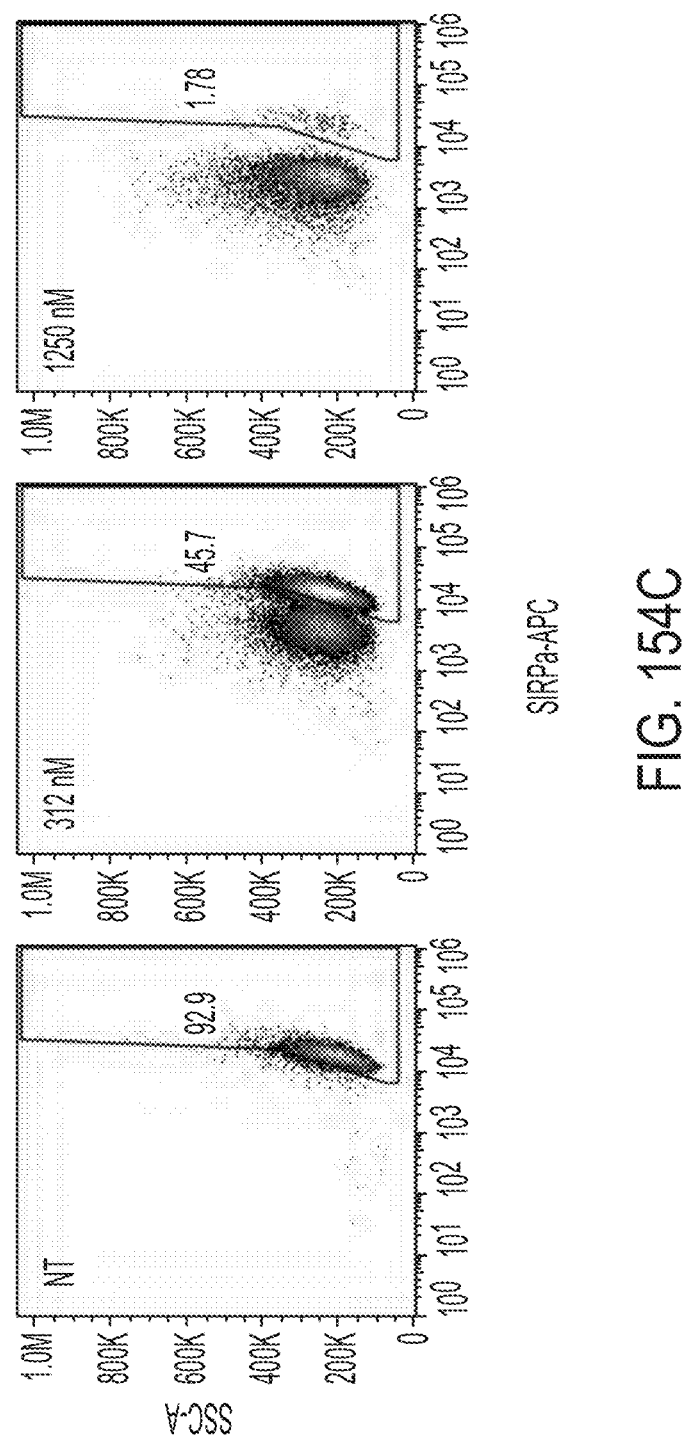
Figure 154D:
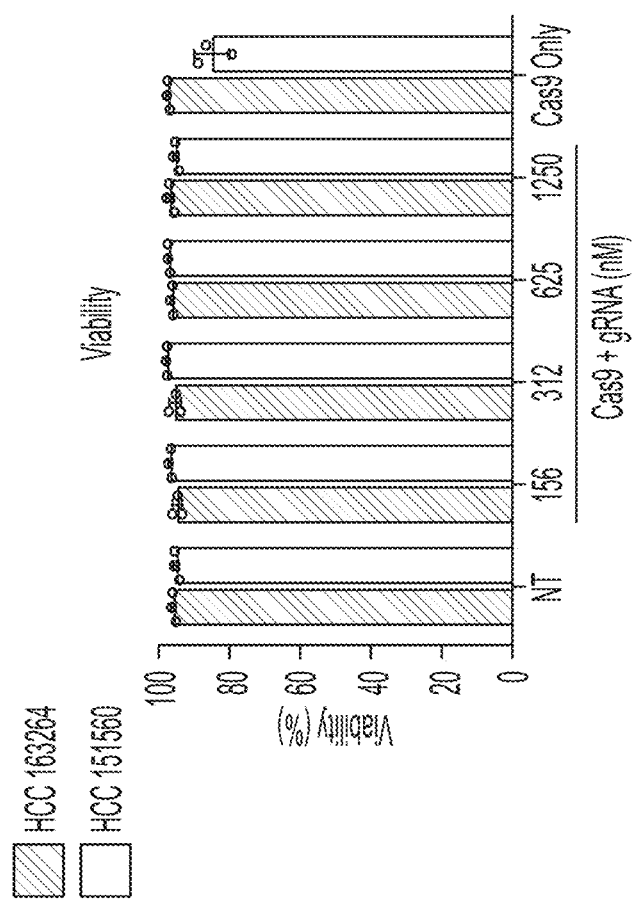

Fresh macrophages from two different donors (HCC 163264 and HCC 151560) were acquired one day before experiments began, macrophages were electroporated with Cas9 at indicated RNP concentrations on Day 0, and expression of SIRPα were evaluated on Day 3. Immunostaining for SIRPα was performed on macrophage surface using flow cytometry. The results showed that in two donors, SIRPα can be knocked out in macrophages in a dose-dependent manner (FIGS. 154A-B). Results showed two distinct CAR macrophage populations in flow cytometry plots at 312 nM RNP (FIG. 154C), which supports an all-or-nothing nature of gene knockout by Cas9, such that SIRPα gene is knocked out or it is not, leading to binary populations, rather than a gradient of SIRPα expression. Importantly, SIRPα knockout did not impact cell viability (FIG. 154D).

Figure 155A:
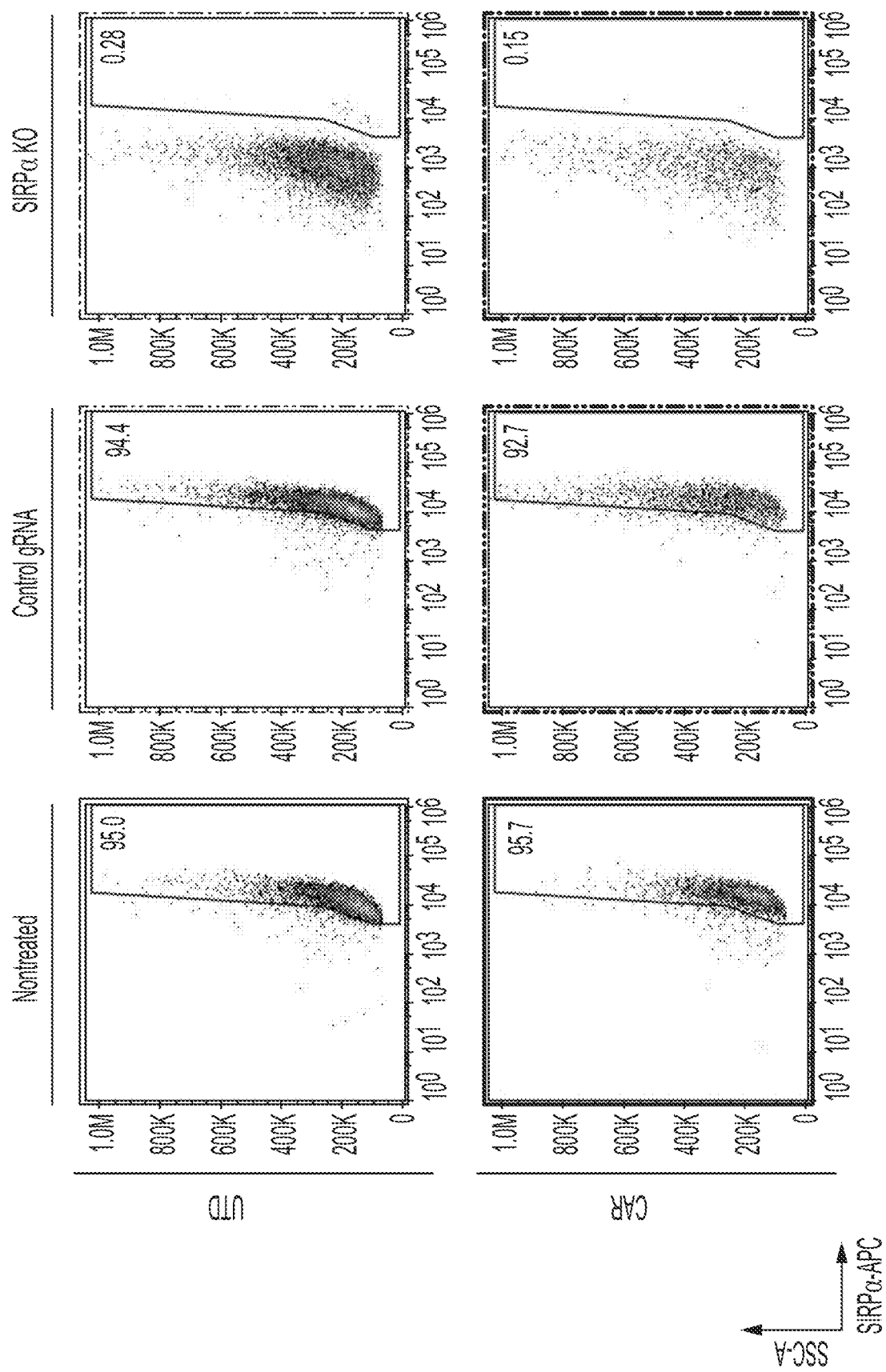
FIG. 155A-D are a series of graphs showing SIRPα knockout in CTX_001 macrophages with Cas9 and gRNA targeting SIRPα using flow cytometry (FIG. 155A), expression of CTX_001 in SIRPα knockout macrophages using flow cytometry (FIG. 155B), phagocytosis by SIRPα knockout CTX_001 macrophages of SKOV-3 ovarian carcinoma cells over 12 hours (FIG. 155C), and total phagocytosis measured over 12 hours quantified as area under the curve (FIG. 155D). Nontreated (NT) CAR macrophages, gRNA only, and UTD macrophages were used as controls.
Figure 155B:
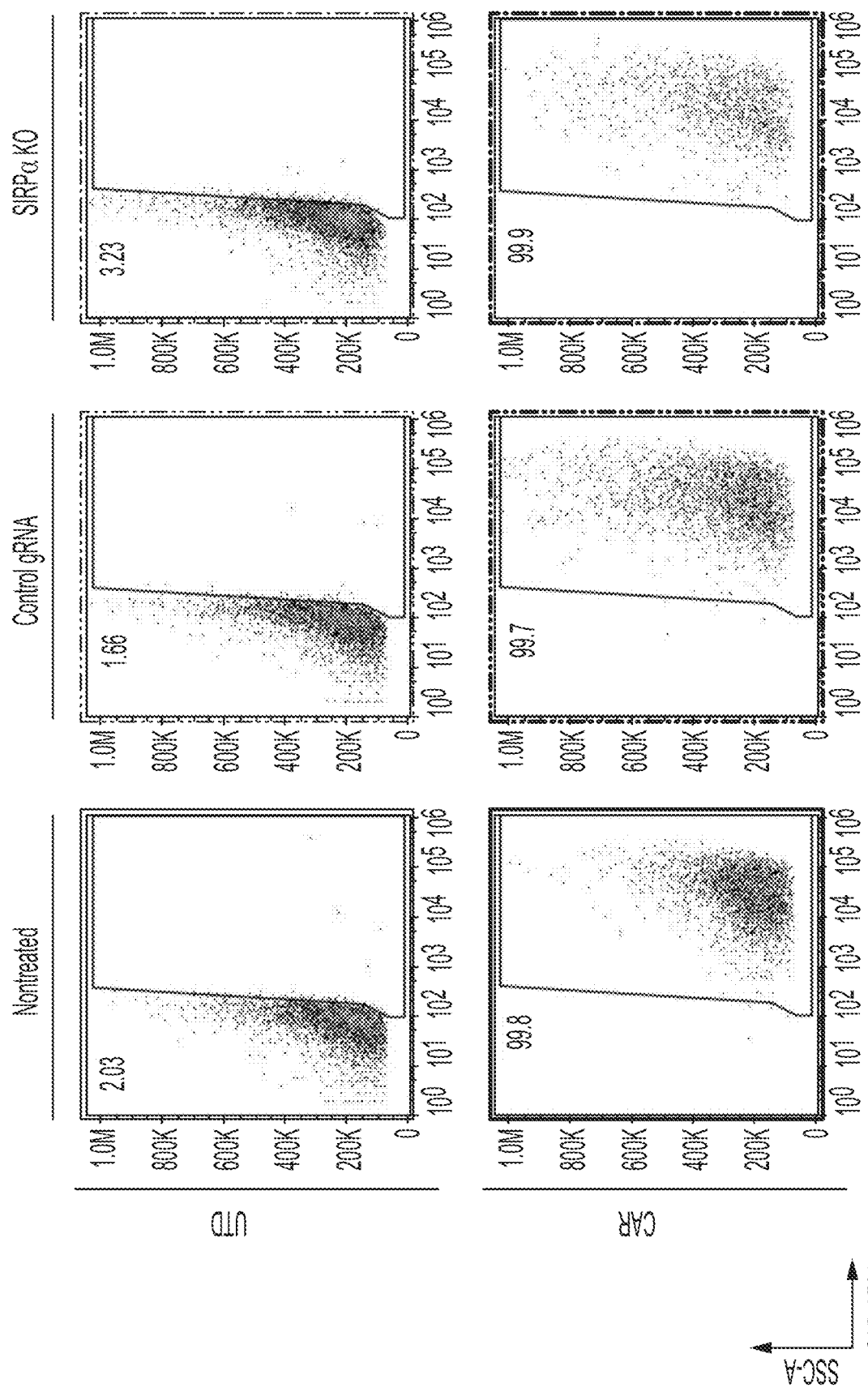
Figure 155C:
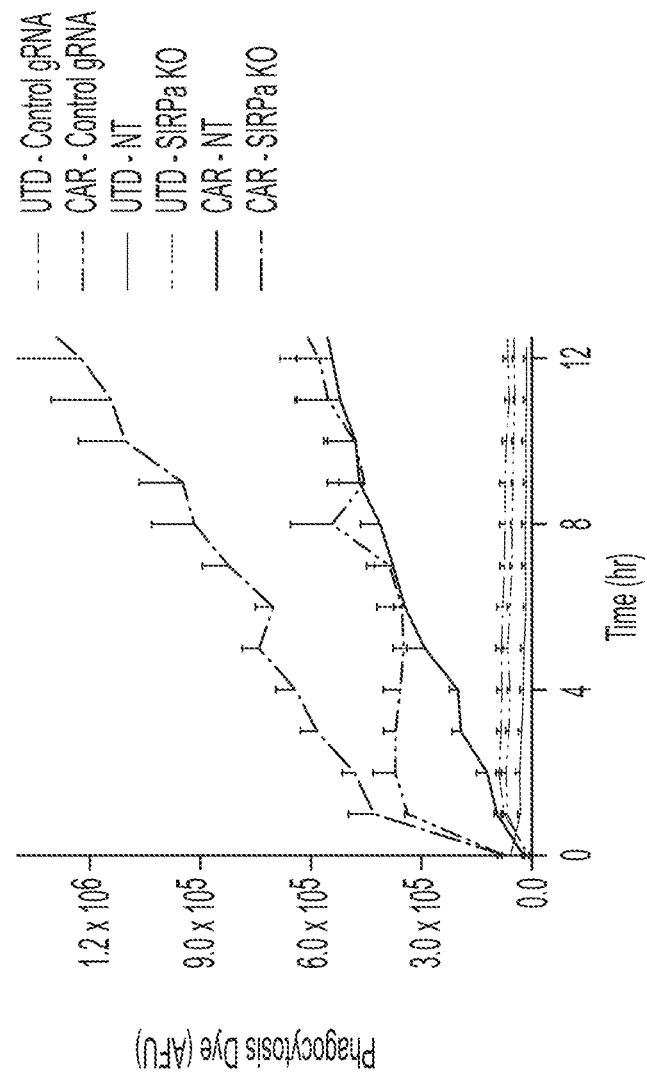
Figure 155D:
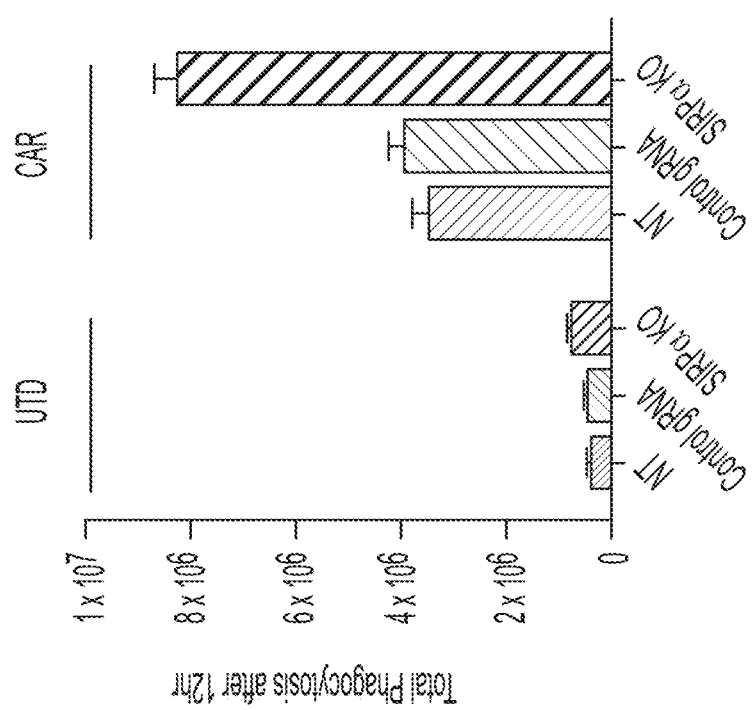

SIRPα knockout was also shown to enhance CAR macrophage phagocytosis in SKOV-3 ovarian carcinoma cells. Macrophages were thawed and transduced with adenovirus encoding CTX_001 (CAR comprising an anti-HER2 scFv, CD8 hinge, CD8 transmembrane domain, and CD3-zeta intracellular signaling domain; FIG. 8) one day prior to electroporation with Cas9 RNP. Three days later, expression of SIRPα was evaluated, and a phagocytosis assay with SKOV-3 was begun. These results show SIRPα knockout in CTX_001 macrophages with Cas9 and gRNA targeting SIRPα (FIG. 155A). CTX_001 was expressed in transduced macrophages (FIG. 155B). CTX_001 macrophages demonstrated phagocytosis over 12 hours, which was measured using pHrodo-green signal via Incucyte® analysis (FIG. 155C). Total phagocytosis measured over 12 hours was quantified as area under the curve (FIG. 155D). SIRPα knockout along with CAR expression in macrophages resulted in greatest phagocytosis, while SIRPα knockout alone did not greatly enhance phagocytosis in UTD macrophages.

Figure 156A:
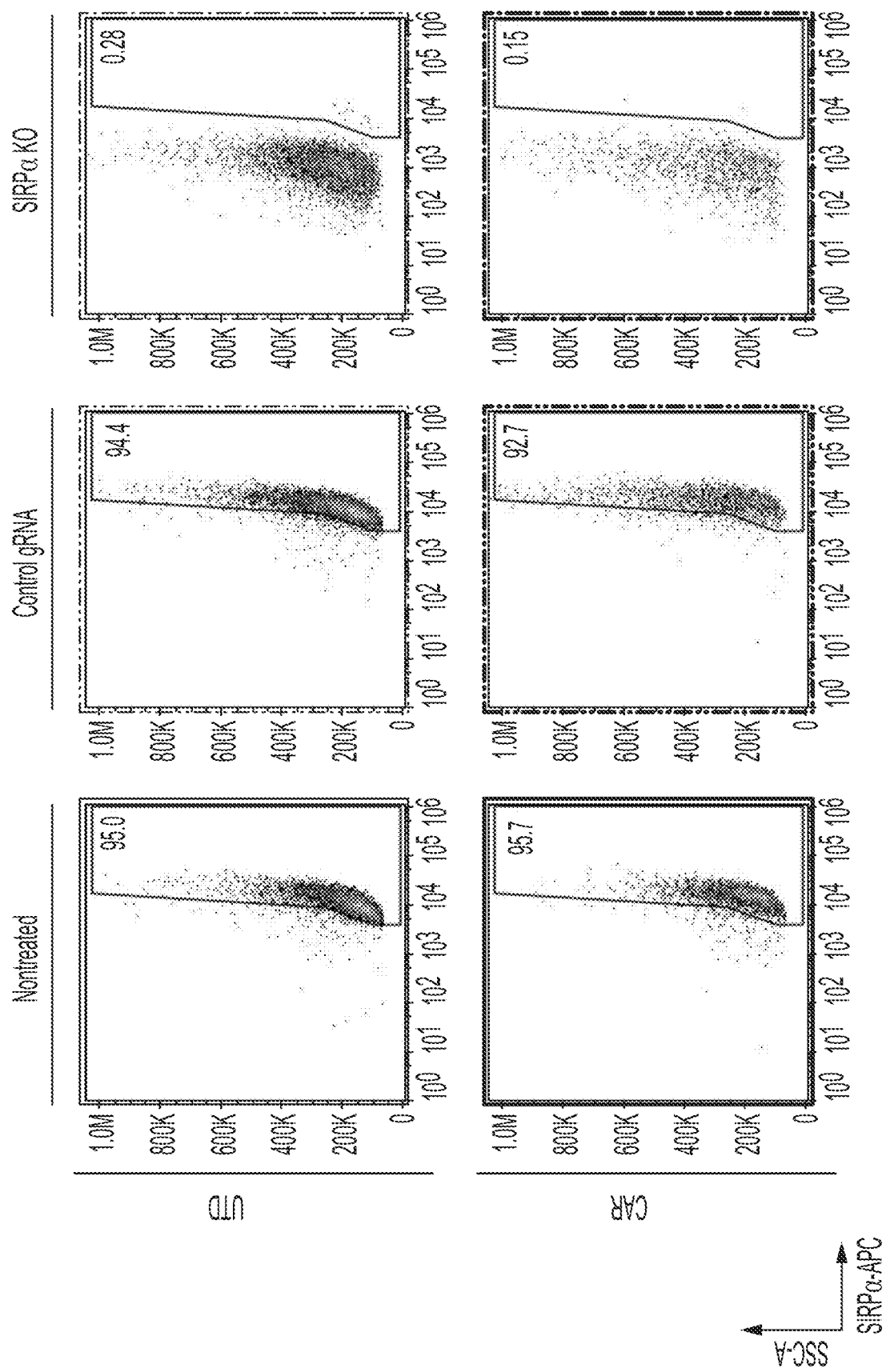
Figure 156B:
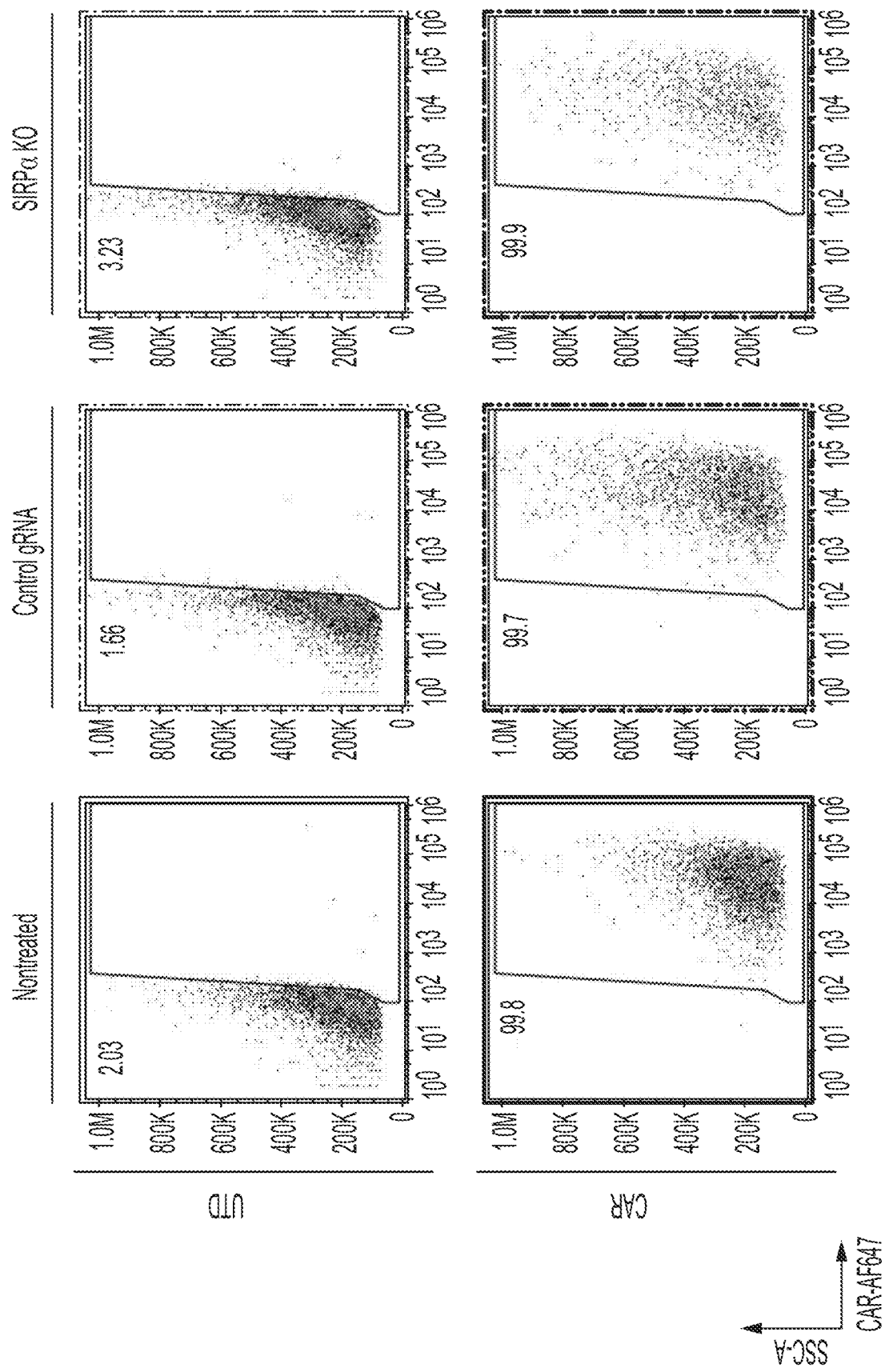
Figure 156C:
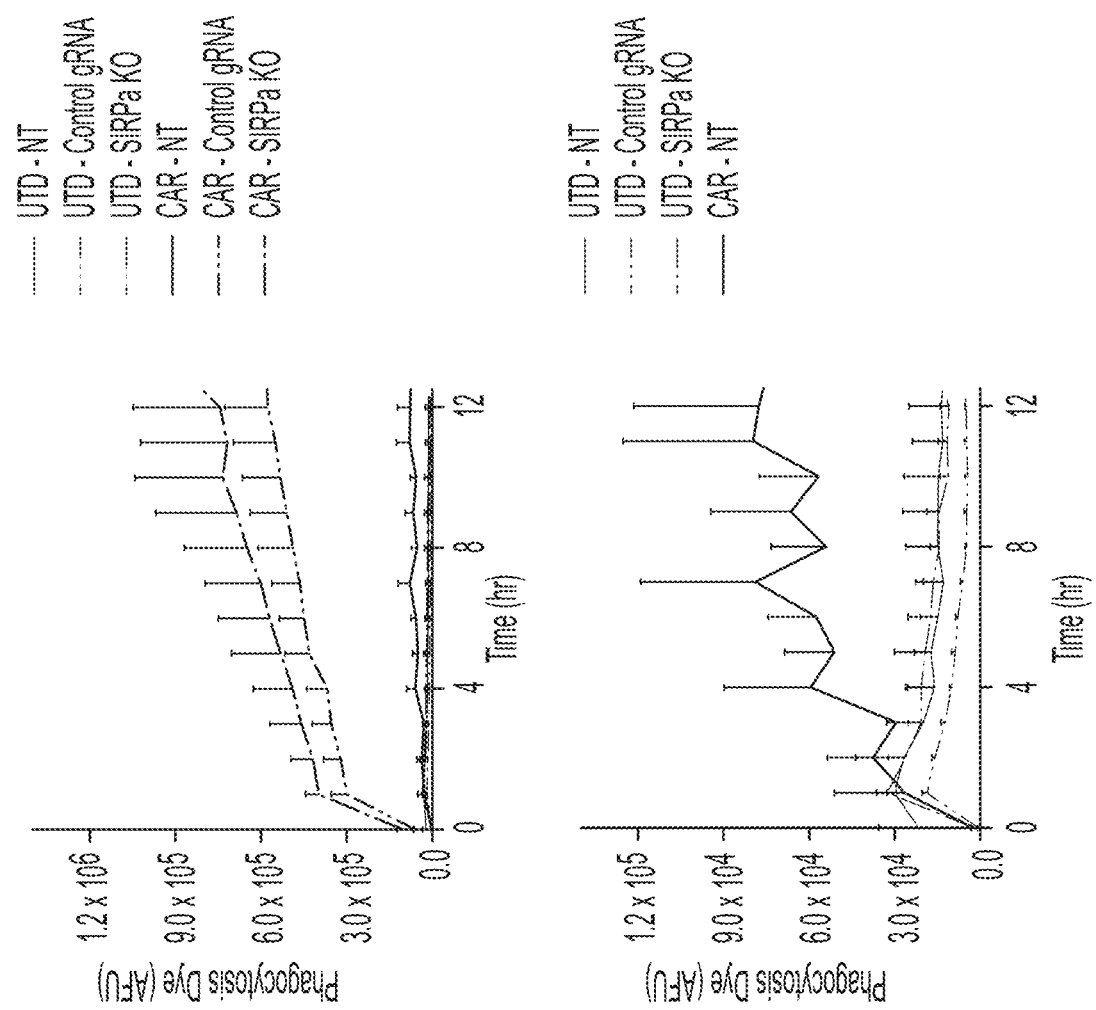

SIRPα KO was also shown to enhance CAR macrophage phagocytosis in HCC-1954 human breast cancer cells. Macrophages were thawed and transduced with adenovirus encoding CTX_001 at one day prior to electroporation with Cas9 RNP. Three days later, expression of SIRPα was evaluated, and a phagocytosis assay with HCC-1954 was begun. These results show SIRPα knockout in CTX_001 macrophages with Cas9 and gRNA targeting SIRPα (FIG. 156A). CTX_001 was expressed in transduced macrophages (FIG. 156B). CTX_001 macrophages demonstrated phagocytosis over 12 hours, which was measured using pHrodo-green signal via Incucyte® analysis with the lower plot re-scaled on the y-axis to show that CTX_001 macrophages demonstrated phagocytosis more than all UTD groups (FIG. 156C). Total phagocytosis measured over 12 hours was quantified as area under the curve (FIG. 156D). These results demonstrate that although the control gRNA increased phagocytosis, SIRPα knockout along with CAR expression in macrophages remained the greatest producer of phagocytosis signal.

Figure 157A:
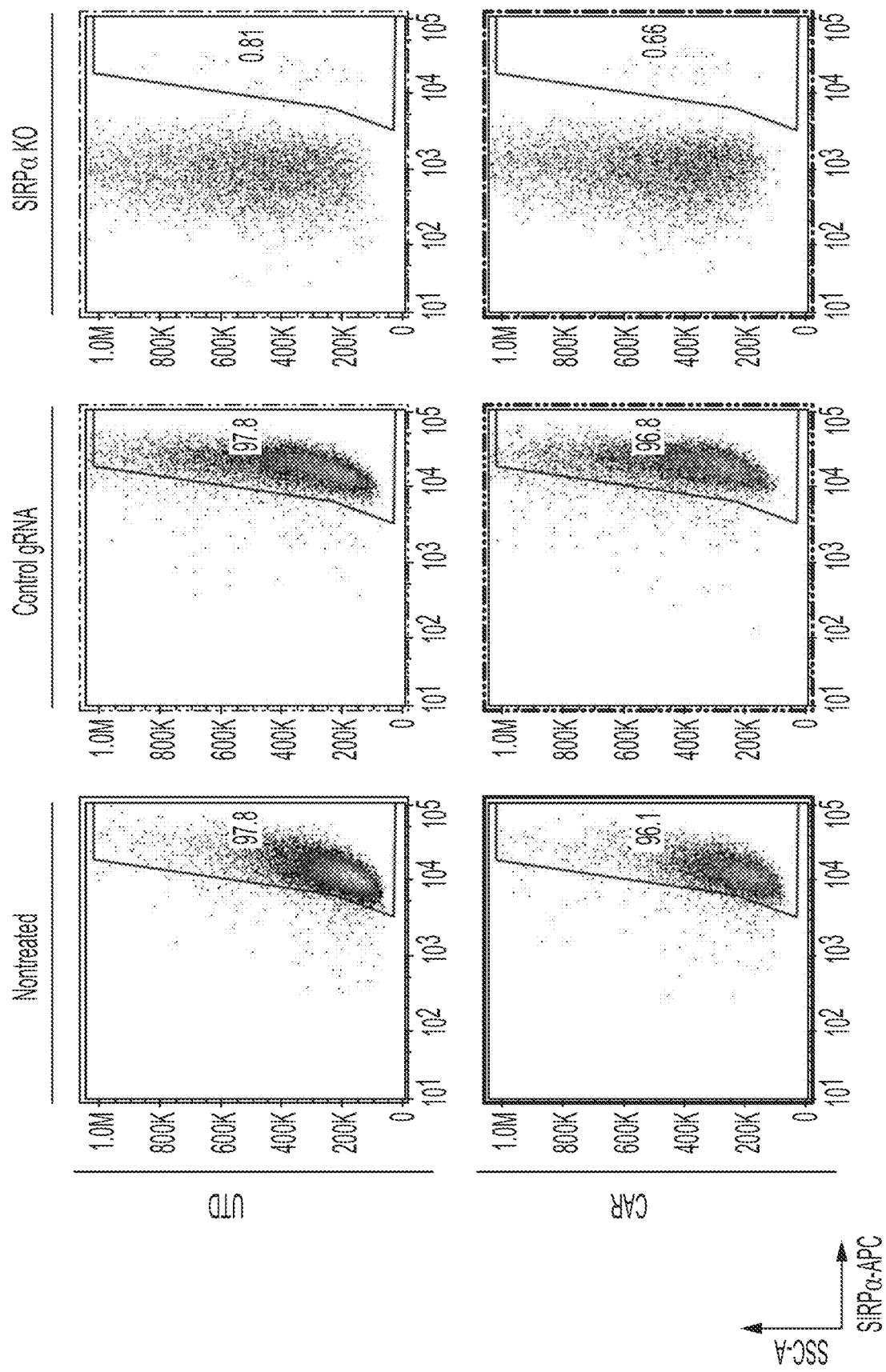
Figure 157B:
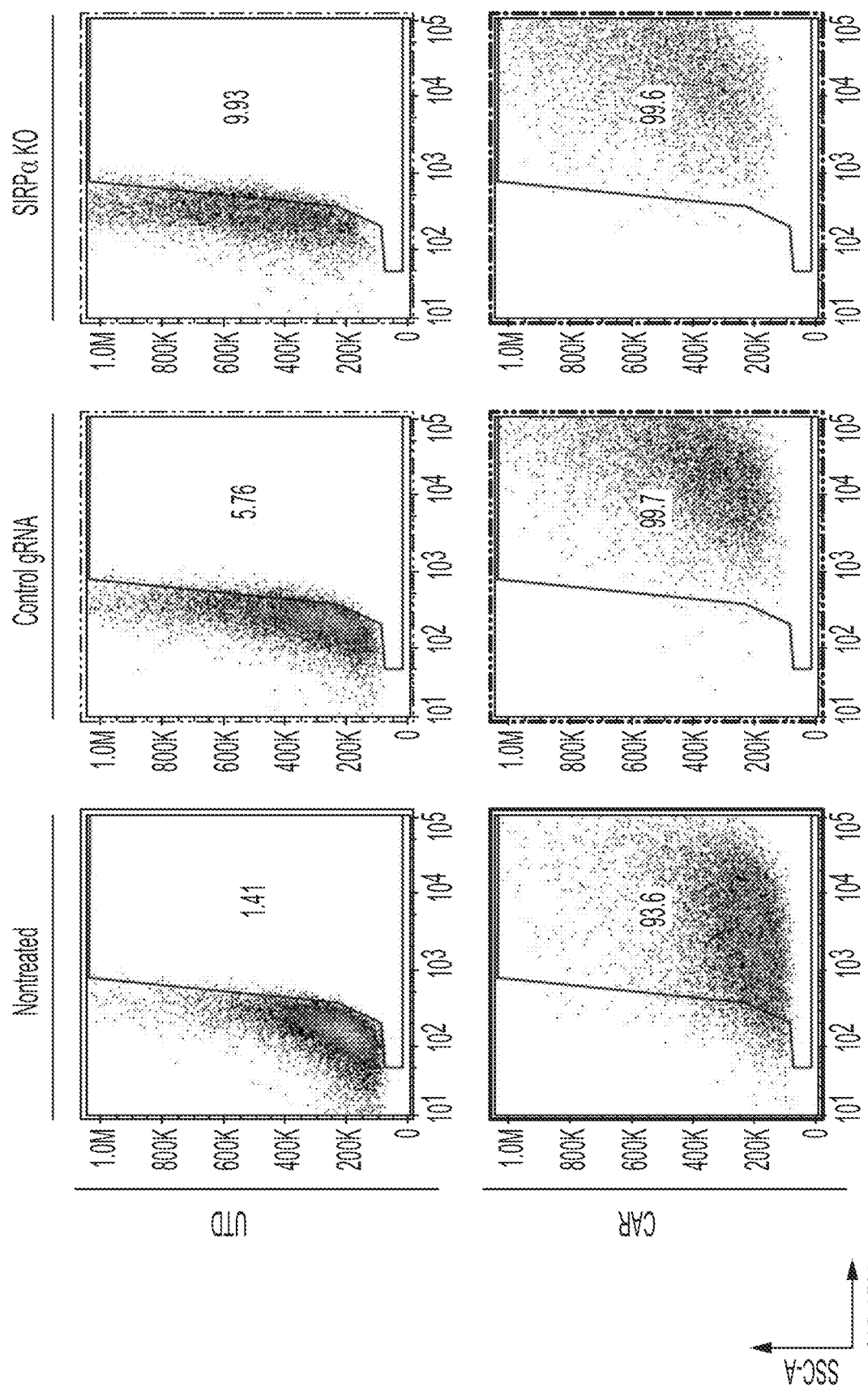
Figure 157C:
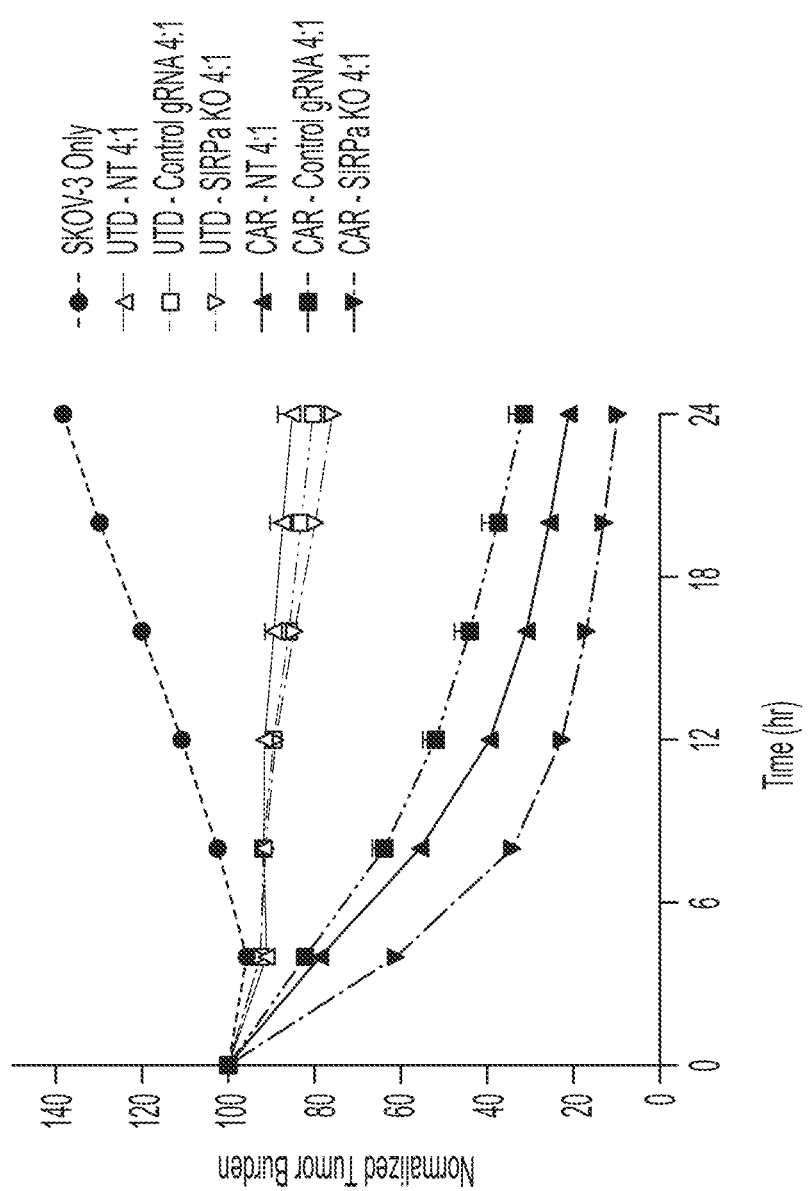
Figure 157E:
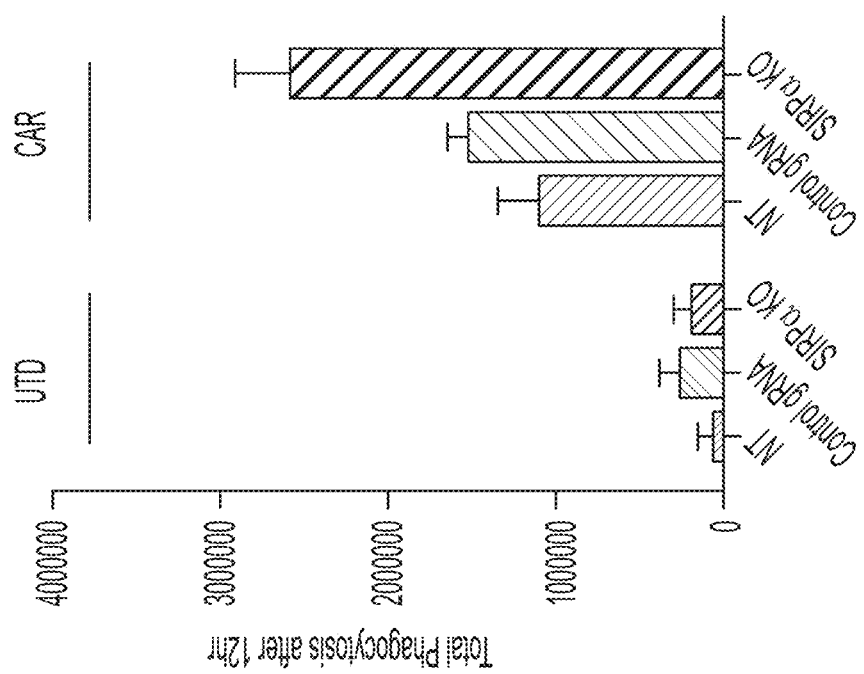

SIRPα knockout was also shown to enhance CAR macrophage killing in SKOV-3 ovarian carcinoma cells using macrophages from different donor cells than in the above experiment. Macrophages were thawed one day prior to electroporation with Cas9 RNP and transduced with adenovirus encoding CTX_001 at three days following electroporation. Two days later, expression of SIRPα was evaluated, and a phagocytosis assay with SKOV-3 was begun. These results show SIRPα knockout in CTX_001 macrophages with Cas9 and gRNA targeting SIRPα (FIG. 157A). CTX_001 was expressed in transduced macrophages (FIG. 157B). SKOV-3 killing was measured as growth of SKOV-3 cells expressing nuclight green fluorescent protein, measured via Incucyte® analysis over 24 hours (FIG. 157C). SIRPα knockout of human CAR macrophages increased kinetics of tumor killing based on hours required for the clearance of 50% of target tumor cells (FIG. 157D). Total phagocytosis was measured over 12 hours (FIG. 157E). SIRPα knockout along with CAR expression in macrophages resulted in greatest phagocytosis, while SIRPα knockout alone did not greatly enhance phagocytosis in UTD macrophages. Phagocytosis results were consistent using a second donor. SIRPα knockout CAR macrophages appeared to kill faster than CAR macrophages without SIRPα knockout.

These results presented herein demonstrate high efficiency SIRPα knockout with a CRISPR/Cas system in primary human CAR macrophages and that SIRPα knockout with a CRISPR/Cas system can consistently be performed on primary human CAR macrophages. These results are paired with functional data showing increased phagocytosis and killing by SIRPα knockout CAR macrophages compared to CAR macrophages without SIRPα knockout. In two separate donors and experimental runs, SIRPα knockout increased phagocytosis of SKOV-3 cells by CAR macrophages. Notably, SIRPα knockout in macrophages not expressing a CAR did not increase phagocytosis or tumor killing; thus, the effect can be considered synergistic.

EQUIVALENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

The invention claimed is:

1. A method of modifying ex vivo a macrophage or monocyte comprising a chimeric antigen receptor (CAR) comprising:
   (a) an extracellular domain,
   (b) a transmembrane domain, and
   (c) an intracellular domain, and
   wherein the method comprises treating the macrophage or monocyte with a CD40 agonist,
   thereby producing a modified macrophage or monocyte which exhibits increased tumor killing ability relative to an unmodified macrophage or monocyte.

2. The method of claim 1, wherein the modified macrophage or monocyte exhibits increased polarization to M1 phenotype relative to an unmodified macrophage or monocyte.

3. The method of claim 1, wherein the modified macrophage or monocyte exhibits increased expression of one or more markers of M1 phenotype relative to an unmodified macrophage or monocyte.

4. The method of claim 3, wherein the one or more markers of M1 phenotype comprise or are one or more of CD86, CD80, MHC II, IL-1R, TLR2, TLR4, iNOS, SOCS3, CD83, PD-L1, CD69, MHC I, CD64, CD32, CD16, IL1R, a IFIT family member, or an ISG family member.

5. The method of claim 1, wherein the modified macrophage or monocyte exhibits decreased expression of one or more markers of M2 phenotype relative to an unmodified macrophage or monocyte.

6. The method of claim 5, wherein the one or more markers of M2 phenotype comprises or are one or more of CD206, CD163, or CD209.

7. The method of claim 1, wherein the CD40 agonist comprises or is CD40L.

8. The method of claim 1, wherein the CAR further comprises a CD28 extracellular hinge domain and a CD28 transmembrane domain.

9. The method of claim 1, wherein the intracellular domain comprises one or more of: a CD3-zeta, FcRγ, CD64, CD32a, CD32c, CD16a, TLR1, TLR2, TLR3, TLR4, TLR5, TLR6, TLR7, TLR8, TLR9, ALK, AXL, DDR2, EGFR, EphA1, INSR, cMET, MUSK, PDGFR, PTK7, RET, ROR1, ROS1, RYK, TIE2, TRK, VEGFR, CD40, CD19, CD20, 41BB, CD28, OX40, GITR, TREM-1, TREM-2, DAP12, MR, ICOS, MyD88, V/I/LxYxxL/V, SIRPα, CD45, Siglec-10, PD1, SHP-1, SHP-2, KIR-2DL, KIR-3DL, NKG2A, CD170, CD33, BTLA, CD32b, SIRPb, CD22, PIR-B, LILRB1, 41BBL (TNFSF9), CD27, OX4OL, CD32b, CD11b, ITGAM, SLAMF7, CD206, CD163, CD209, Dectin-2, IL1R, IL2R, IL3R, IL4R, IL5R, IL6R, IL7R, IL8R, IL9R, IL10R, IL11R, IL12R, IL13R, IL14R, IL15R, IL17R, IFNaR, IFNgR, TNFR, CSF1R, CSF2R, Dap10, CD36, Dectin-1, ICOSL, CD2, CD7, CD96, CRTAM, DC-SIGN, NKG2D, NTB-A, CD30, or Syk intracellular signaling domain.

10. The method of claim 9, wherein the intracellular domain comprises a CD3-zeta intracellular signaling domain.

* * * * *